US012616761B2

(12) United States Patent
Bénard et al.

(10) Patent No.: US 12,616,761 B2
(45) **Date of Patent: *May 5, 2026**

(54) CXCR4-TARGETING COMPOUNDS

(71) Applicants: PROVINCIAL HEALTH SERVICES AUTHORITY, Vancouver (CA); The University of British Columbia, Vancouver (CA)

(72) Inventors: François Bénard, Vancouver (CA); Kuo-Shyan Lin, Richmond (CA); Zhengxing Zhang, Vancouver (CA); Daniel Kwon, Coquitlam (CA); David Perrin, Vancouver (CA); Mijhajlo Todorovic, Vancouver (CA); Jerome Lozada, Vancouver (CA); Lee Lee Li, Vancouver (CA)

(73) Assignees: The University of British Columbia, Vancouver (CA); Provincial Health Services Authority, Vancouver (CA)

(*) Notice: Subject to any disclaimer, the term of this patent is extended or adjusted under 35 U.S.C. 154(b) by 0 days.

This patent is subject to a terminal disclaimer.

(21) Appl. No.: 18/756,500

(22) Filed: Jun. 27, 2024

(65) Prior Publication Data

US 2024/0342321 A1 Oct. 17, 2024

Related U.S. Application Data

(63) Continuation of application No. 18/032,680, filed as application No. PCT/CA2021/051486 on Oct. 21, 2021.

(60) Provisional application No. 63/094,839, filed on Oct. 21, 2020.

(51) Int. Cl.

| | |
|---|---|
| ***A61K 38/00*** | (2006.01) |
| ***A61K 51/08*** | (2006.01) |
| ***A61P 35/00*** | (2006.01) |
| ***C07K 7/64*** | (2006.01) |

(52) U.S. Cl.

CPC ............ *A61K 51/088* (2013.01); *A61P 35/00* (2018.01); *C07K 7/64* (2013.01)

(58) Field of Classification Search

CPC ......... A61K 51/088; A61P 35/00; C07K 7/54; C07K 7/64; Y02P 20/55

See application file for complete search history.

(56) References Cited

U.S. PATENT DOCUMENTS

| | | | | |
|---|---|---|---|---|
| 5,650,134 | A | 7/1997 | Albert et al. | |
| 6,166,226 | A | 12/2000 | Buchwald et al. | |
| 7,041,859 | B1 | 5/2006 | Kabalka | |
| 8,114,381 | B2 | 2/2012 | Perrin et al. | |
| 8,153,101 | B2 | 4/2012 | McBride et al. | |
| 8,574,546 | B2 | 11/2013 | Perrin et al. | |
| 8,691,761 | B2 | 4/2014 | Rivier et al. | |
| 10,150,804 | B2 | 12/2018 | Benard et al. | |
| 10,556,023 | B2 | 2/2020 | Perrin et al. | |
| 11,207,432 | B2 | 12/2021 | Perrin et al. | |
| 12,427,209 | B2 | 9/2025 | Perrin et al. | |
| 2006/0128664 | A1 | 6/2006 | Holmes-Farley et al. | |
| 2008/0300177 | A1 | 12/2008 | Kohn et al. | |
| 2009/0028791 | A1 | 1/2009 | Balatoni et al. | |
| 2014/0147381 | A1 | 5/2014 | Espenan | |
| 2016/0311858 | A1* | 10/2016 | Kariyuki | C40B 40/10 |
| 2016/0333068 | A1 | 11/2016 | Benard et al. | |
| 2020/0222563 | A1 | 7/2020 | Perrin et al. | |
| 2021/0024605 | A1 | 1/2021 | Perrin et al. | |
| 2022/0062445 | A1 | 3/2022 | Perrin et al. | |
| 2022/0062446 | A1 | 3/2022 | Perrin et al. | |
| 2022/0218852 | A1 | 7/2022 | Benard et al. | |
| 2024/0100203 | A1 | 3/2024 | Bénard et al. | |

FOREIGN PATENT DOCUMENTS

| | | | |
|---|---|---|---|
| CA | 2267153 | A1 | 4/1998 |
| CA | 2710923 | A1 | 2/2010 |
| CA | 2810241 | A1 | 3/2012 |
| CA | 2931554 | A1 | 6/2015 |
| CN | 102066974 | A | 5/2011 |
| CN | 105636924 | A | 6/2016 |
| CN | 106967152 | A | 7/2017 |
| CN | 108699087 | A | 10/2018 |
| CN | 109517039 | A | 3/2019 |
| EP | 1027316 | A1 | 8/2000 |
| EP | 1089305 | A2 | 4/2001 |
| EP | 2226328 | A1 | 9/2010 |
| EP | 2555796 | A1 | 2/2013 |
| EP | 3459559 | A1 | 3/2019 |
| WO | WO-2005077967 | A1 | 8/2005 |
| WO | WO-2007032005 | A2 | 3/2007 |
| WO | WO-2008150689 | A1 | 12/2008 |
| WO | WO-2009012596 | A1 | 1/2009 |

(Continued)

OTHER PUBLICATIONS

Translation of WO-2020009093-A1 provided by Espacenet (Year: 2020).*

Merriam-Webster Inc., "Definition of *Derivative*" [online]. Retrieved from: http://beta.www.merriam-webster.com/dictionary/derivative; retrieved on Dec. 9, 2015; 10 pages.

Roxin et al., "The case for DOTA as a pharmacokinetic modulator for 18F-labeled peptides: DOTA-[18F]AMBF3-LLP2A for improved PET imaging of VLA-4 over-expression in murine melanoma," Journal of Nuclear Medicine. May 2019; 60 (supplement 1):1008, 2 pages.

Antunes, P. et al., "Influence of Different Spacers on the Biological Profile of a DOTA-Somatostatin Analogue," Bioconjugate Chemistry, 2007, vol. 18, pp. 84-92.

(Continued)

*Primary Examiner* — Lianko G Garyu
*Assistant Examiner* — Mercy H Sabila
(74) *Attorney, Agent, or Firm* — COOLEY LLP

(57) ABSTRACT

The present disclosure relates to peptidic compounds of Formula A, A-II, A-III, B, or C, or salt or solvate thereof, compositions thereof, and methods of use thereof. The compounds of the present disclosure are useful for targeting CXCR4 for purposes such as imaging and/or therapeutics.

28 Claims, 5 Drawing Sheets

Specification includes a Sequence Listing.

(56) References Cited

FOREIGN PATENT DOCUMENTS

| | | | |
|---|---|---|---|
| WO | WO-2009135015 A2 | 11/2009 | |
| WO | WO-2011124931 A1 | 10/2011 | |
| WO | WO-2012094334 A1 | 7/2012 | |
| WO | WO-2012118909 A1 | 9/2012 | |
| WO | WO-2014134716 A1 | 9/2014 | |
| WO | WO-2015055318 A1 | 4/2015 | |
| WO | WO-2015100498 A1 | 7/2015 | |
| WO | WO-2017117687 A1 | 7/2017 | |
| WO | WO-2019050564 A1 | 3/2019 | |
| WO | WO-2019057445 A1 | 3/2019 | |
| WO | WO-2020009093 A1 * | 1/2020 | |
| WO | WO-2020018700 A1 | 1/2020 | |
| WO | WO-2020210919 A1 * | 10/2020 | ............ A61K 51/04 |
| WO | WO-2020252598 A1 | 12/2020 | |
| WO | WO-2021168567 A1 | 9/2021 | |
| WO | WO-2022082312 A1 | 4/2022 | |
| WO | WO-2023201435 A1 | 10/2023 | |

OTHER PUBLICATIONS

Bagutski, V. et al. "Improved method for the conversion of pinacolboronic esters into trifluoroborate salts: facile synthesis of chiral secondary and tertiary trifluoroborates," Tetrahedron, Nov. 2009, vol. 65, Issue 48, pp. 9956-9960.

Balkwill, F., "Cancer and the chemokine network," Nat. Rev. Cancer, Jul. 2004, vol. 4, pp. 540-550.

Banerjee, S.R. and M.G. Pomper, "Clinical applications of Gallium-68," Applied Radiation and Isotopes, 2013, vol. 76, pp. 2-13.

Berge et al. "Pharmaceutical salts," Journal of Pharmaceutical Sciences (1977); 66(1): 1-19.

Bernard-Gauthier, V. et al., "18F-Labeled Silicon-Based Fluoride Acceptors: Potential Opportunities for Novel Positron Emitting Radiopharmaceuticals," Biomed Res Int, 2014, vol. 2014, Article ID: 454503, 20 pages.

Bernard-Gauthier, V. et al., "From Unorthodox to Established: The Current Status of 18F-Trifluoroborate- and 18F-SIFA-Based Radiopharmaceuticals in PET Nuclear Imaging," Bioconjugate Chemistry, 2016, vol. 27, pp. 267-279.

Bleul, C. et al., "The HIV coreceptors CXCR4 and CCR5 are differentially expressed and regulated on human T lymphocytes," PNAS, Mar. 1997, vol. 94, pp. 1925-1930.

Boutorine, A.S. et al., "Rapid Routes of Synthesis of Chemically Reactive and Highly Radioactive Labeled α- and β-Oligonucleotide Derivatives for in Vivo Studies," Bioconjugate Chemistry, 1:350-356, (1990).

Breeman, W.A.P. et al., "Somatostatin receptor-mediated imaging and therapy: basic science, current knowledge, limitations and future perspectives," European Journal of Nuclear Medicine, Sep. 2001, vol. 28, No. 9, pp. 1421-1429.

Buchmann, I. et al., "Comparison of $^{68}$Ga-DOTATOC PET and $^{111}$In-DTPAOC (Octreoscan)Spect in patients with neuroendocrine tumours," Eur J Nucl Med Mol Imaging, 2007, vol. 34, pp. 1617-1626.

Cai, H. et al., "RGD-based PET tracers for imaging receptor integrin αvβ3 expression," Journal of Labelled Compounds and Radiopharmaceuticals, 2013, vol. 56, pp. 264-279.

Chatterjee, S. et al., "The Intricate Role of CXCR4 in Cancer," Adv Cancer Res, 2014, 124:31-82.

Chin, F.T. et al., "First Experience with Clinical-Grade [18F]FP-P(RGD)2: An Automated Multi-step Radiosynthesis for Clinical PET Studies," Mol Imaging Biol, 2012, vol. 14, pp. 88-95.

Clayden et al., "The definition of pKa" Organic Chemistry. Oxford University Press, 2001, pp. 185-188.

ClinicalTrials.gov, "LY2510924, Idarubicin and Cytarabine in Patients With Relapsed or Refractory Acute Myeloid Leukemia," ClinicalTrials.gov identifier: NCT02652871, Jan. 12, 2016, 9 pages.

De Clerq, E. "The AMD3100 story: the path to the discovery of a stem cell mobilizer (Mozobil)," Biochem Pharmacol, 2009, vol. 77, No. 11, pp. 1655-1664 (32 pages total).

Demmer, O. et al., "PET Imaging of CXCR4 Receptors in Cancer by a New Optimized Ligand," ChemMedChem, 2011, vol. 6, pp. 1789-1791.

Domanska, U.M. et al. "A review on CXCR4/CXCL12 axis in oncology: No place to hide" Eur J Cancer, 2013, vol. 49, pp. 219-230.

Doring, Y. et al., "The CXCL12/CXCR4 chemokine ligand/receptor axis in cardiovascular disease," Front Physiol, Jun. 2014, vol. 5, Article 212, 23 pages.

Duda, D.G. et al., "CXCL12 (SDF1a)-CXCR4/CXCR7 Pathway Inhibition: An Emerging Sensitizer for Anticancer Therapies?" Clin Cancer Res, Apr. 2011, vol. 17, No. 8, pp. 2074-2080.

Dumas, A.M. et al., "Amide-Forming Ligation of Acyltrifluorborates and Hydroxylamines in Water," Angew Chem Int Ed Engl, 51:5683-5686 (Jun. 2012).

Dumas, A.M. et al., "Synthesis of Acyltrifluoroborates," Organic Letters, 14:2138-2141, (2012).

Eberl, S. et al., "High beam current operation of a PETtrace™ cyclotron for $^{18}$F production," Applied Radiation and Isotopes, 2012, vol. 70, pp. 922-930.

European Patent Application No. 14759809.8: Office Action, mailed Mar. 10, 2020 (19 pages).

European Patent Application No. 14759809.8: Office Action, mailed Oct. 10, 2018 (17 pages).

European Patent Application No. 21881418.4: Partial Supplementary European Search Report, dated Aug. 13, 2024, 20 pages.

European Patent Application No. 05706491.7: Supplemental Search Report, dated Mar. 26, 2010, 4 pages.

Extended European Search Report for Application No. 14759809.8, mailed Oct. 4, 2016, 12 pages.

Extended European Search Report for Application No. 15733077.0, dated Jun. 19, 2017, 6 pages.

Extended European Search Report for Application No. 19900988.7, dated Oct. 31, 2022,7 pages.

Extended European Search Report for Application No. 20791838.4, mailed on Dec. 20, 2022, and received Dec. 15, 2022, 10 pages.

Fani, M. et al., "Unexpected Sensitivity of sst2 Antagonists to N-Terminal Radiometal Modifications," The Journal of Nuclear Medicine, Sep. 2012, vol. 53, No. 9, pp. 1481-1489.

Feng, Y. et al., "HIV-1 Entry Cofactor: Functional cDNA Cloning of a Seven-Transmembrane, G Protein-Coupled Receptor," Science, 1996, 272:872-877, Abstract, 6 pages.

Fujii, N. et al. "Molecular-Size Reduction of a Potent CXCR4-Chemokine Antagonist Using Orthogonal Combination of Conformation- and Sequence-Based Libraries," Angew. Chemie Int. Ed., 42, 3251-3253 (2003).

Gabriel, M. et al., "$^{68}$Ga-DOTA-Tyr$^{3}$-Octreotide PET in Neuroendocrine Tumors: Comparison with Somatostatin Receptor Scintigraphy and CT," The Journal of Nuclear Medicine, Apr. 2007, vol. 48, No. 4, pp. 508-518.

Gabriel, M. et al., "An Intrapatient Comparison of $^{99}$mTc-EDDA/HYNIC-TOC with $^{111}$In-DTPA-Octreotide for Diagnosis of Somatostatin Receptor-Expressing Tumors," The Journal of Nuclear Medicine, May 2003, vol. 44, No. 5, pp. 708-716.

George, G.P.C. et al., "Positron Emission Tomographic Imaging of CXCR4 in Cancer: Challenges and Promises," Mol. Imaging, 2014, vol. 13, pp. 1-19, DOI: 10.2310/7290.2014.00041.

George, J. et al. "Transfer of Endothelial Progenitor and Bone Marrow Cells Influences Atherosclerotic Plaque Size and Composition in Apolipoprotein E Knockout Mice," Arterioscler. Thromb. Vasc. Biol., 25, 2636-2641 (2005).

Ginj, M. et al., "Design, Synthesis, and Biological Evaluation of Somatostatin-Based Radiopeptides," Chemistry & Biology, Oct. 2006, vol. 13, pp. 1081-1090.

Gourni, E. et al., "PET of CXCR4 Expression by a 68Ga-Labeled Highly Specific Targeted Contrast Agent," J. Nucl. Med., 2011, vol. 52, No. 11, pp. 1803-1810.

Griffith, J.W. et al., "Chemokines and Chemokine Receptors: Positioning Cells for Host Defense and Immunity," Annu. Rev. Immunol., 2014, vol. 32, pp. 659-702.

Guo, F. et al. "CXCL12/CXCR4: a symbiotic bridge linking cancer cells and their stromal neighbors in oncogenic communication networks," Oncogene, 2016, vol. 35, pp. 816-826.

(56) References Cited

OTHER PUBLICATIONS

Guo, Y. et al., "Preparation and Biological Evaluation of $^{64}$Cu Labeled Tyr$^3$-Octreotate Using a Phosphonic Acid-Based Cross-Bridged Macrocyclic Chelator," Bioconjugate Chemistry, 2012, vol. 23, pp. 1470-1477.
Harwig, C.W. et al., "Synthesis and characterization of 2,6-difluoro-4-carboxyphenylboronic acid and a biotin derivative thereof as captors of anionic aqueous [18F]-fluoride for the preparation of [18F/19F]-labeled aiyltrifluoroborates with high kinetic stability," Tetrahedron Letters, 2008, vol. 49, pp. 3152-3156.
Henze, M. et al., "PET Imaging of Somatostatin Receptors Using [$^{68}$GA]DOTA-D-Phe$^1$-Tyr$^3$-Octreotide: First Results in Patients with Meningiomas," The Journal of Nuclear Medicine, Jul. 2001, vol. 42, No. 7, pp. 1053-1056.
Herrmann, K. et al., "First-in-Human Experience of CXCR4-Directed Endoradiotherapy with 177Lu- and 90Y-Labeled Pentixather in Advanced-Stage Multiple Myeloma with Extensive Intra- and Extramedullary Disease," J Nucl Med, Feb. 2016, vol. 57, No. 2, pp. 248-251.
Huang. S. et al., "Improving the Biodistribution of PSMA-targeting tracers with a highly negatively charged linker", The prostate, Feb. 24, 2014, vol. 74, No. 7, pp. 702-713.
Imahori, Y. et al., "Positron Emission Tomography-based Boron Neutron Capture Therapy Using Boronophenylalanine for High-Grade Gliomas: Part I," Clinical Cancer Research, vol. 4, Aug. 1998, pp. 1825-1832.
Imahori, Y. et al., "Positron Emission Tomography-based Boron Neutron Capture Therapy Using Boronophenylalanine for High-Grade Gliomas: Part II," Clinical Cancer Research, vol. 4, Aug. 1998, pp. 1833-1841.
International Preliminary Report on Patentability for International Application No. PCT/CA2008/001368, mailed on Feb. 4, 2010, 8 pages.
International Preliminary Report on Patentability for International Application No. PCT/CA2014/000200, issued Sep. 8, 2015, 5 pages.
International Preliminary Report Patentability, dated Aug. 14, 2006, corresponding to PCT/CA2005/000195, 6 pages.
International Search Report and Written Opinion for International Application No. PCT/CA2021/051486, mailed Jan. 20, 2022, 11 pages.
International Search Report and Written Opinion for International Application No. PCT/CA2023/050538 dated Jul. 9, 2023, 15 pages.
International Search Report and Written Opinion for International (PCT) Patent Application No. PCT/CA2015/000002, mailed May 4, 2015, 10 pages.
International Search Report and Written Opinion of the International Searching Authority for International Application No. PCT/CA2019/051853, dated Feb. 18, 2020, 8 pages.
International Search Report and Written Opinion of the International Searching Authority for International Application No. PCT/CA2020/050521, dated Jul. 29, 2020, 7 pages.
International Search Report for International Application No. PCT/CA2014/000200, mailed Jun. 11, 2014 , 5 pages.
Ishiwata et al., "A unique in vivo assessment of 4-[10B] borono-L-phenylalanine in tumour tissues for boron neutron capture therapy of malignant melanomas using positron emission tomography and 4-borono-2-[18F]fluoro-L-phenylalanine," Melanoma Research, 1992, vol. 2, pp. 171-179.
Ishiwata, K. et al., "4-Borono-2[18F]-D,L-phenylalanine: a Possible Tracer for Melanoma Diagnosis with PET," International Journal of Radiation Applications and Instrumentation, Part B, Nuclear Medicine and Biology, Apr. 1992, vol. 19, No. 3, pp. 311-318.
Jacobson, O. and Weiss, I.D., "CXCR4 chemokine receptor overview: biology, pathology and applications in imaging and therapy," Theranostics, 2013, vol. 3, pp. 1-2.
Kabalka, G., et al., "Evaluation of Fluorine-18-BPA-Fructose for Boron Neutron Capture Treatment Planning," The Journal of Nuclear Medicine, vol. 38, No. 11, Nov. 1997, pp. 1762-1767.
Kabalka, G., et al., "The Development of Boron Neutron Capture Agents Utilizing Positron Emission Tomography," Special publication Royal Society of Chemistry (Great Britain), vol. 253, (2000), Contemporary Boron Chemistry—Medicinal Applications, pp. 120-126.
Kayani, I. et al. "A Comparison of $^{68}$Ga-DOTATATE and $^{18}$F-FDG PET/CT in Pulmonary Neuroendocrine Tumors," The Journal of Nuclear Medicine, Dec. 2009, vol. 50, No. 12, pp. 1927-1932.
Keenan, M.A. et al., "Radar Realistic Animal Model Series for Dose Assessment," J Nucl Med, 2010, vol. 51, No. 3, pp. 471-476.
Kemerink, G.J. et al., "Effect of the positron range of $^{18}$F, $^{68}$Ga and $^{124}$I on PET/CT in lung-equivalent materials," Eur J Nucl Med Mol Imaging, 2011, vol. 38, pp. 940-948.
Kirkham, J.D. et al. "Synthesis of Ynone Trifluoroborates toward Functionalized Pyrazoles," Org. Letters, 2012, vol. 14, No. 20, pp. 5354-5357.
Kostikov, A.P. et al., "Oxalic Acid Supported Si—18F-Radiofluorination: One-Step Radiosynthesis of N—Succinimidyl 3-(Di-tert-butyl[18F]fluorosilyl) benzoate ([18F]SiFB) for Protein Labeling," Bioconjug Chem, Jan. 2012, vol. 23, pp. 106-114.
Kostikov, A.P. et al., "Synthesis of [18F]SiFB: a prosthetic group for direct protein radiolabeling for application in positron emission tomography," Nature Protocols, Nov. 2012, vol. 7, pp. 1956-1963, Abstract, 9 pages.
Krausz, Y. et al., "SPECT/CT hybrid imaging with $^{111}$In-pentetreotide in assessment of neuroendocrine tumours," Clinical Endocrinology, 2003, vol. 59, pp. 565-573.
Kuil, J. et al., "Imaging agents for the chemokine receptor 4 (CXCR4)," Chem. Soc. Rev., 2012, 41, 5239-5261.
Kuo, H-T. et al., "One-Step $^{18}$F-Labeling and Preclinical Evaluation of Prostate-Specific Membrane Antigen Trifluoroborate Probes for Cancer Imaging," J Nucl Med, 2019; 60:1160-1166, DOI: 10.2967/jnumed.118.216598.
Kwekkeboom, D.J. et al. "Somatostatin receptor-based imaging and therapy of gastroenteropancreatic neuroendocrine tumors," Endocr Relat Cancer, 2010, vol. 17, pp. R53-R73.
Kwekkeboom, D.J. et al. "Peptide Receptor Radionuclide Therapy in Patients With Gastroenteropancreatic Neuroendocrine Tumors," Seminars in Nuclear Medicine, Mar. 2010, vol. 40, No. 2, pp. 78-88.
Kwon, D. et al. "[18F]Trifluoroborate-based CXCR4-targeting PET Agents Based on a Potent and Novel Pharmacophore," Journal of Nuclear Medicine, Aug. 2022:63(supplement 2): Abstract 2579 [online]. Retrieved from the Internet: URL:https://jnm.snmjournals.org/content/63 /supplement_2/2579, 4 pages.
Kwon, D. et al., "A CXCR4-Targeting Radiotheranostic Based on a Potent Novel Peptide Antagonist", Journal of Nuclear Medicine, Aug. 2022:63(supplement 2): Abstract 2566 [online]. Retrieved from the Internet: URL:https://jnm.snmjournals.org/content/63 /supplement_2/2566, 4 pages.
Kwon, D. et al. "High-Contrast CXCR4-Targeted 18F-PET Imaging Using a Potent and Selective Antagonist," Mol Pharm. Jan. 4, 2021;18(1):187-197. doi: 10.1021/acs.molpharmaceut.0c00785. Epub Nov. 30, 2020.
Laforest, R and X. Liu, "Image quality with non-standard nuclides in PET," QJ Nucl Med Mol Imaging, 2008, vol. 52, pp. 151-158.
Lau et al., "[68Ga]Ga/[177Lu]Lu—BL01, a Novel Theranostic Pair for Targeting C-X-C Chemokine Receptor 4," Mol. Pharmaceutics, Nov. 2019, 16(11):4688-4695.
Laverman, P. et al., "A Novel Facile Method of Labeling Octreotide with $^{18}$F-Fluorine," The Journal of Nuclear Medicine, Mar. 2010, vol. 51(3), pp. 454-461.
Laverman, P. et al., "Optimized labeling of NOTA-conjugated octreotide with F-18," Tumor Biol., 2012, vol. 33, pp. 427-434.
Laverman, P. et al., "Radiolabelled peptides for oncological diagnosis," Eur J Nucl Med Mol Imaging, Feb. 2012; 39(Suppl 1):S78-S92.
Lawrence, J.D. et al. "Regiospecific Functionalized of Methyl C—H Bonds of Alkyl Groups in Reagents with Heteroatom Functionality," J. Am. Chem. Soc., 2004, vol. 126, pp. 15334-15335.
Lennox , A.J.J. et al., "Organotrifluoroborate Hydrolysis: Boronic Acid Release Mechanism and an Acid-Base Paradox in Cross-Coupling," JACS, 134:7431-7441, (2012).

(56) References Cited

OTHER PUBLICATIONS

Lepage, M., et al., "Toward 18 F-Labeled Theranostics: A Single Agent that Can Be Labeled with 18 F, 64 Cu, or 177 Lu," Chembiochem, vol. 21, No. 7 (Oct. 16, 2019), pp. 943-947.

Leyton, J. et al., "Targeting Somatostatin Receptors: Preclinical Evaluation of Novel $^{18}$F-Fluoroethyltriazole-Tyr$^{3}$-Octreotate Analogs for PET," The Journal of Nuclear Medicine, Sep. 2011, vol. 52, No. 9, pp. 1441-1448.

Li, Y. et al. "Hydrolytic stability of nitrogenous-heteroaryltrifluoroborates under aqueous conditions at near neutral pH," Journal of Fluorine Chemistry, 130:377-382, (Apr. 2009).

Li, Y. et al., "One-step and one-pot-two-step radiosynthesis of cyclo-RGD-$^{18}$F-aryltrifluoroboronate conjugates for functional imaging," Am J Nucl Med Mol Imaging, 2013, vol. 3, No. 1, pp. 44-56.

Lin, K-S. et al., "In vivo radioimaging of bradykinin receptor b1, a widely overexpressed molecule in human cancer," Cancer Res. Jan. 2015; 75(2):387-393. doi:10.1158/0008-5472.CAN-14-1603.

Liu et al., "Rapid, one-step, high yielding 18F-labeling of an aryltrifluoroborate bioconjugate by isotope exchange at very high specific activity," Journal of Labelled Compounds and Radiopharmaceuticals, 2012, vol. 55, pp. 491-496.

Liu, Z. et al., "$^{18}$F-trifluoroborate derivatives of [des-arg$^{10}$]kallidin for imaging bradykinin B1 receptor expression with positron emission tomography," Molecular Pharmaceutics, 2015, vol. 12, No. 3, pp. 974-982.

Liu, Z. et al., "An Organotrifluoroborate for Broadly Applicable One-Step$^{18}$F-Labeling," Angewandte Chemie International Edition, Sep. 2014, vol. 53, No. 44, pp. 11876-11880.

Liu, Z. et al., "Facile synthesis and biological evaluation of an 18F-labeled 4-(2-aminoethyl) benzenesulfonamide (AEBS) trimer for imaging carbonic anhydrase IX expression with positron emission tomography," World Molecular Imaging Congress, Sep. 19, 2013, Presentation No. LBAP 029, 2 pages.

Liu, Z. et al., "Kit-like $^{18}$F-labeling of RGD-$^{19}$F-Arytrifluroborate in high yield and at extraordinarily high specific activity with preliminary in vivo tumor imaging," Nuclear Medicine and Biology, vol. 40, 2013, pp. 841-849.

Liu, Z. et al., ""Kit-like" radiosynthesis and biological evaluation of an F-labeled 4-(2-Aminoethyl)-benzenesulfonamide (AEBS) trimer for imaging carbonic anhydrase IX expression with positron emission tomography," World Molecular Imaging Congress, Sep. 19, 2013; Poster, 1 page.

Liu, Z. et al., "One-step 18F labeling of biomolecules using organotrifluoroborates," Nat Protoc, Sep. 2015, vol. 10, No. 9, pp. 1423-1432.

Liu, Z. et al., "Preclinical evaluation of a high affinity 18F-trifluoroborate octreotate derivative for somatostatin receptor imaging-poster," University of British Columbia, 2014, 1 page.

Liu, Z. et al., "Preclinical Evaluation of a High-Affinity $^{18}$F-Trifluoroborate Octreotate Derivative for Somatostatin Receptor Imaging," Journal of Nuclear Medicine, Sep. 2014, vol. 55(9), pp. 1499-1505.

Liu, Z. et al., "Preclinical Evaluation of a Novel 18F-Labelled Somatostatin Receptor-Binding Peptide—Abstract Proof," ScholarOne, Inc., 2014, Control ID: 1931699, 4 pages.

Liu, Z. et al., "Preclinical evaluation of a novel$^{18}$F-labelled somatostatin receptor-binding peptide," The Journal of Nuclear Medicine, 2014, vol. 55 (Supplement 1):1089, 1 page.

Liu, Z. et al., "Stoichiometric Leverage: Rapid 18F-Aryltrifluoroborate Radiosynthesis at High Specific Activity for Click Conjugation," Angew Chem Int Ed, 2013, vol. 52, pp. 2303-2307.

Matteson, D.S. et al., "Iodomethaneboronic Esters and Aminomethaneboronic Esters," Journal of Organometallic Chemistry, 1979, vol. 170, pp. 259-264.

Means, G.E. and R.E. Feeney, "Chemical Modifications of Proteins: History and Applications," Bioconjugate Chemistry, 1990, vol. 1, No. 1, pp. 2-12.

Molander , G.A. et al., "Functionalization of Organotrifluoroborates: Reductive Amination," J. Org. Chem., 2008, vol. 73, pp. 3885-3891.

Molander, G.A. et al., "Synthesis of an Acyltrifluoroborate and its Fusion with Azides to Form Amides," J. Org. Chem., 75:4304-4306, (Jun. 2010).

Molander, G.A. et al., "Synthesis of Functionalized Organotriflurorborates via Halomethyltrifluoroborates", Organic Letters, 8(10):2031-2034 (May 2006).

Murdoch, C. "CXCR4: chemokine receptor extraordinaire," Immunol. Rev., 177, 175-184 (2000).

Nichols, T. et al., "Improved treatment planning for boron neutron capture therapy for glioblastoma multiforme using fluorine-18 labeled boronophenylalanine and positron emission tomography," Med. Phys., Oct. 2002, vol. 29, No. 10, pp. 2351-2358.

Okarvi, S.M. "Recent Progress in Fluorine-18 labelled peptide radiopharmaceuticals," European Journal of Nuclear Medicine, 2001, vol. 28, pp. 929-938.

Onufriev, A. et al., "A Novel View of pH Titration in Biomolecules," Biochemistry, Mar. 27, 2001, vol. 40, No. 12, pp. 3413-3419.

Peng, S.B. et al., "Identification of LY2510924, a novel cycllic peptide CXCR4 antagonist that exhibits antitumor activities in solid tumor and breast cancer metastatic models," Mol Cancer Ther, Feb. 2015, 14(2):480-490.

Poeppel, T.D. et al., "$^{68}$GA-DOTATOC Versus $^{68}$Ga-DOTATATE PET/CT in Functional Imaging of Neuroendocrine Tumors," The Journal of Nuclear Medicine, Dec. 2011, vol. 52(12), pp. 1864-1870.

Poethko, T. et al., "Two-Step Methodology for High-Yield Routine Radiohalogenation of Peptides: 18F-Labeled RGD and Octreotide Analogs," The Journal of Nuclear Medicine, May 2004, vol. 45, No. 5, pp. 892-902.

Poole, R.T. et al., "Radiotracers in Fluorine Chemistry. Part IV. Fluorine-18 Exchange between labelled Alkyfluorosilanes and Fluorides or Fluoride Methoxides, of Tungsten(vi), Molybdenum,(vi), Tellurium(vi), and lodine(v)," J.C.S. Dalton, (1976), pp. 1557-1560.

Poschenrieder. A. et al., "The influence of different metal-chelate conjugates of pentixafor on the CXCR4 affinity", EJNMMI Research, Dec. 26, 2016; 6(1):36, 8 pages.

Poty, S. et al., "AMD3100: A Versatile Platform for CXCR4 Targeting (68)Ga-Based Radiopharmaceuticals," Bioconjug Chem, Mar. 2016, 27(3):752-761.

Pourghisian, M. et al., "$^{18}$F-AmBF$_3$-MJ9: a novel radiofluorinated bombesin derivative for prostate cancer imaging," Bioorganic & Medicinal Chemistry, 2015, vol. 23, No. 7, pp. 1500-1506.

Price et al. "Matching chelators to radiometals for radiopharmaceuticals" Chemical Society Reviews (2014); 43(1):260-290.

Ratajczak, M. Z. et al. "The pleiotropic effects of the SDF-1-CXCR4 axis in organogenesis, regeneration and tumorigenesis," Leukemia, 20, 1915-1924 (2006).

Raushel, J. et al. "Reinvestigation of Aminomethyltrifluoroborates and Their Application in Suzuki-Miyaura Cross-Coupling Reactions," J. Org. Chem, 2011, vol. 76, pp. 2762-2769.

Reubi, J.C. et al., "Affinity profiles for human somatostatin receptor subtypes SST1-SST5 of somatostatin radiotracers selected for scintigraphic and radiotherapeutic use," European Journal of Nuclear Medicine, Mar. 2000, vol. 27, No. 3, pp. 273-282.

Roxin, A. et al., "A metal-free DOTA-conjugated $^{18}$F-labeledradiotracer: [$^{18}$F]DOTA-AMBF$_3$-LLP2A for imaging VLA-4 over-expression in murine melanoma with improved tumor uptake and greatly enhanced renal clearance," Bioconjugate Chem, 2019, vol. 30, pp. 1210-1219.

Roxin, A. et al., "Preliminary evaluation of 18F-labeled LLP2A-trifluoroborate conjugates as VLA-4 ($\alpha 4\beta 1$ integrin) specific radiotracers for PET imaging of melanoma," Nuclear Medicine and Biology, Jun. 2018 vol. 61, pp. 11-20.

Salgia, R. et al., "A randomized phase II study of LY2510924 and carboplatin/etoposide versus carboplatin/etoposide in extensive-disease small cell lung cancer," Lung Cancer, 2017, 105:7-13, Abstract, 10 pages.

Schirrmacher, R. et al., "18F-labeling of peptides by means of an organisilicon-based fluoride acceptor," Angew. Chem. Int. Ed., 2006, vol. 45, pp. 6047-6050.

Schottelius, M. et al., "[$^{111}$ In]PSMA-I&T: expanding the spectrum of PSMA-I&T applications towards SPECT and radioguided surgery," EJNMMI Research, 2015, vol. 5, Article 68, 5 pages.

(56) References Cited

OTHER PUBLICATIONS

Segars, William Paul. Development and application of the new dynamic NURBS-based cardiac-torso (NCAT) phantom. Dissertation, The University of North Carolina at Chapel Hill, 2001; 24 pages.
Shoup, T.M. et al., "Synthesis of Fluorine-18-Labeled Biotin Derivatives: Biodistribution and Infection Localization," The Journal of Nuclear Medicine, (1994), vol. 35, pp. 1685-1690.
Smith, M. et al., March's Advanced Organic Chemistry: Reactions, Mechanisms, and Structure, 7th ed. Jun. 13, 2013, John Wiley & Sons, vol. 116, pp. 334-346.
Sprague, J.E. et al., "Preparation and Biological Evaluation of Copper-64-Labeled Tyr3-Octreotate Using a Cross-Bridged Macrocyclic Chelator," Clinical Cancer Research, Dec. 2004, vol. 10, pp. 8674-8682.
Sprik and Ciccotti, "Free energy from constrained molecular dynamics," J Chem Phys, 109(18):7737-7744, (1998).
Stabin, M.G. et al., "OLINDA/EXM: the second-generation personal computer software for internal dose assessment in nuclear medicine," J Nucl Med.;46:1023-1027 (2005).
Stabin, M.G. et al., "Radar reference adult, pediatric, and pregnant female phantom series for internal and external dosimetry," J Nucl Med; 53:1807-1813 (2012).
Storch, D. et al., "Evaluation of [$^{99m}$Tc/EDDA/HYNIC$^{0}$]Octreotide Derivatives Compared with [$^{111}$In-DOTA$^{0}$, Tyr$^{3}$, Thr$^{8}$]Octreotide and [$^{111}$In-DTPA$^{0}$]Octreotide: Does Tumor or Pancreas Uptake Correlate with the Rate of Internalization?" J Nucl Med, Sep. 2005, vol. 46, No. 9, pp. 1561-1569.
Sun, Na et al., "Biorelevant pKa (37° C.) predicted from the 2D structure of the molecule and its pKa at 25 ° C. ," Journal of Pharmaceutical and Biomedical Analysis, Sep. 2011, vol. 56, No. 2, pp. 173-182.
Suzuki, K. et al., "C-terminal-modified LY2510924: a versatile scaffold for targeting C-X-C chemokine receptor type 4," Scientific Reports, Oct. 2019, 9(1):Article No. 15284, 10 pages.
Tamamura, H. et al. "A Low-Molecular-Weight Inhibitor against the Chemokine Receptor CXCR4: A Strong Anti-HIV Peptide T140," Biochem. Biophys. Res. Commun. 253, 877-882 (1998).
Ting, R. et al., "Arylfluoroborates and Alkylfluorosilicates as Potential PET Imaging Agents: High-Yielding Aqueous Biomolecular 18F-Labeling," J. Am. Chem. Soc., 127:13094-13095, (2005).
Ting, R. et al. "Capturing aqueous [18F]-fluoride with an arylboronic ester for PET: Synthesis and aqueous stability of a fluorescent [18F]-labeled aryltrifluoroborate," Journal of Fluorine Chemistry, 129:349-358, (2008).
Ting, R. et al. "Toward [18F]-Labeled Aryltrifluoroborate Radiotracers: In Vivo Positron Emission Tomography Imaging of Stable Aryltrifluoroborate Clearance in Mice," J. Am. Chem. Soc., 130:12045-12055, (2008).
Ting, R. et al., "Substitutent effects on aryitrifluoroborate solvolysis in water: Implications for Suzuki-Miyaura coupling and the design of stable 18F-labeled aryitrifluoroborates for use in PET imaging," J. Org. Chem., 73:4662-4670, (2008).
Todorovic, M. et al., "Fluorescent Isoindodole Crosslink (FIICκ) Chemistry: A Rapid, User-friendly Stapling Reaction", Angewandte Chemie, 2019;58(40):14120-14124.
Toyokuni, T. et al., "Synthesis of a New Heterobiofunctional Linker, N-[4-(Aminooxy)butylmaleimide, for Facile Access to a Thiol-Reactive 18F-Labeling Agent," Bioconjugate Chem, 2003, vol. 14, pp. 1253-1259.
Vag, T. et al., "PET imaging of chemokine receptor CXCR4 in patients with primary and recurrent breast carcinoma," European Journal of Nuclear Medicine and Molecular Imaging Research, Sep. 2018, vol. 8(1):90, 9 pages.
Vallabhajosula, S. et al., "Preclinical Evaluation of Technetium-99m-Labeled Somatostatin Receptor-Binding Peptides," The Journal of Nuclear Medicine, Jun. 1996, vol. 37, No. 6, pp. 1016-1022.
Virgolini, I. et al., "Somatostatin Receptor Subtype Specificity and in Vivo Binding of a Novel Tumor Tracer, $^{99m}$Tc-P829," Cancer Research, May 1998, vol. 58, pp. 1850-1859.
Walenkamp, A.M.E. et al., "CXCR4 Ligands: The Next Big Hit?," J Nucl Med, Sep. 2017, vol. 58, No. 9 (Suppl. 2), pp. 77S-82S.
Walsh, J.C. et al., "Application of Silicon-Fluoride Chemistry to Fluorine-18 Labeling Agents for Biomolecules: A Preliminary Note," J. Labelled Cpd. Radiopharm., 1999, vol. 42 (Suppl. 1), pp. S1-S3.
Wang, A. et al. "CXCR4/CXCL12 Hyperexpression Plays a Pivotal Role in the Pathogenesis of Lupus," J. Immunol., Apr. 2009; 182:4448-4458.
Wang, A. et al. "Dysregulated expression of CXCR4/CXCL12 in subsets of patients with systemic lupus erythematosus," Arthritis Rheum., Nov. 2010;62:3436-3446.
Weiss, I.D. et al., "Molecular Imaging of Chemokine Receptor CXCR4," Theranostics, 2013, vol. 3, Issue 1, pp. 76-84.
Wester, H.J. et al., "PET imaging of somatostatin receptors: design, synthesis and preclinical evaluation of a novel 18F-labelled, carbohydrated analogue of octreotide," European Journal of Nuclear Medicine and Molecular Imaging, Jan. 2003, vol. 30, No. 1, pp. 117-122.
Wängler, C. et al., "One-Step $^{18}$F-Labeling of Carbohydrate-Conjugated Octreotate-Derivatives Containing a Silicon-Fluoride-Acceptor (SiFA): In Vitro and in Vivo Evaluation as Tumor Imaging Agents for Positron Emission Tomography," Bioconjugate Chem., 2010, vol. 21, No. 12, pp. 2289-2296.
Woodard, L.E. & Nimmagadda, S. "CXCR4-Based Imaging Agents," J. Nucl. Med., 52, 1665-1669 (2011).
Written Opinion of the International Searching Authority for International Application No. PCT/CA2014/000200, mailed Jun. 11, 2014 , 4 pages.
Yang, H. et al., "Synthesis and Evaluation of a Macrocyclic Actinium-225 Chelator, Quality Control and In Vivo Evaluation of 225Ac-crown-αMSH Peptide", Chem Eur J, 2020, 26, 11435-11440.
Zhan, C-G. et al., "Hydration of the Fluoride Anion: Structures and Absolute Hydration Free Energy from First-Principles Electronic Structure Calculations," J Phys Chem A., 2004, vol. 108, pp. 2020-2029.
Zhao, H. et al. "CXCR4 over-expression and survival in cancer: a system review and meta-analysis," Oncotarget, 6, 5022-5040 (2015).
Zlotnik, A. et al. "Homeostatic chemokine receptors and organ-specific metastasis," Nat. Rev. Immunol., 11, 597-606 (2011).
Extended European Search Report for European Application No. 21881418.4 mailed Nov. 5, 2024, 18 pages.

* cited by examiner

CXCR4-TARGETING COMPOUNDS

CROSS REFERENCE TO RELATED APPLICATIONS

This application is a continuation of U.S. patent application Ser. No. 18/032,680, filed Apr. 19, 2023, which is a U.S. National Stage Application under 35 U.S.C. § 371 of International Application No. PCT/CA2021/051486, filed Oct. 21, 2021, which claims priority to U.S. Provisional Application No. 63/094,839, filed Oct. 21, 2020, the disclosures of which are hereby incorporated by reference in their entireties for all purposes.

REFERENCE TO SEQUENCE LISTING SUBMITTED ELECTRONICALLY

The sequence listing associated with this application is provided in xml format in lieu of a paper copy, and is hereby incorporated by reference into the specification. The xml file, created on May 30, 2024, is named "A9TH_012_02US_SeqList_ST26.xml" and is −3733 bytes. The xml file is being submitted electronically via EFS-Web.

FIELD OF INVENTION

The present invention relates to novel peptidic compounds, particularly compounds that target CXCR4 for purposes such as imaging and/or therapeutics.

BACKGROUND OF THE INVENTION

C—X—C chemokine receptor type 4 (CXCR4) is a G protein-coupled transmembrane receptor that is expressed in hematological and immune tissues and systems.[1,2] CXCR4 has only one chemokine as a substrate named stromal-derived-factor-1 (SDF-1), also known as CXCL12.[3] CXCR4 is aberrantly expressed in a number of important pathologies that involve inflammation and immune cell trafficking, including athersclerosis,[4] systemic erythematous lupus[5,6], cancer and others. Importantly, CXCR4 has been found to play key roles in tumourigenesis, chemoresistance and metastasis and its expression has been detected in more than twenty different subtypes of cancers with an accompanying negative prognosis.[7-12] As such, there is a need for non-invasive in vivo molecular probes to image CXCR4-expressing tumours for better detection, staging and monitoring of aggressive cancers.[13-16] Such imaging agents enable the rapid assessment of patients for expression of specific biomarkers without the need for invasive biopsy procedures that may not always properly capture the heterogeneity of a patient's disease. Furthermore, with the largely poor efficacy of CXCR4 inhibitors in clinical trials, an alternative strategy is to couple the inhibitor with a radiotherapeutic isotope to deliver ionizing β, α, or auger electrons to the sites of the disease.

LY2510924 (cyclo[Phe-Tyr-Lys(iPr)-D-Arg-2-Nal-Gly-D-Glu]-Lys(iPr)-$NH_2$) is a cyclic peptide that is reported to block SDF-1α binding to CXCR4 with an $IC_{50}$ value of 79 pM[17]. It was reported that LY2510924 was able to inhibit growth of non-Hodgkin lymphoma, renal cell carcinoma, lung cancer, colorectal cancer, and breast cancer xenograft models. LY2510924 failed to improve treatment efficacy of carboplatin/etoposide chemotherapy for small cell lung cancer patients[18].

Many CXCR4 peptide-based inhibitors rely on key amino acid residues that include 1) one or more cationic charged side chain residues to make contact with several anionic residues present on the CXCR4 pocket, 2) a tyrosine residue and 3) a naphthalene-based unnatural amino acid in order to maintain good binding affinity with CXCR4.[19] This is exemplified in the development of T140, which systematically substituted out each amino acid of a prototype peptide (T22) based on a natural peptide with HIV inhibitory activity via CXCR4 antagonism.[19] This has resulted in a number of strong antagonists to CXCR4, including FC131 (which was later repurposed as Pentixafor and Pentixather for imaging and radionuclide therapeutic purposes, respectively) and LY2510924 for radiotheranostic purposes.[20]

There is therefore an unmet need in the field for improved CXCR4-targeting compounds, e.g. imaging and therapeutic agents for in-vivo diagnosis and treatment, respectively, of diseases/disorders characterized by expression of CXCR4.

No admission is necessarily intended, nor should it be construed, that any of the preceding information constitutes prior art against the present invention.

SUMMARY OF THE DISCLOSURE

The present disclosure relates to compounds useful as imaging agents and/or therapeutic agents. In some embodiments, the compound of the present disclosure relates to a compound of Formula A, Formula B, or Formula C, or a salt or solvate thereof:

[Formula A]

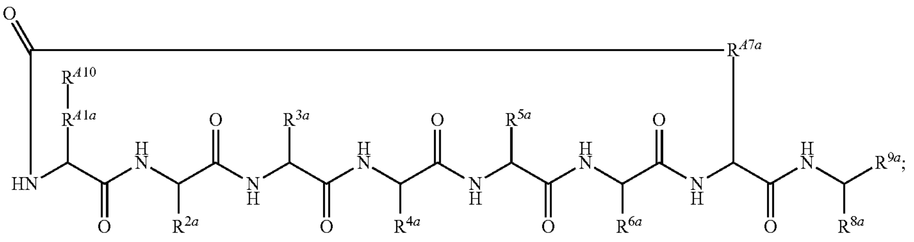

-continued

[Formula B]

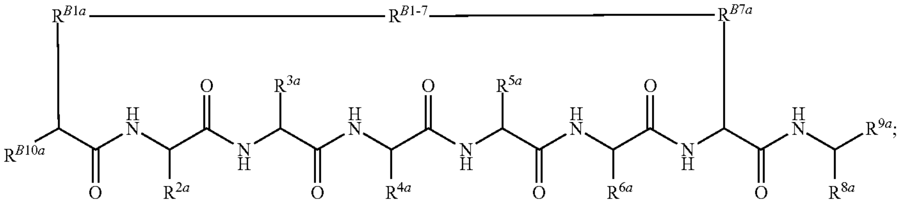

or

[Formula A]

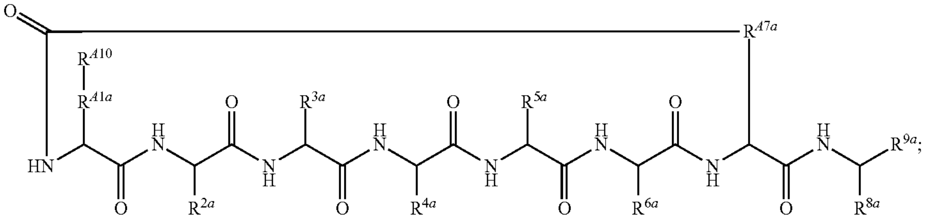

[Formula B]

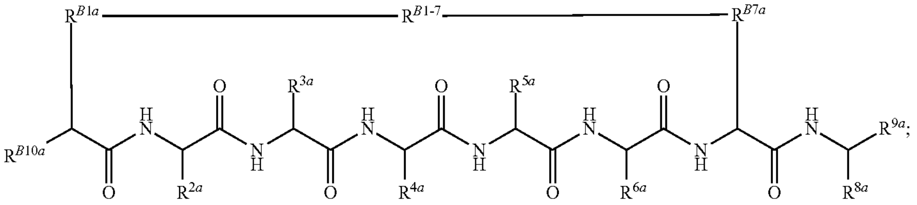

or

[Formula C]

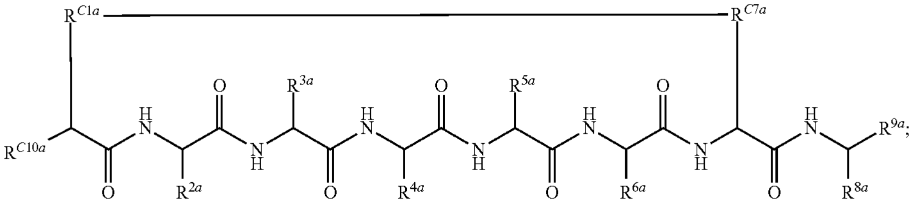

wherein:

$R^{2a}$ is —$(CH_2)$—$(R^{2b})$-(phenyl), wherein $R^{2b}$ is absent, —$CH_2$—, —NH—, —S— or —O—, wherein the phenyl is optionally 4-substituted with —$NH_2$, —$NO_2$, —OH, —$OR^{2c}$, —SH, —$SR^{2c}$, or —O-phenyl, wherein the phenyl is optionally 3-substituted with halogen or —OH, wherein the phenyl is optionally 5-subsituted with halogen or —OH, wherein the —O-phenyl ring is optionally 4-substituted with —$NH_2$, —$NO_2$, —OH, —$OR^{2c}$, —SH, or —$SR^{2c}$, wherein the —O-phenyl ring is optionally 3-substituted with halogen or —OH, wherein the —O-phenyl ring is optionally 5-subsituted with halogen or —OH, wherein each $R^{2c}$ is independently a $C_1$-$C_3$ linear or branched alkyl group;

$R^{3a}$ is $R^{3b}R^{3c}$ wherein $R^{3b}$ is a linear $C_1$-$C_5$ alkylenyl, $C_2$-$C_5$ alkenylenyl, or $C_2$-$C_5$ alkynylenyl, wherein 0-2 carbons in $C_2$-$C_5$ are independently replaced with one or more N, S, and/or O heteroatoms, wherein $R^{3c}$ is —$N(R^{3d})_{2\text{-}3}$ or guanidino, wherein each $R^{3d}$ is independently —H or a linear or branched $C_1$-$C_3$ alkyl;

$R^{4a}$ is $R^{4b}R^{4c}$ wherein $R^{4b}$ is a linear $C_1$-$C_5$ alkylenyl, $C_2$-$C_5$ alkenylenyl, or $C_2$-$C_5$ alkynylenyl, in which 0-2 carbons in $C_2$-$C_5$ are independently replaced with one or more N, S, and/or O heteroatoms, wherein $R^{4c}$ is —$N(R^{4d})_{2\text{-}3}$ or guanidino, wherein each $R^{4d}$ is independently —H or a linear or branched $C_1$-$C_3$ alkyl;

$R^{5a}$ is —$(CH_2)_{1\text{-}3}$—$R^{5b}$, wherein 1 carbon in —$(CH_2)_{2\text{-}3}$— is optionally replaced with a N, S, or O heteroatom, wherein $R^{5b}$ is:

phenyl optionally substituted with one or a combination of the following: 4-substituted with —$NH_2$, —$NO_2$, —OH, —$OR^{5c}$, —SH, —$SR^{5c}$, or —O-phenyl; 3-substituted with halogen or —OH; and/or 5-subsituted with halogen or —OH; wherein the —O-phenyl ring is optionally 4-substituted with —$NH_2$, —$NO_2$, —OH, —$OR^5$—, —SH, or —$SR^{5c}$, wherein the —O-phenyl ring is optionally 3-substituted with halogen or —OH, wherein the —O-phenyl ring is optionally 5-subsituted with halogen or —OH; or a fused bicyclic or fused tricyclic aryl or heteroaryl ring, each optionally substituted with one or more of halogen, —OH, —$OR^{5c}$, amino, —$NHR^{5c}$, and/or $N(R^{5c})_2$;

wherein each $R^{5c}$ is independently a $C_1$-$C_3$ linear or branched alkyl group;

either $R^{6a}$ is H, methyl, ethyl, —C≡CH, —CH≡$CH_2$, —C≡C—$(CH_2)_{1\text{-}3}$—OH, —C≡C—$(CH_2)_{1\text{-}3}$—SH, —C≡C—$(CH_2)_{1\text{-}3}$—$NH_2$, —C≡C—$(CH_2)_{1\text{-}3}$—COOH, —C≡C—$(CH_2)_{1\text{-}3}$—CONH, —C≡C—$(CH_2)_{1\text{-}}$ $_3R^{6b}R^{6c}$, —CH═CH—$(CH_2)_{1-3}$—OH, —CH═CH—$(CH_2)_{1-3}$—SH, —CH═CH—$(CH_2)_{1-3}$—$NH_2$, —CH═CH—$(CH_2)_{1-3}$—COOH, —CH═CH—$(CH_2)_{1-3}$—CONH, —CH═CH—$(CH_2)_{1-3}R^{6b}R^{6c}$, —$CH_2$—$R^{6b}$—OH, —$CH_2$—$R^{6b}$—COOH, —$CH_2$—$(R^{6b})_{1-3}$—$NH_2$, —$CH_2$—$R^{6b}$—CONH, or —$CH_2$—$R^{6b}R^{6c}$, wherein each $R^{6b}$ is independently absent, —$CH_2$—, —NH—, —S— or —O—, and wherein $R^{6c}$ is:

a 5 or 6 membered aromatic ring wherein one or more carbons are optionally independently replaced by N, S, and/or O heteroatoms, and optionally substituted with one or more groups independently selected from oxo, hydroxyl, sulfhydryl, nitro, amino, and/or halogen;

or —NH—CH($R^{6a}$)—C(O)—NH— is replaced with:

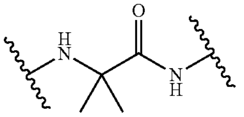,
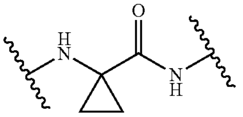,
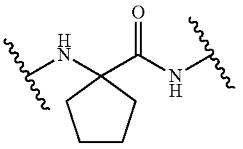,
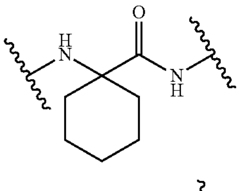,
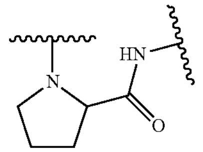, or
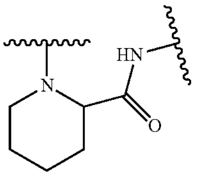;

$R^{A7a}$ is a linear $C_1$-$C_5$ alkylenyl wherein 0-2 carbons in $C_2$-$C_5$ are independently replaced with one or more N, S, and/or O heteroatoms;

$R^{8a}$ is $R^{8b}R^{8c}$ wherein $R^{8b}$ is a linear $C_1$-$C_5$ alkylenyl, $C_2$-$C_5$ alkenylenyl, or $C_2$-$C_5$ alkynylenyl, in which 0-2 carbons in $C_2$-$C_5$ alkylenyl, alkenylenyl, or alkynylenyl are independently replaced with one or more N, S, and/or O heteroatoms, wherein $R^{8c}$ is —N$(R^{8d})_{2-3}$ or guanidino, wherein each $R^{8d}$ is independently —H or a linear or branched $C_1$-$C_3$ alkyl;

$R^{9a}$ is: —C(O)$NH_2$, —C(O)—OH, —$CH_2$—C(O)$NH_2$, —$CH_2$—C(O)—OH, —$CH_2$—$NH_2$, —$CH_2$—OH, —$CH_2$—$CH_2$—$NH_2$, —$R^{9b}$—$R^{9c}$, or —$R^{9b}$-[linker]-$R^X{}_{n1}$, wherein:

$R^{9b}$ is —$CH_2$—NH—C(O)—, —$CH_2$—C(O)—, —$CH_2$—O—, —C(O)NH—, —C(O)—N($CH_3$)—, —$CH_2$—NHC(S)—, —C(S)NH—, —$CH_2$—N($CH_3$)C(S)—, —C(O)N($CH_3$)—, —$CH_2$—N($CH_3$)C(O)—, —C(S)N($CH_3$)—, —$CH_2$—NHC(S)NH—, —$CH_2$—NHC(O)NH—, —$CH_2$—S—, —$CH_2$—S(O)—, —$CH_2$—$S(O)_2$—, —$CH_2$—$S(O)_2$—NH—, —$CH_2$—S(O)—NH—, —$CH_2$—Se—, —$CH_2$—Se(O)—, —$CH_2$—$Se(O)_2$—, —$CH_2$—NHNHC(O)—, —C(O)NHNH—, —$CH_2$—OP(O)($O^-$)O—, —$CH_2$-phosphamide-, —$CH_2$-thiophosphodiester-, —$CH_2$—S-tetrafluorophenyl-S—,

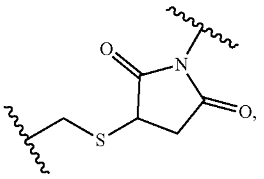,
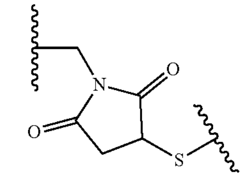,
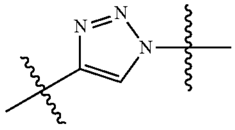,
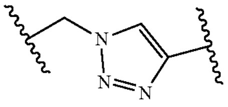, or polyethylene glycol; and $R^{9c}$ is hydrogen or a linear, branched, and/or cyclic $C_1$-$C_{20}$ alkyl, $C_2$-$C_{20}$ alkenyl or $C_2$-$C_{20}$ alkynyl, wherein 0-6 carbons in $C_2$-$C_{20}$ alkyl, alkenyl or alkynyl are independently replaced by N, S, and/or O heteroatoms, and substituted with 0-3 groups independently selected from one or a combination of oxo, hydroxyl, sulfhydryl, halogen, guanidino, carboxylic acid, sulfonic acid, sulfinic acid, and/or phosphoric acid;

$R^{A10}$ is absent or -[linker]-$R^X{}_{n1}$;

when $R^{A10}$ is absent, then $R^{A1a}$ is:

a linear $C_1$-$C_5$ alkyl, $C_2$-$C_5$ alkenyl, or $C_2$-$C_5$ alkynyl, wherein 0-2 carbons in $C_2$-$C_5$ alkyl, alkenyl, or alkynyl, are independently replaced by one or more N, S, and/or O heteroatoms, optionally C-substituted with a single substituent selected from: —SH, —OH, amino, carboxy, guanidino, —NH—C(O)—$CH_3$, —S—C(O)—$CH_3$, —O—C(O)—$CH_3$, —NH—C(O)-(phenyl), —S—C(O)-(phenyl), —O—C(O)-(phenyl), —NH—$(CH_3)_{1-2}$, —$NH_2$—$CH_3$, —N$(CH_3)_{2-3}$, —S—$CH_3$, or —O—$CH_3$;

a branched $C_1$-$C_{10}$ alkyl, $C_2$-$C_{10}$ alkenyl, or $C_2$-$C_{10}$ alkynyl, wherein 0-3 carbons in $C_2$-$C_{10}$ alkyl, alkenyl, or alkynyl, are independently replaced by one or more N, S, and/or O heteroatoms; or $R^{A1b}R^{A1c}$, wherein $R^{A1b}$ is a linear $C_1$-$C_3$ alkylenyl, wherein $C_2$ alkylenyl or $C_3$ alkylenyl is optionally replaced with a N, S, or O heteroatom, wherein $R^{A1c}$ is:

a 5 or 6 membered aromatic ring wherein one or more carbons are optionally independently replaced by N, S, and/or O heteroatoms, and optionally substituted with one or more groups independently selected from oxo, hydroxyl, sulfhydryl, nitro, amino, and/or halogen; or a fused bicyclic or fused tricyclic aryl group wherein one or more carbons are optionally independently replaced by N, S, and/or O heteroatoms, and optionally substituted with one or more groups independently selected from halogen, —OH, —$OR^{A1d}$, amino, —$NHR^{A1d}$, and/or N$(R^{A1d})_2$, wherein each $R^{A1d}$ is independently a $C_1$-$C_3$ linear or branched alkyl group;

when $R^{A10}$ is -[linker]-$R^X{}_{n1}$, then $R^{A1a}$ is $R^{A1e}R^{A1f}$, wherein $R^{A1e}$ is a linear $C_1$-$C_5$ alkylenyl, $C_2$-$C_5$ alkenylenyl, or $C_2$-$C_5$ alkynylenyl, in which 0-2 carbons in $C_2$-$C_5$ alkylenyl, alkenylenyl, or alkynylenyl are independently replaced with N, S, and/or O heteroatoms, and $R^{A1f}$ is —NH—C(O)—, —C(O)—, —O—, —C(O)NH—, —C(O)—N($CH_3$)—, —NHC(S)—, —C(S)NH—, —N($CH_3$)C(S)—, —C(O)N($CH_3$)—, —N($CH_3$)C(O)—, —C(S)N($CH_3$)—, —NHC(S)NH—, —NHC(O)NH—, —S—, —S(O)—, —S(O)—O—, —$S(O)_2$—, —$S(O)_2$—O—, —$S(O)_2$—NH—, —S(O)—NH—, —Se—, —Se(O)—, —$Se(O)_2$—, —NHNHC(O)—, —C(O)NHNH—, —OP(O)($O^-$)O—, -phosphamide-, -thiophosphodiester-, —S-tetrafluorophenyl-S—,

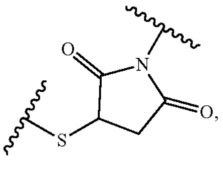
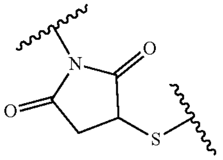
,

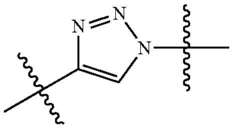
,
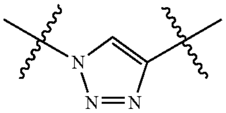
, or polyethylene glycol;

$R^{B1a}$ is a linear, branched, and/or cyclic $C_1$-$C_{10}$ alkylenyl, $C_2$-$C_{10}$ alkenylenyl, or $C_2$-$C_{10}$ alkynylenyl, wherein one or more carbons in $C_2$-$C_{10}$ alkylenyl, alkenylenyl, or alkynylenyl are optionally independently replaced with N, S, and/or O heteroatoms;

$R^{B1-7}$ is:

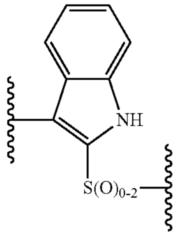
,
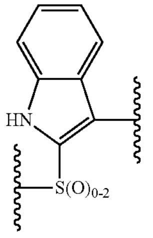
,

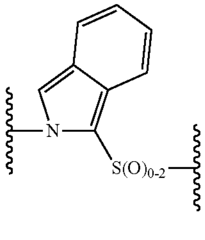
, or
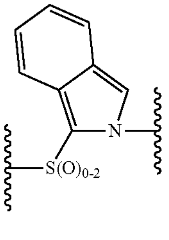
, wherein the indole ring and the isoindole ring are each optionally substituted with one or more of —F, —Br, —Cl, —I, —OH, —O—$R^{B1-7b}$, —CO—, —COOH, —$CONH_2$, —CN, —O-aryl, —$NH_2$, —$NHR^{B1-7b}$, $N_3$, —NH, —CHO, and/or —$R^{B1-7b}$, wherein each $R^{B1-7b}$ is a linear or branched $C_1$-$C_3$ alkyl, alkenyl, or alkynyl;

$R^{B7a}$ is a linear $C_1$-$C_5$ alkylenyl wherein 0-2 carbons in $C_2$-$C_5$ are independently replaced with one or more N, S, and/or O heteroatoms;

$R^{C1a}$ is:

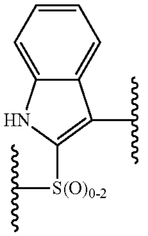
or
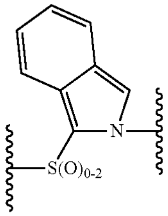
, wherein the indole ring and the isoindole ring are each optionally substituted with one or more of —F, —Br, —Cl, —I, —OH, —O—$R^{C1b}$, —CO—, —COOH, —$CONH_2$, —CN, —O-aryl, —$NH_2$, —$NHR^{C1b}$, $N_3$, —NH, —CHO, and/or —$R^{C1b}$, wherein each $R^{C1b}$ is a linear or branched $C_1$-$C_3$ alkyl, $C_2$-$C_3$ alkenyl, or $C_2$-$C_3$ alkynyl;

$R^{C7a}$ is a linear $C_1$-$C_5$ alkylenyl wherein optionally 0-2 carbons in $C_2$-$C_5$ are independently replaced with one or more N, S, and/or O heteroatoms;

$R^{C10a}$ is $R^{C10b}$—$R^{C10c}$-[linker]-$R^{X}_{n1}$ or $R^{C10d}$, wherein:

$R^{C10b}$ is a linear $C_1$-$C_5$ alkylenyl, $C_2$-$C_5$ alkenylenyl, or $C_2$-$C_5$ alkynylenyl, in which 0-2 carbons in $C_2$-$C_5$ alkylenyl, alkenylenyl, or alkynylenyl are independently replaced with N, S, and/or O heteroatoms;

$R^{C10c}$ is —NH—C(O)—, —C(O)—, —O—, —C(O)NH—, —C(O)—N($CH_3$)—, —NHC(S)—, —C(S)NH—, —N($CH_3$)C(S)—, —C(O)N($CH_3$)—, —N($CH_3$)C(O)—, —C(S)N($CH_3$)—, —NHC(S)NH—, —NHC(O)NH—, —S—, —S(O)—, —S(O)—O—, —$S(O)_2$—, —$S(O)_2$—O—, —$S(O)_2$—NH—, —S(O)—NH—, —Se—, —Se(O)—, —$Se(O)_2$—, —NHNHC(O)—, —C(O)NHNH—, —OP(O)($O^-$)O—, -phosphamide-, -thiophosphodiester-, —S-tetrafluorophenyl-S—,

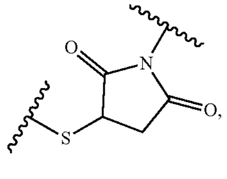
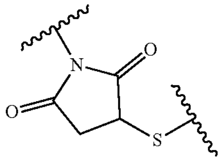
,

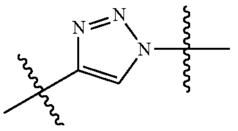
,
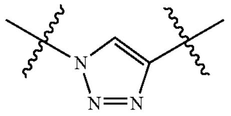
, or polyethylene glycol; and $R^{C10d}$ is:

a linear $C_1$-$C_5$ alkyl, $C_2$-$C_5$ alkenyl, or $C_2$-$C_5$ alkynyl, wherein 0-2 carbons in $C_2$-$C_5$ are independently replaced by N, S, and/or O heteroatoms, optionally C-substituted with a single substituent selected from: —SH, —OH, amino, carboxy, guanidino, —NH—C(O)—$CH_3$, —S—C(O)—$CH_3$, —O—C(O)—$CH_3$, —NH—C(O)-(phenyl), —S—C(O)-(phenyl), —O—C(O)-(phenyl), —NH—$(CH_3)_{1-2}$, —$NH_2$—$CH_3$, —$N(CH_3)_{2-3}$, —S—$CH_3$, or —O—$CH_3$;

a branched $C_1$-$C_{10}$ alkyl, $C_2$-$C_{10}$ alkenyl, or $C_2$-$C_{10}$ alkynyl, wherein 0-3 carbons in $C_2$-$C_{10}$ are independently replaced by N, S, and/or O heteroatoms; or $R^{C10e}R^{C10f}$, wherein $R^{C10e}$ is a linear $C_1$-$C_3$ alkyl, wherein $C_2$ alkyl or $C_3$ alkyl is optionally replaced with N, S, or O heteroatom, wherein $R^{C10f}$ is:

a 5 or 6 membered aromatic ring wherein one or more carbons are optionally independently replaced by N, S, and/or O heteroatoms, and optionally substituted with one or more groups independently selected from oxo, hydroxyl, sulfhydryl, nitro, amino, and/or halogen;

a fused bicyclic or fused tricyclic aryl group wherein one or more carbons are optionally independently replaced by N, S, and/or O heteroatoms, and optionally substituted with one or more groups independently selected from halogen, —OH, —$OR^{C10g}$, amino, —$NHR^{C10g}$, and/or $N(R^{C10g})_2$, wherein $R^{C10g}$ is $C_1$-$C_3$ linear or branched alkyl;

each n1 is independently 0, 1 or 2;

each $R^X$ is a therapeutic moiety, a fluorescent label, a radiolabeled group, or a group capable of being radiolabelled;

wherein 0-3 peptide backbone amides are independently replaced with

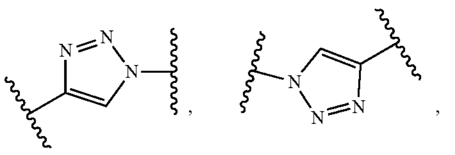 [SMILES: *c1cn(*)nn1 ; *c1cn(*)nn1]

or thioamide;

wherein 0-3 peptide backbone amides are N-methylated;

with the proviso that Formula A excludes the following combination:

—NH—CH($R^{2a}$)—C(O)— forms a Tyr residue;

—NH—CH($R^{4a}$)—C(O)— forms a D-Arg residue;

—NH—CH($R^{5a}$)—C(O)— forms a 2Nal residue; and $R^{6a}$ is H.

The present disclosure also relates to one or more compounds of Table A.

In some embodiments, one or more of the compounds of Table A are bound to a radiolabeled group or a group capable of being radiolabelled, optionally through a linker.

In some embodiments of the compounds of the present disclosure, the compound is complexed with a radioisotope.

The present disclosure also relates to use of any one of the compounds disclosed herein for imaging a CXCR4-expressing tissue in a subject.

The present disclosure also relates to use of any one of the compounds disclosed herein for imaging an inflammatory condition or disease.

The present disclosure also relates to a method of treating a disease or a condition characterized by expression of CXCR4 in a subject, comprising administering an effective amount of the compound to a subject in need thereof. In some embodiments, the disease or condition is a CXCR4-expressing cancer.

The present disclosure also relates to a method of imaging a CXCR4-expressing tissue in a subject, comprising administering an effective amount of the compound to the subject in need of such imaging.

DETAILED DESCRIPTION

Figure 1:
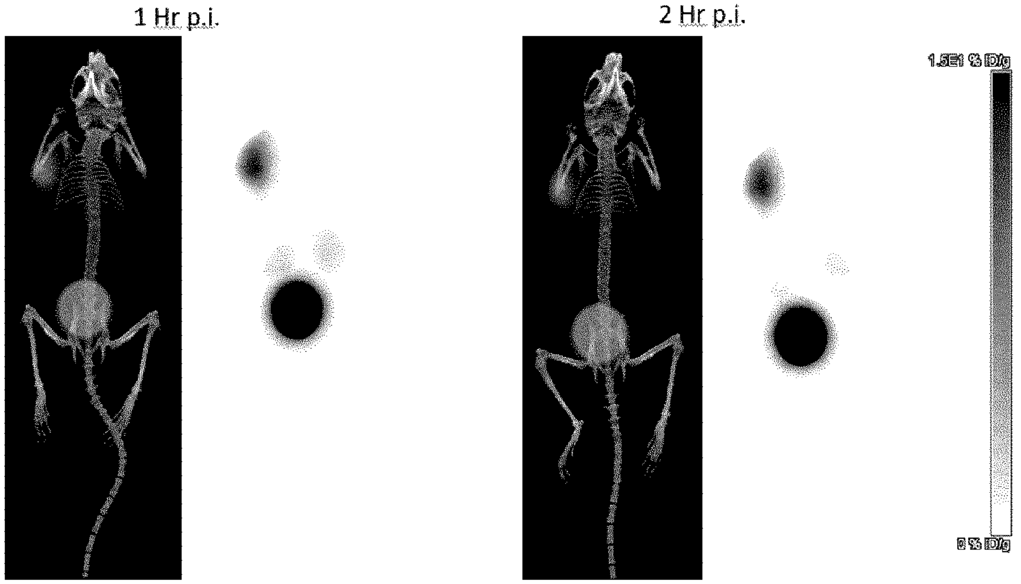
FIG. 1 shows PET/CT images of [$^{68}$Ga]Ga-BL34 in mice bearing Z-138-cell tumors acquired at 1 or 2 hrs post-injection.
Figure 2:
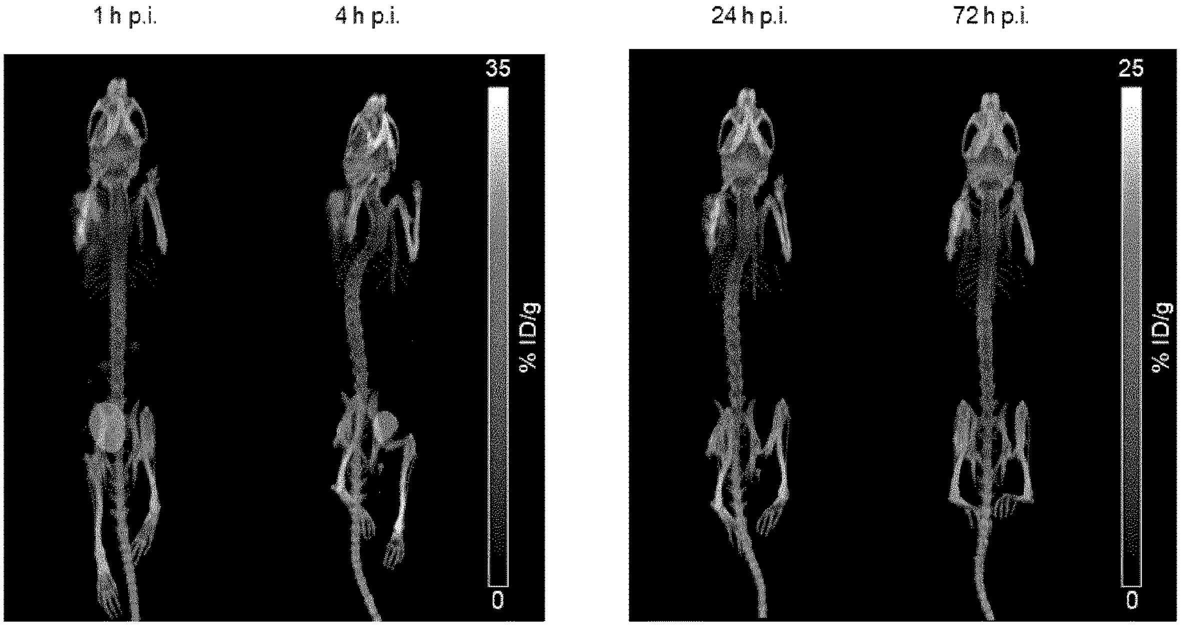
FIG. 2 shows SPECT/CT images of [$^{177}$Lu]Lu-BL34 in mice bearing Z-138-cell tumors acquired at 1, 4, 24 or 72 hrs post-injection.
Figure 3:
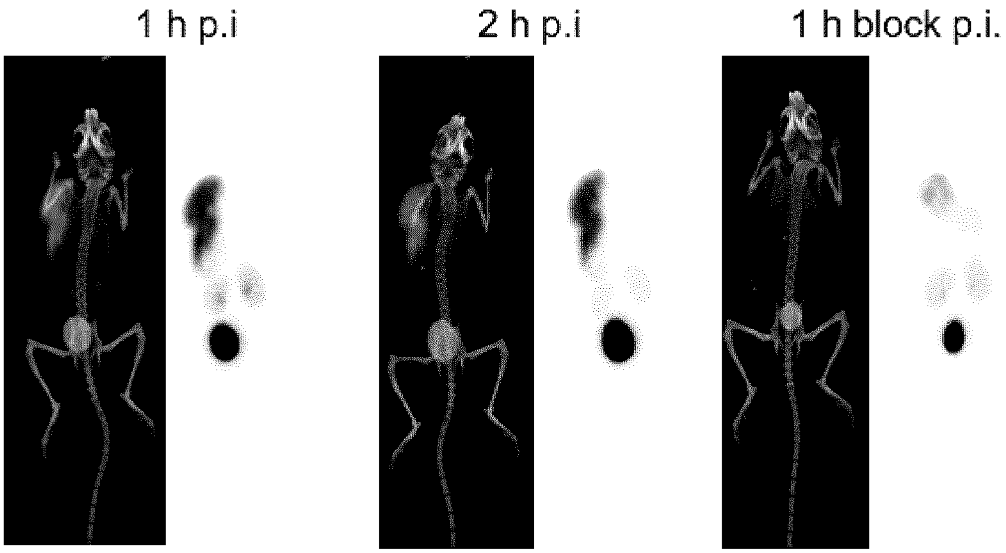
FIG. 3 shows PET/CT images of [$^{18}$F]BL40 in mice bearing Z-138-cell tumors acquired at 1 or 2 hrs post-injection or 1 hrs post-injection after pre-injection by 15 minutes of 7.5 μg of LY2510924 for blocking.
Figure 4:
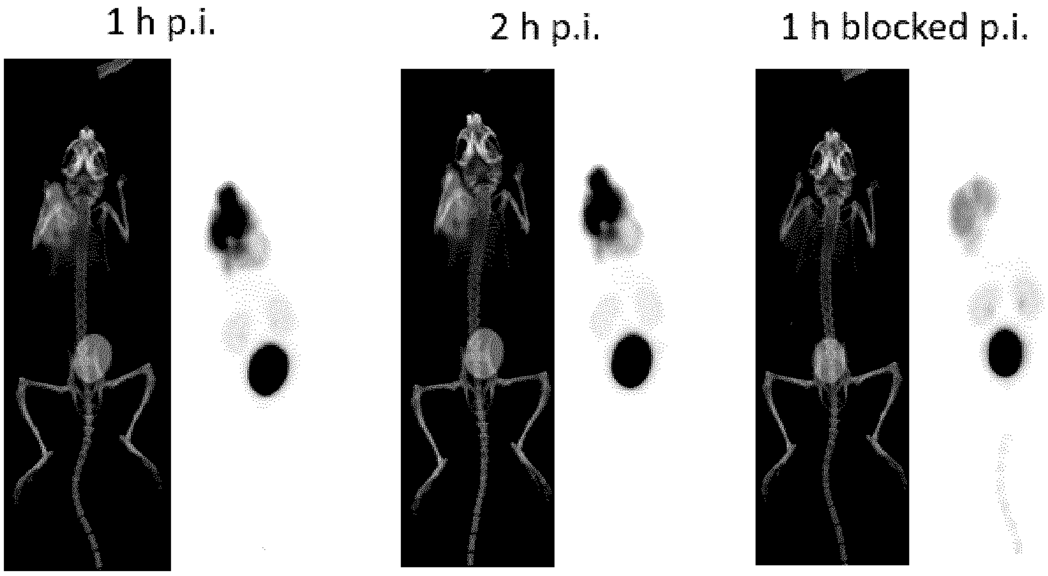
FIG. 4 shows PET/CT images of [$^{18}$F]BL41 in mice bearing Z-138-cell tumors acquired at 1 or 2 hrs post-injection or 1 hrs post-injection after pre-injection by 15 minutes of 7.5 μg of LY2510924 for blocking.
Figure 5:
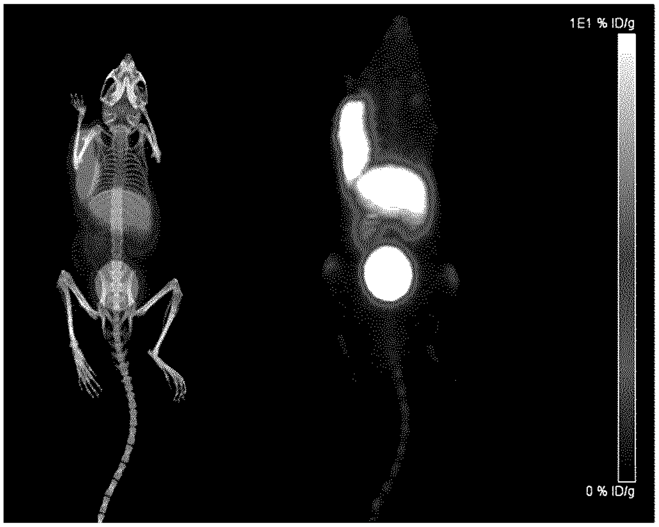
FIG. 5 shows PET/CT images of [$^{68}$Ga]Ga-BL42 in mice bearing Z-138-cell tumors acquired at 1 post-injection
Figure 6:
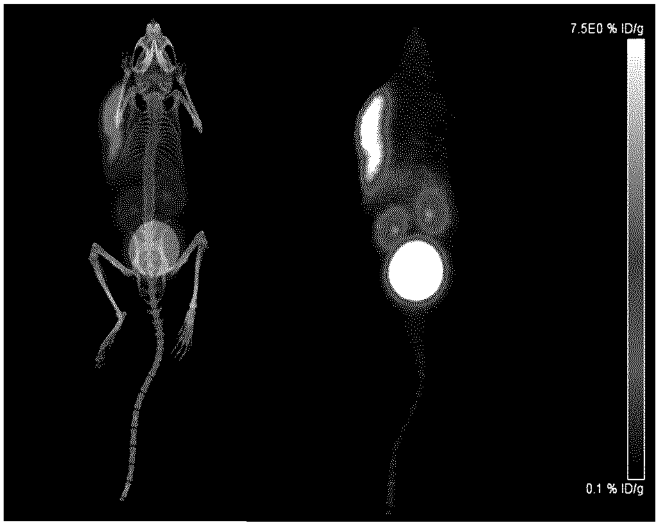
FIG. 6 shows PET/CT images of [$^{68}$Ga]Ga-BL43 in mice bearing Z-138-cell tumors acquired at 1 post-injection
Figure 7:
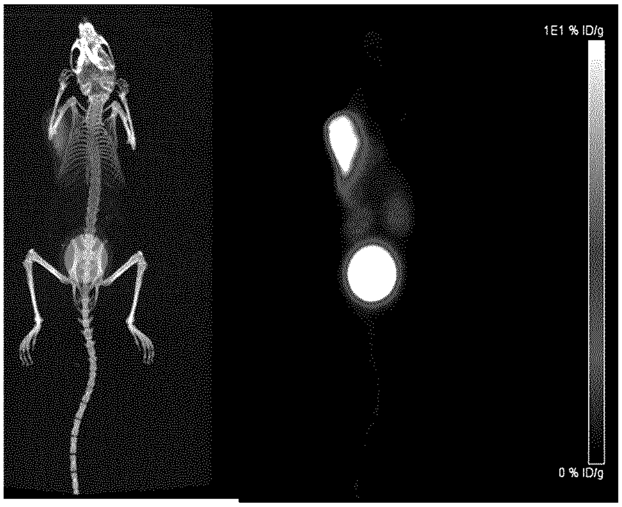
FIG. 7 shows PET/CT images of [$^{68}$Ga]Ga-BL44 in mice bearing Z-138-cell tumors acquired at 1 post-injection
Figure 8:
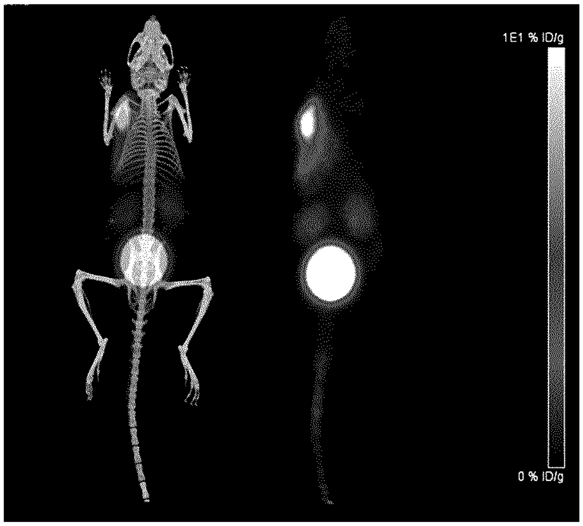
FIG. 8 shows PET/CT images of [$^{68}$Ga]Ga-BL45 in mice bearing Z-138-cell tumors acquired at 1 post-injection
Figure 9A:
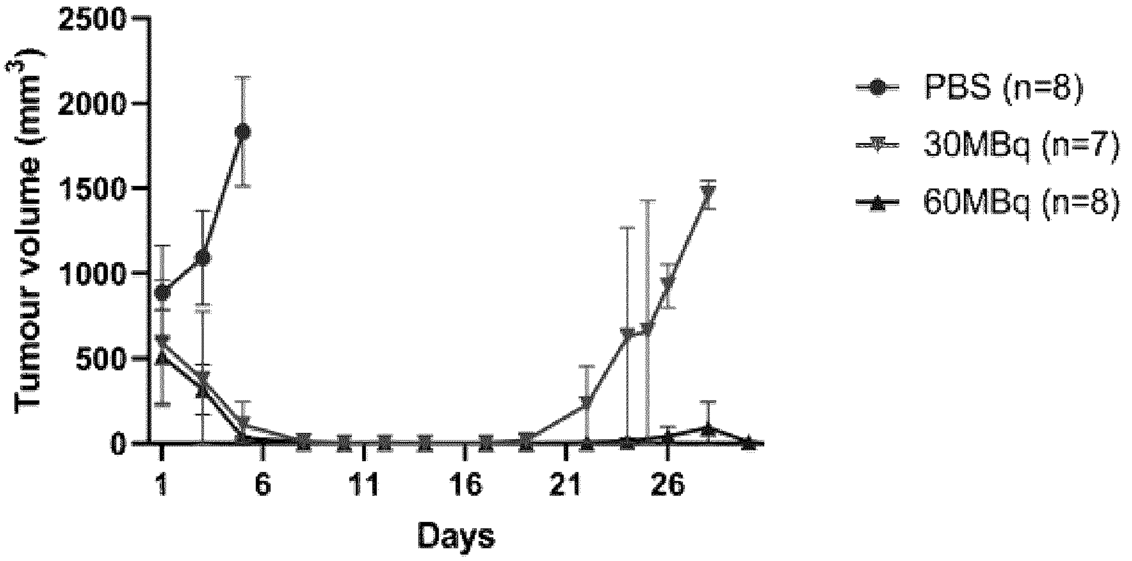
FIGS. 9A-9B shows the Therapeutic efficacy of [$^{177}$Lu]Lu-BL34 in Z138 xenograft-bearing mice. The mean tumor volumes are shown for the treated mice that received either 30 or 60 MBq (FIG. 9A) as compared to PBS (FIG. 98).
Figure 9B:
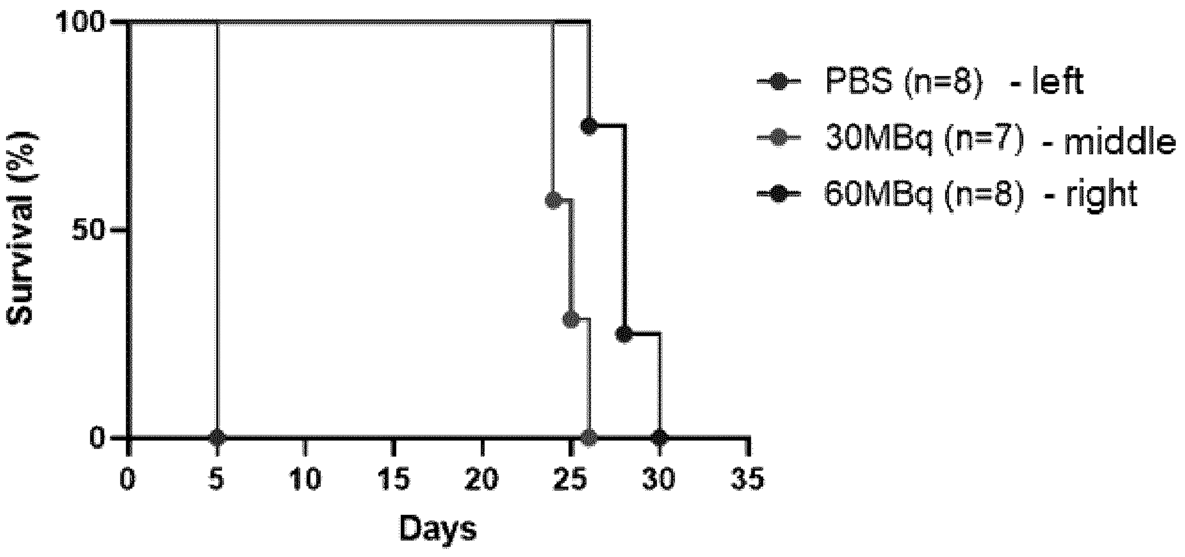

All publications, patents and patent applications, including any drawings and appendices therein are incorporated by reference in their entirety for all purposes to the same extent as if each individual publication, patent or patent application, drawing, or appendix was specifically and individually indicated to be incorporated by reference in its entirety for all purposes.

As used herein, the terms "comprising," "having", "including" and "containing," and grammatical variations thereof, are inclusive or open-ended and do not exclude additional, unrecited elements and/or method steps. The term "consisting essentially of" if used herein in connection with a composition, use or method, denotes that additional elements and/or method steps may be present, but that these additions do not materially affect the manner in which the recited composition, method or use functions. The term "consisting of" if used herein in connection with a composition, use or method, excludes the presence of additional elements and/or method steps. A composition, use or method described herein as comprising certain elements and/or steps may also, in certain embodiments consist essentially of those elements and/or steps, and in other embodiments consist of those elements and/or steps, whether or not these embodiments are specifically referred to. A use or method described herein as comprising certain elements and/or steps may also, in certain embodiments consist essentially of those elements and/or steps, and in other embodiments consist of those elements and/or steps, whether or not these embodiments are specifically referred to.

A reference to an element by the indefinite article "a" does not exclude the possibility that more than one of the elements is present, unless the context clearly requires that there be one and only one of the elements. The singular forms "a", "an", and "the" include plural referents unless the content clearly dictates otherwise. The use of the word "a" or "an" when used herein in conjunction with the term "comprising" may mean "one," but it is also consistent with the meaning of "one or more," "at least one" and "one or more than one."

Unless otherwise specified, "certain embodiments", "various embodiments", "an embodiment" and similar terms includes the particular feature(s) described for that embodiment either alone or in combination with any other embodiment or embodiments described herein, whether or not the other embodiments are directly or indirectly referenced and regardless of whether the feature or embodiment is described in the context of a method, product, use, composition, compound, et cetera.

As used herein, the terms “treat”, “treatment”, “therapeutic” and the like includes ameliorating symptoms, reducing disease progression, improving prognosis and reducing recurrence (e.g. reducing cancer recurrence).

As used herein, the term “diagnostic agent” includes an “imaging agent”. As such, a “diagnostic radiometal” includes radiometals that are suitable for use in imaging agents and “diagnostic radioisotope” includes radioisotopes that are suitable for use in imaging agents. Without limitation, diagnostic and imaging agents include compounds comprising at least one fluorescent moiety and/or at least one radioisotope that is suitable for imaging.

The term “subject” refers to an animal (e.g. a mammal or a non-mammal animal). The subject may be a human or a non-human primate. The subject may be a laboratory mammal (e.g., mouse, rat, rabbit, hamster and the like). The subject may be an agricultural animal (e.g., equine, ovine, bovine, porcine, camelid and the like) or a domestic animal (e.g., canine, feline and the like). In some embodiments, the subject is a human.

The compounds disclosed herein may also include free-base forms, salts or pharmaceutically acceptable salts thereof. Unless otherwise specified, the compounds claimed and described herein are meant to include all racemic mixtures and all individual enantiomers or combinations thereof, whether or not they are explicitly represented herein.

The compounds disclosed herein may be shown as having one or more charged groups, may be shown with ionizable groups in an uncharged (e.g. protonated) state or may be shown without specifying formal charges. As will be appreciated by the person of skill in the art, the ionization state of certain groups within a compound (e.g. without limitation, carboxylic acid, sulfonic acid, sulfinic acid, phosphoric acid and the like) is dependent, inter alia, on the pKa of that group and the pH at that location. For example, but without limitation, a carboxylic acid group (i.e. COOH) would be understood to usually be deprotonated (and negatively charged) at neutral pH and at most physiological pH values, unless the protonated state is stabilized. Likewise, sulfonic acid groups, sulfinic acid groups, and phosphoric acid groups would generally be deprotonated (and negatively charged) at neutral and physiological pH values.

As used herein, the terms “salt” and “solvate” have their usual meaning in chemistry. As such, when the compound is a salt or solvate, it is associated with a suitable counter-ion. It is well known in the art how to prepare salts or to exchange counter-ions. Generally, such salts can be prepared by reacting free acid forms of these compounds with a stoichiometric amount of a suitable base (e.g. without limitation, Na, Ca, Mg, or K hydroxide, carbonate, bicarbonate, or the like), or by reacting free base forms of these compounds with a stoichiometric amount of a suitable acid. Such reactions are generally carried out in water or in an organic solvent, or in a mixture of the two. Counter-ions may be changed, for example, by ion-exchange techniques such as ion-exchange chromatography. Solvates may be made any methodology known in the art, e.g. by dissolving the compound in hot solvent (e.g. water or another solvent) followed by cooling and/or evaporation. All zwitterions, salts, solvates and counter-ions are intended, unless a particular form is specifically indicated.

In certain embodiments, the salt or counter-ion may be pharmaceutically acceptable, for administration to a subject. More generally, with respect to any pharmaceutical composition disclosed herein, non-limiting examples of suitable excipients include any suitable buffers, stabilizing agents, salts, antioxidants, complexing agents, tonicity agents, cryoprotectants, lyoprotectants, suspending agents, emulsifying agents, antimicrobial agents, preservatives, chelating agents, binding agents, surfactants, wetting agents, non-aqueous vehicles such as fixed oils, or polymers for sustained or controlled release. See, for example, Berge et al. 1977. (*J. Pharm Sci.* 66:1-19), or Remington—The Science and Practice of Pharmacy, 21st edition (Gennaro et al editors. Lippincott Williams & Wilkins Philadelphia), each of which is incorporated by reference in its entirety.

As used herein, the expression “Cy-Cz”, where y and z are integers (e.g. $C_1$-$C_{15}$, $C_1$-$C_5$, and the like), refers to the number of carbons in a compound, R-group or substituent, or refers to the number of carbons plus heteroatoms when a certain number of carbons are specified as being replaced (or optionally replaced) by heteroatoms. Heteroatoms may include any, some or all possible heteroatoms. For example, in some embodiments, the heteroatoms are selected from N, O, S, P and Se. In some embodiments, the heteroatoms are selected from N, S and O. Unless otherwise specified, such embodiments are non-limiting. When replacing a carbon with a heteroatom, it will be understood that the replacements only include those that would be reasonably made by the person of skill in the art. For example, —O—O— linkages are explicitly excluded. The expression “$C_1$-$C_5$ . . . wherein one or more carbons in $C_2$-$C_5$ are optionally independently replaced with N, S, and or O heteroatoms” and similar expressions are intended to specify that the $C_1$ carbon (i.e. the first carbon in the defined group and therefore the carbon directly bonded to the remainder of the compound) is not replaced. Such expressions are also intended to include replacement of one carbon, and replacement of multiple carbons, either with the same heteroatom (e.g. one of N, S, or O) or with a combination of different heteroatoms (e.g. combinations of N, S, and/or O in suitable configurations).

Unless explicitly stated otherwise, the term “alkyl” includes any reasonable combination of the following: (1) linear or branched; (2) acyclic or cyclic, the latter of which may include multi-cyclic (fused rings; multiple non-fused rings or a combination thereof; and (3) unsubstituted or substituted. In the context of the expression “alkyl, alkenyl or alkynyl” and similar expressions, the “alkyl” would be understood to be a saturated alkyl. As used herein, the term “linear” may be used as it is normally understood to a person of skill in the art and generally refers to a chemical entity that comprises a skeleton or main chain that does not split off into more than one contiguous chain. Non-limiting examples of linear alkyls include methyl, ethyl, n-propyl, and n-butyl. As used herein, the term “branched” may be used as it is normally understood to a person of skill in the art and generally refers to a chemical entity that comprises a skeleton or main chain that splits off into more than one contiguous chain. The portions of the skeleton or main chain that split off in more than one direction may be linear, cyclic or any combination thereof. Non-limiting examples of a branched alkyl group include tert-butyl and isopropyl.

The term “alkylenyl” refers to a divalent analog of an alkyl group. In the context of the expression “alkylenyl, alkenylenyl or alkynylenyl", and similar expressions, the "alkylenyl" would be understood to be a saturated alkylenyl.

As used herein, the term "saturated" when referring to a chemical entity may be used as it is normally understood to a person of skill in the art and generally refers to a chemical entity that comprises only single bonds, and may include linear, branched, and/or cyclic groups. Non-limiting examples of a saturated $C_1$-$C_{20}$ alkyl group may include methyl, ethyl, n-propyl, i-propyl, sec-propyl, n-butyl, i-butyl, sec-butyl, t-butyl, n-pentyl, i-pentyl, sec-pentyl, t-pentyl, n-hexyl, i-hexyl, 1,2-dimethylpropyl, 2-ethylpropyl, 1-methyl-2-ethylpropyl, I-ethyl-2-methylpropyl, 1,1,2-trimethylpropyl, 1,1,2-triethylpropyl, 1,1-dimethylbutyl, 2,2-dimethylbutyl, 2-ethylbutyl, 1,3-dimethylbutyl, 2-methylpentyl, 3-methylpentyl, sec-hexyl, t-hexyl, n-heptyl, i-heptyl, sec-heptyl, t-heptyl, n-octyl, i-octyl, sec-octyl, t-octyl, n-nonyl, i-nonyl, sec-nonyl, t-nonyl, n-decyl, i-decyl, sec-decyl, t-decyl, cyclopropanyl, cyclobutanyl, cyclopentanyl, cyclohexanyl, cycloheptanyl, cyclooctanyl, cyclononanyl, cyclodecanyl, and the like. Unless otherwise specified, a $C_1$-$C_{20}$ alkylenyl therefore encompasses, without limitation, all divalent analogs of the above-listed saturated alkyl groups.

As used herein, an expression such as "$C_3$-$C_5$ alkylenyl, alkenylenyl or alkynylenyl" is understood to mean $C_3$-$C_5$ alkylenyl, $C_3$-$C_5$ alkenylenyl, or $C_3$-$C_5$ alkynylenyl and expression such as "$C_1$-$C_5$ alkylenyl, alkenylenyl or alkynylenyl" is understood to mean $C_1$-$C_5$ alkylenyl, $C_2$-$C_5$ alkenylenyl, or $C_2$-$C_5$ alkynylenyl. Similarly, as used herein, an expression such as "$C_5$-$C_{20}$ alkyl, alkenyl or alkynyl" is understood to mean $C_5$-$C_{20}$ alkyl, $C_5$-$C_{20}$ alkenyl or $C_5$-$C_{20}$ alkynyl and expression such as "$C_1$-$C_{20}$ alkyl, alkenyl or alkynyl" is understood to mean $C_1$-$C_{20}$ alkyl, $C_2$-$C_{20}$ alkenyl or $C_2$-$C_{20}$ alkynyl.

As used herein, the term "unsaturated" when referring to a chemical entity may be used as it is normally understood to a person of skill in the art and generally refers to a chemical entity that comprises at least one double or triple bond, and may include linear, branched, and/or cyclic groups. Non-limiting examples of a $C_2$-$C_{20}$ alkenyl group may include vinyl, allyl, isopropenyl, I-propene-2-yl, 1-butene-1-yl, 1-butene-2-yl, 1-butene-3-yl, 2-butene-1-yl, 2-butene-2-yl, octenyl, decenyl, cyclopropenyl, cyclobutenyl, cyclopentenyl, cyclohexenyl, cycloheptenyl, cyclooctenyl, cyclononanenyl, cyclodecanenyl, and the like. Unless otherwise specified, a $C_1$-$C_{20}$ alkenylenyl therefore encompasses, without limitation, all divalent analogs of the above-listed alkenyl groups. Non-limiting examples of a $C_2$-$C_{20}$ alkynyl group may include ethynyl, propynyl, butynyl, pentynyl, hexynyl, heptynyl, octynyl, nonynyl, decynyl, and the like. Unless otherwise specified, a $C_1$-$C_{20}$ alkynylenyl therefore encompasses, without limitation, all divalent analogs of the above-listed alkynyl groups.

Where it is specified that 1 or more carbons in an alkyl, alkenyl, alkynyl, alkylenyl, alkenylenyl, alkynylenyl, etc., are independently replaced by a heteroatom, the person of skill in the art would understand that various combinations of different heteroatoms may be used. Non-limiting examples of non-aromatic heterocyclic groups include aziridinyl, azetidinyl, diazetidinyl, pyrrolidinyl, pyrrolinyl, piperidinyl, piperazinyl, imidazolinyl, pyrazolidinyl, imidazolydinyl, phthalimidyl, succinimidyl, oxiranyl, tetrahydropyranyl, oxetanyl, dioxanyl, thietanyl, thiepinyl, morpholinyl, oxathiolanyl, and the like. The expression "a linear, branched, and/or cyclic . . . alkyl, alkenyl or alkynyl" includes, inter alia, aryl groups. Unless further specified, an "aryl" group includes both single aromatic rings as well as fused rings containing at least one aromatic ring. Non-limiting examples of $C_3$-$C_{20}$ aryl groups include phenyl (Ph), pentalenyl, indenyl, naphthyl and azulenyl. Non-limiting examples of $C_3$-$C_{20}$ aromatic rings with one or more carbons replaced with heteroatoms include pyrrolyl, imidazolyl, pyrazolyl, pyridinyl, pyridazinyl, pyrimidinyl, pirazinyl, quinolinyl, isoquinolinyl, acridinyl, indolyl, isoindolyl, indolizinyl, purinyl, carbazolyl, indazolyl, phthalazinyl, naphthyridinyl, quinoxalinyl, quinazolinyl, cinnolinyl, pteridinyl, phenanthridinyl, phenazinyl, phenanthrolinyl, perimidinyl, furyl, dibenzofuryl, xanthenyl, benzofuryl, thiophenyl, thianthrenyl, benzothiophenyl, phosphorinyl, phosphinolinyl, phosphindolyl, thiazolyl, oxazolyl, isoxazolyl, and the like. Likewise, the expression "a linear, branched, and/or cyclic . . . alkylenyl, alkenylenyl or alkynylenyl" includes, inter alia, divalent analogs of the above-defined linear, branched, and/or cyclic alkyl, alkenyl or alkynyl groups, including all aryl groups encompassed therein.

As used herein, the term "substituted" is used as it would normally be understood to a person of skill in the art and generally refers to a compound or chemical entity that has one chemical group replaced with a different chemical group. Unless otherwise specified, a substituted alkyl is an alkyl in which one or more hydrogen atom(s) are independently each replaced with an atom that is not hydrogen. For example, chloromethyl is a non-limiting example of a substituted alkyl, more particularly an example of a substituted methyl. Aminoethyl is another non-limiting example of a substituted alkyl, more particularly an example of a substituted ethyl. Unless otherwise specified, a substituted compound or group (e.g. alkyl, alkylenyl, aryl, and the like) may be substituted with any chemical group reasonable to the person of skill in the art. For example, but without limitation, a hydrogen bonded to a carbon or heteroatom (e.g. N) may be substituted with halide (e.g. F, I, Br, Cl), amine, amide, oxo, hydroxyl, thiol (sulfhydryl), phosphate (or phosphoric acid), phosphonate, sulfate, $SO_2H$ (sulfinic acid), $SO_3H$ (sulfonic acid), alkyls, aryl, ketones, carboxaldehyde, carboxylic acid, carboxamides, nitriles, guanidino, monohalomethyl, dihalomethyl or trihalomethyl.

As used herein, the term "guanidino" refers to the group $-NHC(=NH)NH_2$ or $-NHC(=NR)NR_2$, wherein each R is independently H or alkyl.

As used herein, the term "unsubstituted" is used as it would normally be understood to a person of skill in the art. Non-limiting examples of unsubstituted alkyls include methyl, ethyl, tert-butyl, pentyl and the like. The expression "optionally . . . substituted" is used interchangeably with the expression "unsubstituted or substituted".

In the structures provided herein, hydrogen may or may not be shown. In some embodiments, hydrogens (whether shown or implicit) may be protium (i.e. $^1H$), deuterium (i.e. $^2H$) or combinations of $^1H$ and $^2H$. Methods for exchanging $^1H$ with $^2H$ are well known in the art. For solvent-exchangeable hydrogens, the exchange of $^1H$ with $^2H$ occurs readily in the presence of a suitable deuterium source, without any catalyst. The use of acid, base or metal catalysts, coupled with conditions of increased temperature and pressure, can facilitate the exchange of non-exchangeable hydrogen atoms, generally resulting in the exchange of all $^1H$ to $^2H$ in a molecule.

The compounds disclosed herein incorporate amino acids, e.g. as residues in a peptide chain (linear or branched) or as amino acids that are otherwise part of a compound. Amino acids have both an amino group and a carboxylic acid group, either or both of which can be used for covalent attachment.

In attaching to the remainder of the compound, the amino group and/or the carboxylic acid group may be converted to an amide or other structure; e.g. a carboxylic acid group of a first amino acid is converted to an amide (e.g. a peptide bond) when bonded to the amino group of a second amino acid. As such, amino acid residues may have the formula —N($R^a$)$R^b$C(O)—, where $R^a$ and $R^b$ are R-groups. $R^a$ will typically be hydrogen or methyl. The amino acid residues of a peptide may comprise typical peptide (amide) bonds and may further comprise bonds between side chain functional groups and the side chain or main chain functional group of another amino acid. For example, the side chain carboxylate of one amino acid residue in the peptide (e.g. Asp, Glu, etc.) may be bonded to and the amine of another amino acid residue in the peptide (e.g. Dap, Dab, Orn, Lys). Further details are provided below. The term "amino acid" includes proteinogenic and nonproteinogenic amino acids. Non-limiting examples of nonproteinogenic amino acids are shown in Table 1 and include: D-amino acids (including without limitation any D-form of the following amino acids), ornithine (Orn), 3-(1-naphtyl)alanine (Nal), 3-(2-naphtyl)alanine (2-Nal), α-aminobutyric acid, norvaline, norleucine (Nle), homonorleucine, beta-(1,2,3-triazol-4-yl)-L-alanine, 1,2,4-triazole-3-alanine, Phe(4-F), Phe(4-Cl), Phe(4-Br), Phe(4-1), Phe(4-$NH_2$), Phe(4-$NO_2$), $N^\varepsilon$, $N^\varepsilon$, $N^\varepsilon$-trimethyl-lysine, homoarginine (hArg), 2-amino-4-guanidinobutyric acid (Agb), 2-amino-3-guanidinopropionic acid (Agp), B-alanine, 4-aminobutyric acid, 5-aminovaleric acid, 6-aminohexanoic acid, 7-aminoheptanoic acid, 8-aminooctanoic acid, 9-aminononanoic acid, 10-aminodecanoic acid, 2-aminooctanoic acid, 2-amino-3-(anthracen-2-yl)propanoic acid, 2-amino-3-(anthracen-9-yl)propanoic acid, 2-amino-3-(pyren-1-yl)propanoic acid, Trp(5-Br), Trp(5-$OCH_3$), Trp(6-F), Trp(5-OH) or Trp(CHO), 2-aminoadipic acid (2-Aad), 3-aminoadipic acid (3-Aad), propargylglycine (Pra), homopropargylglycine (Hpg), beta-homopropargylglycine (Bpg), 2,3-diaminopropionic acid (Dap), 2,4-diaminobutyric acid (Dab), azidolysine (Lys($N_3$)), azido-ornithine (Orn ($N_3$)), 2-amino-4-azidobutanoic acid Dab($N_3$), Dap($N_3$), 2-(5'-azidopentyl)alanine, 2-(6'-azidohexyl)alanine, 4-amino-1-carboxymethyl-piperidine (Pip), 4-(2-aminoethyl)-1-carboxymethyl-piperazine (Acp), and tranexamic acid. If not specified as an L- or D-amino acid, an amino acid shall be understood to be an L-amino acid.

TABLE 1

List of non-limiting examples of non-proteinogenic amino acids.

| | |
|---|---|
| Any D-amino acid of a proteinogenic amino acid | 10-aminodecanoic acid |
| ornithine (Orn) | 2-aminooctanoic acid |
| 3-(1-naphtyl)alanine (Nal) | 2-amino-3-(anthracen-2-yl)propanoic acid |
| 3-(2-naphtyl)alanine (2-Nal) | 2-amino-3-(anthracen-9-yl)propanoic acid |
| a-aminobutyric acid | 2-amino-3-(pyren-1-yl)propanoic acid |
| norvaline | Trp(5-Br) |
| norleucine (Nle) | Trp(5-$OCH_3$) |
| homonorleucine | Trp(6-F) |
| beta-(1,2,3-triazol-4-yl)-L-alanine | Trp(5-OH) |
| 1,2,4-triazole-3-alanine | Trp(CHO) |
| Phe(4-F) or (4-F)Phe | 2-aminoadipic acid (2-Aad) |
| Phe(4-Cl) or (4-Cl)Phe | 3-aminoadipic acid (3-Aad) |
| Phe(4-Br) or (4-Br)Phe | propargylglycine (Pra) |
| Phe(4-I) or (4-I)Phe | homopropargylglycine (Hpg) |
| Phe(4-$NH_2$) or (4-$NH_2$)Phe | beta-homopropargylglycine (Bpg) |
| Phe(4-$NO_2$) or (4-$NO_2$)Phe | 2,3-diaminopropionic acid (Dap) |
| (3-I)Tyr | 2,4-diaminobutyric acid (Dab) |
| homoarginine (hArg) | Cysteic acid (CysAcid) |
| homotyrosine (hTyr) | Nε-isopropyl-lysine (Lys(iPr)) |
| 3-(2-phenanthryl)-L-alanine (2-(Ant)Ala) | Arg(Me) |
| 3-(9-phenanthryl)-L-alanine (9-(Ant)Ala) | Arg$(Me)_2$ (symmetrical or asymmetrical) |
| 4-(2-aminoethyl)-1-carboxymethyl-piperazine (Acp) | azidolysine (Lys($N_3$)) |
| 2-(5'-azidopentyl)alanine | azido-ornithine (Orn($N_3$)) |
| 2-(6'-azidohexyl)alanine | amino-4-azidobutanoic acid Dab($N_3$) |
| 2-amino-4-guanidinobutyric acid (Agb) | tranexamic acid |
| 2-amino-3-guanidinopropionic acid (Agp) | 4-amino-1-carboxymethyl-piperidine (Pip) |
| β-alanine | $NH_2(CH_2)_2O(CH_2)_2C(O)OH$ |
| 4-aminobutyric acid | $NH_2(CH_2)_2[O(CH_2)_2]_2C(O)OH$ |
| 5-aminovaleric acid | $NH_2(CH_2)_2[O(CH_2)_2]_3C(O)OH$ |
| 6-aminohexanoic acid | $NH_2(CH_2)_2[O(CH_2)_2]_4C(O)OH$ |
| 7-aminoheptanoic acid | $NH_2(CH_2)_2[O(CH_2)_2]_5C(O)OH$ |
| 8-aminooctanoic acid | $NH_2(CH_2)_2[O(CH_2)_2]_6C(O)OH$ |
| 9-aminononanoic acid | Nε-acetyl-lysine (Lys(Ac)) |

As used herein, "peptide backbone amides" refers to the amides (—C(O)—NH—) drawn in the structures of Formula A-I, A-II, A-III, B, or C, for example, including the amide bond between carbon atoms bonded to $R^{2a}$ and $R^{3a}$. One or more peptide backbone amides can be methylated or N-methylated, unless otherwise discussed herein. For example, the amide bond between carbon atoms bonded to $R^{2a}$ and $R^{3a}$ can methylated (—C(O)—$NCH_3$—).

The wavy line "∿∿" symbol shown through or at the end of a bond in a chemical formula (e.g. in the definition $L^1$) is intended to define the R group on one side of the wavy line, without modifying the definition of the structure on the opposite side of the wavy line. Where an R group is bonded on two or more sides (e.g. certain definitions of $X^1$), any atoms shown outside the wavy lines are intended to clarify orientation of the R group. As such, only the atoms between the two wavy lines constitute the definition of the R group. When atoms are not shown outside the wavy lines, or for a chemical group shown without wavy lines but does have bonds on multiple sides (e.g. —C(O)NH—, and the like), the chemical group should be read from left to right matching the orientation in the formula that the group relates to (e.g. for formula —$R^a$—$R^b$—$R^c$—, the definition of $R^b$ as —C(O)NH— would be incorporated into the formula as $—R^a—C(O)NH—R^c—$ not as $—R^a—NHC(O)—R^c—$).

In various aspects, there is disclosed a compound of Formula A, B, or C, or a salt or solvate of Formula A, B, or C:

[Formula A]

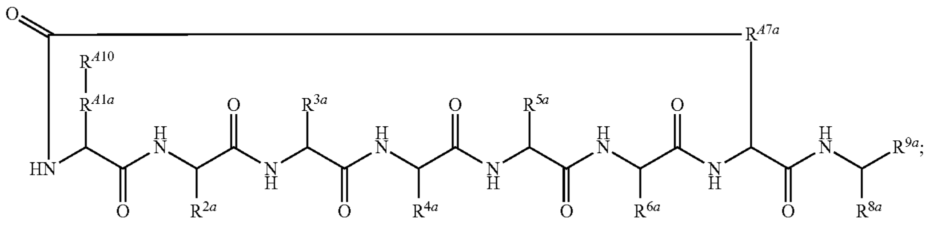

[Formula B]

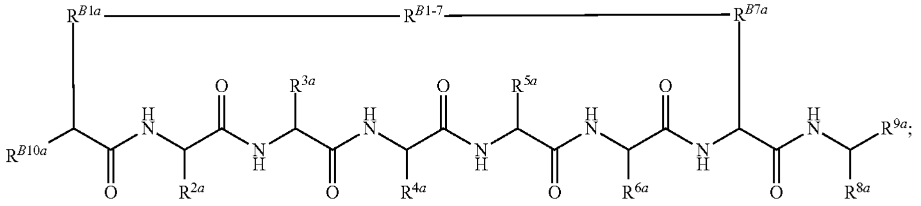

[Formula C]

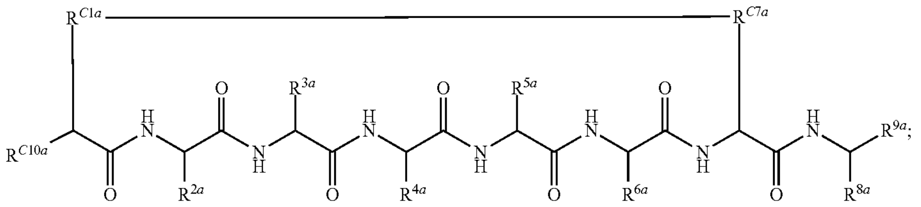

R-groups are defined below;

with the proviso that Formula A excludes the following combination:

—NH—CH($R^{2a}$)—C(O)— forms a Tyr residue;

—NH—CH($R^{4a}$)—C(O)— forms a D-Arg residue;

—NH—CH($R^{5a}$)—C(O)— forms a 2-Nal residue; and $R^{6a}$ is H;

wherein 0-3 peptide backbone amides are independently replaced with

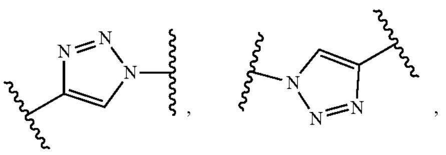 [SMILES: *c1cn(*)nn1 ; *c1cn(*)nn1]

or thioamide; and wherein 0-3 peptide backbone amides are N-methylated.

In some embodiments, the compound has the structure of Formula A. In some embodiments, the compound is a salt of Formula A. In some embodiments, the compound is a solvate of Formula A.

In some embodiments, the compound has the structure of Formula B. In some embodiments, the compound is a salt of Formula B. In some embodiments, the compound is a solvate of Formula B.

In some embodiments, the compound has the structure of Formula C. In some embodiments, the compound is a salt of Formula C. In some embodiments, the compound is a solvate of Formula C.

In some embodiments of the compounds of Formula A, B, and/or C, 1 peptide backbone amide is replaced with

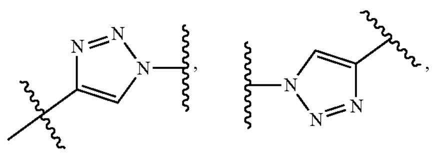 [SMILES: *c1cn(*)nn1 ; *c1cn(*)nn1]

or thioamide. In some embodiments, two peptide backbone amides are replaced. In some embodiments, three peptide backbone amides are replaced. In some embodiments, zero peptide backbone amides are replaced.

In some embodiments of the compounds of Formula A, B, and/or C, 1 peptide backbone amide is N-methylated. In some embodiments, two peptide backbone amides are N-methylated. In some embodiments, three peptide backbone amides are N-methylated. In some embodiments, zero peptide backbone amides are N-methylated.

In some embodiments of the compounds of Formula A, B, and/or C, $R^{2a}$ is $—(CH_2)—(R^{2b})$-(phenyl), wherein $R^{2b}$ is absent, $—CH_2—$, —NH—, —S— or —O—, wherein the phenyl is 4-substituted with $—NH_2$, $—NO_2$, —OH, $—OR^{2c}$, —SH, $—SR^{2c}$, or —O-phenyl, wherein the phenyl is optionally 3-substituted with halogen or —OH, wherein the phenyl is optionally 5-subsituted with halogen or —OH, wherein the —O-phenyl ring is optionally 4-substituted with $—NH_2$, —$NO_2$, —OH, —$OR^{2c}$, —SH, or —$SR^2C$, wherein the —O-phenyl ring is optionally 3-substituted with halogen or —OH, wherein the —O-phenyl ring is optionally 5-subsituted with halogen or —OH, wherein each $R^{2c}$ is independently a $C_1$-$C_3$ linear or branched alkyl group.

In some embodiments of the compounds of Formula A, B, and/or C, $R^{2b}$ is absent. In some embodiments, $R^{2b}$ is —$CH_2$—. In some embodiments, $R^{2b}$ is —NH—. In some embodiments, $R^{2b}$ is —S—. In some embodiments, $R^{2b}$ is —O—.

In some embodiments of the compounds of Formula A, B, and/or C, $R^{2a}$ is —($CH_2$)—($R^2$)-(phenyl), wherein $R^{2b}$ is absent or —$CH_2$—, wherein the phenyl is 4-substituted with —$NH_2$, —$NO_2$, —OH, —$OR^{2c}$, —SH, —$SR^{2c}$, or —O-phenyl. In some embodiments, the phenyl is 4-substituted with —$NH_2$. In some embodiments, the phenyl is 4-substituted with —$NO_2$. In some embodiments, the phenyl is 4-substituted with —OH. In some embodiments, the phenyl is 4-substituted with —SH. In some embodiments, the phenyl is 4-substituted with —O-phenyl. In some embodiments, the phenyl is 3,5-unsubstituted. In some embodiments, the phenyl is 3-substituted. In some embodiments, phenyl is 5-substituted. In some embodiments, the phenyl is 3,5-substituted. In some embodiments, the halogen substituent is iodine. The 3,5-substituents may be the same or different (e.g. different halogens, or a mix of halogen and —OH).

In some embodiments of the compounds of Formula A, B, and/or C, —NH—CH($R^{2a}$)—C(O)— forms an L-amino acid residue. In some embodiments, —NH—CH($R^{2a}$)—C(O)— forms a D-amino acid residue. In some embodiments, —NH—CH($R^{2a}$)—C(O)— forms a Tyr residue. In some embodiments, —NH—CH($R^{2a}$)—C(O)— forms a Phe residue. In some embodiments, —NH—CH($R^{2a}$)—C(O)— forms a (4-$NO_2$)-Phe residue. In some embodiments, —NH—CH($R^{2a}$)—C(O)— forms a (4-$NH_2$)-Phe residue. In some embodiments, —NH—CH($R^{2a}$)—C(O)— forms a hTyr residue. In some embodiments, —NH—CH($R^{2a}$)—C(O)— forms a (3-I)Tyr residue. In some embodiments, —NH—CH($R^{2a}$)—C(O)— forms a Glu residue. In some embodiments, —NH—CH($R^{2a}$)—C(O)— forms a Gln residue. In some embodiments, —NH—CH($R^{2a}$)—C(O)— forms a D-Tyr residue.

In some embodiments, of the compounds of Formula A, B, and/or C, $R^{3a}$ is $R^{3b}R^{3c}$ wherein $R^{3b}$ is a linear $C_1$-$C_5$ alkylenyl, alkenylenyl, or alkynylenyl, wherein 0-2 carbons in $C_2$-$C_5$ alkylenyl, alkenylenyl, or alkynylenyl are independently replaced with one or more N, S, and/or O heteroatoms, wherein $R^{3c}$ is —$N(R^{3d})_{23}$ or guanidino, wherein each $R^{3d}$ is independently —H or a linear or branched $C_1$-$C_3$ alkyl.

In some embodiments of the compounds of Formula A, B, and/or C, $R^{3b}$ is a linear $C_1$-$C_5$ alkylenyl, alkenylenyl, or alkynylenyl (i.e. no heteroatoms). In some embodiments, $R^{3b}$ comprises a single heteroatom (N, S or O) in any one of $C_2$-$C_5$ alkylenyl, alkenylenyl, or alkynylenyl. In some embodiments, $R^{3b}$ is a linear $C_1$-$C_5$ alkylenyl.

In some embodiments of the compounds of Formula A, B, and/or C, $R^{3c}$ is guanidino. In some embodiments, $R^{3c}$ is —$N(R^{3d})_{2-3}$. In some embodiments, $R^{3c}$ is —$N(R^{3d})_{2-3}$ wherein each $R^{3d}$ is a linear or branched $C_1$-$C_3$ alkyl. In some embodiments, $R^{3c}$ is —$N(R^{3d})_{2-3}$ wherein each $R^{3d}$ is methyl. In some embodiments, $R^{3c}$ is —$N(R^{3d})_{2-3}$ wherein each $R^{3d}$ is independently —H or methyl. In some embodiments, $R^{3c}$ is —$NH_2$ or —$NH_3$.

In some embodiments of the compounds of Formula A, B, and/or C, —NH—CH($R^{3a}$)—C(O)— forms an L-amino acid residue. In some embodiments, —NH—CH($R^{3a}$)—C(O)— forms a D-amino acid residue. In some embodiments, —NH—CH($R^{3a}$)—C(O)— forms a Lys(iPr) residue. In some embodiments, —NH—CH($R^{3a}$)—C(O)— forms an Arg$(Me)_2$ (asymmetrical) residue. In some embodiments, —NH—CH($R^{3a}$)—C(O)— forms an Arg(Me) residue.

In some embodiments of the compounds of Formula A, B, and/or C, $R^{4a}$ is $R^{4b}R^{4c}$ wherein $R^{4b}$ is a linear $C_1$-$C_5$ alkylenyl, alkenylenyl, or alkynylenyl, in which 0-2 carbons in $C_2$-$C_5$ are independently replaced with one or more N, S, and/or O heteroatoms, wherein $R^{4c}$ is —$N(R^{4d})_{2-3}$ or guanidino, wherein each $R^{4d}$ is independently —H or a linear or branched $C_1$-$C_3$ alkyl.

In some embodiments of the compounds of Formula A, B, and/or C, $R^{4b}$ is a linear $C_1$-$C_5$ alkylenyl, alkenylenyl, or alkynylenyl (i.e. no heteroatoms). In some embodiments, $R^{4b}$ comprises a single heteroatom (N, S or O) in any one of $C_2$-$C_5$. In some embodiments, $R^{4b}$ is a linear $C_1$-$C_5$ alkylenyl.

In some embodiments of the compounds of Formula A, B, and/or C, $R^{4c}$ is guanidino. In some embodiments, $R^{4c}$ is —$N(R^{4d})_{2-3}$. In some embodiments, $R^{4c}$ is —$N(R^{4d})_{2-3}$ wherein each $R^{4d}$ is a linear or branched $C_1$-$C_3$ alkyl. In some embodiments, $R^{4c}$ is —$N(R^{4d})_{2-3}$ wherein each $R^{4d}$ is methyl. In some embodiments, $R^{4c}$ is —$N(R^{4d})_{2-3}$ wherein each $R^{4d}$ is independently —H or methyl. In some embodiments, $R^{4c}$ is —$NH_2$ or —$NH_3$.

In some embodiments of the compounds of Formula A, B, and/or C, —NH—CH($R^{4a}$)—C(O)— forms a D-amino acid residue. In some embodiments, —NH—CH($R^{4a}$)—C(O)— forms an L-amino acid residue. In some embodiments, —NH—CH($R^{4a}$)—C(O)— forms a D-Arg residue. In some embodiments, —NH—CH($R^{4a}$)—C(O)— forms a D-hArg residue.

In some embodiments of the compounds of Formula A, B, and/or C, $R^{5a}$ is —$(CH_2)_{1-3}R^{5b}$, wherein 1 carbon in —$(CH_2)_{2-3}$— is optionally replaced with a N, S, or O heteroatom, wherein $R^{5b}$ is:

- phenyl optionally substituted with one or a combination of the following: 4-substituted with —$NH_2$, —$NO_2$, —OH, —$OR^{5c}$, —SH, —$SR^{5c}$, or —O-phenyl; 3-substituted with halogen or —OH; and/or 5-subsituted with halogen or —OH; wherein the —O-phenyl ring is optionally 4-substituted with —$NH_2$, —$NO_2$, —OH, —$OR^{5c}$, —SH, or —$SR^{5c}$, wherein the —O-phenyl ring is optionally 3-substituted with halogen or —OH, wherein the —O-phenyl ring is optionally 5-subsituted with halogen or —OH; or
- a fused bicyclic or fused tricyclic aryl group wherein one or more carbons are optionally independently replaced by N, S, and/or O heteroatoms, and independently optionally substituted with one or a combination of halogen, —OH, —$OR^{5c}$, amino, —$NHR^{5c}$, and/or $N(R^{5c})_2$;
- wherein each $R^{5c}$ is independently a $C_1$-$C_3$ linear or branched alkyl group.

In some embodiments of the compounds of Formula A, B, and/or C, $R^{5a}$ is —$CH_2$—$R^{5b}$. In some embodiments, $R^{5a}$ is —$CH_2$—$CH_2$—$R^{5b}$. In some embodiments, $R^{5a}$ is —$CH_2$—$CH_2$—$CH_2$—$R^{5b}$.

In some embodiments of the compounds of Formula A, B, and/or C, $R^{5b}$ is phenyl optionally substituted with one or a combination of the following: 4-substituted with —$NH_2$, —$NO_2$, —OH, —$OR^{5c}$, —SH, —$SR^{5c}$, or —O-phenyl; 3-substituted with halogen or —OH; and/or 5-subsituted with halogen or —OH; wherein the —O-phenyl ring is optionally 4-substituted with —$NH_2$, —$NO_2$, —OH, —$OR^{5c}$, —SH, or —$SR^{5c}$, wherein the —O-phenyl ring is optionally 3-substituted with halogen or —OH, wherein the —O-phenyl ring is optionally 5-subsituted with halogen or —OH. In some embodiments, $R^{5b}$ is phenyl optionally substituted with one or a combination of the following: 4-substituted with —$NH_2$, —$NO_2$, —OH, —SH, or —O-phenyl; 3-substituted with halogen or —OH; and/or 5-subsituted with halogen or —OH. In some embodiments, the phenyl is 4-unsubstituted. In some embodiments, the phenyl is 4-substituted with —$NH_2$. In some embodiments, the phenyl is 4-substituted with —$NO_2$. In some embodiments, the phenyl is 4-substituted with —OH. In some embodiments, the phenyl is 4-substituted with —$OR^{5c}$. In some embodiments, the phenyl is 4-substituted with —SH. In some embodiments, the phenyl is 4-substituted with —$SR^{5c}$. In some embodiments, the phenyl is 4-substituted with —O-phenyl. In some embodiments, each $R^{5c}$ is independently a $C_1$-$C_3$ linear or branched alkyl group. In some embodiments, each $R^{5c}$ is methyl. In some embodiments, the phenyl is 3-unsubstituted. In some embodiments, the phenyl is 3-substituted with halogen. In some embodiments, the phenyl is 3-substituted with —OH. In some embodiments, the phenyl is 5-substituted with halogen. In some embodiments, the phenyl is 5-substituted with —OH. In some embodiments, the halogen is iodine. In some embodiments, the —O-phenyl ring is unsubstituted. In some embodiments, the —O-phenyl ring is 4-substituted. In some embodiments, the —O-phenyl ring is 3-substituted. In some embodiments, the —O-phenyl ring is 5-substituted.

In some embodiments of the compounds of Formula A, B, and/or C, $R^{5b}$ is a fused bicyclic or fused tricyclic aryl group wherein one or more carbons are optionally independently replaced by N, S, and/or O heteroatoms, and optionally independently substituted with one or a combination of halogen, —OH, —$OR^{5c}$, amino, —$NHR^{5c}$, and/or $N(R^{5c})_2$. In some embodiments, each $R^{5c}$ is independently a $C_1$-$C_3$ linear or branched alkyl group. In some embodiments, each $R^{5c}$ is methyl. In some embodiments, $R^{5b}$ is a fused bicyclic or fused tricyclic aryl group wherein 0-3 carbons are independently replaced by N, S, and/or O heteroatoms, and optionally independently substituted with one or a combination of halogen, —OH, and/or amino. In some embodiments, $R^{5b}$ is a fused bicyclic or fused tricyclic aryl group optionally independently substituted with one or a combination of halogen, —OH, and/or amino. In some embodiments, $R^{5b}$ is a fused bicyclic or fused tricyclic aryl group optionally independently substituted with 0-3 groups selected from halogen, —OH, and/or amino. In some embodiments, $R^{5b}$ is a fused bicyclic or fused tricyclic aryl group. In some embodiments, $R^{5b}$ excludes 9-linked anthracenyl. In some embodiments, each ring in the fused bicyclic or fused tricyclic aryl group independently has 4, 5 or 6 ring carbons, wherein 0-3 carbons are independently replaced by N, S, and/or O heteroatoms; such embodiments may be substituted or unsubstituted as defined above.

In some embodiments of the compounds of Formula A, B, and/or C, —NH—$CH(R^{5a})$—C(O)— forms an L-amino acid residue. In some embodiments, —NH—$CH(R^{5a})$—C(O)— forms a D-amino acid residue. In some embodiments, —NH—$CH(R^{5a})$—C(O)— forms a 2-(Ant)Ala residue. In some embodiments, —NH—$CH(R^{5a})$—C(O)— forms a 2-Nal residue. In some embodiments, —NH—$CH(R^{5a})$—C(O)— forms a Trp residue. In some embodiments, —NH—$CH(R^{5a})$—C(O)— forms a (4-$NH_2$)Phe residue. In some embodiments, —NH—$CH(R^{5a})$—C(O)— forms a hTyr residue. In some embodiments, —NH—$CH(R^{5a})$—C(O)— forms a Tyr residue.

In some embodiments of the compounds of Formula A, B, and/or C, either:

(a) $R^{6a}$ is H, methyl, ethyl, —C≡CH, —CH═$CH_2$, —C≡C—$(CH_2)_{1-3}$—OH, —C≡C—$(CH_2)_{1-3}$—SH, —C≡C—$(CH_2)_{1-3}$—$NH_2$, —C≡C—$(CH_2)_{1-3}$—COOH, —C≡C—$(CH_2)_{1-3}$—CONH, —C≡C—$(CH_2)_{1-3}R^{6b}R^{6c}$, —CH═CH—$(CH_2)_{1-3}$—OH, —CH≡CH—$(CH_2)_{1-3}$—SH, —CH≡CH—$(CH_2)_{1-3}$—$NH_2$, —CH═CH—$(CH_2)_{1-3}$—COOH, —CH═CH—$(CH_2)_{1-3}$—CONH, —CH═CH—$(CH_2)_{1-3}R^{6b}R^{6c}$, —$CH_2$—$R^{6b}$—OH, —$CH_2$—$R^{6b}$—COOH, —$CH_2$—$(R^{6b})_{1-3}$—$NH_2$, —$CH_2$—$R^{6b}$—CONH, or —$CH_2$—$R^{6b}R^{6c}$, wherein each $R^{6b}$ is independently absent, —$CH_2$—, —NH—, —S— or —O—, and wherein $R^{6c}$ is:
   a 5 or 6 membered aromatic ring wherein one or more carbons are optionally independently replaced by N, S, and/or O heteroatoms, and optionally substituted with one or more groups independently selected from oxo, hydroxyl, sulfhydryl, nitro, amino, and/or halogen; or (b) —NH—$CH(R^{6a})$—CO—NH— is replaced with:

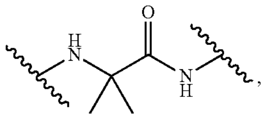, 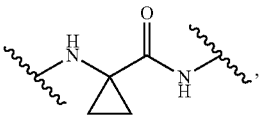, 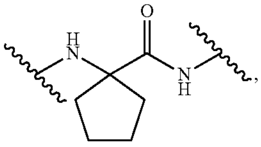, 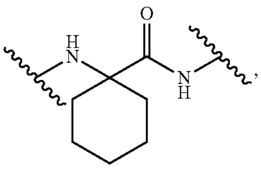, 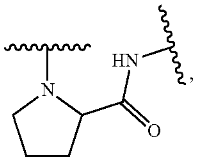, or 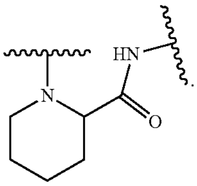.

In some embodiments of the compounds of Formula A, B, and/or C, $R^{6a}$ is H. In some embodiments, $R^{6a}$ is methyl. In some embodiments, $R^{6a}$ is ethyl. In some embodiments, Rea is —C≡CH. In some embodiments, $R^{6a}$ is —CH═$CH_2$. In some embodiments, $R^{6a}$ is —$CH_2$—$R^{6b}$—OH. In some embodiments, $R^{6a}$ is —$CH_2$—$R^{6b}$—COOH. In some embodiments, $R^{6a}$ is —$CH_2$—$(R^{6b})_{1-3}$—$NH_2$. In some embodiments, $R^{6a}$ is —$CH_2$—$R^{6b}$—CONH. In some embodiments, $R^{6a}$ is —C≡C—$(CH_2)_{1-3}$—OH. In some embodiments, $R^{6a}$ is —C≡C—$(CH_2)_{1-3}$—SH. In some embodiments, $R^{6a}$ is —C≡C—$(CH_2)_{1-3}$—$NH_2$. In some embodiments, $R^{6a}$ is —C≡C—$(CH_2)_{1-3}$—COOH. In some embodiments, $R^{6a}$ is —C≡C—$(CH_2)_{1-3}$—CONH. In some embodiments, $R^{6a}$ is —C≡C—$(CH_2)_{1-3}R^{6b}R^{6c}$. In some embodiments, $R^{6a}$ is —CH═CH—$(CH_2)_{1-3}$—OH. In some embodiments, $R^{6a}$ is —CH═CH—$(CH_2)_{1-3}$—SH. In some embodiments, $R^{6a}$ is —CH═CH—$(CH_2)_{1-3}$—$NH_2$. In some embodiments, $R^{6a}$ is —CH═CH—$(CH_2)_{1-3}$—COOH. In some embodiments, $R^{6a}$ is —CH═CH—$(CH_2)_{1-3}$—CONH. In some embodiments, $R^{6a}$ is —CH═CH—$(CH_2)_{1-3}R^{6b}R^{6c}$. Each $R^{6b}$ is independently absent, —$CH_2$—, —NH—, —S— or —O—. In some embodiments, $R^{6b}$ is absent. In some embodiments, $R^{6b}$ is —$CH_2$—.

In some embodiments of the compounds of Formula A, B, and/or C, $R^{6a}$ is H, methyl, ethyl, —C≡CH, —CH═$CH_2$, —$CH_2$—$R^{6b}$—OH, —$CH_2$—$R^{6b}$—COOH, —$CH_2$—$(R^{6b})_{1-3}$—$NH_2$, —$CH_2$—$R^{6b}$—CONH, or —$CH_2$—$R^{6b}R^{6c}$. In some embodiments, $R^{6a}$ is —$CH_2$—$R^{6b}R^{6c}$. Each $R^{6b}$ is independently absent, —$CH_2$—, —NH—, —S— or —O—. In some embodiments, $R^{6b}$ is absent. In some embodiments, $R^{6b}$ is —$CH_2$—. In some embodiments, $R^{6c}$ is a 5 or 6 membered aromatic ring wherein 0-3 carbons are independently replaced by N, S, and/or O heteroatoms, and optionally substituted with 0-3 groups independently selected from oxo, hydroxyl, sulfhydryl, nitro, amino, and/or halogen; in some embodiments, the ring is unsubstituted. In some embodiments, $R^{6c}$ is a 5 or 6 membered aryl, optionally substituted with 0-3 groups independently selected from oxo, hydroxyl, sulfhydryl, nitro, amino, and/or halogen; in some embodiments, the aryl is unsubstituted.

In some embodiments of the compounds of Formula A, B, and/or C, —NH—CH($R^{6a}$)—C(O)—NH— is relaced with:

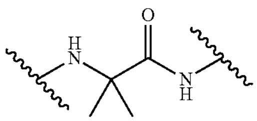,
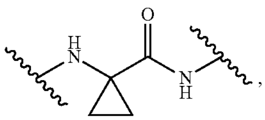,
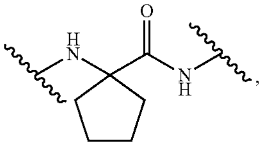, or
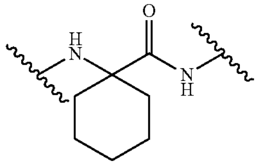.

In some embodiments, —NH—CH($R^{6a}$)—C(O)—NH— is replaced with:

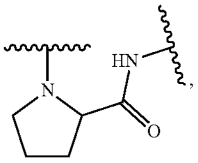, or
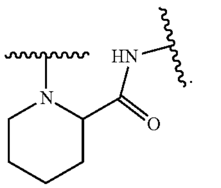.

In some embodiments of the compounds of Formula A, B, and/or C, —NH—CH($R^{6a}$)—C(O)— forms a D-amino acid residue. In some embodiments, —NH—CH($R^{6a}$)—C(O)— forms an L-amino acid residue. In some embodiments, —NH—CH($R^{6a}$)—C(O)— forms a His residue. In some embodiments, —NH—CH($R^{6a}$)—C(O)— forms a D-His residue. In some embodiments, —NH—CH($R^{6a}$)—C(O)— forms a D-Glu residue. In some embodiments, —NH—CH($R^{6a}$)—C(O)— forms a D-Gln residue. In some embodiments, —NH—CH($R^{6a}$)—C(O)— forms a D-Ala residue. In some embodiments, —NH—CH($R^{6a}$)—C(O)— forms a D-Phe residue. In some embodiments, —NH—CH($R^{6a}$)—C(O)— forms a D-Ser residue. In some embodiments, —NH—CH($R^{6a}$)—C(O)— forms a D-Dab residue. In some embodiments, —NH—CH($R^{6a}$)—C(O)— forms a D-Dap residue.

In some embodiments of the compounds of Formula A, B, and/or C, $R^{8a}$ is $R^{8b}R^{8c}$ wherein $R^{8b}$ is a linear $C_1$-$C_5$ alkylenyl, alkenylenyl, or alkynylenyl, in which 0-2 carbons in $C_2$-$C_5$ are independently replaced with one or more N, S, and/or O heteroatoms, wherein $R^{8c}$ is —$N(R^{8d})_{2-3}$ or guanidino, wherein each $R^{8d}$ is independently —H or a linear or branched $C_1$-$C_3$ alkyl.

In some embodiments of the compounds of Formula A, B, and/or C, $R^{8b}$ is a linear $C_1$-$C_5$ alkylenyl, alkenylenyl, or alkynylenyl (i.e. no heteroatoms). In some embodiments, $R^{8b}$ comprises a single heteroatom (N, S or O) in any one of $C_2$-$C_5$. In some embodiments, $R^{8b}$ is a linear $C_1$-$C_5$ alkylenyl.

In some embodiments of the compounds of Formula A, B, and/or C, $R^{8c}$ is guanidino. In some embodiments, $R^{8c}$ is —$N(R^{8d})_{2-3}$. In some embodiments, $R^{8c}$ is —$N(R^{8d})_{2-3}$ wherein each $R^{8d}$ is a linear or branched $C_1$-$C_3$ alkyl. In some embodiments, $R^{8c}$ is —$N(R^{8d})_{2-3}$ wherein each $R^{8d}$ is methyl. In some embodiments, $R^{8c}$ is —$N(R^{8d})_{2-3}$ wherein each $R^{8d}$ is independently —H or methyl. In some embodiments, $R^{8c}$ is —$NH_2$ or —$NH_3$.

In some embodiments of the compounds of Formula A, B, and/or C, —NH—CH($R^{8a}$)—C(O)— forms an L-amino acid residue. In some embodiments, —NH—CH($R^{8a}$)—C(O)— forms a D-amino acid residue. In some embodiments, —NH—CH($R^{8a}$)—C(O)— forms a Lys(iPr) residue. As used herein, in the expression "—NH—CH($R^{8a}$)—C(O)—" made about Formula A, A-I, A-II, B, and/or C, it is understood that the —C(O)— portion is part of $R^{9a}$ definition.

In some embodiments of the compounds of Formula A, B, and/or C, $R^{9a}$ is: —C(O)$NH_2$, —C(O)—OH, —$CH_2$—C(O)$NH_2$, —$CH_2$—C(O)—OH, —$CH_2$—$NH_2$, —$CH_2$—OH, —$CH_2$—$CH_2$—$NH_2$, —$R^{9b}$—$R^{9c}$, or —$R^{9b}$-[linker]-$R^{X}_{n1}$, wherein:

$R^{9b}$ is —$CH_2$—NH—C(O)—, —$CH_2$—C(O)—, —$CH_2$—O—, —C(O)NH—, —C(O)—N($CH_3$)—, —$CH_2$—NHC(S)—, —C(S)NH—, —$CH_2$—N($CH_3$)C(S)—, —C(O)N($CH_3$)—, —$CH_2$—N($CH_3$)C(O)—, —C(S)N($CH_3$)—, —$CH_2$—NHC(S)NH—, —$CH_2$—NHC(O)NH—, —$CH_2$—S—, —$CH_2$—S(O)—, —$CH_2$—$S(O)_2$—, —$CH_2$—$S(O)_2$—NH—, —$CH_2$—S(O)—NH—, —$CH_2$—Se—, —$CH_2$—Se(O)—, —$CH_2$—$Se(O)_2$—, —$CH_2$—NHNHC(O)—, —C(O)NHNH—, —$CH_2$—OP(O)($O^-$)O—, —$CH_2$-phosphamide-, —$CH_2$-thiophosphodiester-, —$CH_2$—S-tetrafluorophenyl-S—,

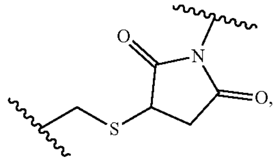,
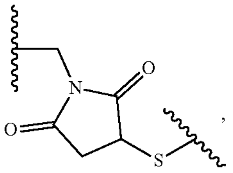,
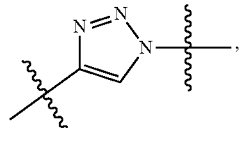,
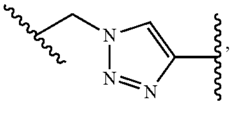, or polyethylene glycol; and $R^{9c}$ is hydrogen or a linear, branched, and/or cyclic $C_1$-$C_{20}$ alkyl, alkenyl or alkynyl, wherein 0-6 carbons in $C_2$-$C_{20}$ are independently replaced by N, S, and/or O heteroatoms, and substituted with 0-3 groups independently selected from one or a combination of oxo, hydroxyl, sulfhydryl, halogen, guanidino, carboxylic acid, sulfonic acid, sulfinic acid, and/or phosphoric acid;

In some embodiments of the compounds of Formula A, B, and/or C, $R^{9a}$ is: —C(O)$NH_2$, —C(O)—OH, —$CH_2$—C(O)$NH_2$, —$CH_2$—C(O)—OH. In some embodiments, $R^{9a}$ is —$R^{9b}$—$R^{9c}$ wherein $R^{9b}$ is —C(O)NH—.

In some embodiments of the compounds of Formula A, B, and/or C, $R^{9c}$ is

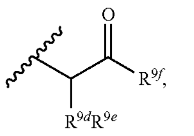

wherein $R^{9d}$ is a linear or branched $C_1$-$C_5$ alkylenyl, alkenylenyl, or alkynylenyl, in which 0-2 carbons in $C_2$-$C_5$ are independently replaced with N, S, and/or O heteroatoms, wherein $R^{9e}$ is carboxylic acid, sulfonic acid, sulfinic acid, phosphoric acid, amino, guanidino, —SH, —OH, —NH—C(O)—$CH_3$, —S—C(O)—$CH_3$, —O—C(O)—$CH_3$, —NH—C(O)-(phenyl), —S—C(O)-(phenyl), —O—C(O)-(phenyl), —NH—$CH_3$, —N$(CH_3)_2$, —S—$CH_3$, —O—$CH_3$, and phenyl, and wherein $R^{9f}$ is amino or —OH. In some embodiments, $R^{9d}$ is a linear or branched $C_1$-$C_5$ alkylenyl, alkenylenyl, or alkynylenyl (i.e. no heteroatoms). In some embodiments, $R^{9d}$ is a linear or branched $C_1$-$C_5$ alkylenyl.

In some embodiments of the compounds of Formula A, B, and/or C, $R^{9a}$ is —$R^{9b}$-[linker]-$R^X{}_{n1}$. In some of these embodiments, $R^{9b}$ is —C(O)NH—.

In some embodiments of the compounds of Formula A, B, and/or C: $R^{9a}$ is —C(O)$NH_2$, —C(O)—OH, —$R^{9b}$—$R^{9c}$, or —$R^{9b}$-[linker]-$R^X{}_{n1}$; and $R^{9b}$ is —C(O)NH—, —C(O)—N$(CH_3)$—, —C(O)N$(CH_3)$—, or —C(O)NHNH—.

In some embodiments of the compounds of Formula A, $R^{A7a}$ is a linear $C_1$-$C_5$ alkylenyl wherein 0-2 carbons in $C_2$-$C_5$ are independently replaced with one or more N, S, and/or O heteroatoms. In some embodiments, $R^{A7}$a is a linear $C_1$-$C_5$ alkylenyl (i.e. no heteroatoms). In some embodiments, $R^{A7a}$ is a linear $C_1$-$C_5$ alkylenyl in which one carbon in $C_2$-$C_5$ is a heteroatom selected from N, S or O. In some embodiments, $R^{A7a}$ is —$CH_2$—. In some embodiments, $R^{A7a}$ is —$CH_2$—$CH_2$—. In some embodiments, —NH—CH($R^{A7a}$)—C(O)— forms a D-amino acid residue. In some embodiments, —NH—CH($R^{A7a}$)—C(O)— forms an L-amino acid residue.

In some embodiments of the compounds of Formula A, $R^{A10}$ is absent or -[linker]-$R^X{}_{n1}$.

In some embodiments of the compounds of Formula A, when $R^{A10}$ is absent, then $R^{A1a}$ is:

- a linear $C_1$-$C_5$ alkyl, alkenyl, or alkynyl, wherein 0-2 carbons in $C_2$-$C_5$ are independently replaced by one or more N, S, and/or O heteroatoms, optionally C-substituted with a single substituent selected from: —SH, —OH, amino, carboxy, guanidino, —NH—C(O)—$CH_3$, —S—C(O)—$CH_3$, —O—C(O)—$CH_3$, —NH—C(O)-(phenyl), —S—C(O)-(phenyl), —O—C(O)-(phenyl), —NH—$(CH_3)_{1-2}$, —$NH_2$—$CH_3$, —N$(CH_3)_{2-3}$, —S—$CH_3$, or —O—$CH_3$;
- a branched $C_1$-$C_{10}$ alkyl, alkenyl, or alkynyl, wherein 0-3 carbons in $C_2$-$C_{10}$ are independently replaced by one or more N, S, and/or O heteroatoms; or
- $R^{A1b}R^{A1c}$, wherein $R^{A1b}$ is a linear $C_1$-$C_3$ alkylenyl, wherein $C_2$ alkylenyl or $C_3$ alkylenyl is optionally replaced with a N, S, or O heteroatom, wherein $R^{A1c}$ is:
  - a 5 or 6 membered aromatic ring wherein one or more carbons are optionally independently replaced by N, S, and/or O heteroatoms, and optionally substituted with one or more groups independently selected from oxo, hydroxyl, sulfhydryl, nitro, amino, and/or halogen; or
  - a fused bicyclic or fused tricyclic aryl group wherein one or more carbons are optionally independently replaced by N, S, and/or O heteroatoms, and optionally substituted with one or more groups independently selected from halogen, —OH, —O$R^{A1d}$, amino, —NH$R^{A1d}$, and/or N$(R^{A1d})_2$, wherein each $R^{A1d}$ is independently a $C_1$-$C_3$ linear or branched alkyl group.

In some embodiments of the compounds of Formula A, when $R^{A10}$ is -[linker]-$R^X{}_{n1}$, then $R^{A1a}$ is $R^{A1e}R^{A1f}$, wherein $R^{A1e}$ is a linear $C_1$-$C_5$ alkylenyl, alkenylenyl, or alkynylenyl, in which 0-2 carbons in $C_2$-$C_5$ are independently replaced with N, S, and/or O heteroatoms, and $R^{A1f}$ is —NH—C(O)—, —C(O)—, —O—, —C(O)NH—, —C(O)—N$(CH_3)$—, —NHC(S)—, —C(S)NH—, —N$(CH_3)$C(S)—, —C(O)N$(CH_3)$—, —N$(CH_3)$C(O)—, —C(S)N$(CH_3)$—, —NHC(S)NH—, —NHC(O)NH—, —S—, —S(O)—, —S(O)—O—, —S$(O)_2$—, —S$(O)_2$—O—, —S$(O)_2$—NH—, —S(O)—NH—, —Se—, —Se(O)—, —Se$(O)_2$—, —NHNHC(O)—, —C(O)NHNH—, —OP(O)($O^-$)O—, -phosphamide-, -thiophosphodiester-, —S-tetrafluorophenyl-S—, polyethylene glycol,

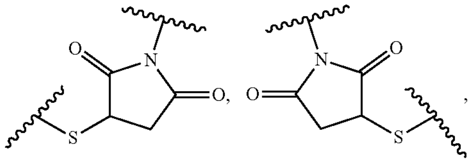
,

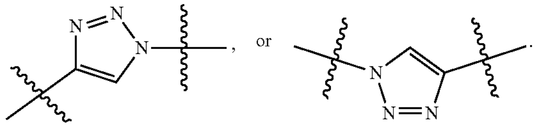

In some embodiments of the compounds of Formula A, —NH—CH($R^{A1a}$)—C(O)— forms an L-amino acid residue. In some embodiments, —NH—CH($R^{A1a}$)—C(O)— forms a D-amino acid residue.

In some embodiments of the compounds of Formula A, $R^{A10}$ is absent.

In some of embodiments of the compounds of Formula A, where $R^{A10}$ is absent, $R^{A1a}$ is a linear $C_1$-$C_5$ alkyl, alkenyl, or alkynyl, optionally substituted with a single substituent selected from: —SH, —OH, amino, carboxy, guanidino, —NH—C(O)—$CH_3$, —S—C(O)—$CH_3$, —O—C(O)—$CH_3$, —NH—C(O)-(phenyl), —S—C(O)-(phenyl), —O—C(O)-(phenyl), —NH—$(CH_3)_{1-2}$, —$NH_2$—$CH_3$, —N$(CH_3)_{2-3}$, —S—$CH_3$, or —O—$CH_3$. In some of embodiments where $R^{A10}$ is absent, $R^{A1a}$ is a linear $C_1$-$C_5$ alkyl optionally substituted with a single substituent selected from: —SH, —OH, amino, carboxy, guanidino, —NH—C(O)—$CH_3$, —S—C(O)—$CH_3$, —O—C(O)—$CH_3$, —NH—C(O)-(phenyl), —S—C(O)— (phenyl), —O—C(O)-(phenyl), —NH—$(CH_3)_{1-2}$, —$NH_2$—$CH_3$, —N$(CH_3)_{2-3}$, —S—$CH_3$, or —O—$CH_3$.

In some of embodiments of the compounds of Formula A, where $R^{A10}$ is absent, $R^{A1a}$ is a branched $C_1$-$C_{10}$ alkyl, alkenyl, or alkynyl. In some of embodiments where $R^{A10}$ is absent, $R^{A1a}$ is a branched $C_1$-$C_{10}$ alkyl.

In some of embodiments of the compounds of Formula A, where $R^{A10}$ is absent, $R^{A1a}$ is $R^{A1b}R^{A1c}$. In some embodiments, $R^{A1b}$ is a linear $C_1$-$C_3$ alkylenyl. In some embodiments, $R^{A1c}$ is a 5 or 6 membered aromatic ring wherein 0-4 carbons are independently replaced by N, S, and/or O heteroatoms, and substituted with 0-4 groups independently selected from oxo, hydroxyl, sulfhydryl, nitro, amino, and/or halogen. In some embodiments, $R^{A1c}$ is a fused bicyclic or fused tricyclic aryl group wherein 0-6 carbons are independently replaced by N, S, and/or O heteroatoms, and optionally substituted with 0-6 groups independently selected from halogen, —OH, —$OR^{A1d}$, amino, —$NHR^{A1d}$, and/or $N(R^{A1d})_2$. In some embodiments, $R^{A1d}$ is methyl. In some embodiments, each ring in the fused bicyclic or fused tricyclic aryl group independently has 4, 5 or 6 ring carbons, wherein 0-3 carbons are independently replaced by N, S, and/or O heteroatoms; such embodiments may be substituted or unsubstituted as defined above.

In some embodiments of the compounds of Formula A, —NH—CH($R^{A1a}$)—C(O)— forms a Phe residue, a 1-Nal residue, a 2-Nal residue, a Tyr residue, a Trp residue, a Lys residue, a hLys residue, a Lys(Ac) residue, a Dap residue, a Dab residue, or an Orn residue. n some embodiments of the compounds of Formula A, —NH—CH($R^{A1a}$)—C(O)— forms an L-Phe residue, an L-1-Nal residue, an L-2-Nal residue, an L-Tyr residue, an L-Trp residue, an L-Lys residue, an L-hLys residue, an L-Lys(Ac) residue, an L-Dap residue, an L-Dab residue, or an L-Orn residue. In some embodiments of the compounds of Formula A, —NH—CH ($R^{A1a}$)—C(O)— forms a Phe residue. In some embodiments, —NH—CH($R^{A1a}$)—C(O)— forms a 1-Nal residue. In some embodiments, —NH—CH($R^{A1a}$)—C(O)— forms a 2-Nal residue. In some embodiments, —NH—CH($R^{A1a}$)—C(O)— forms a Tyr residue. In some embodiments, —NH—CH($R^{A1a}$)—C(O)— forms a Trp residue. In some embodiments, —NH—CH($R^{A1a}$)—C(O)— forms a Lys residue. In some embodiments, —NH—CH($R^{A1a}$)—C(O)— forms a hLys residue. In some embodiments, —NH—CH($R^{A1a}$)—C(O)— forms a Lys(Ac) residue. In some embodiments, —NH—CH($R^{A1a}$)—C(O)— forms a Dap residue. In some embodiments, —NH—CH($R^{A1a}$)—C(O)— forms a Dab residue. In some embodiments, —NH—CH($R^{A1a}$)—C(O)— forms an Orn residue.

In some embodiments of the compounds of Formula A, $R^{A10}$ is -[linker]-$R^{X}_{n1}$ and $R^{A1a}$ is $R^{A1e}R^{A1f}$. In some embodiments, $R^{A1e}$ is a linear $C_1$-$C_5$ alkylenyl, alkenylenyl, or alkynylenyl. In some embodiments, $R^{A1e}$ is a linear $C_1$-$C_5$ alkylenyl. In some embodiments, $R^{A1f}$ is —NH—C(O)—, —C(O)—, —O—, —C(O)NH—, —C(O)—N($CH_3$)—, —NHC(S)—, —C(S)NH—, —N($CH_3$)C(S)—, —C(O)N ($CH_3$)—, —N($CH_3$)C(O)—, —C(S)N($CH_3$)—, —NHC(S) NH—, —NHC(O)NH—, —S—, —S(O)—, —S(O)—O— $S(O)_2$—, —$S(O)_2$—NH—, —S(O)—NH—, —NHNHC (O)—, —C(O)NHNH—, polyethylene glycol,

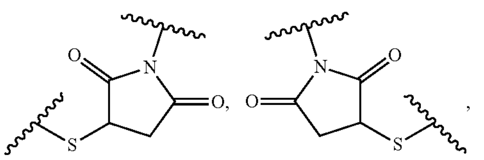

-continued

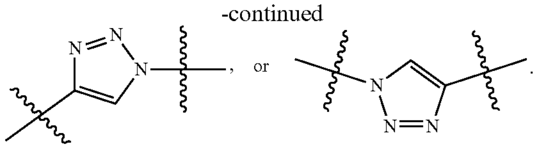

All embodiments described herein for Formula A can be embodiments for Formula A-I and/or Formula A-II to the extent the definitions are encompassed by Formula A-I and/or Formula A-II.

In some embodiments of the compounds of Formula B, $R^{B1a}$ is a linear, branched, and/or cyclic $C_1$-$C_{10}$ alkylenyl, alkenylenyl, or alkynylenyl, wherein one or more carbons in $C_2$-$C_{10}$ are optionally independently replaced with N, S, and/or O heteroatoms.

In some embodiments of the compounds of Formula B, $R^{B1-7}$ is:

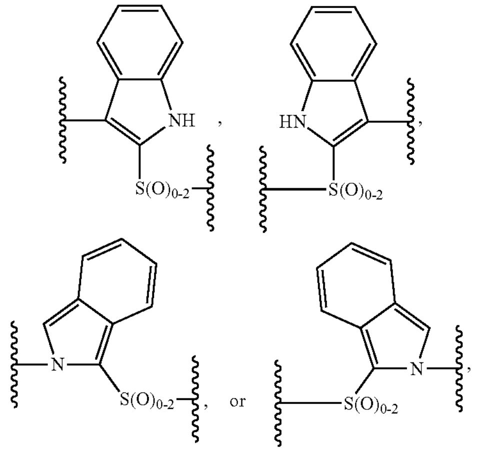

wherein the indole and the isoindole are optionally substituted with one or more of —F, —Br, —Cl, —I, —OH, —O—$R^{B1-7b}$, —CO—, —COOH, —$CONH_2$, —CN, —O-aryl, —$NH_2$, —$NHR^{B1-7b}$, $N_3$, —NH, —CHO, and/or —$R^{B1-7b}$, wherein each $R^{B1-7b}$ is a linear or branched $C_1$-$C_3$ alkyl, alkenyl, or alkynyl. In some embodiments, the indole and the isoindole are not substituted. In some embodiments, the indole and the isoindole are substituted with 1-3 groups selected from —F, —Br, —Cl, —I, —OH, —O—$R^{C1b}$, —CO—, —COOH, —$CONH_2$, —CN, —O-aryl, —$NH_2$, —$NHR^{C1b}$, $N_3$, —NH, —CHO, and/or —$R^{C1b}$. In some embodiments, each $R^{C1b}$ is methyl. In some embodiments, the aryl is a 5 or 6 membered aromatic ring.

In some embodiments of the compounds of Formula B, $R^{B7a}$ is a linear $C_1$-$C_5$ alkylenyl wherein optionally 0-2 carbons in $C_2$-$C_5$ are independently replaced with one or more N, S, and/or O heteroatoms. In some embodiments, $R^{B7a}$ is a linear $C_1$-$C_5$ alkylenyl (i.e. no heteroatoms). In some embodiments, $R^{B7a}$ is a linear $C_1$-$C_5$ alkylenyl in which one carbon in $C_2$-$C_5$ is a heteroatom selected from N, S or O. In some embodiments, $R^{B7a}$ is —$CH_2$—. In some embodiments, $R^{B7a}$ is —$CH_2$—$CH_2$—. In some embodiments, —NH—CH($R^{C7a}$)—C(O)— forms a D-amino acid residue. In some embodiments, —NH—CH($R^{C7a}$)—C (O)— forms an L-amino acid residue.

In some embodiments of the compounds of Formula B, $R^{B1-7}$ is

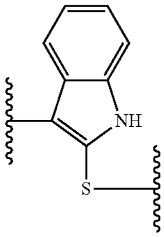, 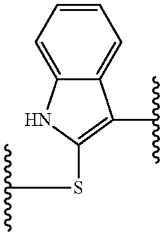,

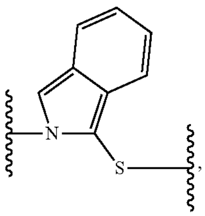, or 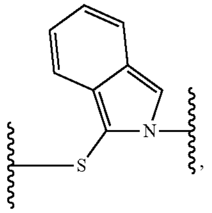, wherein the indole and the isoindole are optionally substituted with one or more of —F, —Br, —Cl, —I, —OH, —O—$R^{B1\text{-}7b}$, —CO—, —COOH, —$CONH_2$, —CN, —O-aryl, —$NH_2$, —$NHR^{B1\text{-}7b}$, $N_3$, —NH, —CHO, and/or —$R^{B1\text{-}7b}$, wherein each $R^{B1\text{-}7b}$ is a linear or branched $C_1$-$C_3$ alkyl, alkenyl, or alkynyl. In some embodiments, the indole and the isoindole are substituted with 1-3 groups selected from —F, —Br, —Cl, —I, —OH, —O—$R^{C1b}$, —CO—, —COOH, —$CONH_2$, —CN, —O-aryl, —$NH_2$, —$NHR^{C1b}$, $N_3$, —NH, —CHO, and/or —$R^{C1b}$. In some embodiments, each $R^{C1b}$ is methyl. In some embodiments, the aryl is a 5 or 6 membered aromatic ring. In some embodiments, $R^{B17}$ is

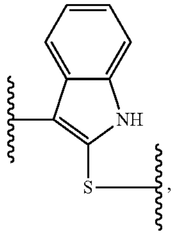, 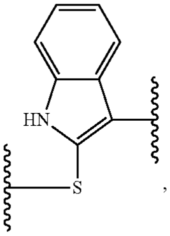,

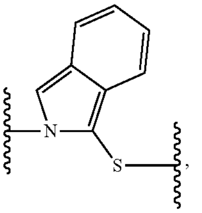, or 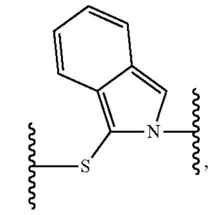,

In some embodiments of the compounds of Formula B, $R^{B1a}$ is —$(CH_2)_{1\text{-}2}$—, $R^{B1\text{-}7}$ is

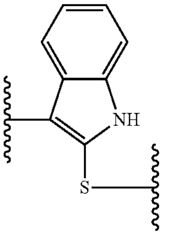 or 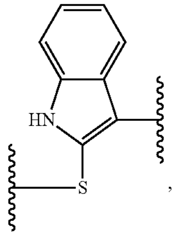, and $R^{B7a}$ is —$(CH_2)_{1\text{-}2}$—.

In some embodiments of the compounds of Formula B, $R^{B1a}$—$R^{B1\text{-}7}$—$R^{B7a}$ is

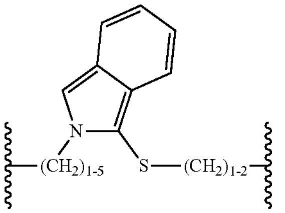 or

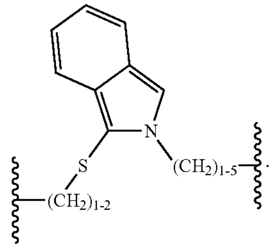.

In some embodiments of the compounds of Formula B, —NH—CH($R^{B7a}$)—C(O)— forms a D-amino acid residue. In some embodiments, —NH—CH($R^{B7a}$)—C(O)— forms an L-amino acid residue.

In some embodiments of the compounds of Formula B, $R^{B10a}$ is: amine, —NH—$(CH_3)_{1\text{-}2}$, —$N(CH_3)_{2\text{-}3}$, —NH—C(O)—$CH_3$, —NH—C(O)-(phenyl), or —$R^{B10b}$-[linker]-$R^X{}_{n1}$ wherein $R^{B10b}$ is:

—NH—C(O)—, —C(O)—, —O—, —C(O)NH—, —C(O)—N($CH_3$)—, —NHC(S)—, —C(S)NH—, —N($CH_3$)C(S)—, —C(O)N($CH_3$)—, —N($CH_3$)C(O)—, —C(S)N($CH_3$)—, —NHC(S)NH—, —NHC(O)NH—, —S—, —S(O)—, —S(O)—O—, —$S(O)_2$—, —$S(O)_2$—O—, —$S(O)_2$—NH—, —S(O)—NH—, —Se—, —Se(O)—, —$Se(O)_2$—, —NHNHC(O)—, —C(O)NHNH—, —OP(O)($O^-$)O—, -phosphamide-, -thiophosphodiester-, —S-tetrafluorophenyl-S—,

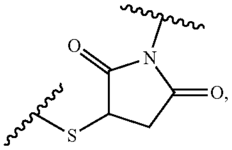, 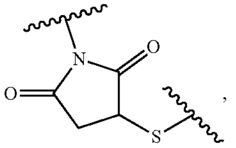,

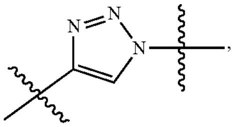, 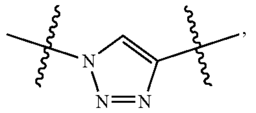, or polyethylene glycol.

In some embodiments of the compounds of Formula B, $R^{B10a}$ is: amine, —NH—$(CH_3)_{1\text{-}2}$, —$N(CH_3)_{2\text{-}3}$, —NH—C(O)—$CH_3$, or —NH—C(O)-(phenyl).

In some embodiments of the compounds of Formula B, $R^{B10a}$ is —$R^{B10b}$-[linker]-$R^X{}_{n1}$. In some of these embodiments $R^{B10b}$ is: —NH—C(O)—, —C(O)—, —O—, —C(O)NH—, —C(O)—N($CH_3$)—, —NHC(S)—, —C(S)NH—, —N($CH_3$)C(S)—, —C(O)N($CH_3$)—, —N($CH_3$)C(O)—, —C(S)N($CH_3$)—, —NHC(S)NH—, —NHC(O)NH—, —NHNHC(O)—, —C(O)NHNH—,

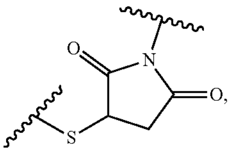 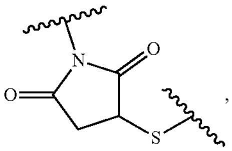 ,

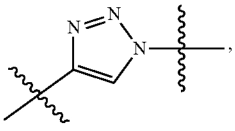 , 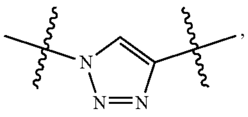 , or polyethylene glycol. In some embodiments, $R^{B10a}$ is —NHC(O)—[linker]-$R^{X}_{n1}$ or —N($CH_3$)C(O)—[linker]-$R^{X}_{n1}$.

In some embodiments of the compounds of Formula C, $R^{C1a}$ is:

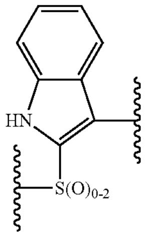 or 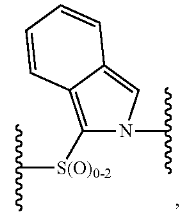 , wherein the indole and the isoindole are optionally substituted with one or more of —F, —Br, —Cl, —I, —OH, —O—$R^{C1b}$, —CO—, —COOH, —$CONH_2$, —CN, —O-aryl, —$NH_2$, —NH$R^{C1b}$, $N_3$, —NH, —CHO, and/or —$R^{C1b}$, wherein each $R^{C1b}$ is a linear or branched $C_1$-$C_3$ alkyl, alkenyl, or alkynyl. In some embodiments, the indole and the isoindole are not substituted. In some embodiments, the indole and the isoindole are substituted with 1-3 groups selected from —F, —Br, —Cl, —I, —OH, —O—$R^{C1b}$, —CO—, —COOH, —$CONH_2$, —CN, —O-aryl, —$NH_2$, —NH$R^{C1b}$, $N_3$, —NH, —CHO, and/or —$R^{C1b}$. In some embodiments, each $R^{C}_{1}$b is methyl. In some embodiments, the aryl is a 5 or 6 membered aromatic ring.

In some embodiments of the compounds of Formula C, $R^{C7a}$ is a linear $C_1$-$C_5$ alkylenyl wherein optionally 0-2 carbons in $C_2$-$C_5$ are independently replaced with one or more N, S, and/or O heteroatoms. In some embodiments, $R^{C7a}$ is a linear $C_1$-$C_5$ alkylenyl (i.e. no heteroatoms). In some embodiments, $R^{C7a}$ is a linear $C_1$-$C_5$ alkylenyl in which one carbon in $C_2$-$C_5$ is a heteroatom selected from N, S or O. In some embodiments, $R^{C7a}$ is —$(CH_2)_{1-2}$—. In some embodiments, —NH—CH($R^{C7a}$)—C(O)— forms a D-amino acid residue. In some embodiments, —NH—CH($R^{C7a}$)—C(O)— forms an L-amino acid residue.

In some embodiments of the compounds of Formula C, $R^{C10a}$ is $R^{C10b}$—$R^{C10c}$-[linker]-$R^{X}_{n1}$ or $R^{C10d}$, wherein:

$R^{C10b}$ is a linear $C_1$-$C_5$ alkylenyl, alkenylenyl, or alkynylenyl, in which 0-2 carbons in $C_2$-$C_5$ are independently replaced with N, S, and/or O heteroatoms;

$R^{C10c}$ is —NH—C(O)—, —C(O)—, —O—, —C(O)NH—, —C(O)—N($CH_3$)—, —NHC(S)—, —C(S)NH—, —N($CH_3$)C(S)—, —C(O)N($CH_3$)—, —N($CH_3$)C(O)—, —C(S)N($CH_3$)—, —NHC(S)NH—, —NHC(O)NH—, —S—, —S(O)—, —S(O)—O—, —$S(O)_2$—, —$S(O)_2$—O—, —$S(O)_2$—NH—, —S(O)—NH—, —Se—, —Se(O)—, —$Se(O)_2$—, —NHNHC(O)—, —C(O)NHNH—, —OP(O)($O^-$)O—, -phosphamide-, -thiophosphodiester-, —S-tetrafluorophenyl-S—,

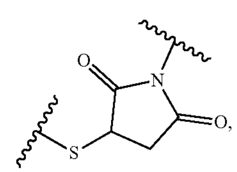 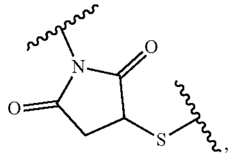

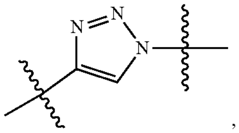 , 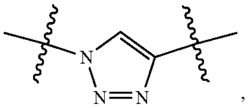 , or polyethylene glycol; and $R^{C10d}$ is:

a linear $C_1$-$C_5$ alkyl, alkenyl, or alkynyl, wherein 0-2 carbons in $C_2$-$C_5$ are independently replaced by N, S, and/or O heteroatoms, optionally C-substituted with a single substituent selected from: —SH, —OH, amino, carboxy, guanidino, —NH—C(O)—$CH_3$, —S—C(O)—$CH_3$, —O—C(O)—$CH_3$, —NH—C(O)-(phenyl), —S—C(O)-(phenyl), —O—C(O)-(phenyl), —NH—$(CH_3)_{1-2}$, —$NH_2$—$CH_3$, —$N(CH_3)_{2-3}$, —S—$CH_3$, or —O—$CH_3$;

a branched $C_1$-$C_{10}$ alkyl, alkenyl, or alkynyl, wherein 0-3 carbons in $C_2$-$C_{10}$ are independently replaced by N, S, and/or O heteroatoms; or $R^{C10e}R^{C10f}$, wherein $R^{C10e}$ is a linear $C_1$-$C_3$ alkyl, wherein $C_2$ alkyl or $C_3$ alkyl is optionally replaced with N, S, or O heteroatom, wherein $R^{C10f}$ is:

a 5 or 6 membered aromatic ring wherein one or more carbons are optionally independently replaced by N, S, and/or O heteroatoms, and optionally substituted with one or more groups independently selected from oxo, hydroxyl, sulfhydryl, nitro, amino, and/or halogen; or a fused bicyclic or fused tricyclic aryl group wherein one or more carbons are optionally independently replaced by N, S, and/or O heteroatoms, and optionally substituted with one or more groups independently selected from halogen, —OH, —O$R^{C10g}$, amino, —NH$R^{C10g}$ and/or N$(R^{C10g})_2$, wherein $R^{C10g}$ is $C_1$-$C_3$ linear or branched alkyl.

In some embodiments of the compounds of Formula C, $R^{C10a}$ is $R^{C10b}$—$R^{C10c}$-[linker]-$R^{X}_{n1}$. In some embodiments, $R^{C10b}$ is a linear $C_1$-$C_5$ alkylenyl, alkenylenyl, or alkynylenyl. In some embodiments, $R^{C10b}$ is a linear $C_1$-$C_5$ alkylenyl. In some embodiments, $R^{C10c}$ is: —NH—C(O)—, —C(O)—, —O—, —C(O)NH—, —C(O)—N($CH_3$)—, —NHC(S)—, —C(S)NH—, —N($CH_3$)C(S)—, —C(O)N($CH_3$)—, —N($CH_3$)C(O)—, —C(S)N($CH_3$)—, —NHC(S)NH—, —NHC(O)NH—, —NHNHC(O)—, —C(O)NHNH—,

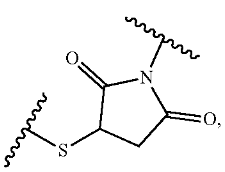 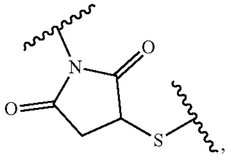

-continued

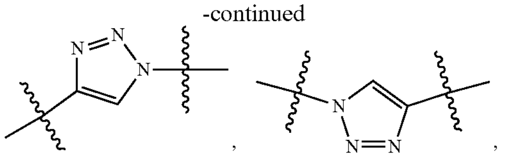

or polyethylene glycol. In some embodiments, $R^{C10c}$ is —NHC(O)— or —N($CH_3$)C(O)—.

In some embodiments of the compounds of Formula C, $R^{C10a}$ is $R^{C10d}$.

In some embodiments of the compounds of Formula C, $R^{C10d}$ is a linear $C_1$-$C_5$ alkyl, alkenyl, or alkynyl, wherein 0-2 carbons in $C_2$-$C_5$ are independently replaced by N, S, and/or O heteroatoms, optionally C-substituted with a single substituent selected from the group consisting of: —SH, —OH, amino, carboxy, guanidino, —NH—C(O)—$CH_3$, —S—C(O)—$CH_3$, —O—C(O)—$CH_3$, —NH—C(O)-(phenyl), —S—C(O)-(phenyl), —O—C(O)-(phenyl), —NH—$(CH_3)_{1-2}$, —$NH_2$—$CH_3$, —$N(CH_3)_{2-3}$, —S—$CH_3$, and —O—$CH_3$.

In some embodiments of the compounds of Formula C, $R^{C10d}$ is a linear $C_1$-$C_5$ alkyl, alkenyl, or alkynyl, optionally C-substituted with a single substituent selected from the group consisting of: —SH, —OH, amino, carboxy, guanidino, —NH—C(O)—$CH_3$, —S—C(O)—$CH_3$, —O—C(O)—$CH_3$, —NH—C(O)-(phenyl), —S—C(O)-(phenyl), —O—C(O)-(phenyl), —NH—$(CH_3)_{1-2}$, —$NH_2$—$CH_3$, —$N(CH_3)_{2-3}$, —S—$CH_3$, and —O—$CH_3$. In some embodiments, $R^{C10d}$ is a linear $C_1$-$C_5$ alkyl optionally C-substituted with a single substituent selected from the group consisting of: —SH, —OH, amino, carboxy, guanidino, —NH—C(O)—$CH_3$, —S—C(O)—$CH_3$, —O—C(O)—$CH_3$, —NH—C(O)-(phenyl), —S—C(O)— (phenyl), —O—C(O)-(phenyl), —NH—$(CH_3)_{1-2}$, —$NH_2$—$CH_3$, —$N(CH_3)_{2-3}$, —S—$CH_3$, and —O—$CH_3$.

In some embodiments of the compounds of Formula C, $R^{C10d}$ is a branched $C_1$-$C_{10}$ alkyl, alkenyl, or alkynyl, wherein 0-3 carbons in $C_2$-$C_{10}$ are independently replaced by N, S, and/or O heteroatoms. In some embodiments, $R^{C10d}$ is a branched $C_1$-$C_{10}$ alkyl, alkenyl, or alkynyl. In some embodiments, $R^{C10d}$ is a branched $C_1$-$C_{10}$ alkyl.

In some embodiments of the compounds of Formula C, $R^{C10d}$ is $R^{C10e}R^{C10f}$. In some embodiments, $R^{C10e}$ is a linear $C_1$-$C_3$ alkyl. In some embodiments, $R^{C10f}$ is a 5 or 6 membered aromatic ring wherein 0-4 carbons are independently replaced by N, S, and/or O heteroatoms, and substituted with 0-4 groups independently selected from oxo, hydroxyl, sulfhydryl, nitro, amino, and/or halogen. In some embodiments, $R^{C10f}$ is a fused bicyclic or fused tricyclic aryl group wherein 0-6 carbons are independently replaced by N, S, and/or O heteroatoms, and substituted with 0-6 groups independently selected from halogen, —OH, —$OR^{C10g}$, amino, —$NHR^{C10g}$, and/or $N(R^{C10g})_2$, wherein $R^{C10g}$ is $C_1$-$C_3$ linear or branched alkyl. In some embodiments, $R^{C10g}$ is methyl. In some embodiments, each ring in the fused bicyclic or fused tricyclic aryl group independently has 4, 5 or 6 ring carbons, wherein 0-3 carbons are independently replaced by N, S, and/or O heteroatoms; such embodiments may be substituted or unsubstituted as defined above.

In some embodiments of the compounds of Formula A: —NH—CH($R^{1a}$)—C(O)— forms a Phe residue; —NH—CH($R^{2a}$)—C(O)— forms a (3-I)Tyr residue; —NH—CH($R^{3a}$)—C(O)— forms a Lys(iPr) residue; —NH—CH($R^{4a}$)—C(O)— forms a D-Arg residue; —NH—CH($R^{5a}$)—C(O)— forms a 2—Nal or a (4-$NH_2$)Phe residue; —NH—CH($R^{6a}$)—C(O)— forms a Gly residue; —NH—CH($R^{A7a}$)—C(O)— forms a D-amino acid, wherein $R^{A7a}$ is $C_1$-$C_3$ alkyenyl; and —NH—CH($R^{8a}$)—C(O)— forms a Lys(iPr) residue. In some of these embodiments, —NH—CH($R^{5a}$)—C(O)— forms a 2-Nal residue. In some of these embodiments, —NH—CH($R^{5a}$)—C(O)— forms a (4-$NH_2$) Phe residue.

In some embodiments of the compounds of Formula A: —NH—CH($R^{1a}$)—C(O)— forms a Phe residue; —NH—CH($R^{2a}$)—C(O)— forms a Tyr residue; —NH—CH($R^{3a}$)—C(O)— forms a Lys(iPr) residue; —NH—CH($R^{4a}$)—C(O)— forms a D-Arg residue; —NH—CH($R^{5a}$)—C(O)— forms a 2-Nal residue or a (4-$NH_2$)Phe residue; —NH—CH($R^{6a}$)—C(O)— forms a D-Ala residue; —NH—CH($R^{A7a}$)—C(O)— forms a D-amino acid residue, wherein $R^{A7a}$ is $C_1$-$C_3$ alkyenyl; and —NH—CH($R^{8a}$)—C(O)— forms a Lys(iPr) residue. In some of these embodiments, —NH—CH($R^{5a}$)—C(O)— forms a 2-Nal residue. In some of these embodiments, —NH—CH($R^{5a}$)—C(O)— forms a (4-$NH_2$)Phe residue.

In some embodiments of the compounds of Formula A: —NH—CH($R^{1a}$)—C(O)— forms a Phe residue; —NH—CH($R^{2a}$)—C(O)— forms a (4-$NH_2$)Phe residue; —NH—CH($R^{3a}$)—C(O)— forms a Lys(iPr) residue; —NH—CH($R^{4a}$)—C(O)— forms a D-Arg residue; —NH—CH($R^{5a}$)—C(O)— forms a 2-Nal residue or a (4-$NH_2$)Phe residue; —NH—CH($R^{6a}$)—C(O)— forms a Gly residue; —NH—CH($R^{A7a}$)—C(O)— forms a D-amino acid residue, wherein $R^{A7a}$ is $C_1$-$C_3$ alkyenyl; and —NH—CH($R^{8a}$)—C(O)— forms a Lys(iPr) residue. In some of these embodiments, —NH—CH($R^{5a}$)—C(O)— forms a 2-Nal residue. In some of these embodiments, —NH—CH($R^{5a}$)—C(O)— forms a (4-$NH_2$)Phe residue.

In some embodiments of the compounds of Formula A: —NH—CH($R^{1a}$)—C(O)— forms a Phe residue; —NH—CH($R^{2a}$)—C(O)— forms a (4-$NO_2$)Phe residue; —NH—CH($R^{3a}$)—C(O)— forms a Lys(iPr) residue; —NH—CH($R^{4a}$)—C(O)— forms a D-Arg residue; —NH—CH($R^{5a}$)—C(O)— forms a 2-Nal residue or a (4-$NH_2$)Phe residue; —NH—CH($R^{6a}$)—C(O)— forms a Gly residue; —NH—CH($R^{A7a}$)—C(O)— forms a D-amino acid residue, wherein $R^{A7a}$ is $C_1$-$C_3$ alkyenyl; and —NH—CH($R^{8a}$)—C(O)— forms a Lys(iPr) residue. In some of these embodiments, —NH—CH($R^{5a}$)—C(O)— forms a 2-Nal residue. In some of these embodiments, —NH—CH($R^{5a}$)—C(O)— forms a (4-$NH_2$)Phe residue.

In some embodiments of the compounds of Formula A: —NH—CH($R^{1a}$)—C(O)— forms a Phe residue; —NH—CH($R^{2a}$)—C(O)— forms a hTyr residue; —NH—CH($R^{3a}$)—C(O)— forms a Lys(iPr) residue; —NH—CH($R^{4a}$)—C(O)— forms a D-Arg residue; —NH—CH($R^{5a}$)—C(O)— forms a 2-Nal residue or a (4-$NH_2$)Phe residue; —NH—CH($R^{6a}$)—C(O)— forms a Gly residue; —NH—CH($R^{A7a}$)—C(O)— forms a D-amino acid residue, wherein $R^{A7a}$ is $C_1$-$C_3$ alkyenyl; and —NH—CH($R^{8a}$)—C(O)— forms a Lys(iPr) residue. In some of these embodiments, —NH—CH($R^{5a}$)—C(O)— forms a 2-Nal residue. In some of these embodiments, —NH—CH($R^{5a}$)—C(O)— forms a (4-$NH_2$)Phe residue.

In some embodiments of the compounds of Formula A: —NH—CH($R^{1a}$)—C(O)— forms a Phe residue; —NH—CH($R^{2a}$)—C(O)— forms a Tyr residue; —NH—CH($R^{3a}$)—C(O)— forms a Lys(iPr) residue; —NH—CH($R^{4a}$)—C(O)— forms a D-Arg residue; —NH—CH($R^{5a}$)—C(O)— forms a 2-Nal residue or (4-$NH_2$)Phe residue; —NH—CH($R^{6a}$)—C(O)— forms a D-His residue; —NH—CH($R^{A7a}$)—C(O)— forms a D-amino acid residue, wherein $R^{A7a}$ is $C_1$-$C_3$ alkyenyl; and —NH—CH($R^{8a}$)—C(O)— forms a Lys(iPr) residue. In some of these embodiments, —NH—CH($R^{5a}$)—C(O)— forms a 2-Nal residue. In some of these embodiments, —NH—CH($R^{5a}$)—C(O)— forms a (4-$NH_2$) Phe residue.

In some embodiments of the compounds of Formula A: —NH—CH($R^{1a}$)—C(O)— forms a Phe residue; —NH—CH($R^{2a}$)—C(O)— forms a Tyr residue; —NH—CH($R^{3a}$)—C(O)— forms a Lys(iPr) residue; —NH—CH($R^{4a}$)—C(O)— forms a D-Arg residue; —NH—CH($R^{5a}$)—C(O)— forms a 2-Nal residue or a (4-$NH_2$)Phe residue; —NH—CH($R^{6a}$)—C(O)— forms a His residue; —NH—CH($R^{A7a}$)—C(O)— forms a D-amino acid residue, wherein $R^{A7a}$ is $C_1$-$C_3$ alkyenyl; and —NH—CH($R^{8a}$)—C(O)— forms a Lys(iPr) residue. In some of these embodiments, —NH—CH($R^{5a}$)—C(O)— forms a 2-Nal residue. In some of these embodiments, —NH—CH($R^{5a}$)—C(O)— forms a (4-$NH_2$)Phe residue.

In some embodiments of the compounds of Formula A: —NH—CH($R^{1a}$)—C(O)— forms a Phe residue; —NH—CH($R^{2a}$)—C(O)— forms a Tyr residue; —NH—CH($R^{3a}$)—C(O)— forms a Lys(iPr) residue; —NH—CH($R^{4a}$)—C(O)— forms a D-Arg residue; —NH—CH($R^{5a}$)—C(O)— forms a 2-Nal residue or a (4-$NH_2$)Phe residue; —NH—CH($R^{6a}$)—C(O)— forms a D-Ser residue; —NH—CH($R^{A7a}$)—C(O)— forms a D-amino acid residue, wherein $R^{A7a}$ is $C_1$-$C_3$ alkyenyl; and —NH—CH($R^{8a}$)—C(O)— forms a Lys(iPr) residue. In some of these embodiments, —NH—CH($R^{5a}$)—C(O)— forms a 2-Nal residue. In some of these embodiments, —NH—CH($R^{5a}$)—C(O)— forms a (4-$NH_2$)Phe residue.

In some embodiments of the compounds of Formula A: —NH—CH($R^{1a}$)—C(O)— forms a Phe residue; —NH—CH($R^{2a}$)—C(O)— forms a Tyr residue; —NH—CH($R^{3a}$)—C(O)— forms a Lys(iPr) residue; —NH—CH($R^{4a}$)—C(O)— forms a D-Arg residue; —NH—CH($R^{5a}$)—C(O)— forms a 2-Nal residue or a (4-$NH_2$)Phe residue; —NH—CH($R^{6a}$)—C(O)— forms a D-Glu residue; —NH—CH($R^{A7a}$)—C(O)— forms a D-amino acid residue, wherein $R^{A7a}$ is $C_1$-$C_3$ alkyenyl; and —NH—CH($R^{8a}$)—C(O)— forms a Lys(iPr) residue. In some of these embodiments, —NH—CH($R^{5a}$)—C(O)— forms a 2-Nal residue. In some of these embodiments, —NH—CH($R^{5a}$)—C(O)— forms a (4-$NH_2$)Phe residue.

In some embodiments of the compounds of Formula A: —NH—CH($R^{1a}$)—C(O)— forms a Phe residue; —NH—CH($R^{2a}$)—C(O)— forms a Tyr residue; —NH—CH($R^{3a}$)—C(O)— forms a Lys(iPr) residue; —NH—CH($R^{4a}$)—C(O)— forms a D-Arg residue; —NH—CH($R^{5a}$)—C(O)— forms a 2-Nal residue or a (4-$NH_2$)Phe residue; —NH—CH($R^{6a}$)—C(O)— forms a D-His residue; —NH—CH($R^{A7a}$)—C(O)— forms a D-amino acid residue, wherein $R^{A7a}$ is $C_1$-$C_3$ alkyenyl; and —NH—CH($R^{8a}$)—C(O)— forms a Lys(iPr) residue. In some of these embodiments, —NH—CH($R^{5a}$)—C(O)— forms a 2-Nal residue. In some of these embodiments, —NH—CH($R^{5a}$)—C(O)— forms a (4-$NH_2$)Phe residue.

In some embodiments of the compounds of Formula A: —NH—CH($R^{1a}$)—C(O)— forms a Phe residue; —NH—CH($R^{2a}$)—C(O)— forms a Tyr residue; —NH—CH($R^{3a}$)—C(O)— forms a Lys(iPr) residue; —NH—CH($R^{4a}$)—C(O)— forms a D-Arg residue; —NH—CH($R^{5a}$)—C(O)— forms a (2-Ant)Ala residue; —NH—CH($R^{6a}$)—C(O)— forms a Gly residue; —NH—CH($R^{A7a}$)—C(O)— forms a D-amino acid residue, wherein $R^{A7a}$ is $C_1$-$C_3$ alkyenyl; and —NH—CH($R^{8a}$)—C(O)— forms a Lys(iPr) residue. In some of these embodiments, —NH—CH($R^{5a}$)—C(O)— forms a 2-Nal residue. In some of these embodiments, —NH—CH($R^{5a}$)—C(O)— forms a (4-$NH_2$)Phe residue.

In some embodiments of the compounds of Formula A: —NH—CH($R^{1a}$)—C(O)— forms a Lys(Ac) residue; —NH—CH($R^{2a}$)—C(O)— forms a Tyr residue; —NH—CH($R^{3a}$)—C(O)— forms a Lys(iPr) residue; —NH—CH($R^{4a}$)—C(O)— forms a D-Arg residue; —NH—CH($R^{5a}$)—C(O)— forms a 2-Nal residue or a (4-$NH_2$)Phe residue; —NH—CH($R^{6a}$)—C(O)— forms a D-Ala residue; —NH—CH($R^{A7a}$)—C(O)— forms a D-amino acid residue, wherein $R^{A7a}$ is $C_1$-$C_3$ alkyenyl; and —NH—CH($R^{8a}$)—C(O)— forms a Lys(iPr) residue. In some of these embodiments, —NH—CH($R^{5a}$)—C(O)— forms a 2-Nal residue. In some of these embodiments, —NH—CH($R^{5a}$)—C(O)— forms a (4-$NH_2$)Phe residue.

In some embodiments of the compounds of Formula A: —NH—CH($R^{2a}$)—C(O)— forms a Tyr residue; —NH—CH($R^{3a}$)—C(O)— forms a Lys(iPr) residue; —NH—CH($R^{4a}$)—C(O)— forms a D-Arg residue; —NH—CH($R^{A7a}$)—C(O)— forms a D-amino acid residue, wherein $R^{A7a}$ is $C_1$-$C_3$ alkyenyl; and —NH—CH($R^{8a}$)—C(O)— forms a Lys(iPr) residue. In some of these embodiments, —NH—CH($R^{6a}$)—C(O)— forms a Gly residue. In some of these embodiments, —NH—CH($R^{6a}$)—C(O)— forms a D-Ala residue. In some of these embodiments, —NH—CH($R^{5a}$)—C(O)— forms a 2-Nal residue. In some of these embodiments, —NH—CH($R^{5a}$)—C(O)— forms a (4-$NH_2$) Phe residue. In some of these embodiments, —NH—CH($R^{1a}$)—C(O)— forms a Phe residue and $R^{10a}$ is absent. In some of these embodiments, $R^{A10}$ is -[linker]-$R^X_{n1}$, $R^{A1e}$ is linear $C_1$-$C_5$ alkylenyl, and $R^{A1f}$ is —NH—C(O)—.

In some embodiments of the compounds of Formula A, one or more of the following conditions are met:

a) —NH—CH($R^{2a}$)—C(O)— forms a Tyr residue;

b) —NH—CH($R^{3a}$)—C(O)— forms a Lys(iPr) residue;

c) —NH—CH($R^{4a}$)—C(O)— forms a D-Arg residue;

d) —NH—CH($R^{5a}$)—C(O)— forms a 2-Nal residue; and/or e) —NH—CH($R^{6a}$)—C(O)— forms a D-Ala residue.

In some embodiments of the compounds of Formula A, —NH—CH($R^{2a}$)—C(O)— forms a Tyr residue; —NH—CH($R^{3a}$)—C(O)— forms a Lys(iPr) residue; —NH—CH($R^{4a}$)—C(O)— forms a D-Arg residue; —NH—CH($R^{5a}$)—C(O)— forms a 2-Nal residue; and —NH—CH($R^{6a}$)—C(O)— forms a D-Ala residue.

In some embodiments of the compounds of Formula A, —NH—CH($R^{2a}$)—C(O)— forms a Tyr residue; —NH—CH($R^{3a}$)—C(O)— forms a Lys(iPr) residue; —NH—CH($R^{4a}$)—C(O)— forms a D-Arg residue; —NH—CH($R^{7a}$)—C(O)— forms a D-amino acid residue, wherein $R^{A7a}$ is $C_1$-$C_3$ alkyenyl; and —NH—CH($R^{8a}$)— together with —C(O)— from $R^{9a}$ forms a Lys(iPr) residue. In some embodiments, —NH—CH($R^{6a}$)—C(O)— forms a Gly residue, a D-Ala residue, a D-Gln residue, or a D-Asn residue. In some embodiments, —NH—CH($R^{1a}$)—C(O)— forms a Phe residue and $R^{10a}$ is absent. In some embodiments, $R^{A10}$ is -[linker]-$R^X_{n1}$, $R^{A1e}$ is linear $C_1$-$C_5$ alkylenyl, and $R^{A1f}$ is —NH—C(O)—.

In some embodiments of the compounds of Formula B: —NH—CH($R^{2a}$)—C(O)— forms a Tyr residue; —NH—CH($R^{3a}$)—C(O)— forms a Lys(iPr) residue; —NH—CH($R^{4a}$)—C(O)— forms a D-Arg residue; and —NH—CH($R^{8a}$)—C(O)— forms a Lys(iPr) residue. In some of these embodiments, —NH—CH($R^{6a}$)—C(O)— forms a Gly residue, a D-Ala residue, a D-Gln residue, or a D-Asn residue; and —NH—CH($R^{5a}$)—C(O)— forms a 2-Nal residue, a (2-Ant)Ala residue or a (4—$NH_2$)Phe residue.

In some embodiments of the compound of Formula A, the compound has the structure of Formula A-I or salt or solvate thereof:

[Formula A-I]

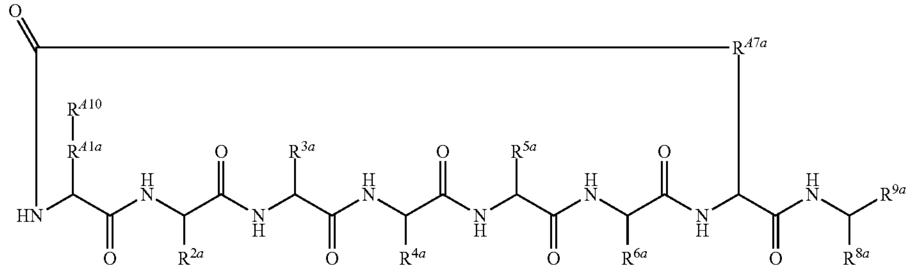

wherein:

$R^{2a}$ is —$(CH_2)$—$(R^{2b})$-(phenyl), wherein $R^{2b}$ is absent, —$CH_2$—, —NH—, —S— or —O—, wherein the phenyl is optionally 4-substituted with —$NH_2$, —$NO_2$, —OH, —$OR^{2c}$, —SH, —$SR^{2c}$, or —O-phenyl or optionally 3-substituted with halogen or —OH, wherein each $R^{2c}$ is independently a $C_1$-$C_3$ linear or branched alkyl group;

$R^{3a}$ is $R^{3b}R^{3c}$ wherein $R^{3b}$ is a linear $C_1$-$C_5$ alkylenyl, $C_2$-$C_5$ alkenylenyl, or $C_2$-$C_5$ alkynylenyl, wherein $R^{3c}$ is —$N(R^{3d})_{2\text{-}3}$ or guanidino, wherein each $R^{3d}$ is independently —H or a linear or branched $C_1$-$C_3$ alkyl;

$R^{4a}$ is $R^{4b}R^{4c}$ wherein $R^{4b}$ is a linear $C_1$-$C_5$ alkylenyl, $C_2$-$C_5$ alkenylenyl, or $C_2$-$C_5$ alkynylenyl, wherein $R^{4c}$ is —$N(R^{4d})_{2\text{-}3}$ or guanidino, wherein each $R^{4d}$ is independently —H or a linear or branched $C_1$-$C_3$ alkyl;

$R^{5a}$ is —$(CH_2)_{1\text{-}3}$—$R^{5b}$, wherein $R^{5b}$ is:

phenyl optionally substituted with one or a more of the following: 4-substituted with —$NH_2$, —$NO_2$, —OH, —SH, or —O-phenyl; 3-substituted with halogen or —OH; and/or 5-subsituted with halogen or —OH;

a fused bicyclic or fused tricyclic aryl or heteroaryl ring which is optionally substituted with one or more of halogen, —OH, —$OR^{5c}$, amino, —$NHR^{5c}$, and/or $N(R^{5c})_2$; and wherein $R^{5c}$ is each independently a $C_1$-$C_3$ linear or branched alkyl group;

$R^{6a}$ is methyl, ethyl, —C≡CH, —CH═$CH_2$, —$CH_2$—$R^{6b}$—OH, —$CH_2$—$R^{6b}$—COOH, —$CH_2$—$(R^{6b})_{1\text{-}3}$—$NH_2$, —$CH_2$—$R^{6b}$—CONH, or —$CH_2$—$R^{6b}R^{6c}$, wherein each $R^{6b}$ is independently absent, —$CH_2$—, —NH—, —S— or —O—; and wherein $R^{6c}$ is a 5 or 6 membered aromatic ring wherein 0-3 carbons are independently replaced by N, S, and/or O heteroatoms, and optionally substituted with 0-3 groups independently selected from oxo, hydroxyl, sulfhydryl, nitro, amino, and/or halogen;

$R^{8a}$ is $R^{8b}R^{8c}$ wherein $R^{8b}$ is a linear $C_1$-$C_5$ alkylenyl, $C_2$-$C_5$ alkenylenyl, or $C_2$-$C_5$ alkynylenyl, wherein $R^{8c}$ is —$N(R^{8d})_{2\text{-}3}$ or guanidino, wherein each $R^{1d}$ is independently —H or a linear or branched $C_1$-$C_3$ alkyl;

$R^{9a}$ is: —C(O)$NH_2$, —C(O)—OH, —$CH_2$—C(O)$NH_2$, —$CH_2$—C(O)—OH, —$R^{9b}$—$R^{9c}$ or —$R^{9b}$-[linker]-$R^{X}{}_{n1}$; wherein $R^{9b}$ is —C(O)NH—; and $R^{9c}$ is

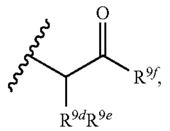

wherein $R^{9d}$ is a linear or branched $C_1$-$C_5$ alkylenyl, Re is carboxylic acid, sulfonic acid, sulfinic acid, phosphoric acid, amino, guanidino, —SH, —OH, —NH—C(O)—$CH_3$, —S—C(O)—$CH_3$, —O—C(O)—$CH_3$, —NH—C(O)— (phenyl), —S—C(O)-(phenyl), —O—C(O)-(phenyl), —NH—$CH_3$, —$N(CH_3)_2$, —S—$CH_3$, —O—$CH_3$, or phenyl, and $R^{9f}$ is amino or —OH;

$R^{A7a}$ is $C_1$-$C_3$ alkylenyl;

$R^{A10}$ is absent or -[linker]$R^{X}{}_{n1}$;

when $R^{A10}$ is absent, then $R^{A1a}$ is:

a linear $C_1$-$C_5$ alkyl, alkenyl, or, alkynyl, wherein 0-2 carbons in $C_2$-$C_5$ are independently replaced by one or more N, S, and/or O heteroatoms, optionally C-substituted with a single substituent selected from: —SH, —OH, amino, carboxy, guanidino, —NH—C(O)—$CH_3$, —S—C(O)—$CH_3$, —O—C(O)—$CH_3$, —NH—C(O)-(phenyl), —S—C(O)-(phenyl), —O—C(O)-(phenyl), —NH—$(CH_3)_{1\text{-}2}$, —$NH_2$—$CH_3$, —$N(CH_3)_{2\text{-}3}$, —S—$CH_3$, or —O—$CH_3$;

a branched $C_1$-$C_{10}$ alkyl, alkenyl, or alkynyl, wherein 0-3 carbons in $C_2$-$C_{10}$ are independently replaced by one or more N, S, and/or O heteroatoms; or $R^{A1b}R^{A1c}$, wherein $R^{A1b}$ is a linear $C_1$-$C_3$ alkylenyl, wherein $C_2$ alkylenyl or $C_3$ alkylenyl is optionally replaced with a N, S, or O heteroatom, wherein $R^{A1c}$ is:

a 5 or 6 membered aromatic ring wherein one or more carbons are optionally independently replaced by N, S, and/or O heteroatoms, and optionally substituted with one or more groups independently selected from oxo, hydroxyl, sulfhydryl, nitro, amino, and/or halogen; or a fused bicyclic or fused tricyclic aryl group wherein one or more carbons are optionally independently replaced by N, S, and/or O heteroatoms, and optionally substituted with one or more groups independently selected from halogen, —OH, —$OR^{A1d}$, amino, —$NHR^{A1d}$, and/or $N(R^{A1d})_2$, wherein each $R^{A1d}$ is independently a $C_1$-$C_3$ linear or branched alkyl group;

when $R^{A10}$ is -[linker]-$R^{X}_{n1}$, then $R^{A1a}$ is $R^{A1e}R^{A1f}$, wherein $R^{A1e}$ is a linear $C_1$-$C_5$ alkylenyl, alkenylenyl, or alkynylenyl, in which 0-2 carbons in $C_2$-$C_5$ are independently replaced with N, S, and/or O heteroatoms, and $R^{A1f}$ is —NH—C(O)—, —C(O)—, —O—, —C(O)NH—, —C(O)—N($CH_3$)—, —NHC(S)—, —C(S)NH—, —N($CH_3$)C(S)—, —C(O)N($CH_3$)—, —N($CH_3$)C(O)—, —C(S)N($CH_3$)—, —NHC(S)NH—, —NHC(O)NH—, —S—, —S(O)—, —S(O)—O—, —$S(O)_2$—, —$S(O)_2$—O—, —$S(O)_2$—NH—, —S(O)—NH—, —Se—, —Se(O)—, —$Se(O)_2$—, —NHNHC(O)—, —C(O)NHNH—, —OP(O)($O^-$)O—, -phosphamide-, -thiophosphodiester-, —S— tetrafluorophenyl-S—,

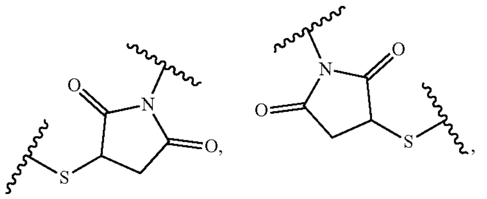

-continued

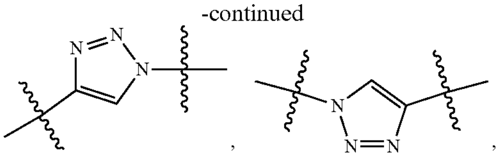

or polyethylene glycol;

each n1 is independently 0, 1 or 2;

each $R^X$ is a therapeutic moiety, a fluorescent label, a radiolabeled group, or a group capable of being radiolabelled;

wherein 0-3 peptide backbone amides are independently replaced with

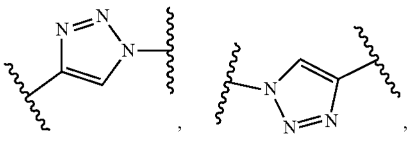 [SMILES: *c1cn(*)nn1 ; *c1cn(*)nn1]

or thioamide; and wherein 0-3 peptide backbone amides are N-methylated.

In some embodiments of the compounds of Formula A or A-I, —NH—CH($R^{A1a}$)—C(O)— forms an L amino acid residue.

In some embodiments of the compounds of Formula A or A-I, —NH—CH($R^{A1a}$)—C(O)— forms a Phe residue, a 1-Nal residue, a 2-Nal residue, a Tyr residue, a Trp residue, a Lys residue, a hLys residue, a Lys(Ac) residue, a Dap residue, a Dab residue, or an Orn residue. n some embodiments of the compounds of Formula A, —NH—CH($R^{A1a}$)—C(O)— forms an L-Phe residue, an L-1-Nal residue, an L-2-Nal residue, an L-Tyr residue, an L-Trp residue, an L-Lys residue, an L-hLys residue, an L-Lys(Ac) residue, an L-Dap residue, an L-Dab residue, or an L-Orn residue.

In some embodiments of the compounds of Formula A or A-I, $R^{A10}$ is -[linker]-$R^{X}_{n1}$ and $R^{9a}$ is —C(O)$NH_2$, —C(O)—OH, —$CH_2$—C(O)$NH_2$, or —$CH_2$—C(O)—OH.

In some embodiments of the compound of Formula A, the compound has the structure of Formula A-II or salt or solvate thereof:

[Formula A-II]

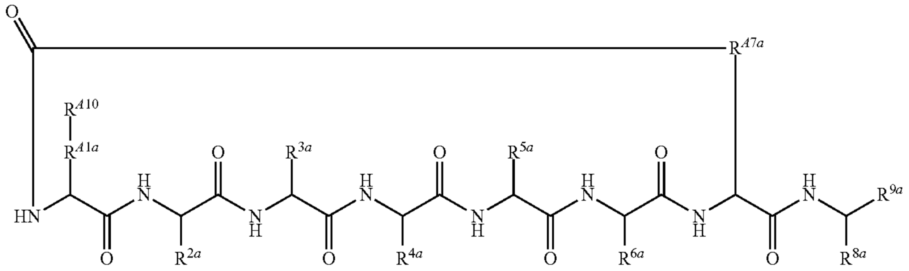

wherein:

—NH—CH($R^{2a}$)—C(O)— in Formula A-II forms a Tyr residue, a Phe residue, a (4—$NO_2$)-Phe residue, a (4-$NH_2$)-Phe residue, a hTyr residue, a (3-I)Tyr residue, a Glu residue, a Gln residue, or a D-Tyr residue;

—NH—CH($R^{3a}$)—C(O)— in Formula A-II forms a Lys(iPr) residue, a $Arg(Me)_2$ (asymmetrical) residue, or a Arg(Me) residue;

—NH—CH($R^{4a}$)—C(O)— in Formula A-II forms a D-Arg residue or a D-hArg residue;

—NH—CH($R^{5a}$)—C(O)— in Formula A-II forms a 2-(Ant)Ala residue, a 2-Nal residue, a Trp residue, a (4-$NH_2$)Phe residue, a hTyr residue, or a Tyr residue;

—NH—CH($R^{6a}$)—C(O)— in Formula A-II forms a His residue, a D-His residue, a D-Glu residue, a D-Gln residue, a D-Ala residue, a D-Phe residue, a D-Ser residue, a D-Dab residue, a D-Dap residue;

$R^{8a}$ is $R^{8b}R^{8c}$, wherein $R^{8b}$ is a linear $C_1$-$C_5$ alkylenyl, $C_2$-$C_5$ alkenylenyl, or $C_2$-$C_5$ alkynylenyl, wherein $R^{8c}$ is —$N(R^{8d})_{2-3}$ or guanidino, wherein each $R^{6d}$ is independently —H or a linear or branched $C_1$-$C_3$ alkyl;

$R^{9a}$ is —C(O)$NH_2$, —C(O)—OH, —$CH_2$—C(O)$NH_2$, —$CH_2$—C(O)—OH, or —$R^{9b}$-[linker]-$R^{X}_{n1}$;

$R^{9b}$ is —C(O)NH—;

$R^{A7a}$ is $C_1$-$C_3$ alkylenyl;

$R^{A10}$ is absent or -[linker]-$R^X{}_{n1}$;

when $R^{A10}$ is absent, then $R^{A1a}$ is a linear $C_1$-$C_5$ alkyl optionally substituted with a single substituent selected from: —SH, —OH, amino, carboxy, guanidino, —NH—C(O)—$CH_3$, —S—C(O)—$CH_3$, —O—C(O)—$CH_3$, —NH—C(O)-(phenyl), —S—C(O)— (phenyl), —O—C(O)-(phenyl), —NH—$(CH_3)_{1-2}$, —$NH_2$—$CH_3$, —$N(CH_3)_{2-3}$, —S—$CH_3$, or —O—$CH_3$, or a branched $C_1$-$C_{10}$ alkyl, alkenyl, or alkynyl;

when $R^{A10}$ is -[linker]-$R^X{}_{n1}$, then $R^{A1a}$ is $R^{A1e}R^{A1f}$, wherein $R^{A1e}$ is a linear $C_1$-$C_5$ alkylenyl, $C_2$-$C_5$ alkenylenyl, or $C_2$-$C_5$ alkynylenyl, and $R^{A1f}$ is —NH—C(O)—, —C(O)—, —O—, —C(O)NH—, —C(O)—N($CH_3$)—, —NHC(S)—, —C(S)NH—, —N($CH_3$)C(S)—, —C(O)N($CH_3$)—, —N($CH_3$)C(O)—, —C(S)N($CH_3$)—, —NHC(S)NH—, —NHC(O)NH—, —S—, —S(O)—, —S(O)—O—, —$S(O)_2$—, —$S(O)_2$—NH—, —S(O)—NH—, —NHNHC(O)—, —C(O)NHNH—,

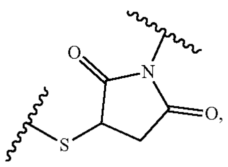

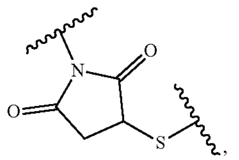

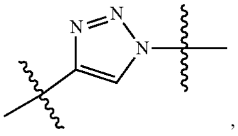

,

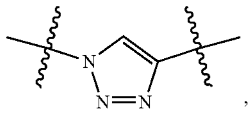

, or polyethylene glycol; the linker is each independently a linear or branched chain of 1-10 units of $X^1L^1$ and/or $X^1(L^1)_2$, wherein:

each $X^1$ is, independently, a linear, branched, and/or cyclic $C_1$-$C_{15}$ alkylenyl, $C_2$-$C_{15}$ alkenylenyl or $C_2$-$C_{15}$ alkynylenyl wherein 0-6 carbons are independently replaced by N, S, and/or O heteroatoms, and substituted with 0-3 groups independently selected from one or a combination of oxo, hydroxyl, sulfhydryl, halogen, guanidino, carboxylic acid, sulfonic acid, sulfinic acid, and/or phosphoric acid;

each $L^1$ is independently —NH—C(O)—, —NH—, —C(O)—, —O—, —C(O)NH—, —C(O)—N($CH_3$)—, —NHC(S)—, —C(S)NH—, —N($CH_3$)C(S)—, —C(O)N($CH_3$)—, —N($CH_3$)C(O)—, —C(S)N($CH_3$)—, —NHC(S)NH—, —NHC(O)NH—, —S—, —S(O)—, —S(O)—O—, —$S(O)_2$—, —$S(O)_2$—O—, —$S(O)_2$—NH—, —S(O)—NH—, —Se—, —Se(O)—, —$Se(O)_2$—, —NHNHC(O)—, —C(O)NHNH—, —OP(O)($O^-$)O—, -phosphamide-, -thiophosphodiester-, —S-tetrafluorophenyl-S—,

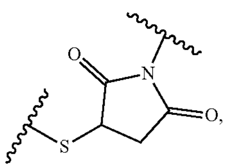

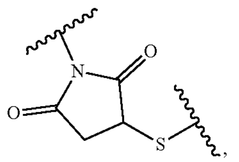

-continued

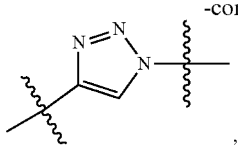

,

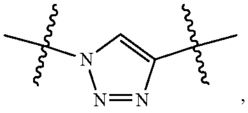

, or polyethylene glycol; or alternatively, the linker together with $R^{A1f}$ forms a linear or branched peptide linker $(Xaa)_{1-5}$, wherein each Xaa is independently selected from a proteinogenic amino acid residue or a nonproteinogenic amino acid residue; and wherein an amino group in each Xaa is optionally methylated;

each n1 is independently 0, 1 or 2;

each $R^X$ is a therapeutic moiety, a fluorescent label, a radiolabeled group, or a group capable of being radiolabelled;

wherein 0-3 peptide backbone amides are independently replaced with

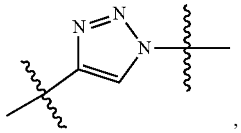

,

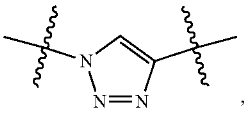

, or thioamide; and wherein 0-3 peptide backbone amides are N-methylated.

In some embodiments of the compounds of Formula A, A-I, A-II, B, or C, —NH—CH($R^{6a}$)—C(O)— forms a Gly residue, a D-Ala residue, a D-Gln residue, or a D-Asn residue. In some embodiments of the compounds of Formula A, A-I, A-II, B, or C, —NH—CH($R^{1a}$)—C(O)— forms a Phe residue and $R^{10a}$ is absent. In some embodiments, $R^{A10}$ is -[linker]-$R^X{}_{n1}$, $R^{A1e}$ is linear $C_1$-$C_5$ alkylenyl, and $R^{A1f}$ is —NH—C(O)—.

The term "[linker]" represents a linker, which may be any linker. Non-limiting examples include peptide and polyethylene glycol-based linkers.

In some embodiments of the compounds of Formula A, A-I, A-II, B, or C, each n1 in $R^X{}_{n1}$ is independently 0, 1 or 2. In some embodiments, each n1 is 0. In some embodiments, each n1 is 1. In some embodiments, each n1 is 2. In some embodiments, each n1 is the same. In some embodiments, each n1 is different.

In some embodiments of the compounds of Formula A, A-I, A-II, B, or C, each $R^X$ is an albumin binder, a therapeutic moiety, a fluorescent label, a radiolabeled group, or a group capable of being radiolabelled. In some embodiments, each $R^X$ is a therapeutic moiety, a fluorescent label, a radiolabeled group, or a group capable of being radiolabelled.

The present disclosure also relates to one or more of compounds selected from Table A, or a salt or solvate thereof; wherein the compound is optionally bound to a radiolabeled group or a group capable of being radiolabelled, optionally through a linker

TABLE A

| |
|---|
| cyclo[Phe-Tyr-Lys(iPr)-D-Arg-2Nal-D-Gln-D-Glu]-Lys(iPr); |
| cyclo[Phe-(3-I) Tyr-Lys(iPr)-D-Arg-2-Nal-Gly-D-Glu]-Lys(iPr); |
| cyclo[Phe-Tyr-Lys(iPr)-D-Arg-2Nal-D-Ala-D-Glu]-Lys(iPr); |
| cyclo[Phe-(4-$NH_2$)Phe-Lys(iPr)-D-Arg-2-Nal-Gly-D-Glu]-Lys(iPr); |

TABLE A-continued

| |
|---|
| cyclo[Phe-(4-$NO_2$) Phe-Lys(iPr)-D-Arg-2-Nal-Gly-D-Glu]-Lys(iPr); |
| cyclo[Phe-hTyr-Lys(iPr)-D-Arg-2-Nal-Gly-D-Glu]-Lys(iPr); |
| cyclo[Phe-hTyr-Lys(iPr)-D-Arg-2-Nal-D-Ala-D-Glu]-Lys(iPr); |
| cyclo[Phe-(4-$NH_2$)Phe-Lys(iPr)-D-Arg-2-Nal-D-Ala-D-Glu]-Lys(iPr); |
| cyclo[Lys(Ac)-Tyr-Lys(iPr)-D-Arg-Trp-D-Ala-D-Glu]-Lys(iPr); |
| cyclo[Phe-Tyr-Lys(iPr)-D-Arg-(4-$NH_2$)Phe-D-Ala-D-Glu]-Lys(iPr); |
| cyclo[Lys(Ac)-Glu-Lys(iPr)-D-Arg-2Nal-D-Ala-D-Glu]-Lys(iPr); |
| cyclo[Phe-Tyr-Lys(iPr)-D-Arg-2Nal-D-His-D-Glu]-Lys(iPr); |
| cyclo[Lys(Ac)-Gln-Lys(iPr)-D-Arg-2Nal-D-Ala-D-Glu]-Lys(iPr); |
| cyclo[Phe-Tyr-Lys(iPr)-D-Arg-2Nal-His-D-Glu]-Lys(iPr); |
| cyclo[Phe-D-Tyr-Lys(iPr)-D-Arg-2Nal-D-Ala-D-Glu]-Lys(iPr); |
| cyclo[Phe-Tyr-Lys(iPr)-D-Arg-2Nal-D-Ser-D-Glu]-Lys(iPr); |
| cyclo[Phe-Tyr-Lys(iPr)-D-Arg-2Nal-D-Leu-D-Glu]-Lys(iPr); |
| cyclo[Phe-Tyr-Lys(iPr)-D-Arg-2Nal-D-Asn-D-Glu]-Lys(iPr); |
| cyclo[Phe-Tyr-Arg(Me)-D-Arg-2Nal-D-Ala-D-Glu]-Lys(iPr); |
| cyclo[Phe-Tyr-Arg($Me_2$)(asym)-D-Arg-2Nal-Gly-D-Glu]-Lys(iPr); |
| cyclo[Phe-Tyr-Lys(iPr)-D-Arg-2Nal-D-Glu-D-Glu]-Lys(iPr); |
| cyclo[Phe-Tyr-Lys(iPr)-D-Arg-2Nal-D-Dab-D-Glu]-Lys(iPr); |
| cyclo[Phe-Tyr-Lys(iPr)-D-Arg-(2-Ant)Ala-Gly-D-Glu]-Lys(iPr); |
| cyclo(isoindole) [Phe-Tyr-Lys(iPr)-D-Arg-(2-Ant) Ala-Gly-D-Cys]-Lys(iPr); |
| cyclo(isoindole) [Phe-Tyr-Lys(iPr)-D-Arg-(2-Ant)Ala-Gly-Cys]-Lys(iPr); |
| cyclo[Lys(Ac)-Tyr-Lys(iPr)-D-Arg-2Nal-Gly-D-Glu]-Lys(iPr); |
| cyclo[Lys(CysAcid)-Tyr-Lys(iPr)-D-Arg-2Nal-D-Ala-D-Glu]-Lys(iPr); |
| cyclo[Orn(CysAcid)-Tyr-Lys(iPr)-D-Arg-2Nal-D-Ala-D-Glu]-Lys(iPr); |
| cyclo[Dap(CysAcid)-Tyr-Lys(iPr)-D-Arg-2Nal-D-Ala-D-Glu]-Lys(iPr); |
| cyclo[Lys(CysAcid)-(3-I)Tyr-Lys(iPr)-D-Arg-2Nal-D-Ala-D-Glu]-Lys(iPr); |
| cyclo[Lys(D-Arg)-Tyr-Lys(iPr)-D-Arg-2Nal-D-Ala-D-Glu]-Lys(iPr); or |
| cyclo(tryptathionine)[Tyr-Lys(iPr)-D-Arg-2Nal-D-Ala-D-Cys]-Lys(iPr) |

In some embodiments of the compounds of Formula A, A-I, B, or C, or Table A, each linker, if present, is independently a linear or branched chain of 1-10 units of $X^1L^1$ and/or $X^1(L^1)_2$, wherein:

each $X^1$ is, independently, a linear, branched, and/or cyclic $C_1$-$C_{15}$ alkylenyl, alkenylenyl or alkynylenyl wherein 0-6 carbons are independently replaced by N, S, and/or O heteroatoms, and substituted with 0-3 groups independently selected from one or a combination of oxo, hydroxyl, sulfhydryl, halogen, guanidino, carboxylic acid, sulfonic acid, sulfinic acid, and/or phosphoric acid;

each $L^1$ is independently —NH—C(O)—, —C(O)—, —O—, —C(O)NH—, —C(O)—N($CH_3$)—, —NHC(S)—, —C(S)NH—, —N($CH_3$)C(S)—, —C(O)N($CH_3$)—, —N($CH_3$)C(O)—, —C(S)N($CH_3$)—, —NHC(S)NH—, —NHC(O)NH—, —S—, —S(O)—, —S(O)—O—, —$S(O)_2$—, —$S(O)_2$—O—, —$S(O)_2$—NH—, —S(O)—NH—, —Se—, —Se(O)—, —$Se(O)_2$—, —NHNHC(O)—, —C(O)NHNH—, —OP(O)($O^-$)O—, -phosphamide-, -thiophosphodiester-, —S-tetrafluorophenyl-S—,

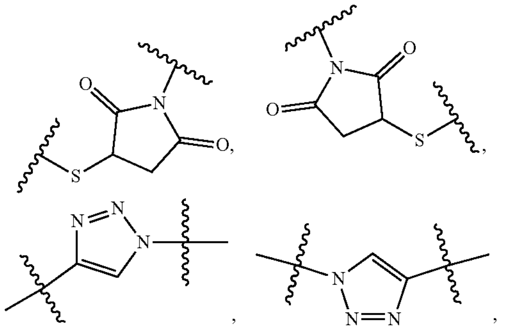

, , or polyethylene glycol.

In some embodiments, each $L^1$ is independently —S—, —NHC(O)—, —C(O)NH—, —N($CH_3$)C(O)—, —C(O)N($CH_3$)—, —NHC(S)—, —C(S)NH—, —N($CH_3$)C(S)—, —C(S)N($CH_3$)—, NHC(S)NH—, —S—, —O—, —S(O)—, —$S(O)_2$—, —Se—, —Se(O)—, —$Se(O)_2$—, —NHNHC(O)—, —C(O)NHNH—, —OP(O)($O^-$)O—, —OP(O)($S^-$)O—, S

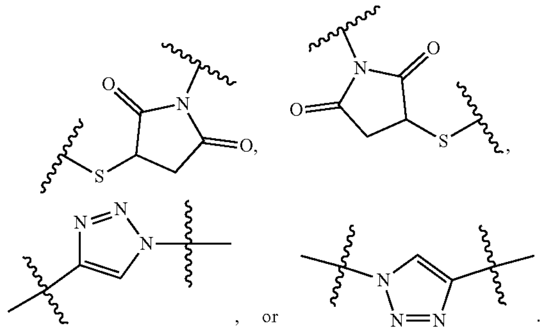

, or .

In some embodiments, each $L^1$ is independently —S—, —NHC(O)—, —C(O)NH—, —N($CH_3$)C(O)—, —C(O)N($CH_3$)—,

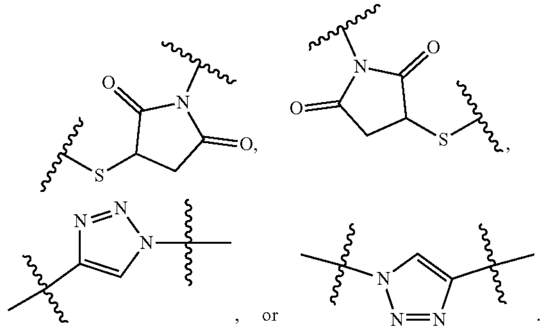

, or .

In some embodiments of the compounds of Formula A, A-I, A-II, B, or C or Table A, at least one linker comprises at least one carboxylic acid, sulfonic acid, sulfinic acid, or phosphoric acid, and has a net negative charge at physiological pH.

In some embodiments of the compounds of Formula A, A-I, A-II, B, or C, or Table A, at least one linker comprises at least one chemical group such as a guanidino or an amino group that has a net positive charge at physiological pH.

In some embodiments of the compounds of Formula A, A-I, A-II, B, or C, or Table A, at least one linker consists of 1-8 units of $X^1L^1$ and 0-2 units of $X^1(L^1)_2$.

In some embodiments, each $X^1$ is independently a linear, branched, and/or cyclic $C_1$-$C_{15}$ alkylenyl.

In some embodiments, each $X^1$ is independently: —CH—;

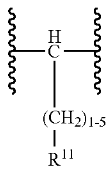

wherein each $R^{11}$ is independently carboxylic acid, sulfonic acid, sulfinic acid, or phosphoric acid; or

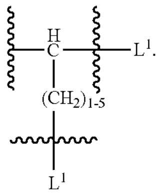

In some embodiments, each $L^1$ between two $X^1$ groups is independently —NHC(O)—, —C(O)NH—, —$N(CH_3)C(O)$—, or —$C(O)N(CH_3)$—, and each $L^1$ linking an $R^X$ is independently —S—, —NHC(O)—, —C(O)NH—, —$N(CH_3)C(O)$—, —$C(O)N(CH_3)$—,

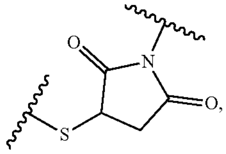
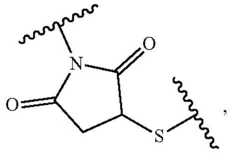
,

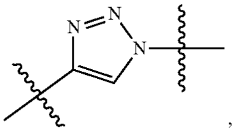
, or
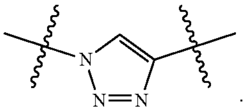
.

In some embodiments of the compounds of Formula A, A-I, A-II, B, or C, or Table A, the linker is $X^1L^1$, $X^1L^1X^1L^1$, or $X^1L^1X^1L^1X^1L^1$, wherein each $X^1$ is same or different, and each $L^1$ is same or different.

In one embodiment, $X^1$ is

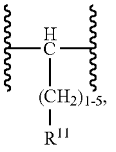

wherein each $R^{11}$ is independently a carboxylic acid, a sulfonic acid, a sulfinic acid, or a phosphoric acid. In one embodiment, $X^1$ is

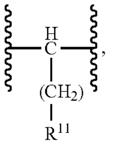

wherein each $R^{11}$ is independently a carboxylic acid, a sulfonic acid, a sulfinic acid, or a phosphoric acid.

In one embodiment, $X^1$ is

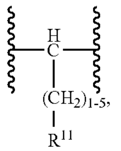

wherein each $R^{11}$ is independently a guanidino or an amino group. In one embodiment, $X^1$ is

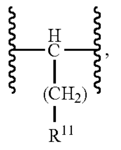

wherein each $R^{11}$ is independently a guanidino or an amino group.

In some embodiments of the compounds of Formula A, A-I, A-II, B, or C, or Table A, the linker together with $R^{A1f}$ forms a linear or branched peptide linker $(Xaa)_{1-5}$, wherein each Xaa is independently selected from a proteinogenic amino acid residue or a nonproteinogenic amino acid residue; and wherein an amino group in each Xaa is optionally methylated. In one embodiment, the amino group in each Xaa is optionally N-methylated.

In some embodiments of the compounds of Formula A, A-I, A-II, B, or C, or Table A, the linker together with $R^{A1f}$ forms a linear or branched peptide linker $(Xaa)_{1-5}$, wherein at least one Xaa is selected from cysteic acid, Glu, Asp, or 2-aminoadipic acid (2-Aad); and wherein an amino group in each Xaa is optionally methylated. In one embodiment, the amino group in each Xaa is optionally N-methylated.

In some embodiments of the compounds of Formula A, A-I, A-II, B, or C, or Table A, the linker together with $R^{A1f}$ forms a single amino acid residue selected from cysteic acid, Glu, Asp, or 2-aminoadipic acid (2-Aad); and wherein an amino group in Xaa is optionally methylated. In one embodiment, the amino group in each Xaa is optionally N-methylated.

In some embodiments of the compounds of Formula A, A-I, A-II, B, or C, or Table A, the linker together with $R^{A1f}$ forms a linear or branched peptide linker $(Xaa)_{1-5}$, wherein at least one Xaa is selected from Dap, Dab, Orn, Arg, hArg, Agb, Agp, Acp, Pip, or NE, N, NE-trimethyl-lysine; and wherein an amino group in each Xaa is optionally methylated. In one embodiment, the amino group in each Xaa is optionally N-methylated.

In some embodiments of the compounds of Formula A, A-I, A-II, B, or C, or Table A, the linker together with $R^{A1f}$ forms a single amino acid residue selected from D-Arg, L-Arg, D-hArg, L-hArg, or Pip; and wherein an amino group in Xaa is optionally methylated. In one embodiment, the amino group in each Xaa is optionally N-methylated.

In some embodiments of the compounds of Formula A, A-I, A-II, B, or C, or Table A, at least one linker is a linear or branched peptide of amino acid residues selected from proteinogenic amino acid residues and/or nonproteinogenic amino acid residues listed in Table 1.

In some embodiments of the compounds of Formula A, A-I, A-II, B, or C, each $L^1$ between two $X^1$ groups in the linker is methylated or unmethylated, and wherein each $L^1$ linking an $R^X$ is independently —S—, —NHC(O)—, —C(O)NH—, —$N(CH_3)C(O)$—, —$C(O)N(CH_3)$—,

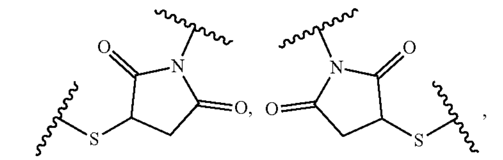

,

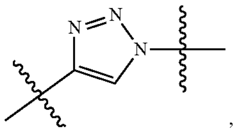

, or

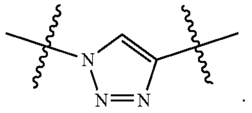

.

In some embodiments, each $L^1$ between two $X^1$ groups is an unmethylated amide.

In some embodiments of the compounds of Formula A, A-I, A-II, B, or C, or Table A, the linker forms a peptide linker of 1 to 3 amino acids selected from one or a combination of: cysteic acid, Glu, Asp, and/or 2-aminoadipic acid (2-Aad) connected via amide bonds. In some embodiments, the linker forms a single amino acid residue selected from cysteic acid, Glu, Asp, or 2-aminoadipic acid (2-Aad). In some embodiments, the linker is a cysteic acid residue.

In some embodiments, each $L^1$ linking an $R^X$ is independently —NHC(O)—, —C(O)NH—,

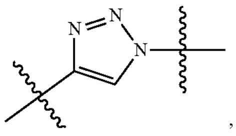

, or

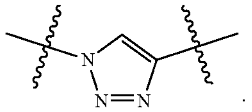

.

In some embodiments, each $L^1$ linking an $R^X$ is independently —NHC(O)— or —C(O)NH—.

In some embodiments of the compounds of Formula A, A-I, A-II, B, or C, at least one $R^X$ is an albumin binder. In some embodiments, the albumin binder is bonded to an $L^1$ of the linker, wherein the albumin binder is: $-(CH_2)_{n2}-CH_3$ wherein n2 is 8-20; $-(CH_2)_{n3}-C(O)OH$ wherein n3 is 8-20, or

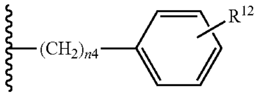

wherein n4=1-4 and $R^{12}$ is I, Br, F, Cl, H, OH, $OCH_3$, $NH_2$, $NO_2$ or $CH_3$;

In some embodiments of the compounds of Formula A, A-I, A-II, B, or C, at least one $R^X$ is a radiolabeled group or a group capable of being radiolabelled (e.g. through conjugation of a radiometal or radiolabeled prosthetic group, or through an isotope-radioisotope exchange reaction).

In some embodiments of the compounds of Formula A, A-I, A-II, B, or C, or Table A, the compound comprises a first linker bonded to a radiolabeled group or to a group capable of being radiolabelled, and further comprises a second linker bonded to an albumin binder.

In some embodiments of the compounds of Formula A, A-I, A-II, B, or C, or Table A, the compound comprises a first linker bonded to a first radiolabeled group or to a first group capable of being radiolabelled, and further comprises a second linker bonded to a second radiolabeled group or to a second group capable of being radiolabelled, wherein the compound optionally further comprises an albumin binder attached to either or both of the first linker and the second linker.

In some embodiments of the compounds of Formula A, A-I, A-II, B, or C, or Table A, the compound comprises only a single linker bonded to 1-2 groups consisting of radiolabeled groups and/or group capable of being radiolabelled, the linker optionally further bonded to an albumin binder.

In some embodiments of the compounds of Formula A, A-I, A-II, B, or C, or Table A, each group capable of being radiolabelled is independently selected from: a metal chelator optionally in complex with a radiometal or radioisotope-bound metal; a prosthetic group containing trifluoroborate ($BF_3$); or a prosthetic group containing a silicon-fluorine-acceptor moiety, a sulphonyl fluoride, or a phosphoryl fluoride.

In some embodiments of the compounds of Formula A, A-I, A-II, B, or C, or Table A, an $R^X$ comprises a metal chelator optionally in complex with a radiometal (e.g. $^{68}Ga$ or $^{177}Lu$) or in complex with a radioisotope-bound metal (e.g. $Al^{18}F$). The chelator may be any metal chelator suitable for binding to the radiometal or to the metal-containing prosthetic group bonded to the radioisotope (e.g. polyaminocarboxylates and the like). Many suitable chelators are known, e.g. as summarized in Price and Orvig, *Chem. Soc. Rev.*, 2014, 43, 260-290, which is incorporated by reference in its entirety. Non-limiting examples of suitable chelators include those selected from the group consisting of: DOTA and derivatives; DOTAGA; NOTA; NODAGA; NODASA; CB-DO2A; 3p-C-DEPA; TCMC; DO3A; DTPA and DTPA analogues optionally selected from CHX-A"-DTPA and 1B4M-DTPA; TETA; NOPO; Me-3,2-HOPO; CB-TE1A1P; CB-TE2P; MM-TE2A; DM-TE2A; sarcophagine and sarcophagine derivatives optionally selected from SarAr, SarAr-NCS, diamSar, AmBaSar, and BaBaSar; TRAP; AAZTA; DATA and DATA derivatives; H2-macropa or a derivative thereof; $H_2$dedpa, $H_4$octapa, $H_4$py4pa, $H_4$Pypa, $H_2$azapa, $H_5$decapa, and other picolinic acid derivatives; CP256; PCTA; C-NETA; C-NE3TA; HBED; SHRED; BCPA; CP256; YM103; desferrioxamine (DFO) and DFO derivatives; and $H_6$phospa. Exemplary non-limiting examples of suitable chelators and example radioisotopes (radiometals) chelated by these chelators are shown in Table 2. In alternative embodiments, an $R^X$ comprises a chelator selected from those listed above or in Table 2, or is any other suitable chelator. One skilled in the art could replace any of the chelators listed herein with another chelator.

TABLE 2

| Exemplary chelators and exemplary isotopes which bind said chelators. | |
|---|---|
| Chelator | Isotopes |
| 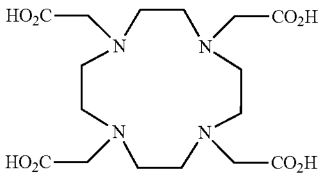<br>DOTA, 1,4,7,10-tetraazacyclododecane-1,4,7,10-tetraacetic acid | Cu-64/67<br>Ga-67/68<br>In-111<br>Lu-177<br>Y-86/90<br>Bi-203/212/213<br>Pb-212<br>Ac-225<br>Gd-159<br>Yb-175<br>Ho-166<br>As-211<br>Sc-44/47<br>Pm-149<br>Pr-142<br>Sn-117m<br>Sm-153<br>Tb-149/161<br>Er-165<br>Ra-223/224<br>Th-227 |
| 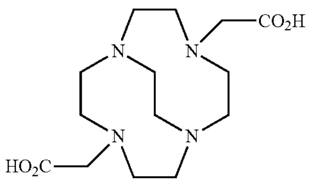 [SMILES: O=C(O)CN1CCN2CCN(CC1)CCN(CC(=O)O)CC2]<br>CB-DO2A, 4,10-bis(carboxymethyl)-1,4,7,10-tetraazabicyclo[5.5.2]tetradecane | Cu-64/67 |
| 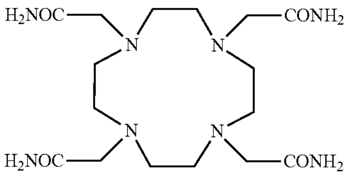 [SMILES: NC(=O)CN1CCN(CC(N)=O)CCN(CC(N)=O)CCN(CC(N)=O)CC1]<br>TCMC, 1,4,7,10-tetrakis(carbamoylmethyl)-1,4,7,10-tetraazacyclododecane | Pb-212 |
| 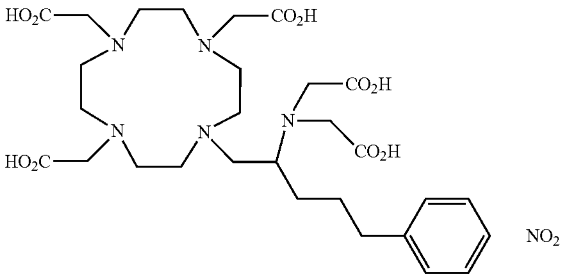<br>3p-C-DEPA | Bi-212/213 |
| 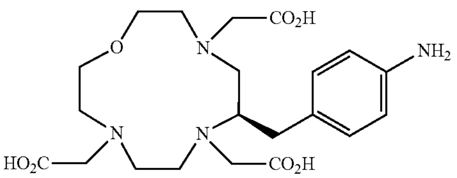<br>p-$NH_2$-Bn-Oxo-DO3A | Cu-64/67 |

TABLE 2-continued

| Exemplary chelators and exemplary isotopes which bind said chelators. | |
|---|---|
| Chelator | Isotopes |
| 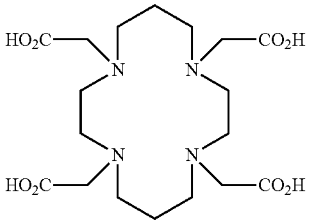 [SMILES: O=C(O)CN1CCCN(CC(=O)O)CCN(CC(=O)O)CCCN(CC(=O)O)CC1] TETA, 1,4,8,11-tetraazacyclotetradecane-1,4,8,11-tetraacetic acid | Cu-64/67 |
| 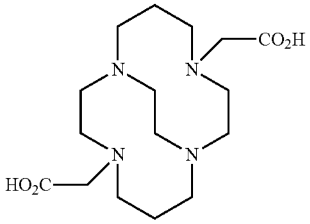 [SMILES: O=C(O)CN1CCCN2CCN(CCCN(CC(=O)O)CC2)CC1] CB-TE2A, 4,11-bis-(carboxymethyl)-1,4,8,11-tetraazabicyclo[6.6.2]-hexadecane | Cu-64/67 |
| 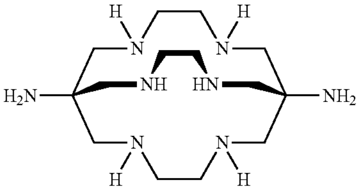 Diamsar | Cu-64/67 |
| 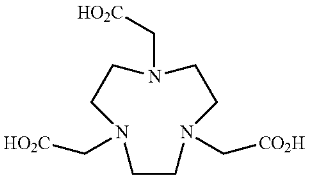 [SMILES: O=C(O)CN1CCN(CC(=O)O)CCN(CC(=O)O)CC1] NOTA, 1,4,7-triazacyclononane-1,4,7-triacetic acid | Cu-64/67<br>Ga-68<br>In-111<br>Sc-44/47 |
| 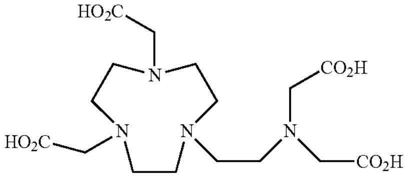 [SMILES: O=C(O)CN1CCN(CCN(CC(=O)O)CC(=O)O)CCN(CC(=O)O)CC1] NETA, {4-[2-(bis-carboxymethylamino)-ethyl]-7-carboxymethyl-[1,4,7]triazonan-1-yl}-acetic acid | Cu-64/67<br>Ga-68<br>Lu-177<br>Y-86/90<br>Bi-213<br>Pb-212 |

TABLE 2-continued

Exemplary chelators and exemplary isotopes which bind said chelators.

| Chelator | Isotopes |
|---|---|
| 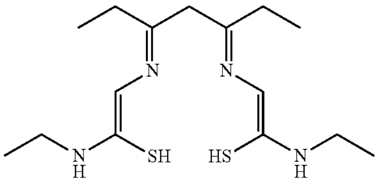 [SMILES: CCN/C(S)=C/N=C(\CC)C/C(CC)=N/C=C(\S)NCC] HxTSE | Au-198/199 |
| 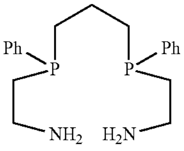 $P_2N_2Ph_2$ | Rh-105 |
| 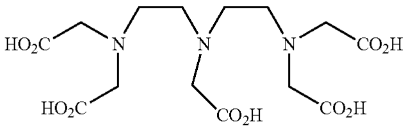 DTPA, diethylenetriaminepentaacetic acid | In-111<br>Sc-44/47<br>Lu-177<br>Y-86/90<br>Sn-117m<br>Pd-109 |
| 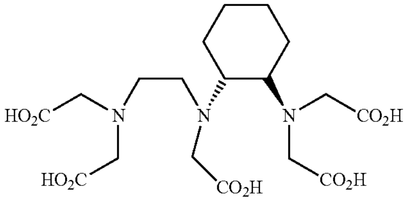 CHX-A00-DTPA, 2-(p-isothiocyanatobenzyl)-Cyclohexyldiethylenetriaminepentaacetic acid | In-111<br>Lu-177<br>Y-86/90<br>Bi-212/213 |
| 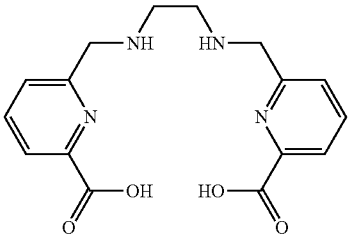 [SMILES: O=C(O)c1cccc(CNCCNCc2cccc(C(=O)O)n2)n1] $H_2$dedpa, 1,2-[[6-(carboxy)-pyridin-2-yl]-methylamino]ethane | Cu-64/67 |

TABLE 2-continued
| Exemplary chelators and exemplary isotopes which bind said chelators. | |
|---|---|
| Chelator | Isotopes |
| 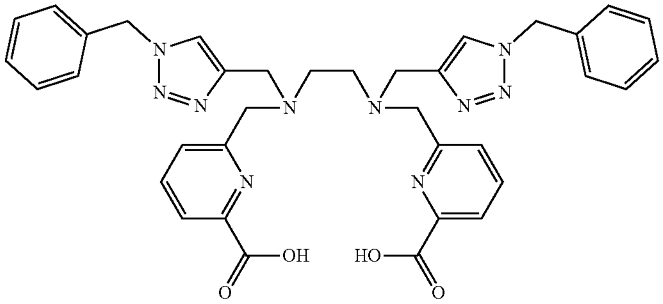 [SMILES: O=C(O)c1cccc(CN(CCN(Cc2cn(Cc3ccccc3)nn2)Cc2cccc(C(=O)O)n2)Cc2cn(Cc3ccccc3)nn2)n1]<br>$H_2$azapa, N,N'-[1-benzyl-1,2,3-triazole-4-yl]methyl-N,N'-[6-(carboxy)pyridin-2-yl]-1,2-diaminoethane | Cu-64/67 |
| 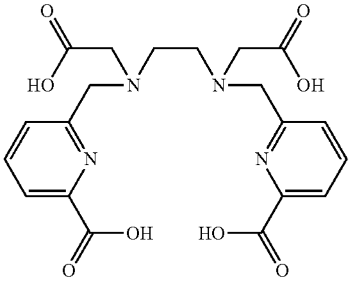 [SMILES: O=C(O)CN(CCN(CC(=O)O)Cc1cccc(C(=O)O)n1)Cc1cccc(C(=O)O)n1]<br>$H_4$octapa | In-111<br>Lu-177<br>Y-86/90<br>Ac-225 |
| 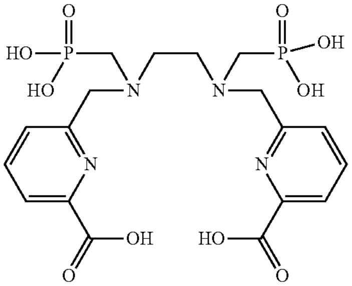 [SMILES: O=C(O)c1cccc(CN(CCN(Cc2cccc(C(=O)O)n2)CP(=O)(O)O)CP(=O)(O)O)n1]<br>$H_{6phospa}$ | Ac-225 |
| 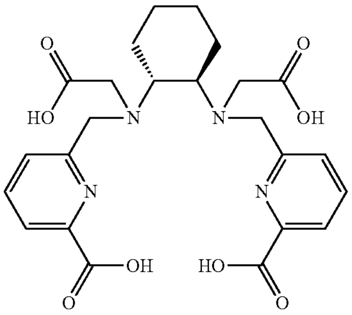 [SMILES: O=C(O)CN(Cc1cccc(C(=O)O)n1)[C@@H]1CCCC[C@H]1N(CC(=O)O)Cc1cccc(C(=O)O)n1]<br>$H_4$CHXoctapa | In-111<br>Ac-225 |

TABLE 2-continued
| Exemplary chelators and exemplary isotopes which bind said chelators. | |
|---|---|
| Chelator | Isotopes |
| 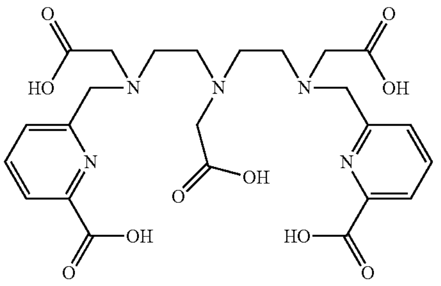 [SMILES: O=C(O)CN(CCN(CC(=O)O)Cc1cccc(C(=O)O)n1)CCN(CC(=O)O)Cc1cccc(C(=O)O)n1] $H_5$decapa | In-111<br>Lu-177<br>Ac-225 |
| 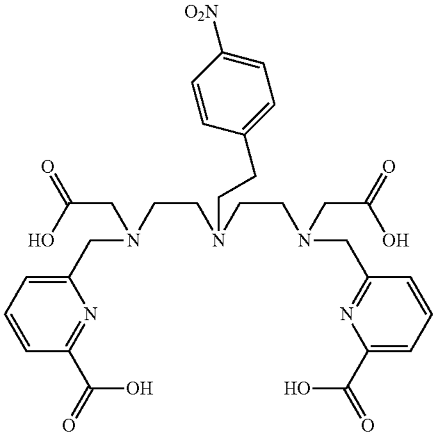 [SMILES: O=C(O)CN(CCN(CCc1ccc([N+](=O)[O-])cc1)CCN(CC(=O)O)Cc1cccc(C(=O)O)n1)Cc1cccc(C(=O)O)n1] $H_4$neunpa-p-Bn-$NO_2$ | In-111<br>Lu-177<br>Ac-225 |
| 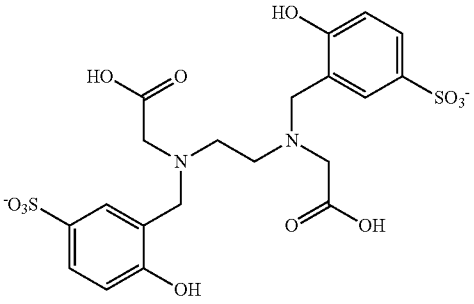 SHBED, N,N'-bis(2-hydroxy-5-sulfobenzyl)-ethylenediamine-N,N'-diacetic acid | In-111<br>Ga-68 |
| 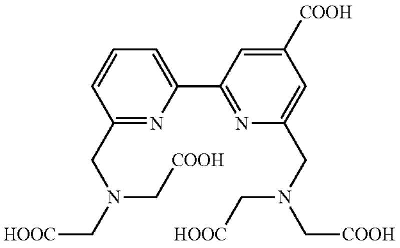 [SMILES: O=C(O)CN(CC(=O)O)Cc1cccc(-c2cc(C(=O)O)cc(CN(CC(=O)O)CC(=O)O)n2)n1] BPCA | In-111 |

TABLE 2-continued

| Exemplary chelators and exemplary isotopes which bind said chelators. | |
|---|---|
| Chelator | Isotopes |
| 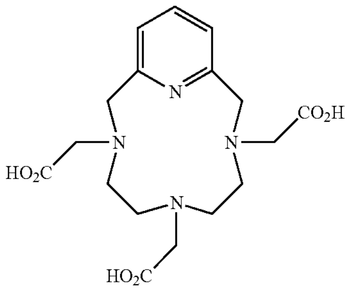<br>PCTA, 3,6,9,15-tetraazabicyclo[9.3.1]-pentadeca-1(15),11,13-triene-3,6,9,-triacetic acid | Cu-64/67 |
| 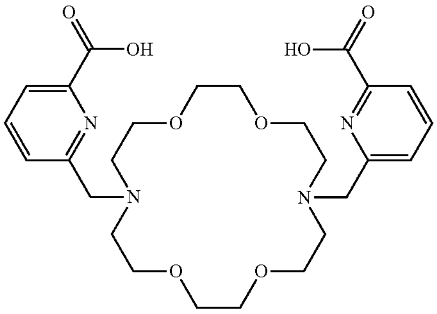 [SMILES: O=C(O)c1cccc(CN2CCOCCOCCN(Cc3cccc(C(=O)O)n3)CCOCCOCC2)n1]<br>H2-MACROPA (N,N'-bis[(6-carboxy-2-pyridil)methyl]-4, 13-diaza-18-crown-6) | Ac-225 |
| 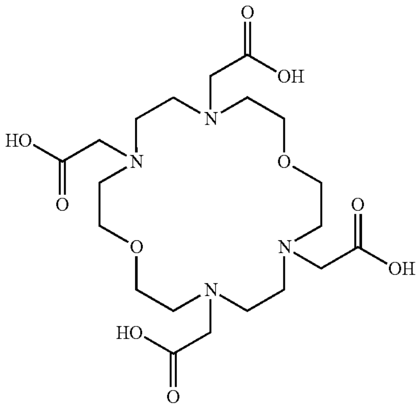 [SMILES: O=C(O)CN1CCOCCN(CC(=O)O)CCN(CC(=O)O)CCOCCN(CC(=O)O)CC1]<br>CROWN, 2,2',2'',2'''-(1,10-dioxa-4,7,13,16-tetraazacyclooctadecane-4,7,13,16-tetrayl)tetraacetic acid | Bis-213<br>Lu-177<br>Ac-225 |

It would be understood by one skilled in the art how the metal chelators, such as those listed in Table 2, can be connected to a linker or the peptide of the present disclosure by replacing one or more atoms or chemical groups of the metal chelators to form the connection. For example, one of the carboxylic acids present in the metal chelator structure can form an amide or an ester bond with the linker or the peptide. In one embodiment, the link formed between the linker and the metal chelator can be covered by the definition of the linker, such as $L^1$ (e.g., if an amide bond connects to the metal chelator to the linker, even if the carbonyl group could be coming from the metal chelator as drawn in Table 2, the definition of $L^1$ (—NH—C(O)—) can encompass the amide under Formula A, A-I, A-II, B, or C).

In some embodiments of the compounds of Table A, the compound is one or more compound selected from Table B, or a salt or solvate thereof.

TABLE B

| |
|---|
| cyclo[Lys(CysAcid-DOTA)-Tyr-Lys(iPr)-D-Arg-2Nal-D-Ala-D-Glu]-Lys(iPr); cyclo[Lys(CysAcid-amido-N,N-dimethyl-ammoniomethyl-trifluoroborate)-Tyr-Lys(iPr)-D-Arg-2Nal-D-Ala-D-Glu]-Lys(iPr); or cyclo[Lys(CysAcid-triazole-N,N-dimethyl-ammoniomethyl-trifluoroborate)-Tyr-Lys(iPr)-D-Arg-2Nal-D-Ala-D-Glu]-Lys(iPr) |

In some embodiments, cyclo[Lys(CysAcid-DOTA)-Tyr-Lys(iPr)-D-Arg-2Nal-D-Ala-D-Glu]-Lys(iPr) is in complex with a radioisotope. In one embodiment, the radioisotope is $^{64}$Cu, $^{67}$Cu, $^{90}$Y, $^{153}$Sm, $^{149}$Tb, $^{161}$Tb, $^{177}$Lu, $^{225}$Ac, $^{213}$Bi, $^{224}$Ra, $^{212}$Bi, $^{212}$Pb, $^{227}$Th, $^{223}$Ra, $^{47}$Sc, $^{186}$Re, $^{188}$Re, $^{94m}$Tc, $^{68}$Ga, $^{61}$Cu, $^{67}$Ga, $^{99m}$Tc, $^{111}$In, $^{44}$Sc, $^{86}$Y, $^{89}$Zr, $^{90}$Nb, $^{117m}$Sn, $^{165}$Er, $^{211}$As, $^{203}$Pb, $^{212}$Pb, $^{47}$Sc, $^{166}$Ho, $^{149}$Pm, $^{159}$Gd, $^{105}$Rh, $^{109}$Pd, $^{198}$Au, $^{199}$Au, $^{175}$Yb, $^{142}$Pr, or $^{114m}$In. In one embodiment, the radioisotope is $^{177}$Lu, $^{111}$In, $^{213}$Bi, $^{68}$Ga, $^{67}$Ga, $^{203}$Pb, $^{212}$Pb, $^{44}$Sc, $^{47}$Sc, $^{90}$Y, $^{86}$Y, $^{225}$Ac, $^{117m}$Sn, $^{153}$Sm, $^{149}$Tb, $^{161}$Tb, $^{165}$Er, $^{224}$Ra, $^{212}$Bi, $^{227}$Th, $^{223}$Ra, $^{64}$Cu, or $^{67}$Cu.

In some embodiments of the compounds of Formula A, A-I, A-II, B, or C, an $R^X$ of the compound is a polyaminocarboxylate chelator. In some such embodiments, the chelator is attached through an amide bond. In some embodiments, $R^X$ is: DOTA or a derivative thereof; TETA or a derivative thereof; SarAr or a derivative thereof; NOTA or a derivative thereof; TRAP or a derivative thereof; HBED or a derivative thereof; 2,3-HOPO or a derivative thereof; PCTA (3,6,9,15-tetraazabicyclo[9.3.1]-pentadeca-1(15),11,13-triene-3,6,9-triacetic acid) or a derivative thereof; DFO or a derivative thereof; DTPA or a derivative thereof; OCTAPA (N,N'-bis(6-carboxy-2-pyridylmethyl)-ethylenediamine-N,N'-diacetic acid) or a derivative thereof; or H2-MACROPA or a derivative thereof. In some embodiments, an $R^X$ is DOTA. In some embodiments, an $R^X$ is a chelator moiety in complex with radioisotope X wherein X is $^{64}$Cu, $^{67}$Cu, $^{90}$Y, $^{111}$In, $^{114m}$In, $^{117m}$Sn, $^{153}$Sm, $^{149}$Tb, $^{161}$Tb, $^{177}$Lu $^{225}$Ac, $^{213}$Bi, $^{224}$Ra, $^{212}$Bi, $^{212}$Pb, $^{227}$Th, $^{223}$Ra, $^{47}$Sc, $^{186}$Re or $^{188}$Re. In some embodiments, X is $^{177}$Lu. In some embodiments, an $R^X$ is a chelator moiety in complex with radioisotope X wherein X is $^{64}$Cu, $^{68}$Ga, $^{86}$Y, $^{111}$In, $^{94m}$Tc, $^{44}$Sc, $^{89}$Zr, or $^{99m}$Tc. In some embodiments, X is $^{68}$Ga.

In some embodiments, the chelator is conjugated with a radioisotope. The conjugated radioisotope may be, without limitation, $^{68}$Ga, $^{61}$Cu, $^{64}$Cu, $^{67}$Ga, $^{99m}$Tc, $^{111}$In, $^{44}$Sc, $^{86}$Y, $^{89}$Zr, $^{90}$Nb, $^{177}$Lu, $^{117m}$Sn, $^{165}$Er, $^{90}$Y, $^{227}$Th, $^{225}$Ac, $^{213}$Bi, $^{212}$Bi, $^{211}$As, $^{203}$Pb, $^{212}$Pb, $^{47}$Sc, $^{166}$Ho, $^{188}$Re, $^{186}$Re, $^{149}$Pm, $^{159}$Gd, $^{105}$Rh, $^{109}$Pd, $^{198}$Au, $^{199}$Au, $^{175}$Yb, $^{142}$Pr, $^{114m}$In, and the like. In some embodiments, the chelator is a chelator from Table 2 and the conjugated radioisotope is a radioisotope indicated in Table 2 as a binder of the chelator.

In some embodiments, the chelator is not conjugated to a radioisotope.

In some embodiments, the chelator is: DOTA or a derivative thereof, conjugated with $^{177}$Lu, $^{111}$In, $^{213}$Bi, $^{68}$Ga, $^{67}$Ga, $^{203}$Pb, $^{212}$Pb, $^{44}$Sc, $^{47}$Sc, $^{90}$Y, $^{86}$Y, $^{225}$Ac, $^{117m}$Sn, $^{153}$Sm, $^{149}$Tb, $^{161}$Tb, $^{165}$Er, $^{224}$Ra, $^{212}$Bi, $^{227}$Th, $^{223}$Ra, $^{64}$Cu or $^{67}$Cu; H2-MACROPA conjugated with $^{225}$Ac; Me-3,2-HOPO conjugated with $^{227}$Th; $H_4$py4pa conjugated with $^{225}$Ac, $^{227}$Th or $^{177}$Lu; $H_4$pypa conjugated with $^{177}$Lu; NODAGA conjugated with $^{68}$Ga; DTPA conjugated with $^{111}$In; or DFO conjugated with $^{89}$Zr.

In some embodiments, the chelator is TETA, SarAr, NOTA, TRAP, HBED, 2,3-HOPO, PCTA, DFO, DTPA, OCTAPA or another picolinic acid derivative.

In some embodiments of the compounds of Formula A, A-I, A-II, B, or C, an $R^X$ is a chelator for radiolabelling with $^{99m}$Tc, $^{94m}$Tc, $^{186}$Re, or $^{188}$Re, such as mercaptoacetyl, hydrazinonicotinamide, dimercaptosuccinic acid, 1,2-ethylenediylbis-L-cysteine diethyl ester, methylenediphosphonate, hexamethylpropyleneamineoxime and hexakis (methoxy isobutyl isonitrile), and the like. In some embodiments, an $R^X$ is a chelator, wherein the chelator is mercaptoacetyl, hydrazinonicotinamide, dimercaptosuccinic acid, 1,2-ethylenediylbis-L-cysteine diethyl ester, methylenediphosphonate, hexamethylpropyleneamineoxime or hexakis(methoxy isobutyl isonitrile). In some of these embodiments, the chelator is bound by a radioisotope. In some such embodiments, the radioisotope is $^{99m}$Tc, $^{94m}$Tc, $^{186}$Re, or $^{188}$Re.

In one embodiment of the compounds of Formula A, A-I, A-II, B, or C, Table A or derivatives thereof (e.g., where compounds of Table A is bound to a radiolabeled group or a group capable of being radiolabelled, optionally through a linker), or Table B, the radioisotope is $^{64}$Cu, $^{67}$Cu, $^{90}$Y, $^{153}$Sm, $^{149}$Tb, $^{161}$Tb, $^{177}$Lu, $^{225}$Ac, $^{213}$Bi, $^{224}$Ra, $^{212}$Bi, $^{212}$Pb, $^{227}$Th, $^{223}$Ra, $^{47}$Sc, $^{186}$Re, $^{188}$Re, $^{94m}$Tc, $^{68}$Ga, $^{61}$Cu, $^{67}$Ga, $^{99m}$Tc, $^{111}$In, $^{44}$Sc, $^{86}$Y, $^{89}$Zr, $^{90}$Nb, $^{117m}$Sn, $^{165}$Er, $^{211}$As, $^{203}$Pb, $^{212}$Pb, $^{47}$Sc, $^{166}$Ho, $^{149}$Pm, $^{159}$Gd, $^{105}$Rh, $^{109}$Pd, $^{198}$Au, $^{199}$Au, $^{175}$Yb, $^{142}$Pr, or $^{114m}$In. In one embodiment, the radioisotope is $^{177}$Lu, $^{111}$In, $^{213}$Bi, $^{68}$Ga, $^{67}$Ga, $^{203}$Pb, $^{212}$Pb, $^{44}$Sc, $^{47}$Sc, $^{90}$Y, $^{86}$Y, $^{225}$Ac, $^{117m}$Sn, $^{153}$Sm, $^{149}$Tb, $^{161}$Tb, $^{165}$Er, $^{224}$Ra, $^{212}$Bi, $^{227}$Th, $^{223}$Ra, $^{64}$Cu, or $^{67}$Cu.

In one embodiment of the compounds of Formula A, A-I, A-II, B, or C, or Table A or derivatives thereof, or Table B, at least one $R^X$ comprises an imaging radioisotope or is complexed with an imaging radioisotope, the compound is bound to a metal chelator complexed with an imaging radioisotope, or the compound is bound to a prosthetic group containing $BF_3$ comprising an imaging radioisotope.

In one embodiment of the compounds of Formula A, A-I, A-II, B, or C, or Table A or derivatives thereof, or Table B, the imaging radioisotope is $_{68}$Ga, $^{67}$Ga, $^{61}$Cu, $^{64}$Cu, $^{99m}$Tc, $^{114m}$In, $^{111}$In, $^{44}$Sc, $^{86}$Y, $^{89}$Zr, $^{90}$Nb, $^{18}$F, $^{131}$I, $^{123}$I, $^{124}$I or $^{72}$As. In one embodiment, the imaging radioisotope is $^{68}$Ga, $^{67}$Ga, $^{61}$Cu, $^{64}$Cu, $^{99m}$Tc, $^{114m}$In, $^{111}$In, $^{44}$Sc, $^{86}$Y, $^{89}$Zr, $^{90}$Nb, $^{131}$I, $^{123}$I, $^{124}$I or $^{72}$As.

In one embodiment of the compounds of Formula A, A-I, A-II, B, or C, or Table A or derivatives thereof, or Table B, at least one $R^X$ comprises an imaging radioisotope or is complexed with a therapeutic radioisotope, or the compound is bound to a metal chelator complexed with a therapeutic radioisotope.

In one embodiment of the compounds of Formula A, A-I, A-II, B, or C, or Table A or derivatives thereof, or Table B, the therapeutic radioisotope is $^{165}$Er, $^{212}$Bi, $^{211}$At, $^{166}$Ho, $^{149}$Pm, $^{159}$Gd, $^{105}$Rh, $^{109}$Pd, $^{198}$Au, $^{199}$Au, $^{175}$Yb, $^{142}$Pr, $^{177}$Lu, $^{111}$In, $^{213}$Bi, $^{203}$Pb, $^{212}$Pb, $^{47}$Sc, $^{90}$Y $^{117m}$Sn, $^{153}$Sm, $^{149}$Tb, $^{161}$Tb, $^{224}$Ra, $^{225}$Ac, $^{227}$Th, $^{223}$Ra, $^{77}$As, $^{131}$I, $^{64}$Cu or $^{67}$Cu.

In some embodiments of the compounds of Formula A, A-I, A-II, B, or C, an $R^X$ is a chelator that can bind $^{18}F$-aluminum fluoride ([$^{18}F$]AlF), such as 1,4,7-triazacyclononane-1,4-diacetate (NODA) and the like. In some embodiments, the chelator is NODA. In some embodiments, the chelator is bound by [$^{18}F$]AlF.

In some embodiments of the compounds of Formula A, A-I, A-II, B, or C, an $R^X$ is a chelator that can bind $^{72}As$ or $^{77}As$, such as a trithiol chelate and the like. In some embodiments, the chelator is a trithiol chelate. In some embodiments, the chelator is conjugated to $^{72}As$. In some embodiments, the chelator is conjugated to $^{77}As$.

In some embodiments of the compounds of Formula A, A-I, A-II, B, or C, an $R^X$ is a prosthetic group containing a trifluoroborate ($BF_3$), capable of $^{18}F/^{19}F$ exchange radiolabeling. Such an $R^X$ group may be the only $R^X$ (n1=1), or may be in addition to additional $R^X$ groups, which may be the same as or different than the first $R^X$. The prosthetic group may be —$R^{13}R^{14}BF_3$, wherein $R^{13}$ is independently —$(CH_2)_{1-5}$— and the group —$R^{14}BF_3$ may independently be selected from one or a combination of those listed in Table 3 (below), Table 4 (below), or

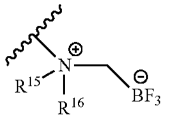

wherein each $R^{15}$ and each $R^{16}$ are independently $C_1$-$C_5$ linear or branched alkyl groups. For Tables 3 and 4, the R in the pyridine substituted with —OR, —SR, —NR—, —NHR or —$NR_2$ groups is $C_1$-$C_5$ branched or linear alkyl.

In some embodiments of the compounds of Formula A, A-I, A-II, B, or C, or Table A or derivatives thereof, or Table B, —$R^{14}BF_3$ is selected from those listed in Table 3. In some embodiments, —$R^{14}BF_3$ is independently selected from one or a combination of those listed in Table 4. In some embodiments, at least one fluorine is $^{18}F$. In some embodiments, all three fluorines are $^{19}F$.

TABLE 3

| Exemplary $R^{14}BF_3$ groups. |
| --- |
| 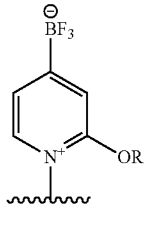 |
| 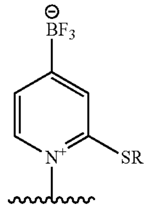 |

TABLE 3-continued

| Exemplary $R^{14}BF_3$ groups. |
| --- |
| 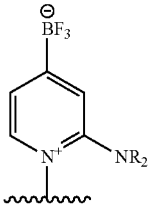 |
| 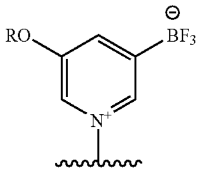 |
| 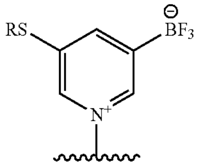 |
| 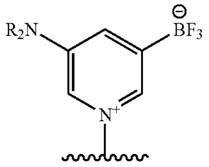 |
| 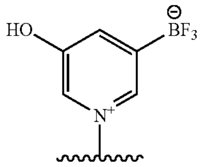 |
| 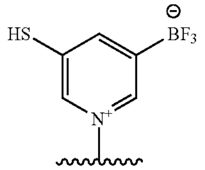 |
| 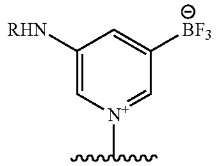 |
| 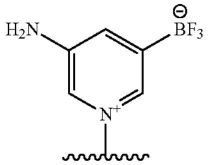 |

TABLE 3-continued
| Exemplary $R^{14}BF_3$ groups. |
|---|
| 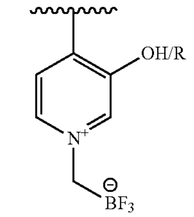 |
| 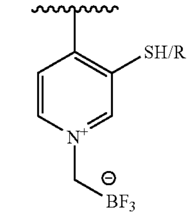 |
| 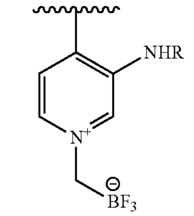 |
| 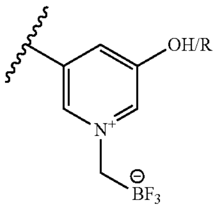 |
| 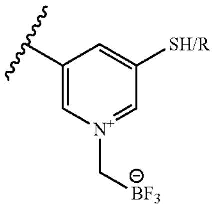 |
| 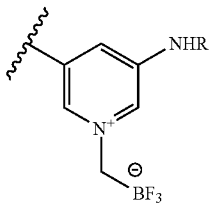 |
| 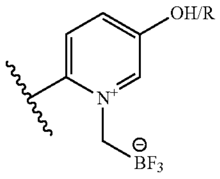 |
TABLE 3-continued
| Exemplary $R^{14}BF_3$ groups. |
|---|
| 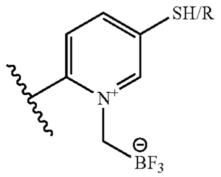 |
| 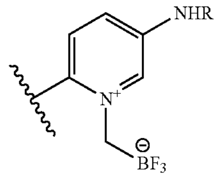 |
| 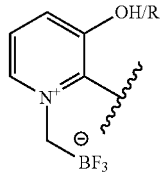 |
| 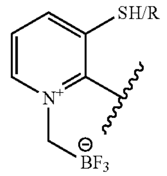 |
| 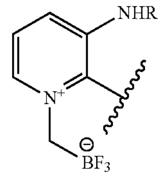 |
| 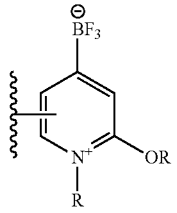 |
| 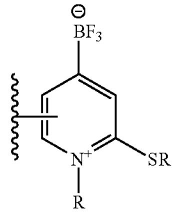 |
| 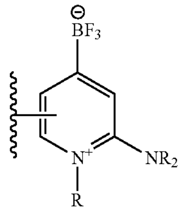 |

TABLE 3-continued
| Exemplary $R^{14}BF_3$ groups. |
| --- |
| 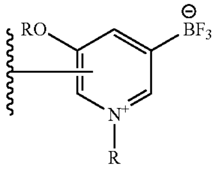 |
| 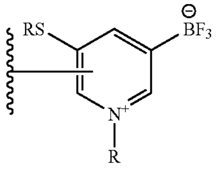 |
| 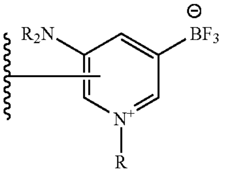 |
| 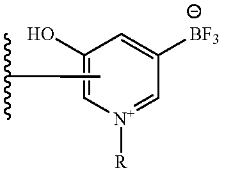 |
| 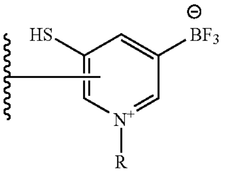 |
| 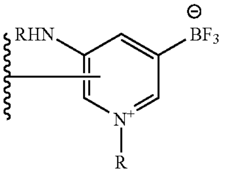 |
| 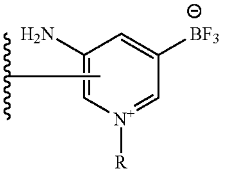 |
| 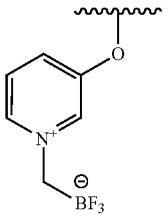 |
| 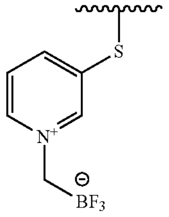 |
| 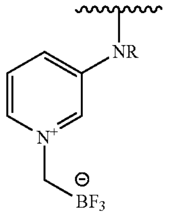 |
| 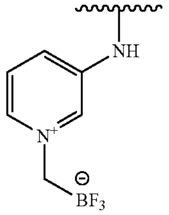 |
| 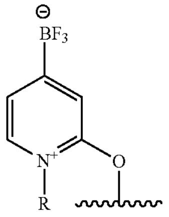 |
| 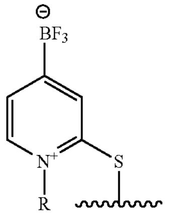 |
| 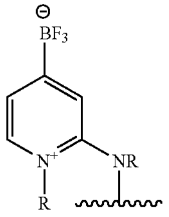 |
| 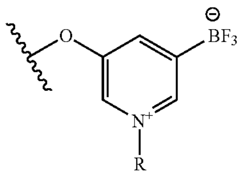 |

TABLE 3-continued
| Exemplary $R^{14}BF_3$ groups. |
|---|
| 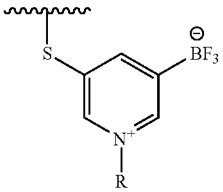 |
| 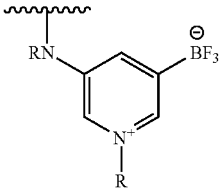 |
| 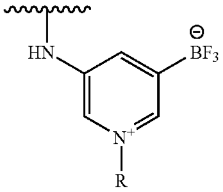 |
| 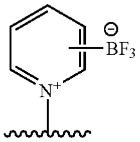 |
TABLE 4
| Exemplary $R^{14}BF_3$ groups. |
|---|
| 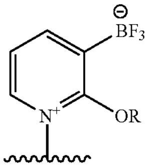 |
| 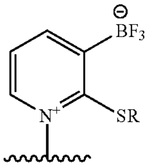 |
| 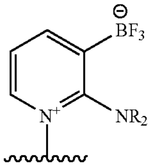 |
TABLE 4-continued
| Exemplary $R^{14}BF_3$ groups. |
|---|
| 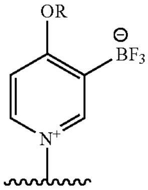 |
| 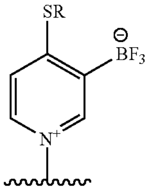 |
| 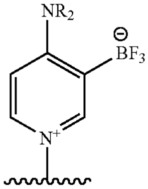 |
| 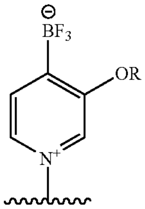 |
| 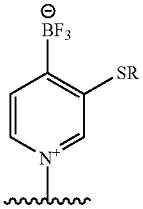 |
| 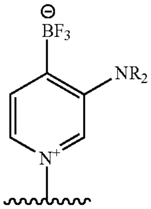 |
| 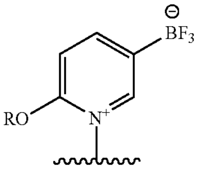 |

TABLE 4-continued
Exemplary $R^{14}BF_3$ groups.
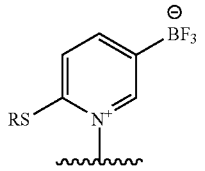
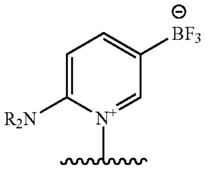
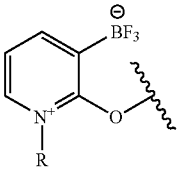
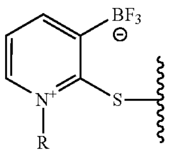
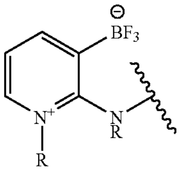
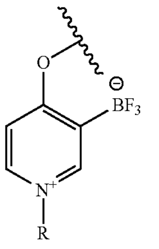
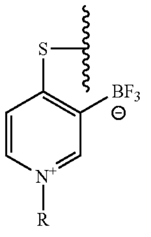
TABLE 4-continued
Exemplary $R^{14}BF_3$ groups.
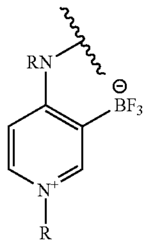
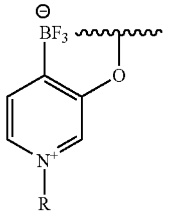
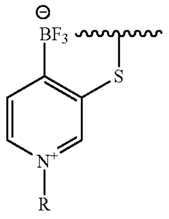
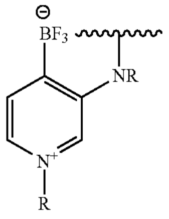
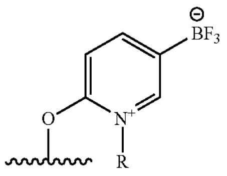
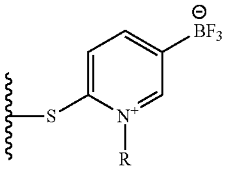
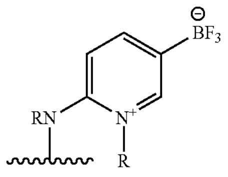

TABLE 4-continued
| Exemplary $R^{14}BF_3$ groups. |
| --- |
| 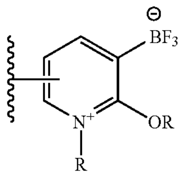 |
| 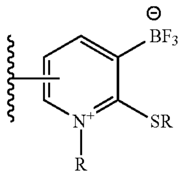 |
| 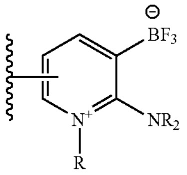 |
| 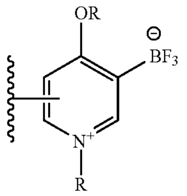 |
| 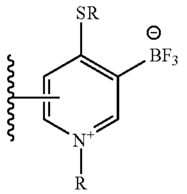 |
| 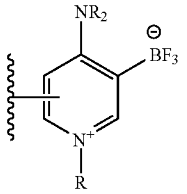 |
| 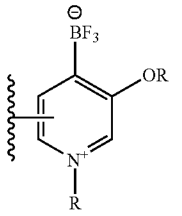 |
| 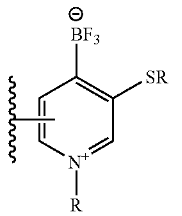 |
TABLE 4-continued
| Exemplary $R^{14}BF_3$ groups. |
| --- |
| 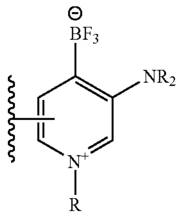 |
| 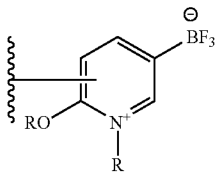 |
| 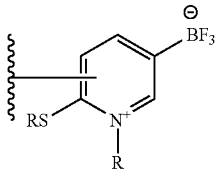 |
| 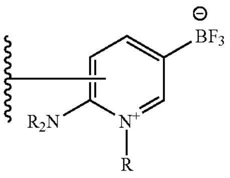 |
| 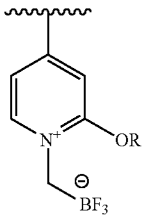 |
| 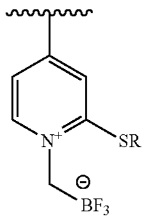 |
| 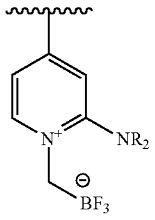 |

TABLE 4-continued
| Exemplary $R^{14}BF_3$ groups. |
| --- |
| 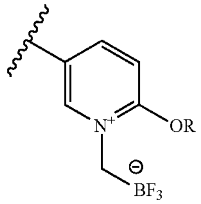 |
| 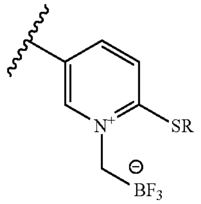 |
| 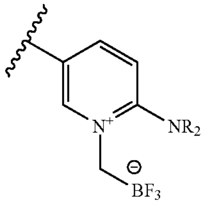 |
| 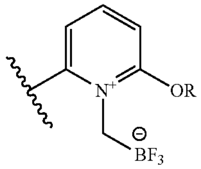 |
| 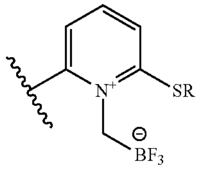 |
| 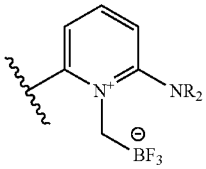 |
| 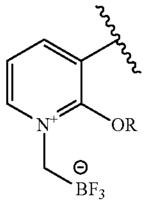 |
TABLE 4-continued
| Exemplary $R^{14}BF_3$ groups. |
| --- |
| 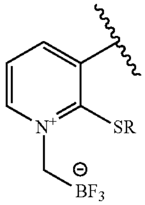 |
| 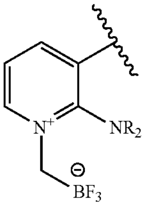 |
| 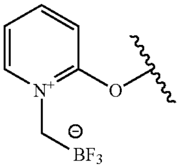 |
| 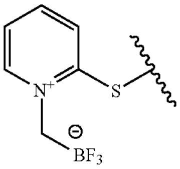 |
| 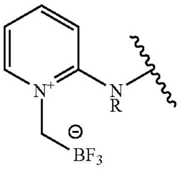 |
| 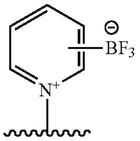 |
In some embodiments, $R^{14}BF_3$ may form
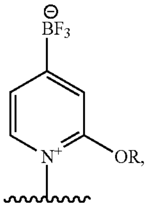
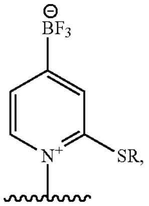
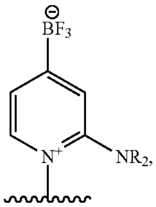
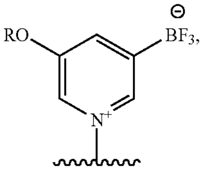
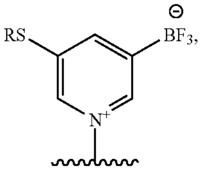

-continued
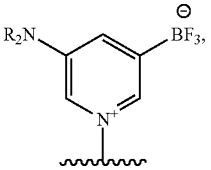
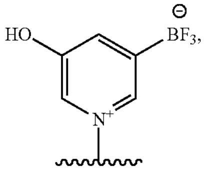
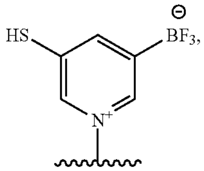
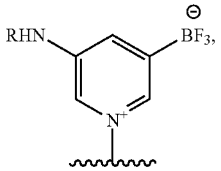
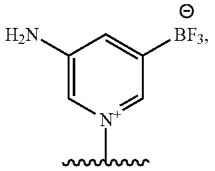
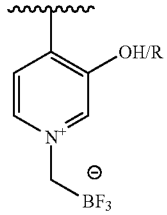
,
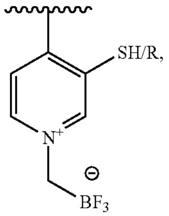
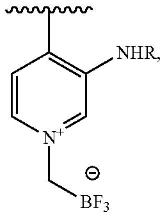
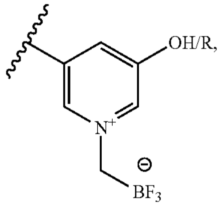
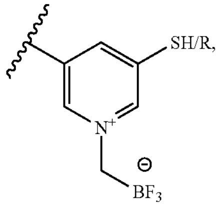
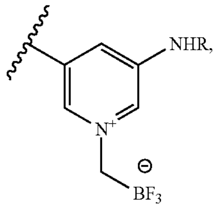
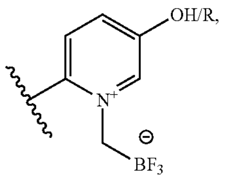
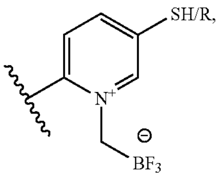
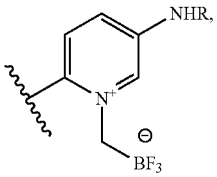
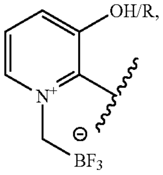
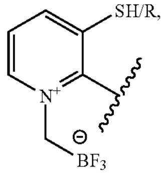
-continued
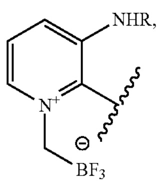
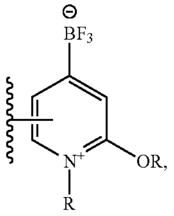
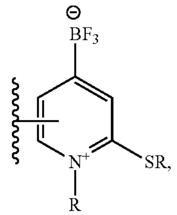
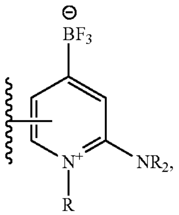
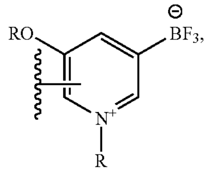
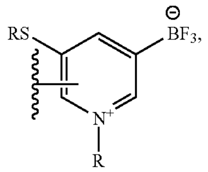
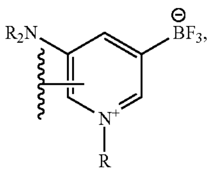
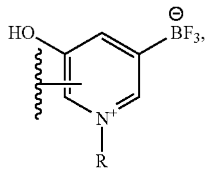
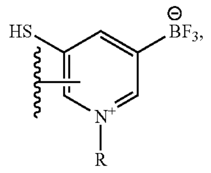
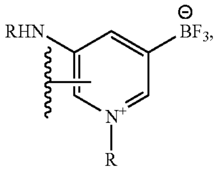
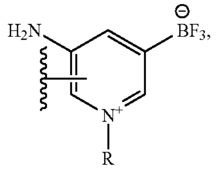
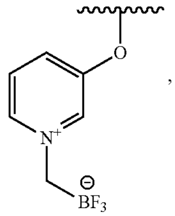
,
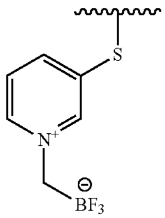
,
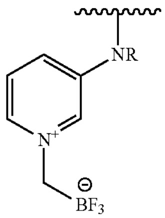
,
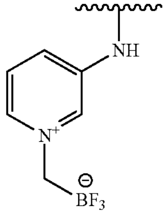
,
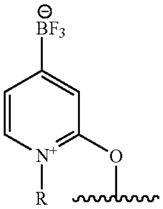
, -continued

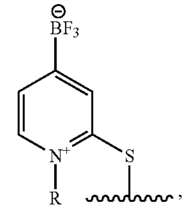,
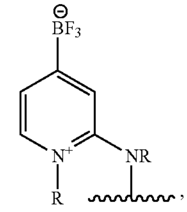,
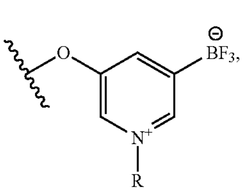
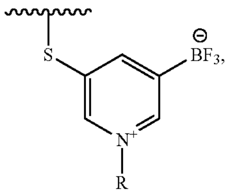
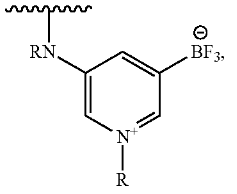
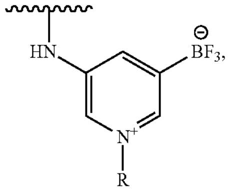 or
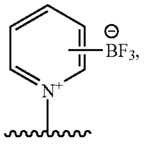

in which the R (when present) in the pyridine substituted —OR, —SR, —NR—, —NHR or —$NR_2$ is a branched or linear $C_1$-$C_5$ alkyl. In some embodiments, R is a branched or linear $C_1$-$C_5$ saturated alkyl. In some embodiments, R is methyl. In some embodiments, R is ethyl. In some embodiments, R is propyl. In some embodiments, R is isopropyl. In some embodiments, R is n-butyl. In some embodiments, one fluorine is $^{18}F$. In some embodiments, all three fluorines are $^{19}F$.

In some embodiments, $R^{14}BF_3$ may form

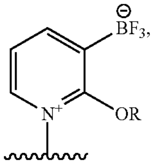
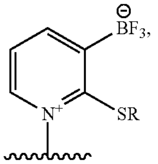
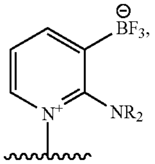
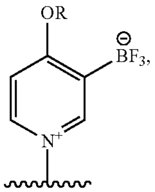
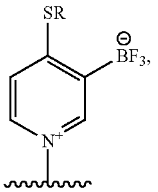
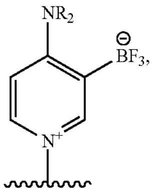
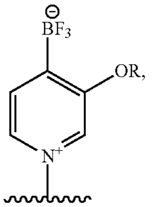
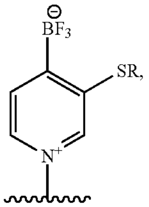
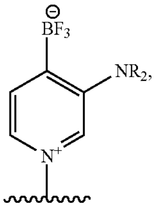

-continued

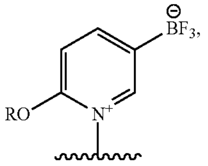
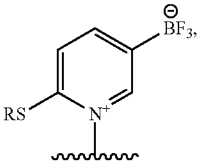
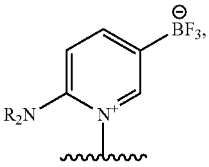
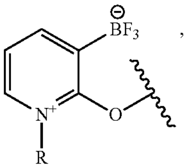,
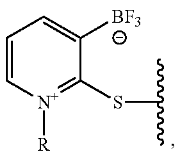,
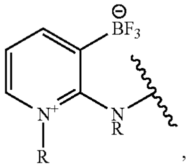,
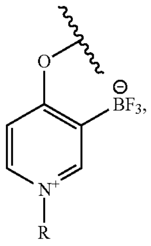
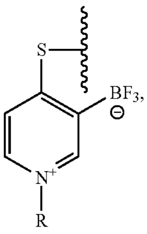
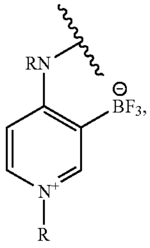
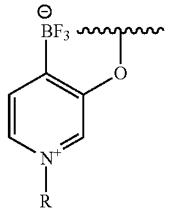,
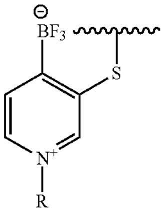,
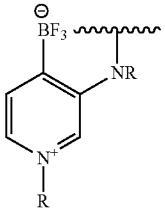,
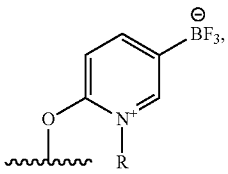
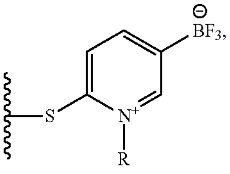
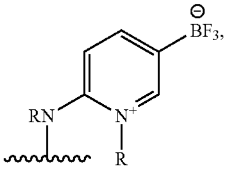
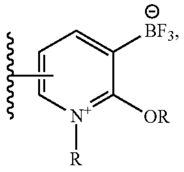
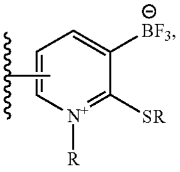
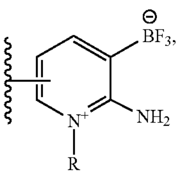
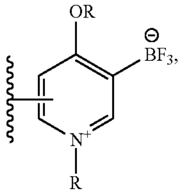

-continued

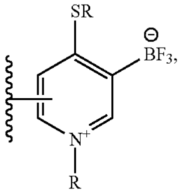

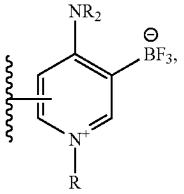

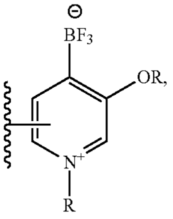

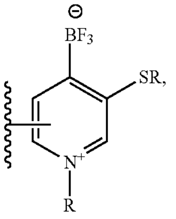

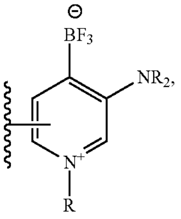

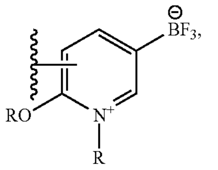

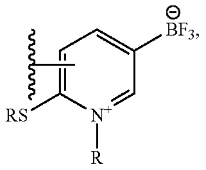

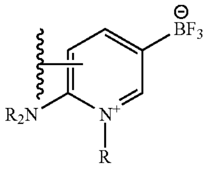

,

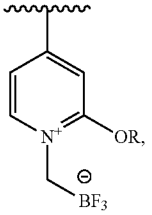

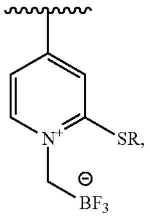

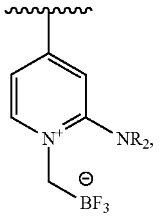

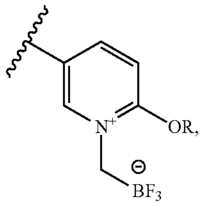

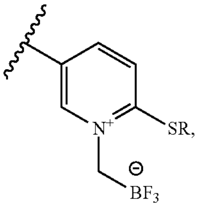

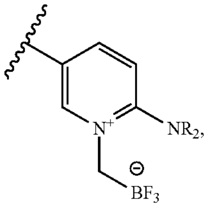

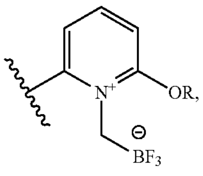

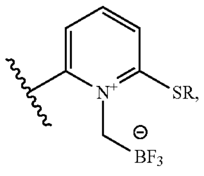

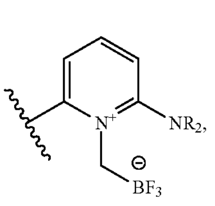

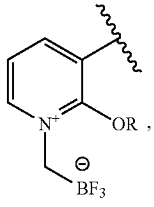

-continued

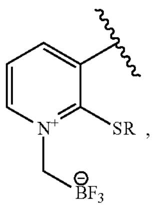

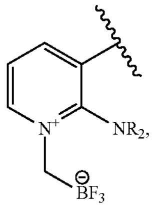

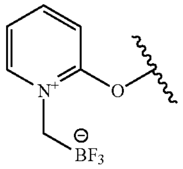

,

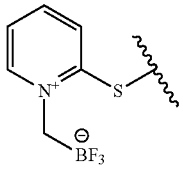

,

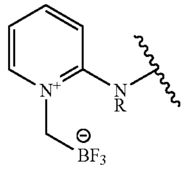

, or

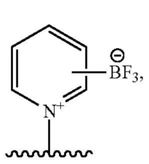

which the R (when present) in the pyridine substituted —OR, —SR, —NR— or —$NR_2$ is branched or linear $C_1$-$C_5$ alkyl. In some embodiments, R is a branched or linear $C_1$-$C_5$ saturated alkyl. In some embodiments, R is methyl. In some embodiments, R is ethyl. In some embodiments, R is propyl. In some embodiments, R is isopropyl. In some embodiments, R is n-butyl. In some embodiments, —$R^{14}BF_3$ is

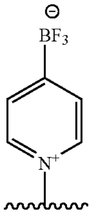

.

In some embodiments, one fluorine is $^{18}F$. In some embodiments, all three fluorines are $^{19}F$.

In some embodiments, —$R^{14}BF_3$ is

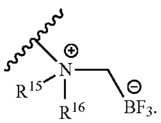

In some embodiments, $R^{15}$ is methyl. In some embodiments, $R^{15}$ is ethyl. In some embodiments, $R^{15}$ is propyl. In some embodiments, $R^{15}$ is isopropyl. In some embodiments, $R^{15}$ is butyl. In some embodiments, $R^{15}$ is n-butyl. In some embodiments, $R^{15}$ is pentyl. In some embodiments, $R^{16}$ is methyl. In some embodiments, $R^{16}$ is ethyl. In some embodiments, $R^{16}$ is propyl. In some embodiments, $R^{16}$ is isopropyl. In some embodiments, $R^{16}$ is butyl. In some embodiments, $R^{16}$ is n-butyl. In some embodiments, $R^{16}$ is pentyl. In some embodiments, $R^{15}$ and $R^{16}$ are both methyl. In some embodiments, at least one fluorine is $^{18}F$. In some embodiments, all three fluorines are $^{19}F$.

In some embodiments of the compounds of Formula A, A-I, A-II, B, or C, an $R^X$ is a prosthetic group containing a silicon-fluorine-acceptor moiety. In some embodiments, the fluorine of the silicon-fluorine acceptor moiety is $^{1}F$. The prosthetic groups containing a silicon-fluorine-acceptor moiety may be independently selected from one or a combination of the following:

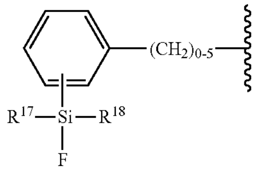

or

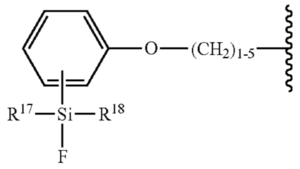

Wherein $R^{17}$ and $R^{18}$ are independently a linear or branched, cyclic or acyclic, and/or aromatic or non-aromatic $C_1$-$C_{10}$ alkyl, alkenyl or alkynyl group. In some embodiments, $R^{17}$ and $R^{18}$ are independently selected from the group consisting of phenyl, tert-butyl, sec-propyl, isopropyl, methyl, pyridyl, 2-indolyl, and 3-indolyl. In some embodiments, the prosthetic group is

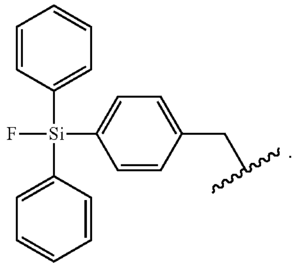 [SMILES: *Cc1ccc([Si](F)(c2ccccc2)c2ccccc2)cc1]

In some embodiments, the prosthetic group is

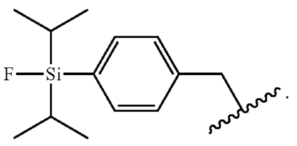 [SMILES: *Cc1ccc([Si](F)(C(C)C)C(C)C)cc1]

In some embodiments, the prosthetic group is

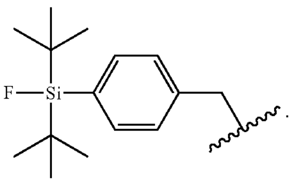 [SMILES: *Cc1ccc([Si](F)(C(C)(C)C)C(C)(C)C)cc1]

In some embodiments, the prosthetic group is

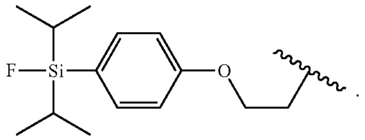 [SMILES: *CCOc1ccc([Si](F)(C(C)C)C(C)C)cc1]

In some embodiments of the compounds of Formula A, A-I, A-II, B, or C, an $R^X$ is a therapeutic moiety, including any chemical moiety capable of producing a therapeutic effect, e.g. small molecule drugs.

In some embodiments of the compounds of Formula A, A-I, A-II, B, or C, $R^X$ is fluorescent label.

The present disclosure also relates to a composition comprising any one of the compounds of Formula A, A-I, A-II, B, or C, or Table A or derivatives thereof, or Table B as described herein.

The present disclosure also relates to any one of the compounds of Formula A, A-I, A-II, B, or C, or Table A or derivatives thereof, or Table B as described herein, for use in imaging a CXCR4-expressing tissue in a subject or for imaging an inflammatory condition or disease. In one embodiment, the compound comprises at least one $R^X$ comprises an imaging radioisotope or is complexed with an imaging radioisotope, the compound is bound to a metal chelator complexed with an imaging radioisotope, or the compound is bound to a prosthetic group containing $BF_3$ comprising an imaging radioisotope. In one embodiment, the imaging radioisotope is $^{68}$Ga, $^{67}$Ga, $^{61}$Cu, $^{64}$Cu, $^{99m}$Tc, $^{114m}$In, $^{111}$In, 44Sc, $^{86}$Y, $^{89}$Zr, $^{90}$Nb, $^{18}$F, $^{131}$I, $^{123}$I, $^{124}$I or $^{72}$As. In one embodiment, the imaging radioisotope is $^{68}$Ga, $^{67}$Ga, $^{61}$Cu, $^{64}$Cu, $^{99m}$Tc, $^{114m}$In, $^{111}$In, $^{44}$Sc, $^{86}$Y, $^{89}$Zr, $^{90}$Nb, $^{131}$I, $^{123}$I, $^{124}$I or $^{72}$As.

The present disclosure also relates to a method of imaging a CXCR4-expressing tissue, comprising administering an effective amount of any one of the compounds of Formula A, A-I, A-II, B, or C, or Table A or derivatives thereof, or Table B as described herein, to a subject in need of such imaging. In one embodiment, the compound comprises at least one $R^X$ comprises an imaging radioisotope or is complexed with an imaging radioisotope, the compound is bound to a metal chelator complexed with an imaging radioisotope, or the compound is bound to a prosthetic group containing $BF_3$ comprising an imaging radioisotope. In one embodiment, the imaging radioisotope is $^{68}$Ga, $^{67}$Ga, $^{61}$Cu, $^{64}$Cu, $^{99m}$Tc, $^{114m}$In, $^{111}$In, $^{44}$Sc, $^{86}$Y, $^{89}$Zr, $^{90}$ Nb, $^{18}$F, $^{131}$I, $^{123}$I, $^{124}$I or $^{72}$As. In one embodiment, the imaging radioisotope is $^{68}$Ga, $^{67}$Ga, $^{61}$Cu, $^{64}$Cu, $^{99m}$Tc, $^{114m}$In, $^{111}$In, $^{44}$Sc, $^{86}$Y, $^{89}$Zr, $^{90}$Nb, $^{131}$I, $^{123}$I, $^{124}$I or $^{72}$As.

The present disclosure also relates to any one of the compounds of Formula A, A-I, A-II, B, or C, or Table A or derivatives thereof, or Table B as described herein, for use in treating a disease or condition characterized by expression of CXCR4 in a subject. In one embodiment, the disease or condition is a CXCR4-expressing cancer. In one embodiment, the compound comprises at least one $R^X$ comprises an imaging radioisotope or the compound is complexed with a therapeutic radioisotope, or the compound is bound to a metal chelator complexed with a therapeutic radioisotope. In one embodiment, the therapeutic radioisotope is $^{165}$Er, $^{212}$Bi, $^{211}$At, $^{166}$Ho, $^{149}$Pm, $^{159}$Gd, $^{105}$Rh, $^{109}$Pd, $^{198}$Au, $^{199}$Au, $^{175}$Yb, $^{142}$Pr, $^{177}$Lu, $^{111}$In, $^{213}$Bi, $^{203}$Pb, $^{212}$Pb, $^{47}$Sc, $^{90}$Y, $^{117m}$Sn, $^{153}$Sm, $^{149}$Tb, $^{161}$Tb, $^{224}$Ra, $^{225}$Ac, $^{227}$Th, $^{223}$Ra, $^{77}$As, $^{131}$I, $^{64}$Cu or $^{67}$Cu.

The present disclosure also relates to a method of treating a disease or condition characterized by expression of CXCR4, comprising administering an effective amount of any one of the compounds of Formula A, A-I, A-II, B, or C, or Table A or derivatives thereof, or Table B as described herein, to a subject in need thereof. In one embodiment, the disease or condition is a CXCR4-expressing cancer. In one embodiment, the compound comprises at least one $R^X$ comprises an imaging radioisotope or the compound is complexed with a therapeutic radioisotope, or the compound is bound to a metal chelator complexed with a therapeutic radioisotope. In one embodiment, the therapeutic radioisotope is $^{165}Er$, $^{212}Bi$, $^{211}At$, $^{166}Ho$, $^{149}Pm$, $^{159}Gd$, $^{105}Rh$, $^{109}Pd$, $^{198}Au$, $^{199}Au$, $^{175}Yb$, $^{142}Pr$, $^{177}Lu$, $^{111}In$, $^{231}Bi$, $^{203}Pb$, $^{212}Pb$, $^{47}Sc$, $^{90}Y$, $^{117m}Sn$, $^{153}Sm$ $^{149}Tb$, $^{161}Tb$, $^{224}Ra$, $^{225}Ac$, $^{227}Th$, $^{223}Ra$, $^{77}As$, $^{131}I$, $^{64}Cu$ or $^{67}Cu$.

In some embodiments, the compounds of Formula A, A-I, A-II, B, or C, or Table A or derivatives thereof, or Table B, inhibit SDF-1α binding to CXCR4 in vitro with an $IC_{50}$ of 50 nM or lower. In some embodiments, the compounds inhibit SDF-1α binding to CXCR4 in vitro with an $IC_{50}$ of 25 nM or lower. In some embodiments, the compounds inhibit SDF-1α binding to CXCR4 in vitro with an $IC_{50}$ of 10 nM or lower.

The overexpression of CXCR4 has been observed in over 23 types of malignancies, including brain, breast, and prostate cancers. Moreover, leukemia, lymphoma and myeloma have significant CXCR4 expression. Retrospective studies have shown that CXCR4 expression is correlated with lowered survival for prostate and melanoma patients. Furthermore, CXCR4 expression is a prognostic factor of disease relapse for acute and chronic myeloid leukemia, acute myelogenous leukemia and multiple myeloma. The SDF-1/CXCR4 axis mediates cancer growth, potentiates metastasis, recruits stromal and immune cells to support malignant growth, and confers chemotherapeutic resistance. Radiolabeled CXCR4 probes could be used in the early diagnosis of solid and hematological malignancies that express CXCR4. Such imaging agents could be used to confirm the diagnostic of malignancy, or guide focal ablative treatment if the disease is localized. Such ligands could also be used to monitor response to therapy, by providing an independent assessment of the residual cellular content of a tumour known to overexpress CXCR4. [$^{68}Ga$]Ga-Pentixafor has been used by the Wester group for cancer imaging and to identify potential responders to endoradiotherapy.

Dysregulation of the SDF-1/CXCR4 axis also mediates a number of inflammatory conditions. In rheumatoid arthritis (RA), SDF-1/CXCR4 signaling is responsible for the pro-inflammatory migration of activated T-cells into the site of inflammation; specifically, the synovium of patients with RA showed that the presence of T-cells with increased expression of CXCR4. Given the burden of RA on the population with respect to morbidity and mortality, there is a significant amount of research into developing therapeutics to mediate the inflammatory response, especially with novel biologics being approved by the FDA in the past few years. Radiolabeled CXCR4 probes for positron emission tomography imaging would enable diagnosis and prognosis of the rheumatoid arthritis and also be used to monitor therapy of emerging disease-modifying antirheumatic drugs in clinical trials. CXCR4 expression has been detected with PET imaging using [$^{68}Ga$]Ga-Pentixafor in diseases with an inflammatory component, including infectious bone diseases, urinary tract infections as a complication after kidney transplantation, myocardial infarctions, and ischemic strokes. CXCR4 imaging may have a significant role in diagnosing and monitoring other inflammatory diseases in the future.

In the setting of cardiac pathology, inflammatory diseases of the cardiac vessel walls are mediated in part by the dysregulation of the SDF-1/CXCR4 axis. In the early stages of atherosclerosis, the SDF-1/CXCR4 axis recruits endothelial progenitor cells towards sites of peripheral vascular damage, thereby initiating plaque formation, though there is some evidence towards an atheroprotective effect. Atherosclerotic plaques are characterized by the presence of hypoxia, which has been shown to upregulate the expression of CXCR4 and influence cell trafficking. Finally, in a rabbit model of atherosclerosis, [$^{68}Ga$]Ga-Pentixafor enabled visualization of atherosclerotic plaques by PET. In the same study, atherosclerotic plaques were identified in patients with a history of atherosclerosis using [$^{68}Ga$]Ga-Pentixafor. As such, PET diagnostic agents targeting CXCR4 are potentially viable as an alternative method of diagnosing and obtaining prognostic information about atherosclerosis.

In some embodiments, the disease or condition characterized by expression of CXCR4 is leukemia, lymphoma and myeloma. In some embodiments, the disease or condition characterized by expression of CXCR4 is a hematological malignancy. In some embodiments, the disease or condition characterized by expression of CXCR4 is an inflammatory disease.

In some embodiments, the disease or condition characterized by expression of CXCR4 is a disease or condition characterized by an overexpression of CXCR4 or an abnormal expression of CXCR4.

In some embodiment, the CXCR4-expressing cancer is a hematologic malignancy. In some embodiment, the CXCR4-expressing cancer is leukemia, lymphoma and myeloma.

In certain embodiments, the compound of Formula A, A-I, A-II, B, or C is conjugated with a radioisotope for positron emission tomography (PET) or single photon emission computed tomography (SPECT) imaging of a CXCR4-expressing tissue or for imaging an inflammatory condition or disease (e.g. rheumatoid arthritis or cardiovascular disease), wherein the compound is conjugated with a radioisotope that is a positron emitter or a gamma emitter. Without limitation, the positron or gamma emitting radioisotope may be $^{68}Ga$, $^{67}Ga$, $^{61}Cu$, $^{64}Cu$, $^{99m}Tc$, $^{110m}In$, $^{111}In$, $^{44}Sc$, $^{86}Y$, $^{89}Zr$, $^{90}Nb$, $^{18}F$, $^{131}I$, $^{123}I$, $^{124}I$ or $^{72}As$.

When the radioisotope (e.g. X) is a diagnostic radioisotope, there is disclosed use of certain embodiments of the compound for preparation of a radiolabelled tracer for imaging. There is also disclosed a method of imaging CXCR4-expressing tissues or an inflammatory condition or disease in a subject, in which the method comprises: administering to the subject a composition comprising certain embodiments of the compound and a pharmaceutically acceptable excipient; and imaging the subject, e.g. using positron emission tomography (PET). When the tissue is a diseased tissue (e.g. a CXCR4-expressing cancer), CXCR4-targeted treatment may then be selected for treating the subject. There is therefore disclosed the use of certain compounds of the invention in imaging a CXCR4-expressing cancer in a subject, wherein $R^X$ comprises or is complexed with a diagnostic or imaging radioisotope. In some embodiments, the subject is human.

Given the broad expression of CXCR4 in cancers, there has been a significant push to develop CXCR4-targeting therapeutics. While CXCR4 inhibitors have demonstrated efficacy in tumor models in mice, in both treating tumors and preventing metastasis, very few pharmaceutical agents have demonstrated efficacy in clinical trials. Plerixafor, also known as AMD3100, developed originally for HIV treatment, is the lone CXCR4 antagonist to receive FDA approval to date. AMD3100 is given to lymphoma and multiple myeloma patients to mobilize hematopoietic stem cells into peripheral blood for collection and autologous transplantation, and not as a method of direct treatment. There is an unmet clinical need for treating CXCR4-expressing cancers, many of which are resistant to the standard of care available today.

Cancers that are CXCR4 positive could be susceptible to endoradiotherapy. In this application, a peptide targeting CXCR4 is radiolabeled with a radioisotope, usually a β- or α-particle emitter, to deliver a high local dose of radiation to lesions. These radioactive emissions usually inflict DNA damage, thereby inducing cellular death. This method of therapy has been exploited in oncology, with the somatostatin receptor (for neuroendocrine tumors) and prostate-specific membrane antigen (for metastatic castration-resistant prostate cancer) being two examples. Unlike external beam radiation therapy, this systemic treatment can be effective even in the metastatic setting. Therapeutic radioisotopes include but are not restricted to $^{177}$Lu, $^{90}$Y, $^{225}$Ac and $^{64}$Cu.

With respect to cardiac pathologies, a small retrospective study with endoradiotherapy by [$^{90}$Y]Y- or [$^{177}$Lu]Lu-Pentixather demonstrated regression of CXCR4 expression and activity in patients with previously identified atherosclerotic plaques. Therefore, radionuclide therapy may present a novel route of therapy for inflammatory diseases such as atherosclerosis.

In certain embodiments the compound of Formula A, A-I, A-II, B, or C is conjugated with a radioisotope that is used for therapy (e.g. cancer therapy). This includes radioisotopes such as $^{165}$Er, $^{212}$Bi, $^{211}$At, $^{166}$Ho, $^{149}$Pm, $^{159}$Gd, $^{105}$Rh, $^{109}$Pd, $^{198}$Au, $^{199}$Au, $^{175}$Yb, $^{142}$Pr, $^{177}$Lu (β-emitter, $t_{2/1}$=6.65 d), $^{111}$In, $^{213}$Bi, $^{203}$Pb, $^{212}$Pb, $^{47}$Sc, $^{90}$Y (β-emitter, $t_{2/1}$=2.66 d), $^{117m}$Sn, $^{153}$Sm, $^{149}$Tb, $^{161}$Tb, $^{224}$Ra, $^{225}$Ac (α-emitter, $t_{2/1}$=9.95 d), $^{227}$Th, $^{223}$Ra, $^{77}$As, $^{131}$I, $^{64}$Cu or $^{67}$Cu.

When the radioisotope (e.g. X) is a therapeutic radioisotope, there is disclosed use of certain embodiments of the compound (or a pharmaceutical composition thereof) for the treatment of a disease or condition characterized by expression of CXCR4 in a subject. Accordingly, there is provided use of the compound in preparation of a medicament for treating a disease or condition characterized by expression of CXCR4 in a subject. There is also provided a method of treating a disease or condition characterized by expression of CXCR4 in a subject, in which the method comprises: administering to the subject a composition comprising the compound of Formula A, A-I, A-II, B, or C, or a salt or solvate thereof and a pharmaceutically acceptable excipient. For example, but without limitation, the disease may be a CXCR4-expressing cancer (e.g. non-Hodgkin lymphoma, lymphoma, multiple myeloma, leukemia, adrenocortical cancer, lung cancer, breast cancer, renal cell cancer, colorectal cancer). There is therefore disclosed the use of certain compounds of the invention for treating a CXCR4-expressing cancer in a subject, wherein $R^X$ comprises or is complexed with a therapeutic radioisotope. In some embodiments, the subject is human.

The compounds presented herein incorporate peptides, which may be synthesized by any of a variety of methods established in the art. This includes but is not limited to liquid-phase as well as solid-phase peptide synthesis using methods employing 9-fluorenylmethoxycarbonyl (Fmoc) and/or t-butyloxycarbonyl (Boc) chemistries, and/or other synthetic approaches.

Solid-phase peptide synthesis methods and technology are well-established in the art. For example, peptides may be synthesized by sequential incorporation of the amino acid residues of interest one at a time. In such methods, peptide synthesis is typically initiated by attaching the C-terminal amino acid of the peptide of interest to a suitable resin. Prior to this, reactive side chain and alpha amino groups of the amino acids are protected from reaction by suitable protecting groups, allowing only the alpha carboxyl group to react with a functional group such as an amine group, a hydroxyl group, or an alkyl halide group on the solid support. Following coupling of the C-terminal amino acid to the support, the protecting group on the side chain and/or the alpha amino group of the amino acid is selectively removed, allowing the coupling of the next amino acid of interest. This process is repeated until the desired peptide is fully synthesized, at which point the peptide can be deprotected and cleaved from the support, and purified. A non-limiting example of an instrument for solid-phase peptide synthesis is the Aapptec Endeavor 90 peptide synthesizer.

To allow coupling of additional amino acids, Fmoc protecting groups may be removed from the amino acid on the solid support, e.g. under mild basic conditions, such as piperidine (20-50% v/v) in DMF. The amino acid to be added must also have been activated for coupling (e.g. at the alpha carboxylate). Non-limiting examples of activating reagents include without limitation 2-(1H-benzotriazol-1-yl)-1,1,3,3-tetramethyluronium hexafluorophosphate (HBTU), 2-(1H-benzotriazol-1-yl)-1,1,3,3-tetramethyluronium tetrafluoroborate (TBTU), 2-(7-Aza-1H-benzotriazole-1-yl)-1,1,3,3-tetramethyluronium hexafluorophosphate (HATU), benzotriazole-1-yl-oxy-tris(dimethylamino)phosphoniumhexafluorophosphate (BOP), benzotriazole-1-yl-oxy-tris(pyrrolidino)phosphoniumhexafluorophosphate (PyBOP). Racemization is minimized by using triazoles, such as 1-hydroxy-benzotriazole (HOBt) and 1-hydroxy-7-aza-benzotriazole (HOAt). Coupling may be performed in the presence of a suitable base, such as N,N-diisopropylethylamine (DIPEA/DIEA) and the like. For long peptides or if desired, peptide synthesis and ligation may be used.

Apart from forming typical peptide bonds to elongate a peptide, peptides may be elongated in a branched fashion by attaching to side chain functional groups (e.g. carboxylic acid groups or amino groups), either: side chain to side chain; or side chain to backbone amino or carboxylate. Coupling to amino acid side chains may be performed by any known method, and may be performed on-resin or off-resin. Non-limiting examples include: forming an amide between an amino acid side chain containing a carboxyl group (e.g. Asp, D-Asp, Glu, D-Glu, Aad, and the like) and an amino acid side chain containing an amino group (e.g. Lys, D-Lys, Orn, D-Orn, Dab, D-Dab, Dap, D-Dap, and the like) or the peptide N-terminus; forming an amide between an amino acid side chain containing an amino group (e.g. Lys, D-Lys, Orn, D-Orn, Dab, D-Dab, Dap, D-Dap, and the like) and either an amino acid side chain containing a carboxyl group (e.g. Asp, D-Asp, Glu, D-Glu, and the like) or the peptide C-terminus; and forming a 1, 2, 3-triazole via click chemistry between an amino acid side chain containing an azide group (e.g. Lys($N_3$), D-Lys($N_3$), and the like) and an alkyne group (e.g. Pra, D-Pra, and the like). The protecting groups on the appropriate functional groups must be selectively removed before amide bond formation, whereas the reaction between an alkyne and an azido groups via the click reaction to form an 1,2,3-triazole does not require selective deprotection. Non-limiting examples of selectively removable protecting groups include 2-phenylisopropyl esters (O-2-PhiPr) (e.g. on Asp/Glu) as well as 4-methyltrityl (Mtt), allyloxycarbonyl (alloc), 1-(4,4-dimethyl-2,6-dioxocyclohex-1-ylidene))ethyl (Dde), and 1-(4,4-dimethyl-2,6-d ioxocyclohex-1-ylidene)-3-methylbutyl (ivDde) (e.g. on Lys/Orn/Dab/Dap). O-2-PhiPr and Mtt protecting groups can be selectively deprotected under mild acidic conditions, such as 2.5% trifluoroacetic acid (TFA) in DCM. Alloc protecting groups can be selectively deprotected using tetrakis(triphenylphosphine)palladium(0) and phenylsilane in DCM. Dde and ivDde protecting groups can be selectively deprotected using 2-5% of hydrazine in DMF. Deprotected side chains of Asp/Glu (L- or D-forms) and Lys/Orn/Dab/Dap (L- or D-forms) can then be coupled, e.g. by using the coupling reaction conditions described above.

Formula A, A-I, and A-II compounds may be cyclized by linking the peptide N-terminus to a side chain carboxylate (at residue 7 in the peptide) using the technologies discussed above (exemplary reaction conditions are described in the Examples). Formula B compounds may be cyclized using an intra-annular tryptathionine stapling reaction or an isoindole stapling reaction, called FIICk[21], to link the side chains of residues 1 and 7 in the peptide (exemplary reaction conditions are described in the Examples); the resulting isoindoles have intrinsic fluorescent properties imaging. Formula C compounds may be similarly cyclized using a thiolactic amino acid at residue 1 in the peptide, e.g. as shown in the following scheme:

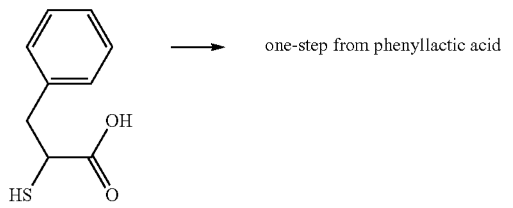

(Or any other thiolactic amino acid)

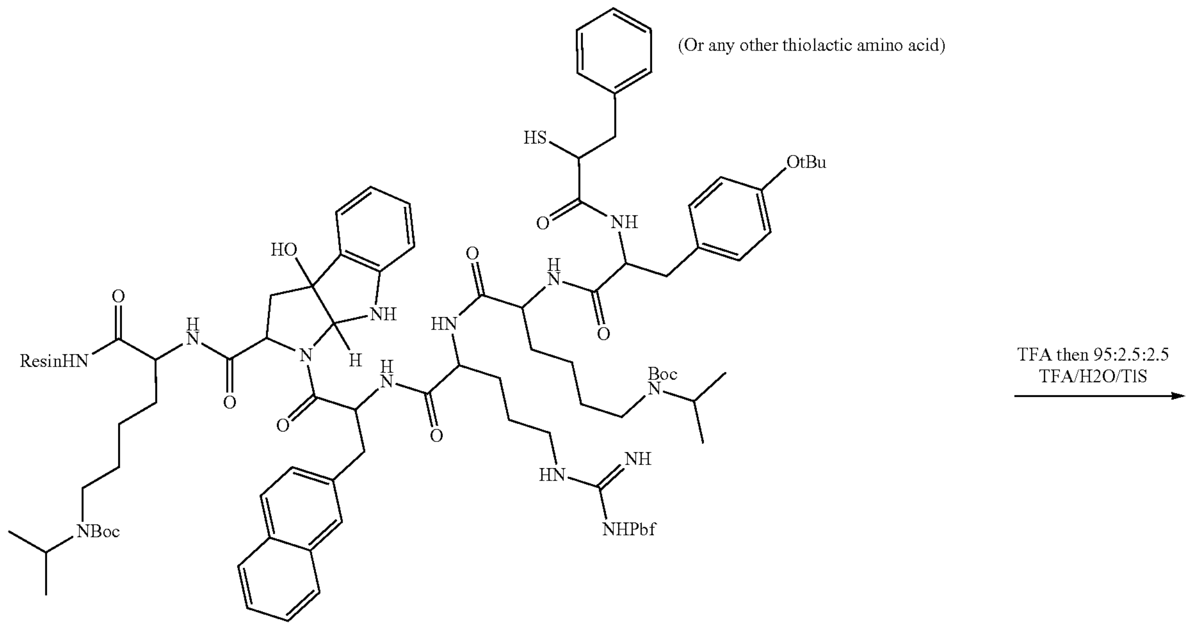

-continued

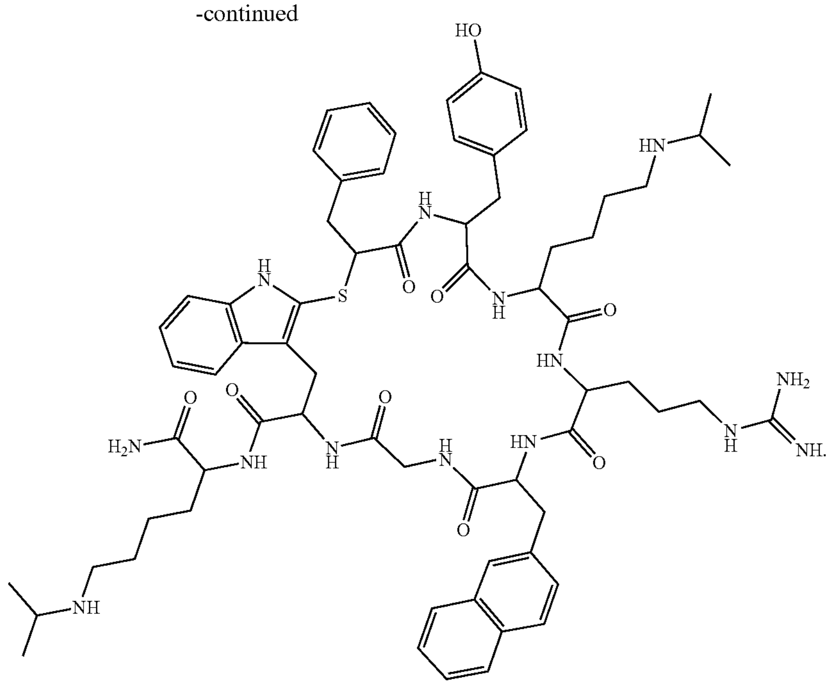

Peptide backbone amides may be N-methylated (i.e. alpha amino methylated). This may be achieved by directly using Fmoc-N-methylated amino acids during peptide synthesis. Alternatively, N-methylation under Mitsunobu conditions may be performed. First, a free primary amine group is protected using a solution of 4-nitrobenzenesulfonyl chloride (Ns-Cl) and 2,4,6-trimethylpyridine (collidine) in NMP. N-methylation may then be achieved in the presence of triphenylphosphine, diisopropyl azodicarboxylate (DIAD) and methanol. Subsequently, N-deprotection may be performed using mercaptoethanol and 1,8-diazabicyclo[5.4.0]undec-7-ene (DBU) in NMP. For coupling protected amino acids to N-methylated alpha amino groups, HATU, HOAt and DIEA may be used.

The formation of the thioether (—S—) linkages (e.g. for $L^1$) can be achieved either on solid phase or in solution phase. For example, the formation of thioether (—S—) linkage can be achieved by coupling between a thiol-containing compound (such as the thiol group on cysteine side chain) and an alkyl halide (such as 3-(Fmoc-amino) propyl bromide and the like) in an appropriate solvent (such as N,N-dimethylformamide and the like) in the presence of base (such as N,N-diisopropylethylamine and the like). If the reactions are carried out in solution phase, the reactants used are preferably in equivalent molar ratio (1 to 1), and the desired products can be purified by flash column chromatography or high performance liquid chromatography (HPLC). If the reactions are carried out on solid phase, meaning one reactant has been attached to a solid phase, then the other reactant is normally used in excess amount (z 3 equivalents of the reactant attached to the solid phase). After the reactions, the excess unreacted reactant and reagents can be removed by sequentially washing the solid phase (resin) using a combination of solvents, such as N,N-dimethylformamide, methanol and dichloromethane, for example.

The formation of the linkage (e.g. for $L^1$) between a thiol group and a maleimide group can be performed using the conditions described above for the formation of the thioether (—S—) linkage simply by replacing the alkyl halide with a maleimide-containing compounds. Similarly, this reaction can be conducted in solid phase or solution phase. If the reactions are carried out in solution phase, the reactants used are preferably in equivalent molar ratio (1 to 1), and the desired products can be purified by flash column chromatography or high performance liquid chromatography (HPLC). If the reactions are carried out on solid phase, meaning one reactant has been attached to a solid phase, then the other reactant is normally used in excess amount (?3 equivalents of the reactant attached to the solid phase). After the reactions, the excess unreacted reactant and reagents can be removed by sequentially washing the solid phase (resin) using a combination of solvents, such as N,N-dimethylformamide, methanol and dichloromethane, for example.

Non-peptide moieties (e.g. radiolabeling groups, albumin-binding groups and/or linkers) may be coupled to the peptide N-terminus while the peptide is attached to the solid support. This is facile when the non-peptide moiety comprises an activated carboxylate (and protected groups if necessary) so that coupling can be performed on resin. For example, but without limitation, a bifunctional chelator, such as 1,4,7,10-tetraazacyclododecane-1,4,7,10-tetraacetic acid (DOTA) tris(tert-butyl ester) may be activated in the presence of N-hydroxysuccinimide (NHS) and N,N'-dicyclohexylcarbodiimide (DCC) for coupling to a peptide. Alternatively, a non-peptide moiety may be incorporated into the compound via a copper-catalyzed click reaction under either liquid or solid phase conditions. Copper-catalyzed click reactions are well established in the art. For example, 2-azidoacetic acid is first activated by NHS and DCC and coupled to a peptide. Then, an alkyne-containing non-peptide moiety may be clicked to the azide-containing peptide in the presence of $Cu^{2+}$ and sodium ascorbate in water and organic solvent, such as acetonitrile (ACN) and DMF and the like. Non-peptide moieties may also be added in solution phase, which is routinely performed.

The synthesis of chelators is well-known and many chelators are commercially available (e.g. from Sigma-Aldrich™/Milipore Sigma™ and others). Protocols for conjugation of radiometals to the chelators are also well known (e.g. see Example 1, below). The synthesis of the silicon-fluorine-acceptor moieties can be achieved following previously reported procedures (e.g. Bernard-Gauthier et al. Biomed Res Int. 2014 2014:454503; Kostikov et al. *Nature Protocols* 2012 7:1956-1963; Kostikov et al. *Bioconjug Chem.* 2012 18:23:106-114; each of which is incorporated by reference in its entirety). The synthesis or acquisition of radioisotope-substituted aryl groups is likewise facile.

The synthesis of the $R^{13}R^{14}BF_3$ component on the compounds can be achieved following previously reported procedures (e.g.: Liu et al. *Angew Chem Int Ed* 2014 53:11876-11880; Liu et al. *J Nucl Med* 2015 55:1499-1505; Liu et al. *Nat Protoc* 2015 10:1423-1432; Kuo et al., *J Nucl Med* 2019 60:1160-1166; each of which is incorporated by reference in its entirety). Generally, the $BF_3$-containing motif can be coupled to the linker via click chemistry by forming a 1,2,3-triazole ring between a $BF_3$-containing azido (or alkynyl) group and an alkynyl (or azido) group on the linker, or by forming an amide linkage between a $BF_3$-containing carboxylate and an amino group on the linker. To make the $BF_3$-containing azide, alkyne or carboxylate, a boronic acid ester-containing azide, alkyne or carboxylate is first prepared following by the conversion of the boronic acid ester to $BF_3$ in a mixture of HCl, DMF and $KHF_2$. For alkyl $BF_3$, the boronic acid ester-containing azide, alkyne or carboxylate can be prepared by coupling boronic acid ester-containing alkyl halide (such as iodomethylboronic acid pinacol ester) with an amine-containing azide, alkyne or carboxylate (such as N,N-dimethylpropargylamine). For aryl $BF_3$, the boronic acid ester can be prepared via Suzuki coupling using aryl halide (iodine or bromide) and bis(pinacolato)diboron, $^{18}F$-Fluorination of the $BF_3$-containing compounds via $^{18}F$-$^{19}F$ isotope exchange reaction can be achieved following previously published procedures (Liu et al. Nat Protoc 2015 10:1423-1432, incorporated by reference in its entirety). Generally, ~100 nmol of the $BF_3$-containing compound is dissolved in a mixture of 15 μl of pyridazine-HCl buffer (pH=2.0-2.5, 1 M), 15 μl of DMF and 1 μl of a 7.5 mM $KHF_2$ aqueous solution. $^{18}F$-Fluoride solution (in saline, 60 μl) is added to the reaction mixture, and the resulting solution is heated at 80° C. for 20 min. At the end of the reaction, the desired product can be purified by solid phase extraction or by reversed high performance liquid chromatography (HPLC) using a mixture of water and acetonitrile as the mobile phase.

When the peptide has been fully synthesized on the solid support, the desired peptide may be cleaved from the solid support using suitable reagents, such as TFA, tri-isopropylsilane (TIS) and water. Side chain protecting groups, such as Boc, pentamethyldihydrobenzofuran-5-sulfonyl (Pbf), trityl (Trt) and tert-butyl (tBu) are simultaneously removed (i.e. deprotection). The crude peptide may be precipitated and collected from the solution by adding cold ether followed by centrifugation. Purification and characterization of the peptides may be performed by standard separation techniques, such as high performance liquid chromatography (HPLC) based on the size, charge and polarity of the peptides. The identity of the purified peptides may be confirmed by mass spectrometry or other similar approaches.

The present invention will be further illustrated in the following examples for the synthesis and evaluation of specific compounds.

Examples

Chemical Synthesis

Reagents and solvents were purchased from commercial sources and used without further purification, unless otherwise stated. Peptides were synthesized on a Liberty Blue automated microwave peptide synthesis (CEM Corporations). High performance liquid chromatography (HPLC) was performed on 1) an Agilent 1260 infinity system equipped with a model 1200 quaternary pump, a model 1200 UV absorbance detector and a Bioscan NaI scintillation detector, 2) an Agilent 1100 HPLC system or 3) an Agilent 1260 Infinity II Preparative System equipped with a model 1260 Infinity II preparative binary pump, a model 1260 Infinity variable wavelength detector (set at 220 nm), and a 1290 Infinity II preparative open-bed fraction collector. The HPLC column used for synthesis was a semi-preparative column (Agilent Eclipse XDB-C18, 5 μm, 9.4×250 mm) or a preparative column (Gemini, NX-C18, 5 μm, 110 Å, 50×30 mm) purchased from Phenomenex. Mass analyses were performed using an AB SCIEX 4000 QTRAP mass spectrometer system with an ESI ion source or a Waters 2695 Separation module and Waters-Micromass ZQ mass spectrometer system.

All Fmoc-amino acids are coupled using a 4/8/4 equiv. of Fmoc-AA-OH/DIC/Oxyma in DMF for 4 min at 90° C. using microwave heating, unless stated otherwise. All Fmoc groups are removed with 20% v/v piperidine in DMF for 1 min at 90° C. unless stated otherwise. Coupled twice implies two cycles of the activated Fmoc amino acid solution. After the coupling of the first Fmoc-protected amino acid to the resin, the free amines on the resin polymer are capped with a solution of 5% 1-acetylimidazole in DMF.

Peptides are C-terminally amidated.

The term “cyclo” in the peptide nomenclature used herein refers to the cyclization shown in Formula A, i.e. an amide linkage formed by the N-terminal amino group of the first amino acid residue and the side chain carboxy group of the seventh amino acid residue. The terms “cyclo(isoindole)” and “cyclo(tryptathionine)” in the peptide nomenclature used herein refers to the cyclization shown in Formula B, i.e. an isoindole linkage or tryptathionine linkage formed by linking the side chain functional groups of the first and seventh side chain amino acid residues using FIICk or a similar reaction.

Synthesis of cyclo[Phe-(4-$NH_2$)Phe-Lys(iPr)-D-Arg-2-Nal-Gly-D-Glu]-Lys(iPr) (1)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-Gly-OH (coupled twice), Fmoc-2Nal-OH (coupled twice), Fmoc-D-Arg(Pbf)-OH (coupled twice), Fmoc-Lys(iPr,Boc)-OH, Fmoc-Phe(4-NH(Boc))—OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The $N^{\alpha}$-Fmoc on Phe was then removed, and cyclization was performed using DIC/HOBt in DMF (3×10 min at 90° C.). Following cyclization, the peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 14-34% acetonitrile (0.1% TFA) in $H_2O$ (0.1% TFA) in 20 mins at a flow rate of 30 mL/min. The retention time of 1 was 7.88 min with the preparative column. ESI-MS: calculated $[M+2H]^{2+}$ for 1 $C_{62}H_{91}N_{15}O_9$ 594.86; found $[M+2H]^{2+}$ 595.12.

Synthesis of cyclo[Phe-(4-$NO_2$)Phe-Lys(iPr)-D-Arg-2-Nal-Gly-D-Glu]-Lys(iPr) (2)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-Gly-OH (coupled twice), Fmoc-2Nal-OH (coupled twice), Fmoc-D-Arg(Pbf)-OH (coupled twice), Fmoc-Lys(iPr,Boc)-OH, Fmoc-Phe(4-$NO_2$)—OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The NP-Fmoc on Phe was then removed, and cyclization was performed using DIC/HOBt in DMF (3×10 min at 90° C.). Following cyclization, the peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 18-38% acetonitrile (0.1% TFA) in $H_2O$ (0.1% TFA) in 20 mins at a flow rate of 30 mL/min. The retention time of 2 was 12.04 min with the preparative column. ESI-MS: calculated $[M+2H]^{2+}$ for 2 $C_{62}H_{89}N_{15}O_{11}$ 609.84; found $[M+2H]^{2+}$ 609.95.

Synthesis of cyclo[Phe-hTyr-Lys(iPr)-D-Arg-2-Nal-Gly-D-Glu]-Lys(iPr) (3)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-Gly-OH (coupled twice), Fmoc-2Nal-OH (coupled twice), Fmoc-D-Arg(Pbf)-OH (coupled twice), Fmoc-Lys(iPr,Boc)-OH, Fmoc-hTyr-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The $N^\alpha$-Fmoc on Phe was then removed, and cyclization was performed using DIC/HOBt in DMF (3×10 min at 90° C.). Following cyclization, the peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 16-36% acetonitrile (0.1% TFA) in $H_2O$ (0.1% TFA) in 20 mins at a flow rate of 30 mL/min. The retention time of 3 was 10.86 min with the preparative column. ESI-MS: calculated $[M+2H]^{2+}$ for 3 $C_{63}H_{92}N_{14}O_{10}$ 602.36; found $[M+2H]^{2+}$ 602.12.

Synthesis of cyclo[Phe-(3-1)Tyr-Lys(iPr)-D-Arg-2-Nal-Gly-D-Glu]-Lys(iPr) (4)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-Gly-OH (coupled twice), Fmoc-2Nal-OH (coupled twice), Fmoc-D-Arg(Pbf)-OH (coupled twice), Fmoc-Lys(iPr,Boc)-OH, Fmoc-(3-I)Tyr-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The $N^\alpha$-Fmoc on Phe was then removed, and cyclization was performed using DIC/HOBt in DMF (3×10 min at 90° C.). Following cyclization, the peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 14-34% acetonitrile (0.1% TFA) in $H_2O$ (0.1% TFA) in 20 mins at a flow rate of 30 mL/min. The retention time of 4 was 14.66 min with the preparative column. ESI-MS: calculated $[M+2H]^{2+}$ for 4 $C_{62}H_{89}IN_{14}O_{10}$ 658.30; found $[M+2H]^{2+}$ 658.40.

Synthesis of cyclo[Phe-Tyr-Arg(Me)$_2$(asym)-D-Arg-2-Nal-Gly-D-Glu]-Lys(iPr) (5)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-Gly-OH (coupled twice), Fmoc-2Nal-OH (coupled twice), Fmoc-D-Arg(Pbf)-OH (coupled twice), Fmoc-Arg(Me)$_2$(asym)-OH, Fmoc-Tyr(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The $N^\alpha$-Fmoc on Phe was then removed, and cyclization was performed using DIC/HOBt in DMF (3×10 min at 90° C.). Following cyclization, the peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 13-33% acetonitrile (0.1% TFA) in $H_2O$ (0.1% TFA) in 20 mins at a flow rate of 30 mL/min. The retention time of 5 was 11.55 min with the preparative column. ESI-MS: calculated $[M+2H]^{2+}$ for 5 $C_{61}H_{88}N_{16}O_{10}$ 602.34; found $[M+2H]^{2+}$ 602.46.

Synthesis of cyclo[Phe-Tyr-Lys(iPr)-D-Arg-(2-Ant)Ala-Gly-D-Glu]-Lys(iPr) (6)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-Gly-OH (coupled twice), Fmoc-(2-Ant)Ala-OH (coupled twice), Fmoc-D-Arg(Pbf)-OH (coupled twice), Fmoc-Lys(iPr, Boc)-OH, Fmoc-Tyr(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The $N^{\alpha}$-Fmoc on Phe was then removed, and cyclization was performed using DIC/HOBt in DMF (3×10 min at 90° C.). Following cyclization, the peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 15-35% acetonitrile (0.1% TFA) in $H_2O$ (0.1% TFA) in 20 mins at a flow rate of 30 mL/min. The retention time of 6 was 11.22 min with the preparative column. ESI-MS: calculated $[M+3H]^{3+}$ for 6 $C_{66}H_{93}N_{14}O_{10}$ 413.91; found $[M+3H]^{3+}$ 414.40.

Synthesis of cyclo[Phe-Tyr-Lys(iPr)-D-Arg-(9-Ant)Ala-Gly-D-G/u]-Lys(iPr) (7)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-Gly-OH (coupled twice), Fmoc-(9-Ant)Ala-OH (coupled twice), Fmoc-D-Arg(Pbf)-OH (coupled twice), Fmoc-Lys(iPr, Boc)-OH, Fmoc-Tyr(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The NA-Fmoc on Phe was then removed, and cyclization was performed using DIC/HOBt in DMF (3×10 min at 90° C.). Following cyclization, the peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 15-35% acetonitrile (0.1% TFA) in $H_2O$ (0.1% TFA) in 20 mins at a flow rate of 30 mL/min. The retention time of 7 was 10.70 min with the preparative column. ESI-MS: calculated $[M+3H]^{3+}$ for 7 $C_{66}H_{93}N_{14}O_{10}$ 413.91; found $[M+3H]^{3+}$ 413.60.

Synthesis of cyclo[Phe-Tyr-Lys(iPr)-D-Arg-(Adamantyl)Ala-Gly-D-Glu]-Lys(iPr) (8)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-Gly-OH (coupled twice), Fmoc-(Adamantyl)Ala-OH (coupled twice), Fmoc-D-Arg(Pbf)-OH (coupled twice), Fmoc-Lys(iPr, Boc)-OH, Fmoc-Tyr(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The NA-Fmoc on Phe was then removed, and cyclization was performed using DIC/HOBt in DMF (3×10 min at 90° C.). Following cyclization, the peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column.

Synthesis of cyclo[Phe-Tyr-Lys(iPr)-D-Arg-2Nal-D-Ala-D-Glu]-Lys(iPr) (9)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Ala-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The NP-Fmoc on Phe was then removed, and cyclization was performed using DIC/HOBt in DMF (3×10 min at 90° C.). Following cyclization, the peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 16-36% acetonitrile (0.1% TFA) in $H_2O$ (0.1% TFA) in 20 mins at a flow rate of 30 mL/min. The retention time of 9 was 10.74 min with the preparative column. ESI-MS: calculated $[M+3H]^{3+}$ for 9 $C_{63}H_{93}N_{14}O_{10}$ 401.91; found $[M+3H]^{3+}$ 401.40.

Synthesis of cyclo[Phe-Tyr-Lys(iPr)-D-Arg-2Nal-D-His-D-Glu]-Lys(iPr) (10)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-His(Trt)-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-Phe-OH (coupled twice) were sequentially coupled to the peptidyl resin following similar procedures, except Fmoc-D-His(Trt)-OH, which was coupled for 10 min at 50° C. The —OAllyl protecting group on D-Glu was removed using $Pd(PPh_3)_4$ (20 mg)/Phenylsilane (300 μL) in DCM (6 mL) (2×6 min at 35° C.). The NP-Fmoc on Phe was then removed, and cyclization was performed using DIC/HOBt in DMF (3×10 min at 90° C.). Following cyclization, the peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 16-36% acetonitrile (0.1% TFA) in $H_2O$ (0.1% TFA) in 20 mins at a flow rate of 30 mL/min. The retention time of 10 was 7.86 min with the preparative column. ESI-MS: calculated $[M+3H]^{3+}$ for 10 $C_{66}H_{95}N_{16}O_{10}$ 423.91; found $[M+3H]^{3+}$ 424.01.

Synthesis of cyclo[Phe-Tyr-Lys(iPr)-D-Arg-2Nal-His-D-Glu]-Lys(iPr) (11)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-His(Trt)-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-Phe-OH (coupled twice) were sequentially coupled to the peptidyl resin following similar procedures, except Fmoc-His(Trt)-OH, which was coupled for 10 min at 50° C. The —OAllyl protecting group on D-Glu was removed using $Pd(PPh_3)_4$ (20 mg)/Phenylsilane (300 μL) in DCM (6 mL) (2×6 min at 35° C.). The $N^{\alpha}$-Fmoc on Phe was then removed, and cyclization was performed using DIC/HOBt in DMF (3×10 min at 90° C.). Following cyclization, the peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 16-36% acetonitrile (0.1% TFA) in $H_2O$ (0.1% TFA) in 20 mins at a flow rate of 30 mL/min. The retention time of 11 was 8.33 min with the preparative column. ESI-MS: calculated $[M+3H]^{3+}$ for 11 $C_{66}H_{95}N_{16}O_{10}$ 423.91; found $[M+3H]^{3+}$ 423.70.

Synthesis of cyclo[Phe-Tyr-Lys(iPr)-D-Arg-2Nal-D-Phe-D-Glu]-Lys(iPr) (12)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Phe)-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The $N^{\alpha}$-Fmoc on Phe was then removed, and cyclization was performed using DIC/HOBt in DMF (3×10 min at 90° C.). Following cyclization, the peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 13-33% acetonitrile (0.1% TFA) in $H_2O$ (0.1% TFA) in 20 mins at a flow rate of 30 mL/min. The retention time of 12 was 14.45 min with the preparative column. ESI-MS: calculated $[M+3H]^{3+}$ for 12 $C_{69}H_{97}N_{14}O_{10}$ 427.25; found $[M+3H]^{3+}$ 427.39.

Synthesis of cyclo[Phe-Tyr-Lys(iPr)-D-Arg-2Nal-D-Leu-D-Glu]-Lys(iPr) (13)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Leu-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The NP-Fmoc on Phe was then removed, and cyclization was performed using DIC/HOBt in DMF (3×10 min at 90° C.). Following cyclization, the peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 17-37% acetonitrile (0.1% TFA) in $H_2O$ (0.1% TFA) in 20 mins at a flow rate of 30 mL/min. The retention time of 13 was 13.44 min with the preparative column. ESI-MS: calculated $[M+3H]^{3+}$ for 13 $C_{66}H_{98}N_{14}O_{10}$ 415.59; found $[M+3H]^{3+}$ 414.98.

Synthesis of cyclo[Phe-Tyr-Lys(iPr)-D-Arg-2Nal-D-Glu-D-Glu]-Lys(iPr) (14)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Glu(tBu)-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The NP-Fmoc on Phe was then removed, and cyclization was performed using DIC/HOBt in DMF (3×10 min at 90° C.). Following cyclization, the peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 17-37% acetonitrile (0.1% TFA) in $H_2O$ (0.1% TFA) in 20 mins at a flow rate of 30 mL/min. The retention time of 14 was 8.71 min with the preparative column. ESI-MS: calculated $[M+3H]^{3+}$ for 14 $C_{65}H_{94}N_{14}O_{12}$ 420.90; found $[M+3H]^{3+}$ 421.21.

Synthesis of cyclo[Phe-Tyr-Lys(iPr)-D-Arg-2Nal-D-Dab-D-Glu]-Lys(iPr) (15)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Dab(Boc)-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The NP-Fmoc on Phe was then removed, and cyclization was performed using DIC/HOBt in DMF (3×10 min at 90° C.). Following cyclization, the peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 13-33% acetonitrile (0.1% TFA) in $H_2O$ (0.1% TFA) in 20 mins at a flow rate of 30 mL/min. The retention time of 15 was 11.0 min with the preparative column. ESI-MS: calculated $[M+3H]^{3}$*for 15 $C_{64}H_{95}N_{15}O_{10}$ 411.25; found $[M+3H]^{3+}$ 411.53.

Synthesis of cyclo[Phe-Tyr-Lys(iPr)-D-Arg-2Nal-D-Dap-D-Gu]-Lys(iPr) (16)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Dap(Boc)-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The NP-Fmoc on Phe was then removed, and cyclization was performed using DIC/HOBt in DMF (3×10 min at 90° C.). Following cyclization, the peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 13-33% acetonitrile (0.1% TFA) in $H_2O$ (0.1% TFA) in 20 mins at a flow rate of 30 mL/min. The retention time of 16 was 11.3 min with the preparative column. ESI-MS: calculated $[M+2H]^{2+}$ for 16 $C_{63}H_{93}N_{15}O_{10}$ 609.86; found $[M+3H]^{3+}$ 610.10.

Synthesis of cyclo[Phe-Tyr-Lys(iPr)-D-Arg-2Nal-D-Ser-D-Glu]-Lys(iPr) (17)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Ser(tBu)-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-Phe-OH (coupled twice) were sequentially coupled to the peptidyl resin following similar procedures. The —OAllyl protecting group. on D-Glu was removed using $Pd(PPh_3)_4$ (20 mg)/Phenylsilane (300 μL) in DCM (6 mL) (2×6 min at 35° C.). The $N^{\alpha}$-Fmoc on Phe was then removed, and cyclization was performed using DIC/HOBt in DMF (3×10 min at 90° C.). Following cyclization, the peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 15-35% acetonitrile (0.1% TFA) in $H_2O$ (0.1% TFA) in 20 mins at a flow rate of 30 mL/min. The retention time of 17 was 10.7 min with the preparative column. ESI-MS: calculated $[M+3H]^{3+}$ for 17 $C_{63}H_{93}N_{14}O_{11}$ 407.24; found [M+3H]3'⁰ 406.52.

Synthesis of cyclo[Phe-Tyr-Lys(iPr)-D-Arg-2Nal-D-Gln-D-Gu]-Lys(iPr) (18)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Gln(Trt)-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The $N^{\alpha}$-Fmoc on Phe was then removed, and cyclization was performed using DIC/HOBt in DMF (3×10 min at 90° C.). Following cyclization, the peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 17-37% acetonitrile (0.1% TFA) in $H_2O$ (0.1% TFA) in 20 mins at a flow rate of 30 mL/min. The retention time of 18 was 7.78 min with the preparative column. ESI-MS: calculated $[M+3H]^{3+}$ for 18 $C_{65}H_{96}N_{15}O_{10}$ 420.91; found $[M+3H]^{3+}$ 420.35.

Synthesis of cyclo[Phe-Tyr-Lys(iPr)-D-Arg-2Nal-D-Asn-D-Glu]-Lys(iPr) (19)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Asn(Trt)-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in $CH_2Cl_2$ (6 mL) (2×6 min at 35° C.). The $N^{\alpha}$-Fmoc on Phe was then removed, and cyclization was performed using DIC/HOBt in DMF (3×10 min at 90° C.). Following cyclization, the peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 15-35% acetonitrile (0.1% TFA) in $H_2O$ (0.1% TFA) in 20 mins at a flow rate of 30 mL/min. The retention time of 19 was 10.19 min with the preparative column. ESI-MS: calculated $[M+3H]^{3+}$ for 19 $C_{64}H_{94}N_{15}O_{11}$ 416.24; found $[M+3H]^{3+}$ 415.75.

Synthesis of cyclo[1Nal-Tyr-Lys(iPr)-D-Arg-2Nal-Gly-D-Glu]-Lys(iPr) (20)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-Gly-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-1-Nal-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The $N^{\alpha}$-Fmoc on 1Nal was then removed, and cyclization was performed using DIC/HOBt in DMF (3×10 min at 90° C.). Following cyclization, the peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 14-34% acetonitrile (0.1% TFA) in $H_2O$ (0.1% TFA) in 20 mins at a flow rate of 30 mL/min. The retention time of 20 was 14.9 min with the preparative column. ESI-MS: calculated $[M+2H]^{24}$for 20 $C_{66}H_{92}N_{14}O_{10}$ 620.36; found $[M+2H]^{2+}$ 620.77.

Synthesis of cyclo[Tyr-Tyr-Lys(iPr)-D-Arg-2Nal-Gly-D-Glu]-Lys(iPr) (21)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-Gly-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-Tyr(tBu)-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The NP-Fmoc on Tyr was then removed, and cyclization was performed using DIC/HOBt in DMF (3×10 min at 90° C.). Following cyclization, the peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 15-35% acetonitrile (0.1% TFA) in $H_2O$ (0.1% TFA) at a flow rate of 30 mL/min. The retention time of 21 was 15.1 min with the preparative column. ESI-MS: calculated $[M+2H]^{2+}$ for 21 $C_{62}H_{90}N_{14}O_{11}$ 603.35; found $[M+2H]^{2+}$ 603.99.

Synthesis of cyclo[Trp-Tyr-Lys(iPr)-D-Arg-2Nal-Gly-D-Glu]-Lys(iPr) (22)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-Gly-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-Trp(Boc)-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The $N^{\alpha}$-Fmoc on Trp was then removed, and cyclization was performed using DIC/HOBt in DMF (3×10 min at 90° C.). Following cyclization, the peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 16-36% acetonitrile (0.1% TFA) in $H_2O$ (0.1% TFA) in 20 mins at a flow rate of 30 mL/min. The retention time of 22 was 10.46 min with the preparative column. ESI-MS: calculated $[M+2H]^{2+}$ for 22 $C_{62}H_{90}N_{14}O_{11}$ 614.85; found $[M+2H]^{2+}$ 615.17.

Synthesis of cyclo(isoindole)[Phe-Tyr-Lys(iPr)-D-Arg-2-Nal-Gly-D-Cys]-Lys(iPr) (23)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. At a 0.05 mmol scale, Fmoc-D-Cys(Trt)-OH, Fmoc-Gly-OH (coupled twice), Fmoc-2-Nal-OH (coupled twice), Fmoc-D-Arg (Pbf)-OH (coupled twice), Fmoc-Lys(iPr, Boc)-OH, Fmoc-Tyr(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The $N^{\alpha}$-Fmoc on Phe was then removed, and cyclization was performed using DIC/HOBt in DMF (3×10 min at 90° C.). The peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The linear crude peptide (~0.5 mg) as a lyophilized powder in a 15 mL falcon tube was dissolved in 80 μL borate Buffer (pH-9-9.5) and 20 μL ortho-phthalaldehyde in EtOH (5×10-2M) was added. After 20 minutes, 0.5 μL of Formic Acid was added to the reaction mixture. The crude peptide was purified by HPLC using the semi-preparative column. ESI-MS: calculated $[M+H]^{+}$ for 23 $C_{68}H_{91}N_{14}O_9S$ 1279.7; found $[M+H]^{+}$ 1279.9.

Synthesis of cyclo(isoindole)[Phe-Tyr-Lys(iPr)-D-Arg-2-Nal-Gly-Cys]-Lys(iPr) (24)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. At a 0.05 mmol scale, Fmoc-Cys(Trt)-OH, Fmoc-Gly-OH (coupled twice), Fmoc-2-Nal-OH (coupled twice), Fmoc-D-Arg (Pbf)-OH (coupled twice), Fmoc-Lys(iPr, Boc)-OH, Fmoc-Tyr(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The NP-Fmoc on Phe was then removed, and cyclization was performed using DIC/HOBt in DMF (3×10 min at 90° C.). The peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The linear crude peptide (~0.5 mg) as a lyophilized powder in a 15 mL falcon tube was dissolved in 80 μL Borate Buffer (pH-9-9.5) and 20 μL ortho-phthalaldehyde in EtOH (5×10-2M) was added. After 20 minutes, 0.5 μL of Formic Acid was added to the reaction mixture. ESI-MS: calculated $[M+H]^{+}$ for 24 $C_{68}H_{91}N_{14}O_9S$ 1279.7; found $[M+H]^{+}$ 1279.9.

Synthesis of cyclo[Phe-Tyr-Lys(iPr)-D-Arg-(carboxy-m-carborane)Dap-Gly-D-Glu]-Lys(iPr) (25)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-Gly-OH (coupled twice), and Fmoc-Dap (Mtt)-OH were sequentially coupled to the peptidyl resin following similar procedures. The Mtt group was removed by three washes with DCM, followed by incubation with 2/1/97 TFA/TIS/DCM five times, then washed three times with DCM and then washed three times with DMF. The m-Carborane-1-carboxylic acid was coupled to the free amine group using a 3/3/6 equiv. of m-Carborane-1-carboxylic acid/HATU/DIEA in 2 mL DMF for 10 mins at 90° C. using microwave heating. After Fmoc deprotection, Fmoc-D-Arg(Pbf)-OH (coupled twice), Fmoc-Lys(iPr, Boc)-OH, Fmoc-Tyr(tBu)-OH, and Fmoc-Phe-OH (coupled twice) were sequentially coupled to the peptidyl resin. The —OAllyl protecting group on D-Glu was removed using $Pd(PPh_3)_4$ (20 mg)/Phenylsilane (300 μL) in DCM (6 mL) (2×6 min at 35° C.). The AlP-Fmoc on Phe was then removed, and cyclization was performed using DIC/HOBt in DMF (3×10 min at 90° C.). Following cyclization, the peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 17-3% acetonitrile (0.1% TFA) in $H_2O$ (0.1% TFA) in 20 mins at a flow rate of 30 mL/min. The retention time of 25 was 14.35 min with the preparative column. ESI-MS: calculated $[M+2H]^{2+}$ for 25 $C_{55}H_{94}B_{10}N_{15}O_{11}$ 624.41; found $[M+2H]^{2+}$ 625.50.

Synthesis of cyclo[Lys(Ac)-Tyr-Lys(iPr)-D-Arg-2Nal-Gly-D-Glu]-Lys(iPr) (26)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-Gly-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-Lys(ivDde)-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The $N^{\alpha}$-Fmoc on Lys(ivDde) was then removed, and cyclization was performed using DIC/HOBt in DMF (3×10 min at 90° C.). Following cyclization, the ivDde group was removed via adding 3 mL of 2% $N_2H_4$ in DMF for 5 minutes, with 5 cycles. The terminal amine was then acetylated using 0.1 w/v of 1-acetylimidazole in DMF for 30 minutes at room temperature. The peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 15-35% acetonitrile (0.1% TFA) in $H_2O$ (0.1% TFA) in 20 mins at a flow rate of 30 mL/min. The retention time of 26 was 8.1 min with the preparative column.

Synthesis of cyclo[Phe-D-Tyr-Lys(iPr)-DArg-2Nal-D-Ala-D-Glu]-Lys(iPr) (27)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Ala-OH (coupled twice), Fmoc-2-Nal-OH (coupled twice), Fmoc-D-Arg(Pbf)-OH (coupled twice), Fmoc-Lys(iPr, Boc)-OH, Fmoc-D-Tyr(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The $N^{\alpha}$-Fmoc on Phe was then removed, and cyclization was performed using DIC/HOBt in DMF (3×10 min at 90° C.). Following cyclization, the peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 14-34% acetonitrile (0.1% TFA) in $H_2O$ (0.1% TFA) in 20 mins at a flow rate of 30 mL/min. The retention time of 27 was 14.04 min with the preparative column. ESI-MS: calculated $[M+2H]^{2+}$ for 27 $C_{63}H_{91}N_{14}O_{10}$ 601.85; found $[M+2H]^{2+}$ 602.01.

Synthesis of cyclo[Phe-Tyr-Lys(iPr)-DArg-(4-NH$_2$)Phe-D-Ala-D-Glu]-Lys(iPr) (28)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Ala-OH (coupled twice), Fmoc-(4-NHBoc)Phe-OH (coupled twice), Fmoc-D-Arg(Pbf)-OH (coupled twice), Fmoc-Lys(iPr, Boc)-OH, Fmoc-Tyr(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The A-Fmoc on Phe was then removed, and cyclization was performed using DIC/HOBt in DMF (3×10 min at 90° C.). Following cyclization, the peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 14-34% acetonitrile (0.1% TFA) in $H_2O$ (0.1% TFA) in 20 mins at a flow rate of 30 mL/min. The retention time of 28 was 9.04 min with the preparative column. ESI-MS: calculated $[M+2H]^{2+}$ for 28 $C_{59}H_{91}N_{15}O_{10}$ 584.85; found $[M+2H]^{2+}$ 585.36.

Synthesis of cyclo[Phe-Tyr-Lys(iPr)-DArg-hTyr-D-Ala-D-Glu]-Lys(iPr) (29)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Ala-OH (coupled twice), Fmoc-hTyr-OH (coupled twice), Fmoc-D-Arg(Pbf)-OH (coupled twice), Fmoc-Lys(iPr, Boc)-OH, Fmoc-Tyr(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The $N^{\alpha}$-Fmoc on Phe was then removed, and cyclization was performed using DIC/HOBt in DMF (3×10 min at 90° C.). Following cyclization, the peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 14-34% acetonitrile (0.1% TFA) in $H_2O$ (0.1% TFA) in 20 mins at a flow rate of 30 mL/min. The retention time of 29 was 8.64 min with the preparative column. ESI-MS: calculated $[M+2H]^{2+}$ for 29 $C_{60}H_{92}N_{14}O_{11}$ 592.35; found $[M+2H]^{2+}$ 592.92.

Synthesis of cyclo[Phe-Tyr-Lys(iPr)-DArg-(COOH) Phe-D-Ala-D-Glu]-Lys(iPr) (30)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Ala-OH (coupled twice), Fmoc-p-carboxy-Phe(OtBu)-OH (coupled twice), Fmoc-D-Arg(Pbf)-OH (coupled twice), Fmoc-Lys(iPr, Boc)-OH, Fmoc-Tyr (tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The A-Fmoc on Phe was then removed, and cyclization was performed using DIC/HOBt in DMF (3×10 min at 90° C.). Following cyclization, the peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 12-32% acetonitrile (0.1% TFA) in $H_2O$ (0.1% TFA) in 20 mins at a flow rate of 30 mL/min. The retention time of 30 was 10.31 min with the preparative column. ESI-MS: calculated $[M+2H]^{2+}$ for 30 $C_{60}H_{90}N_{14}O_{12}$ 599.34; found $[M+2H]^{2+}$ 599.85.

Synthesis of cyclo[Phe-Tyr-Lys(iPr)-DArg-Thyronine-D-Ala-D-Glu]-Lys(iPr) (31)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Ala-OH (coupled twice), Fmoc-Thyronine-OH (coupled twice), Fmoc-D-Arg(Pbf)-OH (coupled twice), Fmoc-Lys(iPr, Boc)-OH, Fmoc-Tyr(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The $N^0$—Fmoc on Phe was then removed, and cyclization was performed using DIC/HOBt in DMF (3×10 min at 90° C.). Following cyclization, the peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 12-32% acetonitrile (0.1% TFA) in $H_2O$ (0.1% TFA) in 20 mins at a flow rate of 30 mL/min. The retention time of 31 was 10.31 min with the preparative column. ESI-MS: calculated $[M+2H]^{2+}$ for 31 $C_{60}H_{90}N_{14}O_{12}$ 631.36; found $[M+2H]^{2+}$ 632.11.

Synthesis of cyclo[Phe-Tyr-Arg(Me)-D-Arg-2Nal-D-Ala-D-Glu]-Lys(iPr) (32)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Ala-OH (coupled twice), Fmoc-2-Nal-OH (coupled twice), Fmoc-D-Arg(Pbf)-OH (coupled twice), Fmoc-Arg(Me,Pbf)-OH (coupled twice), Fmoc-Tyr(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The NA-Fmoc on Phe was then removed, and cyclization was performed using DIC/HOBt in DMF (3×10 min at 90° C.). Following cyclization, the peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 14-34% acetonitrile (0.1% TFA) in $H_2O$ (0.1% TFA) in 20 mins at a flow rate of 30 mL/min. The retention time of 32 was 12.55 min with the preparative column. ESI-MS: calculated $[M+2H]^{2+}$ for 32 $C_{61}H_{88}N_{16}O_{10}$ 602.35; found $[M+2H]^{2+}$ 602.98.

Synthesis of cyclo[Lys(Ac)-Gln-Lys(iPr)-D-Arg-2Nal-D-Ala-D-Glu]-Lys(iPr) (33)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Ala-OH (coupled twice), Fmoc-2-Nal-OH (coupled twice), Fmoc-D-Arg(Pbf)-OH (coupled twice), Fmoc-Lys(iPr, Boc)-OH, Fmoc-Gln(Trt)-OH, and Fmoc-Lys(ivDde)-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The $N^{\alpha}$-Fmoc on Lys(ivDde) was then removed, and cyclization was performed using DIC/HOBt in DMF (3×10 min at 90° C.). Following cyclization, the ivDde group was removed via adding 3 mL of 2% $N_2H_4$ in DMF for 5 minutes, with 5 cycles. The terminal amine was then acetylated using 0.1 w/v of 1-acetylimidazole in DMF for 30 minutes at room temperature. The peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 13-33% acetonitrile (0.1% TFA) in $H_2O$ (0.1% TFA) in 20 mins at a flow rate of 30 mL/min. The retention time of 33 was 7.61 min with the preparative column. ESI-MS: calculated $[M+2H]^{2+}$ for 33 $C_{58}H_{95}N_{16}O_{11}$ 595.87 found $[M+2H]^{2+}$ 595.54.

Synthesis of cyclo[Lys(Ac)-Glu-Lys(iPr)-D-Arg-2Nal-D-Ala-D-Glu]-Lys(iPr) (34)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Ala-OH (coupled twice), Fmoc-2-Nal-OH (coupled twice), Fmoc-D-Arg(Pbf)-OH (coupled twice), Fmoc-Lys(iPr, Boc)-OH, Fmoc-Glu(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The $N^{\alpha}$-Fmoc on Lys(ivDde) was then removed, and cyclization was performed using DIC/HOBt in DMF (3×10 min at 90° C.). Following cyclization, the ivDde group was removed via adding 3 mL of 2% $N_2H_4$ in DMF for 5 minutes, with 5 cycles. The terminal amine was then acetylated using 0.1 w/v of 1-acetylimidazole in DMF for 30 minutes at room temperature. The peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified using preparative HPLC. ESI-MS: calculated $[M+2H]^{2+}$ for 34 $C_{58}H_{94}N_{15}O_{12}$ 596.36; found $[M+2H]^{2+}$ 596.74.

Synthesis of cyclo[Phe-(4-$NH_2$)Phe-Lys(iPr)-D-Arg-2-Nal-D-Ala-D-Glu]-Lys(iPr) (35)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Ala-OH (coupled twice), Fmoc-2-Nal-OH (coupled twice), Fmoc-D-Arg(Pbf)-OH (coupled twice), Fmoc-Lys(iPr, Boc)-OH, Fmoc-4-NHBoc)Phe-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in $CH_2Cl_2$ (6 mL) (2×6 min at 35° C.). The $N^{\alpha}$-Fmoc on Phe was then removed, and cyclization was performed using DIC/HOBt in DMF (3×10 min at 90° C.). Following cyclization, the peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 11-31% acetonitrile (0.1% TFA) in $H_2O$ (0.1% TFA) in 20 mins at a flow rate of 30 mL/min. The retention time of 35 was 7.87 min with the preparative column. ESI-MS: calculated $[M+2H]^{2+}$ for 35 $C_{63}H_{93}N_{15}O_9$ 601.86; found $[M+2H]^{2+}$ 602.36.

Synthesis of cyclo[Lys(Ac)-Tyr-Lys(iPr)-D-Arg-Trp-D-Ala-D-Glu]-Lys(iPr) (36)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Ala-OH (coupled twice), Fmoc-Trp (Boc)-OH (coupled twice), Fmoc-D-Arg(Pbf)-OH (coupled twice), Fmoc-Lys(iPr, Boc)-OH, Fmoc-Tyr(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The NP-Fmoc on Lys(ivDde) was then removed, and cyclization was performed using DIC/HOBt in DMF (3×10 min at 90° C.). Following cyclization, the ivDde group was removed via adding 3 mL of 2% $N_2H_4$ in DMF for 5 minutes, with 5 cycles. The terminal amine was then acetylated using 0.1 w/v of 1-acetylimidazole in DMF for 30 minutes at room temperature. The peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. ESI-MS: calculated $[M+2H]^{2+}$ for 36 $C_{62}H_{97}$N15$O_{11}$ 613.87; found $[M+2H]^{2+}$ 613.81.

Synthesis of cyclo[Lys(D-Glu-Ac)-Tyr-Lys(iPr)-D-Arg-2Nal-D-Ala-D-Glu]-Lys(iPr) (37)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Ala-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The NP-Fmoc on Lys(ivDde) was then removed, and cyclization was performed using DIC/HOBt in DMF (3×10 min at 90° C.). Following cyclization, the ivDde group was removed via adding 3 mL of 2% $N_2H_4$ in DMF for 5 minutes, with 5 cycles. Fmoc-D-Glu(tBu)-OH was then coupled and the Fmoc group removed. The terminal amine was then acetylated using 0.1 w/v of 1-acetylimidazole in DMF for 30 minutes at room temperature. The peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 13-33% acetonitrile (0.1% TFA) in $H_2O$ (0.1% TFA) in 20 mins at a flow rate of 30 mL/min. The retention time of 37 was 9.76 min with the preparative column.

Synthesis of cyclo[Lys(Ac-D-Arg)-Tyr-Lys(iPr)-D-Arg-2Nal-D-Ala-D-Glu]-Lys(iPr) (38)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Ala-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The NP-Fmoc on Lys(ivDde) was then removed, and cyclization was performed using DIC/HOBt in DMF (3×10 min at 90° C.). Following cyclization, the ivDde group was removed via adding 3 mL of 2% $N_2H_4$ in DMF for 5 minutes, with 5 cycles. Fmoc-D-Arg(Pbf)-OH was then coupled and the Fmoc group removed. The terminal amine was then acetylated using 0.1 w/v of 1-acetylimidazole in DMF for 30 minutes at room temperature. The peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 12-32% acetonitrile (0.1% TFA) in $H_2O$ (0.1% TFA) in 20 mins at a flow rate of 25 mL/min. The retention time of 38 was 10.02 min with the preparative column. ESI-MS: calculated $[M+2H]^{2+}$ for 38 $C_{63}H_{109}N_{19}O_{12}$ 691.92; found $[M+2H]^{2+}$ 691.70. The term "Ac-D-Arg" refers to D-Arg that is N(alpha)-acetylated and C-terminally amide-bonded to the sidechain of Lys in position 1.

Synthesis of cyclo[Lys(Ac-D-Arg)-Tyr-Lys(iPr)-D-Arg-2Nal-D-Ala-D-Glu]-Lys(iPr) (39)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Ala-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The $N^{\alpha}$-Fmoc on Lys(ivDde) was then removed, and cyclization was performed using DIC/HOBt in DMF (3×10 min at 90° C.). Following cyclization, the ivDde group was removed via adding 3 mL of 2% $N_2H_4$ in DMF for 5 minutes, with 5 cycles. Fmoc-D-Ala-OH was then coupled and the Fmoc group removed. The terminal amine was then acetylated using 0.1 w/v of 1-acetylimidazole in DMF for 30 minutes at room temperature. The peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 15-35% acetonitrile (0.1% TFA) in $H_2O$ (0.1% TFA) in 20 mins at a flow rate of 30 mL/min. The retention time of 39 was 8.46 min with the preparative column. ESI-MS: calculated $[M+2H]^{2+}$ for 39 $C_{65}H_{102}N_{16}O_{12}$ 649.39; found $[M+2H]^{2+}$ 649.98.

Synthesis of cyclo[Lys(Ac-D-Phe)-Tyr-Lys(iPr)-D-Arg-2Nal-D-Ala-D-Glu]-Lys(iPr) (40)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Ala-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The $N^{\alpha}$-Fmoc on Lys(ivDde) was then removed, and cyclization was performed using DIC/HOBt in DMF (3×10 min at 90° C.). Following cyclization, the ivDde group was removed via adding 3 mL of 2% $N_2H_4$ in DMF for 5 minutes, with 5 cycles. Fmoc-D-Phe-OH was then coupled and the Fmoc group removed. The terminal amine was then acetylated using 0.1 w/v of 1-acetylimidazole in DMF for 30 minutes at room temperature. The peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 14-34% acetonitrile (0.1% TFA) in $H_2O$ (0.1% TFA) in 20 mins at a flow rate of 30 mL/min. The retention time of 40 was 12.51 min with the preparative column. ESI-MS: calculated $[M+2H]^{2+}$ for 40 $C_{71}H_{106}N_{16}O_{12}$ 687.41; found $[M+2H]^{2+}$ 687.01. Note that "Ac-D-Phe" refers to D-Phe that is N-acetylated and C-terminally amide-bonded to the side chain of Lys in position 1.

Synthesis of cyclo[Lys(CysAcid-CysAcid-CysAcid-DOTA-Ga)-Tyr-Lys(iPr)-D-Arg-2NaI-D-Ala-D-Glu]-Lys(iPr) (41)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Ala-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The $N^{\alpha}$-Fmoc on Lys was then removed, and cyclization was performed using DIC/HOBt in DMF (3×10 min at 90° C.). Following cyclization, the ivDde group was removed via adding 3 mL of 2% $N_2H_4$ in DMF for 5 minutes, with 5 cycles. Fmoc-CysAcid-OH was then coupled in succession three times. $DOTA(tBu)_3$ was then coupled at room temperature using HATU and DIEA in DMF using 4/4/8 equivalents. The peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The lyophilized powder was dissolved in 0.1 NaOAc buffer (4.2 pH) and to it was added 5 eq of $GaCl_3$. The solution was heated to 80° C. for 20 minutes and the crude peptide was directly purified by preparative HPLC using the preparative column eluted with 12.5-32.5% acetonitrile (0.1% TFA) in $H_2O$ (0.1% TFA) in 20 mins at a flow rate of 30 mL/min. The retention time of 41 was 9.33 min with the preparative column.

Synthesis of cyclo[Phe-Tyr-Lys(iPr)-D-Arg-2Nal-D-Ala-D-Glu]-Lys(iPr)-Lys(Glu-Ac) (42)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys (ivDde)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-Lys (iPr, Boc)-OH, Fmoc-D-Glu(OAll)-OH, Fmoc-D-Ala-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The $N^{\alpha}$-Fmoc on Phe was then removed, and cyclization was performed using DIC/HOBt in DMF (3×10 min at 90° C.). Following cyclization, the ivDde group was removed via adding 3 mL of 2% $N_2H_4$ in DMF for 5 minutes, with 5 cycles. Fmoc-Glu(tBu)-OH was then coupled. The terminal amine was then acetylated using 0.1 w/v of 1-acetylimidazole in DMF for 30 minutes at room temperature. The peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 16-36% acetonitrile (0.1% TFA) in $H_2O$ (0.1% TFA) in 20 mins at a flow rate of 30 mL/min. The retention time of 42 was 13.32 min with the preparative column.

Synthesis of cyclo[Phe-Tyr-Lys(iPr)-D-Arg-2Nal-D-Ala-D-Glu]-Lys(iPr)-Lys(Ac) (43)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys (ivDde)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-Lys (iPr, Boc)-OH, Fmoc-D-Glu(OAll)-OH, Fmoc-D-Ala-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The NP-Fmoc on Phe was then removed, and cyclization was performed using DIC/HOBt in DMF (3×10 min at 90° C.). Following cyclization, the ivDde group was removed via adding 3 mL of 2% $N_2H_4$ in DMF for 5 minutes, with 5 cycles. The terminal amine was then acetylated using 0.1 w/v of 1-acetylimidazole in DMF for 30 minutes at room temperature. The peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 16-36% acetonitrile (0.1% TFA) in $H_2O$ (0.1% TFA) in 20 mins at a flow rate of 30 mL/min. The retention time of 43 was 13.69 min with the preparative column.

Synthesis of cyclo[Phe-Tyr-Lys(iPr)-D-Arg-2Nal-D-Ala-D-Glu]-Lys(iPr)-Lys(Glu-Glu-Ac) (44)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys (ivDde)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-Lys (iPr, Boc)-OH, Fmoc-D-Glu(OAll)-OH, Fmoc-D-Ala-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The $N^{\alpha}$-Fmoc on Phe was then removed, and cyclization was performed using DIC/HOBt in DMF (3×10 min at 90° C.). Following cyclization, the ivDde group was removed via adding 3 mL of 2% $N_2H_4$ in DMF for 5 minutes, with 5 cycles. Two instances of Fmoc-Glu(tBu)-OH was then coupled. The terminal amine was then acetylated using 0.1 w/v of 1-acetylimidazole in DMF for 30 minutes at room temperature. The peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 13-33% acetonitrile (0.1% TFA) in $H_2O$ (0.1% TFA) in 20 mins at a flow rate of 30 mL/min. The retention time of 44 was 14.00 min with the preparative column.

Synthesis of cyclo[Phe-(4NH$_2$)Phe-Lys(iPr)-D-Arg-2Nal-Gly-D-Glu]-Lys(iPr)-Lys(Glu-Glu-Glu-DOTA-Ga) (45)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys (ivDde)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-Lys (iPr, Boc)-OH, Fmoc-D-Glu(OAll)-OH, Fmoc-Gly-OH (coupled twice), Fmoc-2-Nal-OH (coupled twice), Fmoc-D-Arg(Pbf)-OH (coupled twice), Fmoc-Lys(iPr, Boc)-OH, Fmoc-(4NHBoc)Phe-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The $N^{\alpha}$-Fmoc on Phe was then removed, and cyclization was performed using DIC/HOBt in DMF (3×10 min at 90° C.). Following cyclization, the ivDde group was removed via adding 3 mL of 2% $N_2H_4$ in DMF for 5 minutes, with 5 cycles. Three instances of Fmoc-Glu(tBu)-OH was then coupled. DOTA(tBu)$_3$ was then coupled at room temperature using HATU and DIEA in DMF using 4/4/8 equivalents. The peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The lyophilized powder was dissolved in 0.1 NaOAc buffer (4.2 pH) and to it was added 5 eq of $GaCl_3$. The solution was heated to 80° C. for 20 minutes and the crude peptide was directly purified by preparative HPLC using the preparative column eluted with 13-33% acetonitrile (0.1% TFA) in $H_2O$ (0.1% TFA) in 20 mins at a flow rate of 30 mL/min. The retention time of 45 was 8.11 min with the preparative column. ESI-MS: calculated $[M+2H]^{2+}$ for 45 $C_{99}H_{148}GaN_{24}O_{26}$ 1079.51; found $[M+2H]^{2}$. 1080.21.

Synthesis of cyclo[Phe-(4-NH$_2$)Phe-Lys(iPr)-D-Arg-2Nal-D-Ala-D-Glu]-Lys(iPr)-Lys(Glu-Glu-Glu-DOTA-Ga) (46)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys (ivDde)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-Lys (iPr,Boc)-OH, Fmoc-D-Glu(OAll)-OH, Fmoc-D-Ala-OH (coupled twice), Fmoc-2-Nal-OH (coupled twice), Fmoc-D-Arg(Pbf)-OH (coupled twice), Fmoc-Lys(iPr, Boc)-OH, Fmoc-(4—NHBoc)Phe-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in $CH_2Cl_2$ (6 mL) (2×6 min at 35° C.). The $N^{\alpha}$-Fmoc on Phe was then removed, and cyclization was performed using DIC/HOBt in DMF (3×10 min at 90° C.). Following cyclization, the ivDde group was removed via adding 3 mL of 2% $N_2H_4$ in DMF for 5 minutes, with 5 cycles. Three instances of Fmoc-Glu(tBu)-OH was then coupled. DOTA(tBu)$_3$ was then coupled at room temperature using HATU and DIEA in DMF using 4/4/8 equivalents. The peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The lyophilized powder was dissolved in 0.1 NaOAc buffer (4.2 pH) and to it was added 20 μL of a solution of 0.2 M $GaCl_3$. The solution was heated to 80° C. for 20 minutes and the crude peptide was directly purified by preparative HPLC using the preparative column eluted with 11-31% acetonitrile (0.1% TFA) in $H_2O$ (0.1% TFA) in 20 mins at a flow rate of 30 mL/min. The retention time of 46 was 10.91 min with the preparative column. ESI-MS: calculated $[M+2H]^{2+}$ for 46 $C_{100}H_{150}GaN_{24}O_{26}$ 1086.52; found $[M+2H]^{2+}$ 1086.94.

Synthesis of cyclo[Phe-Tyr-Lys(iPr)-D-Arg-2Nal-D-Ala-D-Glu]-Lys(iPr)-Lys(Glu-Glu-Glu-DOTA-Ga) (47)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys (ivDde)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-Lys (iPr, Boc)-OH, Fmoc-D-Glu(OAll)-OH, Fmoc-D-Ala-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The NP-Fmoc on Phe was then removed, and cyclization was performed using DIC/HOBt in DMF (3×10 min at 90° C.). Following cyclization, the ivDde group was removed via adding 3 mL of 2% $N_2H_4$ in DMF for 5 minutes, with 5 cycles. Three instances of Fmoc-Glu(tBu)-OH was then coupled. DOTA (tBu)$_3$ was then coupled at room temperature using HATU and DIEA in DMF using 4/4/8 equivalents. The peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The lyophilized powder was dissolved in 0.1 NaOAc buffer (4.2 pH) and to it was added 5 eq of $GaCl_3$. The solution was heated to 80° C. for 20 minutes and the crude peptide was directly purified by preparative HPLC using the preparative column eluted with 13-33% acetonitrile (0.1% TFA) in $H_2O$ (0.1% TFA) in 20 mins at a flow rate of 30 mL/min. The retention time of 47 was 12.00 min with the preparative column. ESI-MS: calculated $[M+2H]^{2+}$ for 47 $C_{100}H_{149}GaN_{23}O_{27}$ 1087.01; found $[M+2H]^{2+}$ 1086.97.

Synthesis of cyclo[Phe-hTyr-Lys(iPr)-D-Arg-2Nal-D-Ala-D-Glu]-Lys(iPr)-Lys(Glu-Glu-Glu-DOTA-Ga) (48)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(ivDde)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-Lys(iPr, Boc)-OH, Fmoc-D-Glu(OAll)-OH, Fmoc-D-Ala-OH (coupled twice), Fmoc-2-Nal-OH (coupled twice), Fmoc-D-Arg(Pbf)-OH (coupled twice), Fmoc-Lys(iPr, Boc)-OH, Fmoc-hTyr(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The $N^{\alpha}$-Fmoc on Phe was then removed, and cyclization was performed using DIC/HOBt in DMF (3×10 min at 90° C.). Following cyclization, the ivDde group was removed via adding 3 mL of 2% $N_2H_4$ in DMF for 5 minutes, with 5 cycles. Three instances of Fmoc-Glu(tBu)-OH was then coupled. DOTA(tBu)$_3$ was then coupled at room temperature using HATU and DIEA in DMF using 4/4/8 equivalents. The peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The lyophilized powder was dissolved in 0.1 NaOAc buffer (4.2 pH) and to it was added 5 eq of $GaCl_3$. The solution was heated to 80° C. for 20 minutes and the crude peptide was directly purified by preparative HPLC using the preparative column eluted with 13-33% acetonitrile (0.1% TFA) in $H_2O$ (0.1% TFA) in 20 mins at a flow rate of 30 mL/min. The retention time of 48 was 12.55 min with the preparative column.

Synthesis of cyclo(tryptathionine)[Tyr-Lys(iPr)-D-Arg-2Nal-D-Ala-D-Cys]-Lys(iPr) (49)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Cys(Trt)-OH, Fmoc-D-Ala-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, were sequentially coupled to the peptidyl resin following similar procedures. Next, the resin was suspended in a solution of Fmoc-Hpi-OH, HCTU, and NMM using 10/10/20 equivalents. The resin was then resuspended in TFA, agitated lightly with $N_2$ for 90 min. The TFA was then collected and enough TIS and $H_2O$ were added to make the final solution 95:2.5:2.5 TFA/TIS/H2O and the reaction was allowed to proceed for another 30 minutes. After filtration, the TFA was removed in vacuo and the peptide was precipitated by the addition of cold diethyl ether. After being allowed to dry in air, the precipitated peptide was dissolved in 0.1% Formic Acid $H_2O$/MeCN and purified by preparative HPLC.

Cyclo(isoindole Na-S)[Lys(Cys(Acid)-DOTA-Ga)-Tyr-Lys(iPr)-D-Arg-2-Nal-D-Ala-D-Cys]-Lys(iPr) (50)

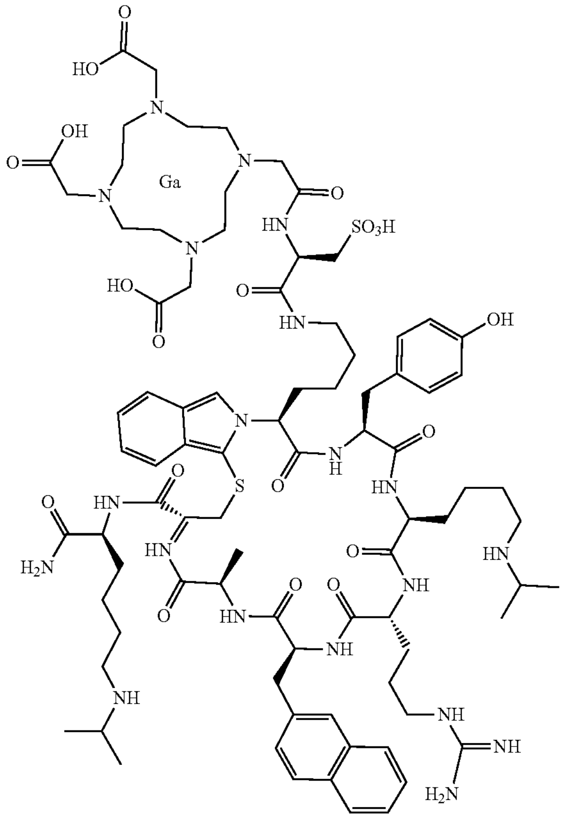

The linear peptide was synthesized using Liberty Blue automated microwave peptide synthesizer from CEM. At a 0.25 mmol scale, Fmoc-Rink Amide MBHA resin (CEM, 0.56 mmol/g) was deprotected with 20% v/v piperidine in DMF for 1 min at 90° C. and washed with DMF (3 mL×3). At a 1 mmol scale, Fmoc-Lys(iPr, Boc)-OH was conjugated to the Rink Amide MBHA resin using OxymaPure in DMF (1 M) and DIC in DMF (1 M) at 90° C. for 4 min. The Fmoc group was removed with 20% v/v piperidine in DMF for 1 min at 90° C. The resin was washed three times with DMF (3 mL) after deprotection. Fmoc-Cys(Trt)-OH, Fmoc-D-Ala-OH (coupled twice), Fmoc-2-Nal-OH (coupled twice), Fmoc-D-Arg(Pbf)-OH(coupled twice), Fmoc-Lys(iPr, Boc)-OH, Fmoc-Tyr(tBu)-OH were sequentially coupled to the peptidyl resin following similar procedures. After standard Fmoc-deprotection, Boc-Lys(Fmoc)-OH was coupled with HATU/HOAt/DIPEA using 4/4/8 equivalents in DMF for 4 min at 75° C. After removal of the Fmoc group, Fmoc-Cys(Acid)-OH was coupled to the side chain amine, followed by DOTA(tBu)$_3$ coupling at 75° C. using HATU/HOAt/DIPEA using 4/4/8 equivalents in DMF (2 mL). The peptide was deprotected and cleaved simultaneously from the resin by treating with a cocktail solution of 92.5/5/2.5 TFA/TIPS/$H_2O$ for 3 h at 35° C. After filtering off the resin, the crude peptide was precipitated by adding the crude solution to cold diethyl ether (10× vol. of the cleavage solution) dropwise. The crude peptide was washed twice with diethyl ether, vortexed and centrifuged. The washed crude peptide pellet was re-dissolved in 30% ACN in $H_2O$ (0.1% TFA) and lyophilized. crude peptide (~2 μmol, lyophilized, in a 15 mL falcon tube) was dissolved in HEPES (2 M, pH=5, 560 μL)

and $Ga(NO_2)_3$ in 1 M HCl (0.0282 M, 400 μL). The solution was transferred to a scintillation vial and heated in a commercial food microwave for 1 min at 20% power. $NaOH_{(aq)}$ (5M) was added to the solution until pH~8. Ortho-phthalaldehyde in EtOH (0.05M, 60 μL) was then added. The solution was vortexed and allowed to reaction at room temperature for 15 minutes. Reaction mixture then adjusted to pH~3-4 with Formic Acid and then directly purified using preparative HPLC eluted with 5-35% acetonitrile (0.1% FA) in $H_2O$ (0.1% FA) from 0 to 7.5 mins, then 35-100% acetonitrile (0.1% FA) in $H_2O$ (0.1% FA) in 7.5 to 8.0 mins. The retention time was 27.0 min. ESI-MS: calculated $[M+2H]^{2+}$ for 50 $C_{85}H_{123}GaN_{20}O_{20}S_2$ 939.9; found $[M+2H]^{2+}$ 940.6.

Cyclo(Me-isoindole Na-S)[Lys(Cys(Acid)-DOTA-Ga)-Tyr-Lys(iPr)-D-Arg-2-Nal-D-Ala-D-Cys]-Lys (iPr) (51)

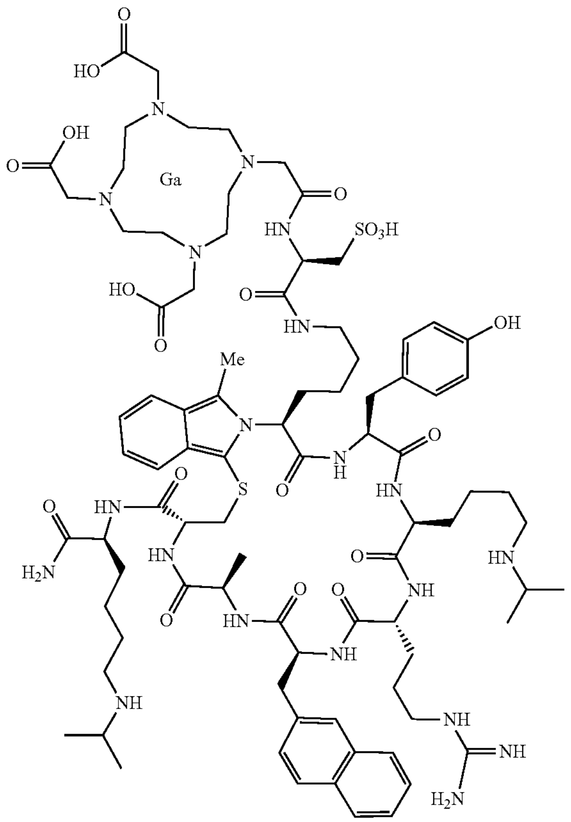

The linear peptide was synthesized using Liberty Blue automated microwave peptide synthesizer from CEM. At a 0.25 mmol scale, Fmoc-Rink Amide MBHA resin (CEM, 0.56 mmol/g) was deprotected with 20% v/v piperidine in DMF for 1 min at 90° C. and washed with DMF (3 mL×3). At a 1 mmol scale, Fmoc-Lys(iPr, Boc)-OH was conjugated to the Rink Amide MBHA resin using OxymaPure in DMF (1 M) and DIC in DMF (1 M) at 90° C. for 4 min. The Fmoc group was removed with 20% v/v piperidine in DMF for 1 min at 90° C. The resin was washed three times with DMF (3 mL) after deprotection. Fmoc-Cys(Trt)-OH, Fmoc-D-Ala-OH (coupled twice), Fmoc-2-Nal-OH (coupled twice), Fmoc-D-Arg(Pbf)-OH(coupled twice), Fmoc-Lys(iPr, Boc)-OH, Fmoc-Tyr(tBu)-OH were sequentially coupled to the peptidyl resin following similar procedures. After standard Fmoc-deprotection, Boc-Lys(Fmoc)-OH was coupled with HATU/HOAt/DIPEA using 4/4/8 equivalents in DMF for 4 min at 75° C. After removal of the Fmoc group, Fmoc-Cys (Acid)-OH was coupled to the side chain amine, followed by $DOTA(tBu)_3$ coupling at 75° C. using HATU/HOAt/DIPEA using 4/4/8 equivalents in DMF (2 mL). The peptide was deprotected and cleaved simultaneously from the resin by treating with a cocktail solution of 92.5/5/2.5 TFA/TIPS/$H_2O$ for 3 h at 35° C. After filtering off the resin, the crude peptide was precipitated by adding the crude solution to cold diethyl ether (10× vol. of the cleavage solution) dropwise. The crude peptide was washed twice with diethyl ether, vortexed and centrifuged. The washed crude peptide pellet was re-dissolved in 30% ACN in $H_2O$ (0.1% TFA) and lyophilized. crude peptide (~2 μmol, lyophilized, in a 15 mL falcon tube) was dissolved in HEPES (2 M, pH=5, 560 μL) and $Ga(NO_2)_3$ in 1 M HCl (0.0282 M, 400 μL). The solution was transferred to a scintillation vial and heated in a commercial food microwave for 1 min at 20% power. $NaOH_{(aq)}$ (5M) was added to the solution until pH ~8. Me-ortho-phthalaldehyde in EtOH (0.05M, 60 μL) was then added. The solution was vortexed and allowed to reaction at room temperature for 15 minutes. Reaction mixture then adjusted to pH~3-4 with Formic Acid and then directly purified using preparative HPLC eluted with 5-35% acetonitrile (0.1% FA) in $H_2O$ (0.1% FA) from 0 to 7.5 mins, then 35-100% acetonitrile (0.1% FA) in $H_2O$ (0.1% FA) in 7.5 to 8.0 mins. The retention time was 25.9 min. ESI-MS: calculated $[M+2H]^{2\prime}$ for 51 $C_{86}H_{125}GaN_{20}O_2OS_2$ 946.9; found $[M+2H]^{2+}$ 947.4.

Cyclo($NO_2$-isoindole Na-S)[Lys(Cys(Acid)-DOT A-Ga)-Tyr-Lys(iPr)-D-Arg-2-Nal-D-Ala-D-Cys]-Lys (iPr) (52)

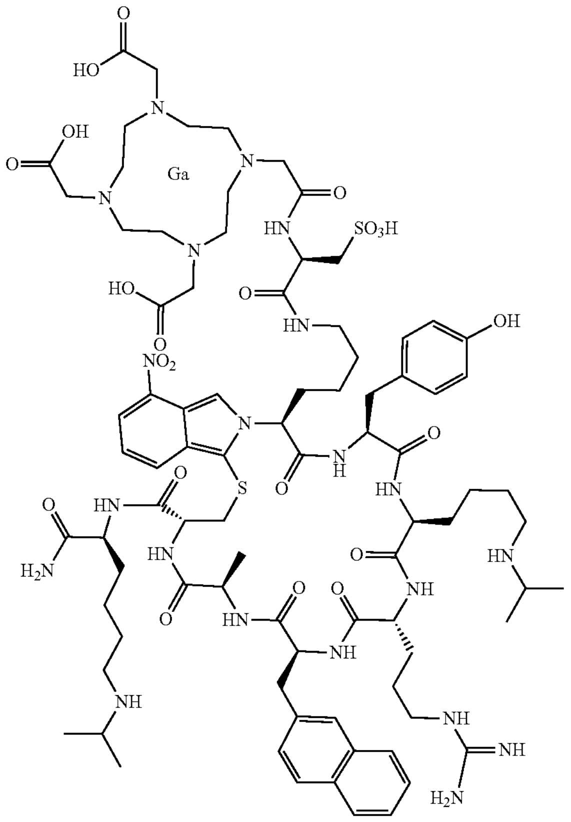

The linear peptide was synthesized using Liberty Blue automated microwave peptide synthesizer from CEM. At a 0.25 mmol scale, Fmoc-RinkAmide MBHA resin (CEM, 0.56 mmol/g) was deprotected with 20% v/v piperidine in DMF for 1 min at 90° C. and washed with DMF (3 mL×3). At a 1 mmol scale, Fmoc-Lys(iPr, Boc)-OH was conjugated to the Rink Amide MBHA resin using OxymaPure in DMF (1 M) and DIC in DMF (1 M) at 90° C. for 4 min. The Fmoc group was removed with 20% v/v piperidine in DMF for 1 min at 90° C. The resin was washed three times with DMF (3 mL) after deprotection. Fmoc-Cys(Trt)-OH, Fmoc-D-Ala-OH (coupled twice), Fmoc-2-Nal-OH (coupled twice), Fmoc-D-Arg(Pb)—OH(coupled twice), Fmoc-Lys(iPr, Boc)-OH, Fmoc-Tyr(tBu)-OH were sequentially coupled to the peptidyl resin following similar procedures. After standard Fmoc-deprotection, Boc-Lys(Fmoc)-OH was coupled with HATU/HOAt/DIPEA using 4/4/8 equivalents in DMF for 4 min at 75° C. After removal of the Fmoc group, Fmoc-Cys(Acid)-OH was coupled to the side chain amine, followed by DOTA(tBu)$_3$ coupling at 75° C. using HATU/HOAt/DIPEA using 4/4/8 equivalents in DMF (2 mL). The peptide was deprotected and cleaved simultaneously from the resin by treating with a cocktail solution of 92.5/5/2.5 TFA/TIPS/$H_2O$ for 3 h at 35° C. After filtering off the resin, the crude peptide was precipitated by adding the crude solution to cold diethyl ether (10× vol. of the cleavage solution) dropwise. The crude peptide was washed twice with diethyl ether, vortexed and centrifuged. The washed crude peptide pellet was re-dissolved in 30% ACN in $H_2O$ (0.1% TFA) and lyophilized. crude peptide (~2 μmol, lyophilized, in a 15 mL falcon tube) was dissolved in HEPES (2 M, pH=9, 400 μL), to which 3-nitro-ortho-phthalaldehyde in EtOH Solution (0.05M, 80 μL) was added. The solution was allowed to react overnight. The reaction mixture was then acidified with 1 M HCl(aq) to pH 4, Ga($NO_2$)$_3$ in 1 M HCl (0.0282M, 300 μL) added (pH~3) and then transferred to a scintillation vial and heated in a commercial food microwave for 1 min at 20% power. The reaction mixture was then directly purified using preparative HPLC eluted with 5-35% acetonitrile (0.1% FA) in $H_2O$ (0.1% FA) from 0 to 7.5 mins, then 35-100% acetonitrile (0.1% FA) in $H_2O$ (0.1% FA) in 7.5 to 8.0 mins. The retention time was 27.2 min. ESI-MS: calculated $[M+2H]^{2+}$ for 52 $C_{85}H_{122}GaN_{21}O_{22}S_2$ 962.4; found $[M+2H]^{2+}$ 963.1.

Cyclo($NO_2$-isoindole N-S)[Lys(Cys(Acid)-DOTA-Ga)-Tyr-Lys(iPr)-D-Arg-2Nal-D-Ala-D-hCys]-Lys (iPr) (53)

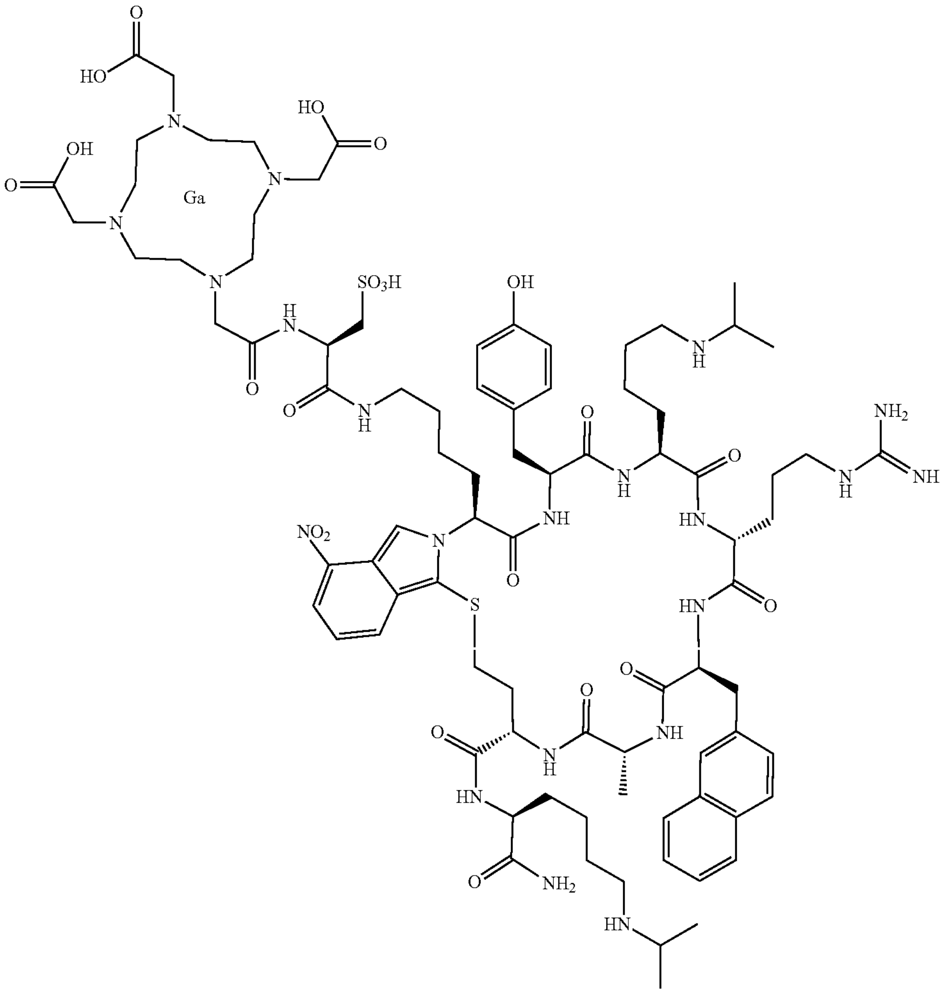

The linear peptide was synthesized using Liberty Blue automated microwave peptide synthesizer from CEM. At a 0.25 mmol scale, Fmoc-Rink Amide MBHA resin (CEM, 0.56 mmol/g) was deprotected with 20% v/v piperidine in DMF for 1 min at 90° C. and washed with DMF (3 mL×3). At a 1 mmol scale, Fmoc-Lys(iPr, Boc)-OH was conjugated to the Rink Amide MBHA resin using OxymaPure in DMF (1 M) and DIC in DMF (1 M) at 90° C. for 4 min. The Fmoc group was removed with 20% v/v piperidine in DMF for 1 min at 90° C. The resin was washed three times with DMF (3 mL) after deprotection. Fmoc-hCys(Trt)-OH, Fmoc-D-Ala-OH (coupled twice), Fmoc-2-Nal-OH (coupled twice), Fmoc-D-Arg(Pbf)-OH(coupled twice), Fmoc-Lys(iPr, Boc)-OH, Fmoc-Tyr(tBu)-OH were sequentially coupled to the peptidyl resin following similar procedures. After standard Fmoc-deprotection, Boc-Lys(Fmoc)-OH was coupled with HATU/HOAt/DIPEA using 4/4/8 equivalents in DMF for 4 min at 75° C. After removal of the Fmoc group, Fmoc-Cys (Acid)-OH was coupled to the side chain amine, followed by $DOTA(tBu)_3$ coupling at 75° C. using HATU/HOAt/DIPEA using 4/4/8 equivalents in DMF (2 mL). The peptide was deprotected and cleaved simultaneously from the resin by treating with a cocktail solution of 92.5/5/2.5 TFA/TIPS/$H_2O$ for 3 h at 35° C. After filtering off the resin, the crude peptide was precipitated by adding the crude solution to cold diethyl ether (10× vol. of the cleavage solution) dropwise. The crude peptide was washed twice with diethyl ether, vortexed and centrifuged. The washed crude peptide pellet was re-dissolved in 30% ACN in $H_2O$ (0.1% TFA) and lyophilized. crude peptide (~2 μmol, lyophilized, in a 15 mL falcon tube) was dissolved in HEPES (2 M, pH=9, 400 μL), to which 3-nitro-ortho-phthalaldehyde in EtOH Solution (0.05M, 80 μL) was added. The solution was allowed to react overnight. The reaction mixture was then acidified with 1 M HCl(aq) to pH ~4, $Ga(NO_2)_3$ in 1 M HCl (0.0282M, 300 μL) added (pH~3) and then transferred to a scintillation vial and heated in a commercial food microwave for 1 min at 20% power. The reaction mixture was then directly purified using preparative HPLC eluted with 5-35% acetonitrile (0.1% FA) in $H_2O$ (0.1% FA) from 0 to 7.5 mins, then 35-100% acetonitrile (0.1% FA) in $H_2O$ (0.1% FA) in 7.5 to 8.0 mins. The retention time was 27.6 min. ESI-MS: calculated $[M+2H]^{2+}$ for 53 $C_{86}H_{124}GaN_{21}O_{22}S_2$ 969.4; found $[M+2H]^{2+}$ 969.8.

Synthesis of cyclo[Lys($CysAcid_2$-DOTA-Ga)-Tyr-Lys(iPr)-D-Arg-2Nal-D-Ala-D-Glu]-Lys(iPr) (BL33) (55)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Ala-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-Lys(ivDde)-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in $CH_2Cl_2$ (6 mL) (2×6 min at 35° C.). The NP-Fmoc on Lys(ivDde) was then removed, and cyclization was performed using DIC/HOBt in DMF (3×10 min at 90° C.). Following cyclization, the ivDde group was removed via adding 3 mL of 2% $N_2H_4$ in DMF for 5 minutes, with 5 cycles. Fmoc-cysteic acid-OH was coupled (coupled twice) in two instances and the Fmoc group removed. $DOTA(tBu)_3$ was then coupled at room temperature using HATU and DIEA in DMF using 4/4/8 equivalents. The peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The lyophilized powder was dissolved in 0.1 NaOAc buffer (4.2 pH) and to it was added 20 μL of a solution of 0.2 M $GaCl_3$. The solution was heated to 80° C. for 20 minutes and the crude peptide was directly purified by preparative HPLC using the preparative column eluted with 14-34% acetonitrile (0.1% TFA) in $H_2O$ (0.1% TFA) in 20 mins at a flow rate of 30 mL/min. The retention time of Ga-BL33 was 7.71 min with the preparative column. ESI-MS: calculated $[M+2H]^{2+}$ for Ga-BL33 $C_{82}H_{129}GaN_{21}O_{25}S_2$ 970.40; found $[M+2H]^{2+}$ 970.97.

Synthesis of cyclo[Lys(CysAcid-DOTA)-Tyr-Lys(iPr)-D-Arg-2Nal-D-Ala-D-Glu]-Lys(iPr) (BL34) (56)

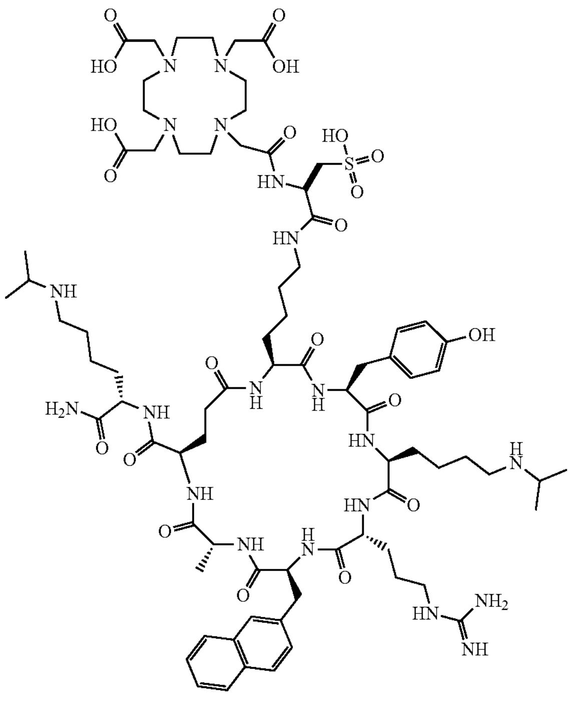 [SMILES: CC(C)NCCCC[C@H](NC(=O)[C@H]1CCC(=O)N[C@@H](CCCCNC(=O)[C@H](CS(=O)(=O)O)NC(=O)CN2CCN(CC(=O)O)CCN(CC(=O)O)CCN(CC(=O)O)CC2)C(=O)N[C@@H](Cc2ccc(O)cc2)C(=O)N[C@@H](CCCCNC(C)C)C(=O)N[C@H](CCCNC(=N)N)C(=O)N[C@@H](Cc2ccc3ccccc3c2)C(=O)N[C@H](C)C(=O)N1)C(N)=O]

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Ala-OH (coupled twice), Fmoc-2-Nal-OH (coupled twice), Fmoc-D-Arg(Pbt)-OH (coupled twice), Fmoc-Lys(iPr, Boc)-OH, Fmoc-Tyr(tBu)-OH, and Fmoc-Lys(ivDde)-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The $N^{\alpha}$-Fmoc on Lys(ivDde) was then removed, and cyclization was performed using DIC/HOBt in DMF (3×10 min at 90° C.). Following cyclization, the ivDde group was removed via adding 3 mL of 2% $N_2H_4$ in DMF for 5 minutes, with 5 cycles. Fmoc-CysAcid-OH was then coupled (coupled twice) to the terminal amine and the Fmoc group removed. DOTA(tBu)$_3$ was then coupled at room temperature using HATU and DIEA in DMF using 4/4/8 equivalents. The peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 12-32% acetonitrile (0.1% TFA) in $H_2O$ (0.1% TFA) in 20 mins at a flow rate of 30 mL/min. The retention time of BL34 was 9.19 min with the preparative column. ESI-MS: calculated $[M+2H]^{2+}$ for BL34 $C_{79}H_{123}N_{20}O_{21}S$ 861.46; found $[M+2H]^{2+}$ 861.98.

Synthesis of cyclo[Lys(CysAcid-DOTA-Ga)-Tyr-Lys(iPr)-D-Arg-2Nal-D-Ala-D-Glu]-Lys(iPr) (Ga-BL34) (57)

1.1 mg of BL34 (0.59 μmol) was dissolved in 0.1 NaOAc buffer (4.2 pH) and to it was added 5 eq of $GaCl_3$ (14.7 μL, 0.2 M, 2.93 μmol). The solution was heated to 80° C. for 20 minutes and the peptide was directly purified by preparative HPLC using the preparative column eluted with 12-32% acetonitrile (0.1% TFA) in $H_2O$ (0.1% TFA) in 20 mins at a flow rate of 30 mL/min. The retention time of Ga-BL34 was 9.64 min with the preparative column and produced 0.79 mg of Ga-BL34 (71% yield). ESI-MS: calculated $[M+2H]^{2+}$ for Ga-BL34 $C_{79}H_{124}GaN_{20}O_{21}S$ 894.91; found $[M+2H]^{2+}$ 891.33.

Synthesis of cyclo[Lys(CysAcid-DOTA-Lu)-Tyr-Lys(iPr)-D-Arg-2Nal-D-Ala-D-Glu]-Lys(iPr) (Lu-BL34) (58)

1.2 mg of BL34 (0.70 μmol) was dissolved in 0.1 NaOAc buffer (4.2 pH) and to it was added 5 eq of $LuCl_3$ (17.4 μL, 0.2 M, 3.48 μmol). The solution was heated to 80° C. for 20 minutes and the peptide was directly purified by preparative HPLC using the preparative column eluted with 12-32% acetonitrile (0.1% TFA) in $H_2O$ (0.1% TFA) in 20 mins at a flow rate of 30 mL/min. The retention time of Lu-BL34 was 9.71 min with the preparative column. ESI-MS: calculated $[M+2H]^{2+}$ for Lu-BL34 $C_{79}H_{123}LuN_{20}O_{21}S$ 947.41; found $[M+2H]^{2+}$ 947.91.

Synthesis of cyclo[Lys(CysAcid-DOTA)-(4-$NH_2$)Phe-Lys(iPr)-D-Arg-2Nal-Gly-D-Glu]-Lys(iPr) (BL36) (59)

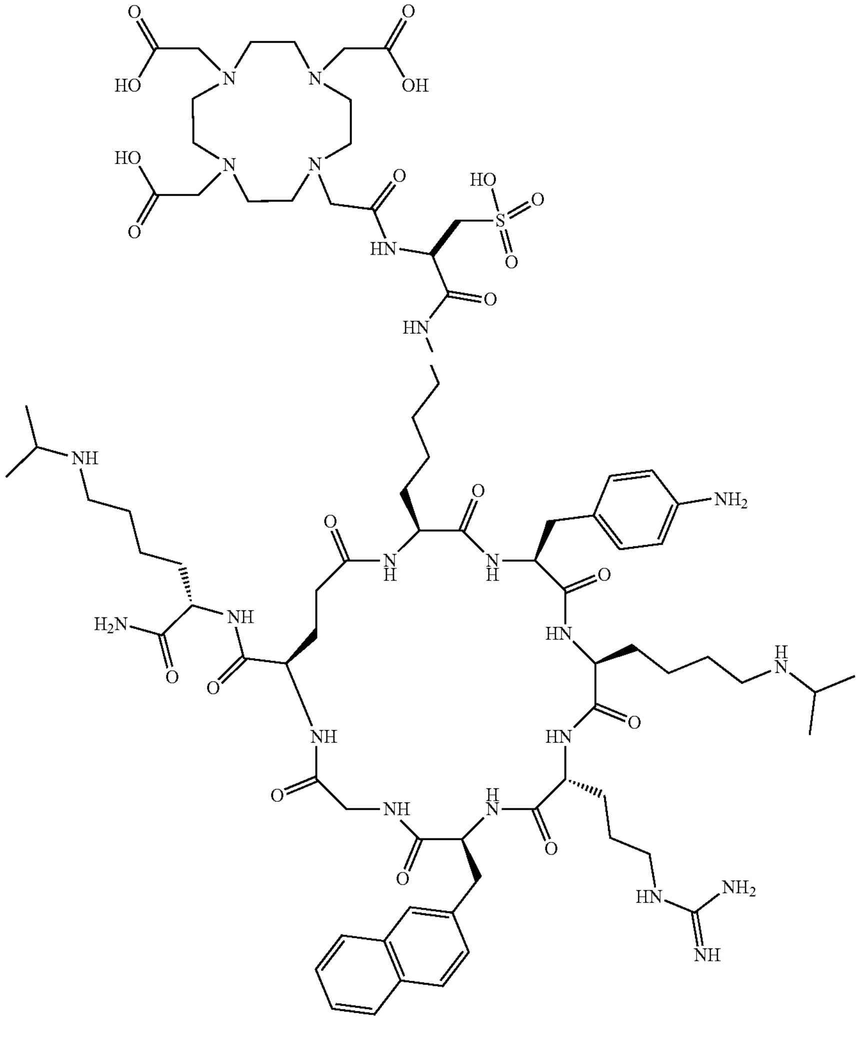

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-Gly-OH (coupled twice), Fmoc-2-Nal-OH (coupled twice), Fmoc-D-Arg(Pbf)-OH (coupled twice), Fmoc-Lys(iPr, Boc)-OH, Fmoc-(4-NHBoc)Phe-OH, and Fmoc-Lys(ivDde)-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in $CH_2Cl_2$ (6 mL) (2×6 min at 35° C.). The $N^{\alpha}$-Fmoc on Lys(ivDde) was then removed, and cyclization was performed using DIC/HOBt in DMF (3×10 min at 90° C.). Following cyclization, the ivDde group was removed via adding 3 mL of 2% $N_2H_4$ in DMF for 5 minutes, with 5 cycles. Fmoc-CysAcid-OH was coupled (coupled twice) and the Fmoc group removed. $DOTA(tBu)_3$was coupled at room temperature using HATU and DIEA in DMF using 4/4/8 equivalents. The peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude was dissolved in water, frozen, and lyophilized overnight. The crude peptide was purified by preparative HPLC using the preparative column eluted with 11-31% acetonitrile (0.1% TFA) in $H_2O$ (0.1% TFA) in 20 mins at a flow rate of 30 mL/min. The retention time of BL36 was 7.55 min with the preparative column. ESI-MS: calculated $[M+2H]^{2+}$ for BL36 $C_{78}H_{125}N_{21}O_{20}S$ 853.96; found $[M+2H]^{2+}$ 853.34

Synthesis of cyclo[Lys(CysAcid-DOTA)-(4-$NH_2$)Phe-Lys(iPr)-D-Arg-2Nal-Gly-D-Glu]-Lys(iPr) (Ga-BL36) (60)

1.5 mg of BL36 (0.87 μmol) was dissolved in 0.1 NaOAc buffer (4.2 pH) and to it was added 5 eq of $GaCl_3$ (21.8 μL, 0.2 M, 4.35 μmol). The solution was heated to 80° C. for 20 minutes and the peptide was directly purified by preparative HPLC using the preparative column eluted with 10-30% acetonitrile (0.1% TFA) in $H_2O$ (0.1% TFA) in 20 mins at a flow rate of 30 mL/min. The retention time of Ga-BL36 was 8.85 min with the preparative column and produced 1.21 mg of Ga-BL36 (77% yield). ESI-MS: calculated $[M+2H]^{2+}$ for Ga-BL36 $C_{78}H_{123}GaN_{21}O_{20}S$ 887.41; found $[M+2H]^{2+}$ 887.12.

Synthesis of cyclo[Lys(CysAcid-DOTA)-Tyr-Lys(iPr)-D-Arg-2Nal-D-Asn-D-Glu]-Lys(iPr) (BL37) (61)

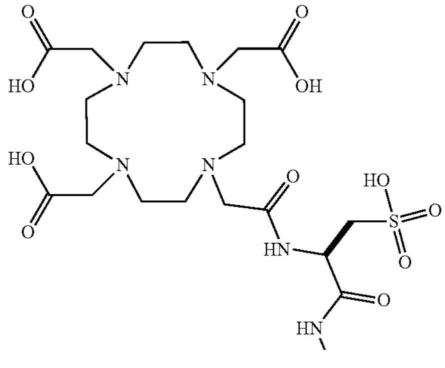

-continued

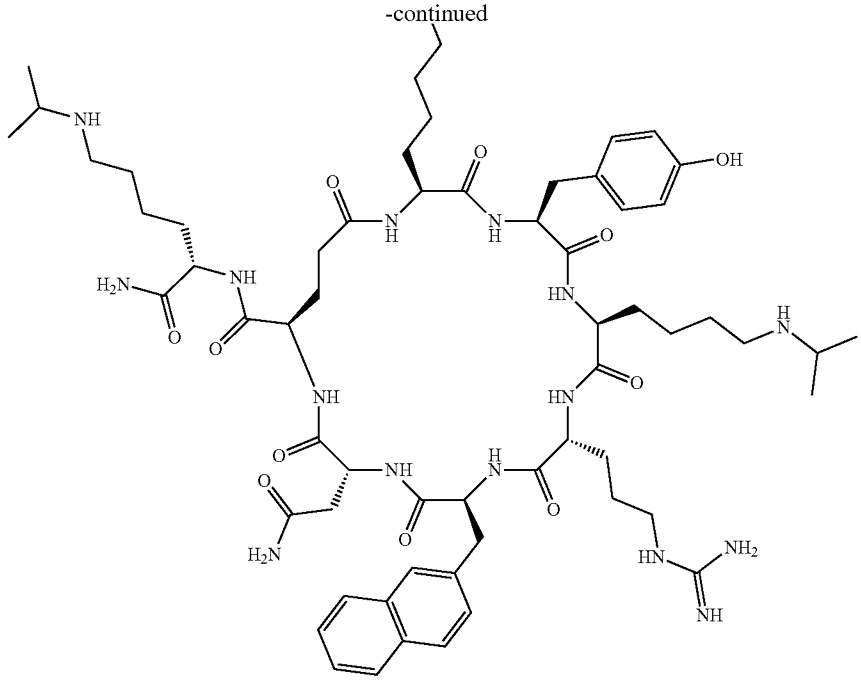

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Asn(Trt)-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-Lys(ivDde)-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in $CH_2Cl_2$ (6 mL) (2×6 min at 35° C.). The $N^{\alpha}$-Fmoc on Lys(ivDde) was then removed, and cyclization was performed using DIC/HOBt in DMF (3×10 min at 90° C.). Following cyclization, the ivDde group was removed via adding 3 mL of 2% $N_2H_4$ in DMF for 5 minutes, with 5 cycles. Fmoc-CysAcid-OH was coupled (coupled twice) and the Fmoc group removed. $DOTA(tBu)_3$was coupled at room temperature using HATU and DIEA in DMF using 4/4/8 equivalents. The peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude was dissolved in water, frozen, and lyophilized overnight. The crude peptide was purified by preparative HPLC using the preparative column eluted with 11-31% acetonitrile (0.1% TFA) in $H_2O$ (0.1% TFA) in 20 mins at a flow rate of 30 mL/min. The retention time of BL37 was 8.70 min with the preparative column. ESI-MS: calculated $[M+2H]^{2+}$ for BL37 $C_{80}H_{127}N_{21}O_{22}S$ 882.96; found $[M+2H]^{2+}$ 882.12.

Synthesis of cyclo[Lys(CysAcid-DOTA)-Tyr-Lys (iPr)-D-Arg-2Nal-D-Asn-D-Glu]-Lys(iPr) (Ga-BL37) (62)

1.1 mg of BL37 (0.62 μmol) was dissolved in 0.1 NaOAc buffer (4.2 pH) and to it was added 5 eq of $GaCl_3$ (15.6 μL, 0.2 M, 3.1 μmol). The solution was heated to 80° C. for 20 minutes and the peptide was directly purified by preparative HPLC using the preparative column eluted with 11-31% acetonitrile (0.1% TFA) in $H_2O$ (0.1% TFA) in 20 mins at a flow rate of 30 mL/min. The retention time of Ga-BL36 was 7.11 min with the preparative column and produced 0.91 mg of Ga-BL37 (80% yield). ESI-MS: calculated $[M+2H]^{2+}$ for Ga-BL37 $C_{80}H_{125}GaN_{21}O_{22}S$ 916.41; found $[M+2H]^{2+}$ 916.32.

Synthesis of cyclo[Phe-Tyr-Lys(iPr)-D-Arg-2Nal-D-Asn-D-Glu]-Lys(iPr)-Lys(CysAcid-DOTA) (BL38) (63)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys (ivDde)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-Lys (iPr, Boc)-OH, Fmoc-D-Glu(OAll)-OH, Fmoc-D-Asn(Trt)-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The $N^{\alpha}$-Fmoc on Phe was then removed, and cyclization was performed using DIC/HOBt in DMF (3×10 min at 90° C.). Following cyclization, the ivDde group was removed via adding 3 mL of 2% $N_2H_4$ in DMF for 5 minutes, with 5 cycles. Fmoc-CysAcid-OH was then coupled (coupled twice) and the Fmoc group removed. DOTA(tBu)$_3$ was then coupled at room temperature using HATU and DIEA in DMF using 4/4/8 equivalents. The peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 12-32% acetonitrile (0.1% TFA) in $H_2O$ (0.1% TFA) in 20 mins at a flow rate of 30 mL/min. The retention time of BL38 was 11.66 min with the preparative column.

Synthesis of cyclo[Phe-Tyr-Lys(iPr)-D-Arg-2Nal-D-Asn-D-Gu]-Lys(iPr)-Lys(CysAcid-DOTA) (Ga-BL38) (64)

1.2 mg of BL38 (0.63 μmol) was dissolved in 0.1 NaOAc buffer (4.2 pH) and to it was added 5 eq of $GaCl_3$ (21.8 μL, 0.2 M, 4.35 μmol). The solution was heated to 80° C. for 20 minutes and the peptide was directly purified by preparative HPLC using the preparative column eluted with 10-30% acetonitrile (0.1% TFA) in $H_2O$ (0.1% TFA) in 20 mins at a flow rate of 30 mL/min. The retention time of Ga-BL38 was 12.31 min with the preparative column and produced 0.9 mg of Ga-BL38 (74% yield). ESI-MS: calculated $[M+2H]^{2+}$ for Ga-BL38 $C_{89}H_{134}GaN_{22}O_{23}S$ 989.95; found $[M+2H]^{2+}$ 989.32.

Synthesis of cyclo[Phe-Tyr-Lys(iPr)-D-Arg-2Nal-D-Asn-D-Gu]-Lys(iPr)-Lys(CysAcid$_2$-DOTA) (BL39) (65)

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(ivDde)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-Lys(iPr, Boc)-OH, Fmoc-D-Glu(OAll)-OH, Fmoc-D-Asn(Trt)-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-Phe-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The $N^{\alpha}$-Fmoc on Phe was then removed, and cyclization was performed using DIC/HOBt in DMF (3×10 min at 90° C.). Following cyclization, the ivDde group was removed via adding 3 mL of 2% $N_2H_4$ in DMF for 5 minutes, with 5 cycles. Fmoc-CysAcid-OH was then coupled (coupled twice) in two instances and the Fmoc group removed. DOTA(tBu)$_3$was then coupled at room temperature using HATU and DIEA in DMF using 4/4/8 equivalents. The peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 12-32% acetonitrile (0.1% TFA) in $H_2O$ (0.1% TFA) in 20 mins at a flow rate of 30 mL/min. The retention time of BL39 was 12.18 min with the preparative column.

Synthesis of cyclo[Phe-Tyr-Lys(iPr)-D-Arg-2Nal-D-Asn-D-Glu]-Lys(iPr)-Lys(CysAcid$_2$-DOTA-Ga) (Ga-BL39) (66)

1.4 mg of BL39 (0.79 μmol) was dissolved in 0.1 NaOAc buffer (4.2 pH) and to it was added 5 eq of $GaCl_3$ (21.8 μL, 0.2 M, 4.35 μmol). The solution was heated to 80° C. for 20 minutes and the peptide was directly purified by preparative HPLC using the preparative column eluted with 10-30% acetonitrile (0.1% TFA) in $H_2O$ (0.1% TFA) in 20 mins at a flow rate of 30 mL/min. The retention time of Ga-BL36 was 12.57 min with the preparative column and produced 1.2 mg of Ga-BL39 (86% yield). ESI-MS: calculated $[M+2H]^{2+}$ for Ga-BL39 $C_{92}H_{139}GaN_{23}O_{27}S_2$ 1065.44; found $[M+2H]^{2+}$ 1065.98.

Synthesis of cyclo[Lys(CysAcid-amido-N,N-dimethyl-ammoniomethyl-trifluoroborate)-Tyr-Lys(iPr)-D-Arg-2Nal-D-Ala-D-Glu]-Lys(iPr) (PepBF$_3$—BL40) (67)

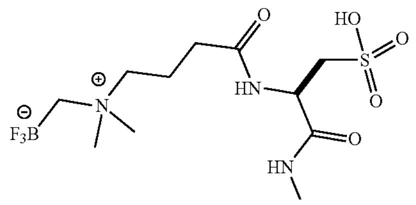

-continued

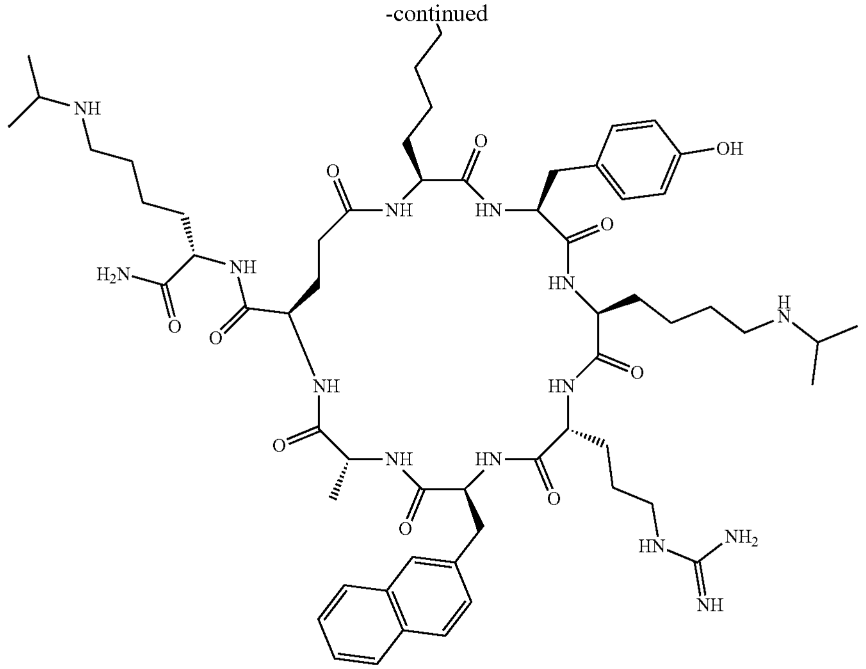

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Ala-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-Lys(ivDde)-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The $N^{\alpha}$-Fmoc on Lys(ivDde) was then removed, and cyclization was performed using DIC/HOBt in DMF (3×10 min at 90° C.). Following cyclization, the ivDde group was removed via adding 3 mL of 2% $N_2H_4$ in DMF for 5 minutes, with 5 cycles. Fmoc-CysAcid-OH was then coupled (coupled twice) and the Fmoc group removed. The resin was placed into a spin column and was swelled using degassed and freshly distilled DMF (10 mL) for 30 mins. The solution was then drained and rinsed with DCM. At a 0.025 mmol scale, (3-Carboxy-propyl)-N,N-dimethyl-ammoniummethyl-trifluoroborate (32 mg, 149 μmol) was dissolved in DMF (5 mL) and was transferred to the spin column. HBTU (54.5 mg, 144 μmol) was directly added to the bead solution followed by DIPEA (52 μL, 609 μmol). The mixture was mixed for 4 hours using a tube rotator. The solution was drained and rinsed with DCM, DMF, and DCM three times in 10 mL portions each followed by a rinse of $Et_2O$ and dried in vacuo for 30 minutes. The beads were transferred into a falcon tube and were suspended in 500 μL DCM and added with 50 μL TIPS, 10 μL $H_2O$, and a stir bar. $KHF_2$ (200 mg) was placed into a separate falcon tube. TFA (1 mL) was added to the falcon tube of $KHF_2$ using a hypodermic needle and 1 mL syringe. The tube was then sealed and sonicated until all the solids were observed to completely dissolve. After complete dissolution, the mixture was added to the falcon tube containing the beads. The mixture was stirred uncapped for 1 hour. Afterwards, the mixture was cooled then diluted with $H_2O$ (1 mL) in an ice bath followed by the slow addition of excess $NH_4OH$ until basic. ACN was then added to the mixture and the solution was filtered into a falcon tube and concentrated at low heat to remove the organic solvents. The resulting mixture was further diluted into water, frozen, and lyophilized to yield a white powder. This was then triturated with ACN and centrifuged, and was purified by preparative HPLC eluted with 8-18% acetonitrile (0.1% FA) in $H_2O$ (0.1% FA) in 15 mins at a flow rate of 30 mL/min. The retention time of $PepBF_3$—BL40 was 9.57 min with the preparative column. ESI-MS: calculated $[M+2H]^{2+}$ for $C_{70}H_{115}BF_3N_{17}O_{15}S$ 765.9; found $[M+2H]^{2+}$ 766.3.

Synthesis of cyclo[Lys(CysAcid-triazole-N,N-dimethyl-ammoniomethyl-trifluoroborate)-Tyr-Lys(iPr)-D-Arg-2Nal-D-Ala-D-Glu]-Lys(iPr) ($AMBF_3$-BL41) (68)

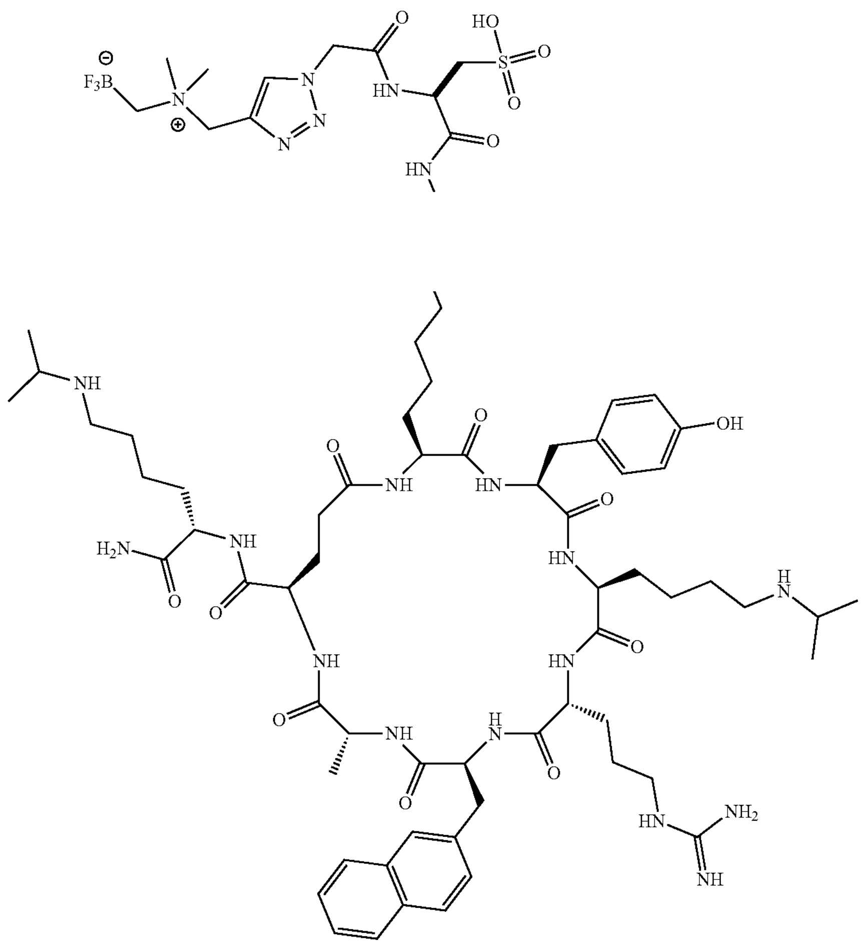

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Ala-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-Lys(ivDde)-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The $N^{\alpha}$-Fmoc on Lys(ivDde) was then removed, and cyclization was performed using DIC/HOBt in DMF (3×10 min at 90° C.). Following cyclization, the ivDde group was removed via adding 3 mL of 2% $N_2H_4$ in DMF for 5 minutes, with 5 cycles. Fmoc-CysAcid-OH was then coupled (coupled twice) and the Fmoc group removed. 2-Azidoacetic acid was then coupled at 50° C. using HATU and DIEA in DMF using 4/4/8 equivalents. The azido-peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the azido-peptide was precipitated by the addition of cold diethyl ether. The crude peptide was purified by preparative HPLC using the preparative column eluted with 13-33% acetonitrile (0.1% TFA) in $H_2O$ (0.1% TFA) in 20 mins at a flow rate of 30 mL/min. The retention time was 10.98 min with the preparative column. ESI-MS: calculated $[M+2H]^{2+}$ for the azido-peptide $C_{65}H_{101}N_{19}O_{15}S$ 709.87; found $[M+2H]^{2+}$ 710.58. The fractions containing the pure azido-peptide were collected and lyophilized and dissolved in 1 mL of $H_2O$. 5 μL of 1 M $CuSO_4$, 5 μL of 1 M N-propargyl-N,N-dimethylammoniomethyl-trifluoroborate, 500 μL of 0.1 M $NH_4OH$ solution, and 6 μL of 1 M sodium ascorbate were added sequentially and heated to 45° C. until the reaction mixture turned clear and starting material was consumed based on HPLC. The reaction mixture was purified again by HPLC using the preparative column eluted with 10-20% acetonitrile (0.1% FA) in $H_2O$ (0.1% FA) in 15 mins at a flow rate of 30 mL/min. The retention time was 6.22 min. ESI-MS: calculated $[M+2H]^{2+}$ for $AMBF_3$—BL41 $C_{71}H_{112}BF_3N_{20}O_{15}S$ 792.42; found $[M+2H]^2$+792.62.

Synthesis of cyclo[Lys(D-Arg-DOTA)-Tyr-Lys(iPr)-D-Arg-2Nal-D-Ala-D-Glu]-Lys(iPr) (BL42) (69)

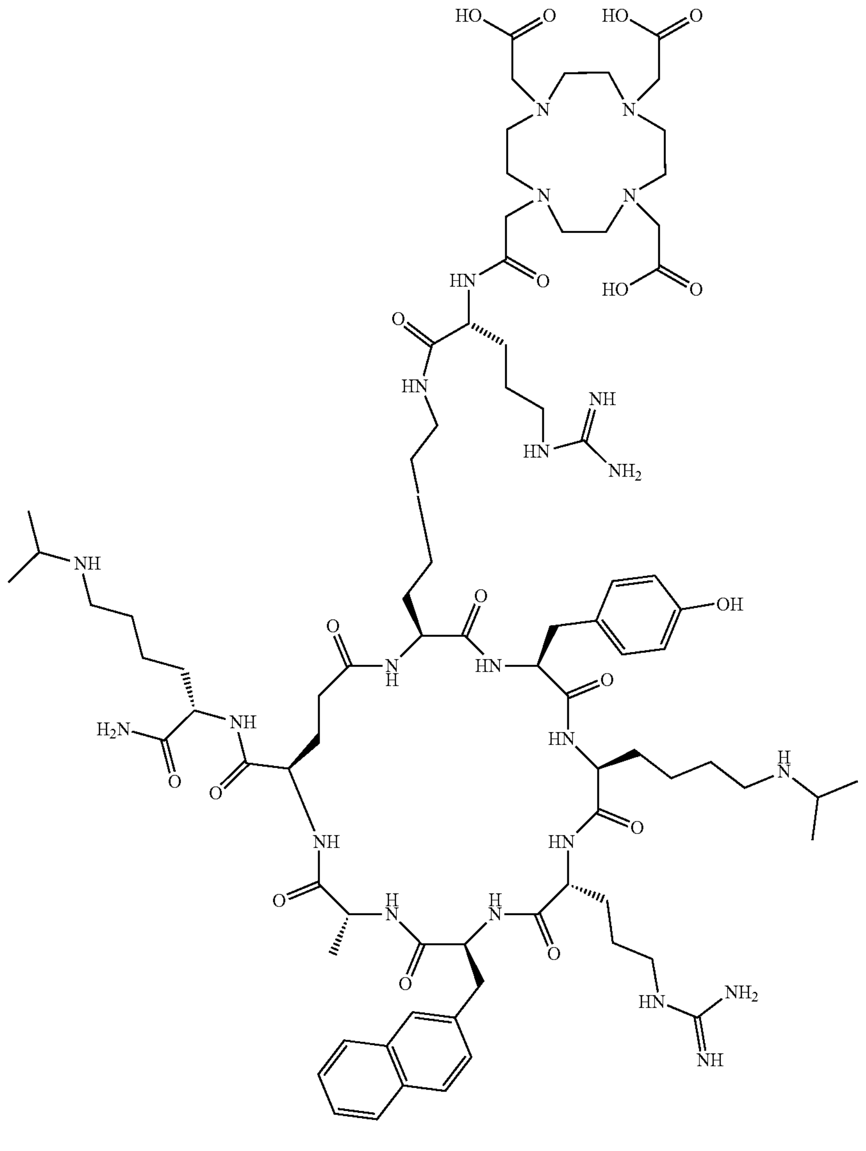 [SMILES: CC(C)NCCCC[C@H](NC(=O)[C@H]1CCC(=O)N[C@@H](CCCCNC(=O)[C@@H](CCCNC(=N)N)NC(=O)CN2CCN(CC(=O)O)CCN(CC(=O)O)CCN(CC(=O)O)CC2)C(=O)N[C@@H](Cc2ccc(O)cc2)C(=O)N[C@@H](CCCCNC(C)C)C(=O)N[C@H](CCCNC(=N)N)C(=O)N[C@@H](Cc2ccc3ccccc3c2)C(=O)N[C@H](C)C(=O)N1)C(N)=O]

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Ala-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-Lys(ivDde)-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The $N^{\alpha}$-Fmoc on Lys(ivDde) was then removed, and cyclization was performed using DIC/HOBt in DMF (3×10 min at 90° C.). Following cyclization, the ivDde group was removed via adding 3 mL of 2% $N_2H_4$ in DMF for 5 minutes, with 5 cycles. Fmoc-D-Arg(Pbf)-OH was then coupled (coupled twice) and the Fmoc group removed. $DOTA(tBu)_3$ was then coupled at room temperature using HATU and DIEA in DMF using 4/4/8 equivalents. The peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 11-31% acetonitrile (0.1% TFA) in $H_2O$ (0.1% TFA) in 20 mins at a flow rate of 30 mL/min. The retention time of BL42 was 10.08 min with the preparative column.

Synthesis of cyclo[Lys(D-Arg-DOTA-Ga)-Tyr-Lys(iPr)-D-Arg-2Nal-D-Ala-D-Glu]-Lys(iPr) (Ga-BL42) (70)

1.2 mg of BL42 (0.69 μmol) was dissolved in 0.1 NaOAc buffer (4.2 pH) and to it was added 5 eq of $GaCl_3$ (17.4 μL, 0.2 M, 3.47 μmol). The solution was heated to 80° C. for 20 minutes and the peptide was directly purified by preparative HPLC using the preparative column eluted with 11-31% acetonitrile (0.1% TFA) in $H_2O$ (0.1% TFA) in 20 mins at a flow rate of 30 mL/min. The retention time of Ga-BL42 was 10.18 min with the preparative column and produced 0.9 mg of Ga-BL42 (73% yield). ESI-MS: calculated $[M+2H]^{2+}$ for Ga-BL42 $C_{82}H_{131}GaN_{23}O_{18}$ 897.5; found $[M+2H]^{2+}$ 897.3.

Synthesis of cyclo[Lys(CysAcid-DOTA)-(3-I)Tyr-Lys(iPr)-D-Arg-2Nal-D-Ala-D-Glu]-Lys(iPr) (BL43) (71)

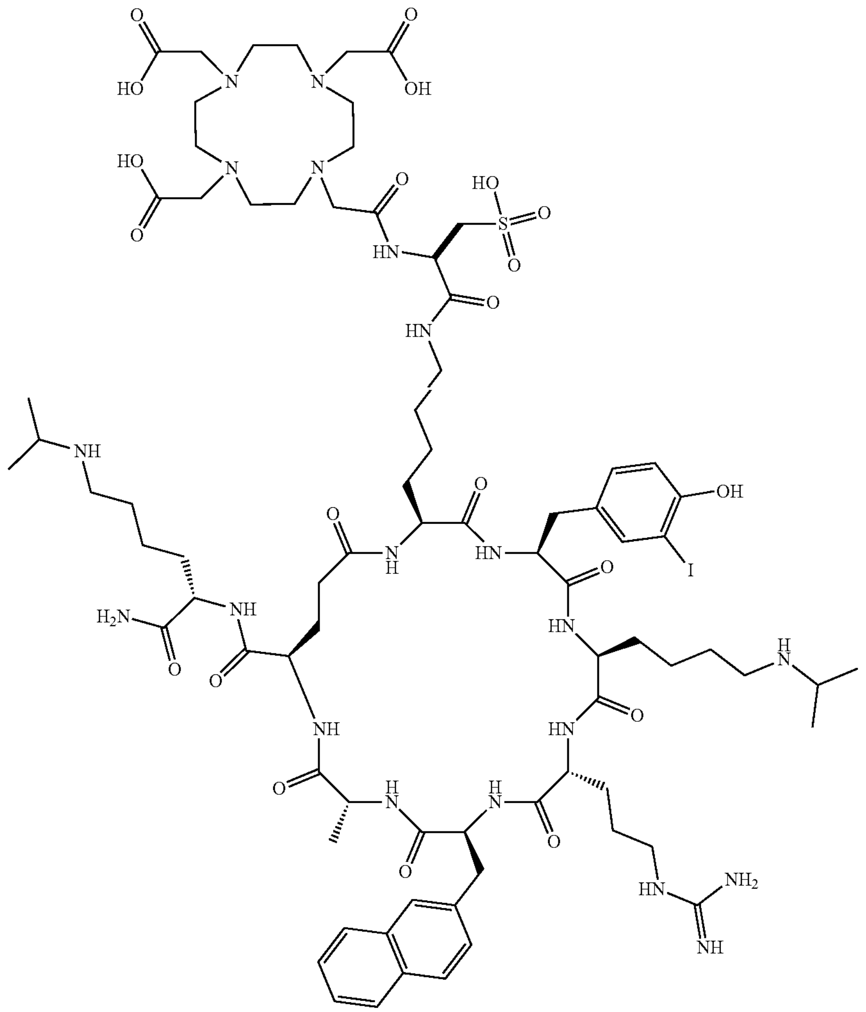 [SMILES: CC(C)NCCCC[C@H](NC(=O)[C@H]1CCC(=O)N[C@@H](CCCCNC(=O)[C@H](CS(=O)(=O)O)NC(=O)CN2CCN(CC(=O)O)CCN(CC(=O)O)CCN(CC(=O)O)CC2)C(=O)N[C@@H](Cc2ccc(O)c(I)c2)C(=O)N[C@@H](CCCCNC(C)C)C(=O)N[C@H](CCCNC(=N)N)C(=O)N[C@@H](Cc2ccc3ccccc3c2)C(=O)N[C@H](C)C(=O)N1)C(N)=O]

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Ala-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(3-I)—OH (coupled twice), and Fmoc-Lys(ivDde)-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The $N^{\alpha}$-Fmoc on Lys(ivDde) was then removed, and cyclization was performed using DIC/HOBt in DMF (3×10 min at 90° C.). Following cyclization, the ivDde group was removed via adding 3 mL of 2% $N_2H_4$ in DMF for 5 minutes, with 5 cycles. Fmoc-CysAcid-OH was then coupled (coupled twice) and the Fmoc group removed. $DOTA(tBu)_3$ was then coupled at room temperature using HATU and DIEA in DMF using 4/4/8 equivalents. The peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 12-32% acetonitrile (0.1% TFA) in $H_2O$ (0.1% TFA) in 20 mins at a flow rate of 30 mL/min. The retention time of BL43 was 11.63 min with the preparative column.

Synthesis of cyclo[Lys(CysAcid-DOTA-Ga)-(3-I) Tyr-Lys(iPr)-D-Arg-2Nal-D-Ala-D-Glu]-Lys(iPr) (Ga-BL43) (72)

0.8 mg of BL43 (0.43 μmol) was dissolved in 0.1 NaOAc buffer (4.2 pH) and to it was added 5 eq of $GaCl_3$ (10.8 μL, 0.2 M, 2.17 μmol). The solution was heated to 80° C. for 20 minutes and the peptide was directly purified by preparative HPLC using the preparative column eluted with 13-33% acetonitrile (0.1% TFA) in $H_2O$ (0.1% TFA) in 20 mins at a flow rate of 30 mL/min. The retention time of Ga-BL34 was 10.98 min with the preparative column and produced 0.8 mg of Ga-BL43 (97% yield). ESI-MS: calculated $[M+2H]^{2+}$ for Ga-BL43 $C_{79}H_{123}GaIN_{20}O_{21}S$ 957.9; found $[M+2H]^{2+}$ 957.8.

Synthesis of cyclo[Orn(CysAcid-DOTA)-Tyr-Lys (iPr)-D-Arg-2Nal-D-Ala-D-Glu]-Lys(iPr) (BL44) (73)

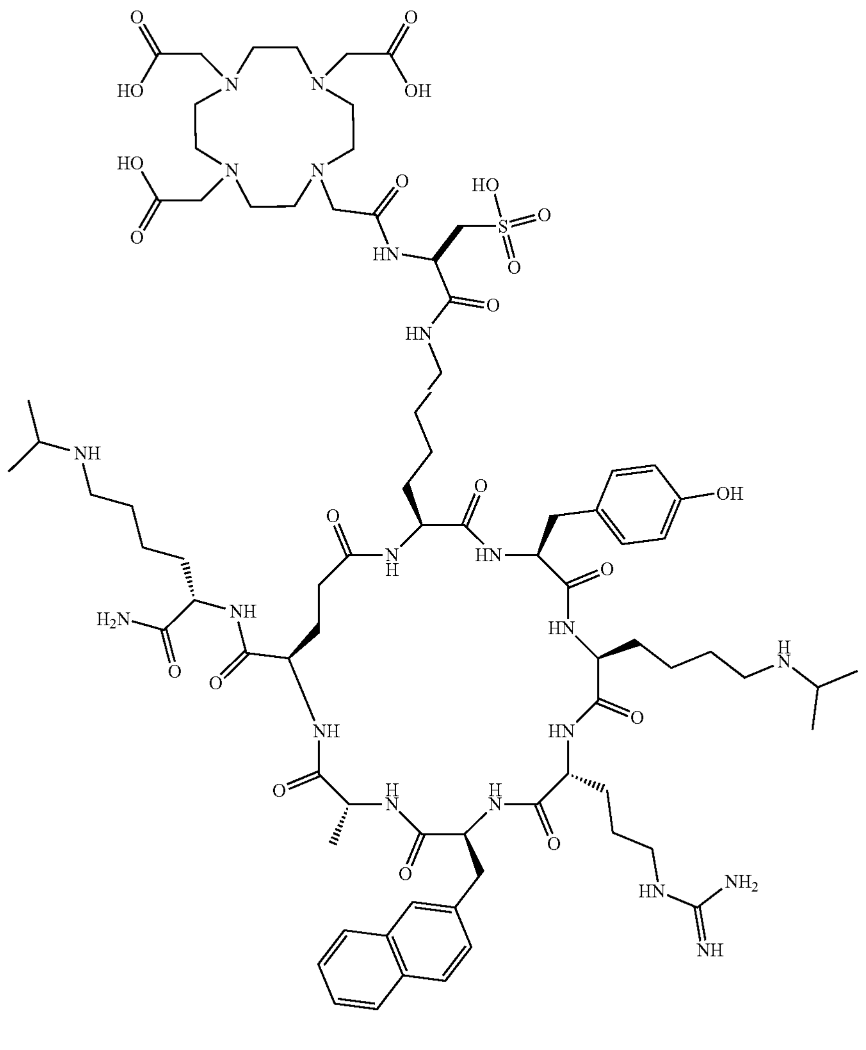 [SMILES: CC(C)NCCCC[C@H](NC(=O)[C@H]1CCC(=O)N[C@@H](CCCCNC(=O)[C@H](CS(=O)(=O)O)NC(=O)CN2CCN(CC(=O)O)CCN(CC(=O)O)CCN(CC(=O)O)CC2)C(=O)N[C@@H](Cc2ccc(O)cc2)C(=O)N[C@@H](CCCCNC(C)C)C(=O)N[C@H](CCCNC(=N)N)C(=O)N[C@@H](Cc2ccc3ccccc3c2)C(=O)N[C@H](C)C(=O)N1)C(N)=O]

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Ala-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-Orn(ivDde)-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The $N^{\alpha}$-Fmoc on Lys(ivDde) was then removed, and cyclization was performed using DIC/HOBt in DMF (3×10 min at 90° C.). Following cyclization, the ivDde group was removed via adding 3 mL of 2% $N_2H_4$ in DMF for 5 minutes, with 5 cycles. Fmoc-CysAcid-OH was then coupled (coupled twice) and the Fmoc group removed. $DOTA(tBu)_3$ was then coupled at room temperature using HATU and DIEA in DMF using 4/4/8 equivalents. The peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 12-32% acetonitrile (0.1% TFA) in $H_2O$ (0.1% TFA) in 20 mins at a flow rate of 30 mL/min. The retention time of BL44 was 9.24 min with the preparative column. ESI-MS: calculated $[M+2H]^{2+}$ for $C_{71}H_{124}N_{20}O_{21}S$ 854.45; found $[M+2H]^{2+}$ 854.98.

Synthesis of cyclo[Dap(CysAcid-DOTA)-Tyr-Lys (iPr)-D-Arg-2Nal-D-Ala-D-Glu]-Lys(iPr) (BL45) (74)

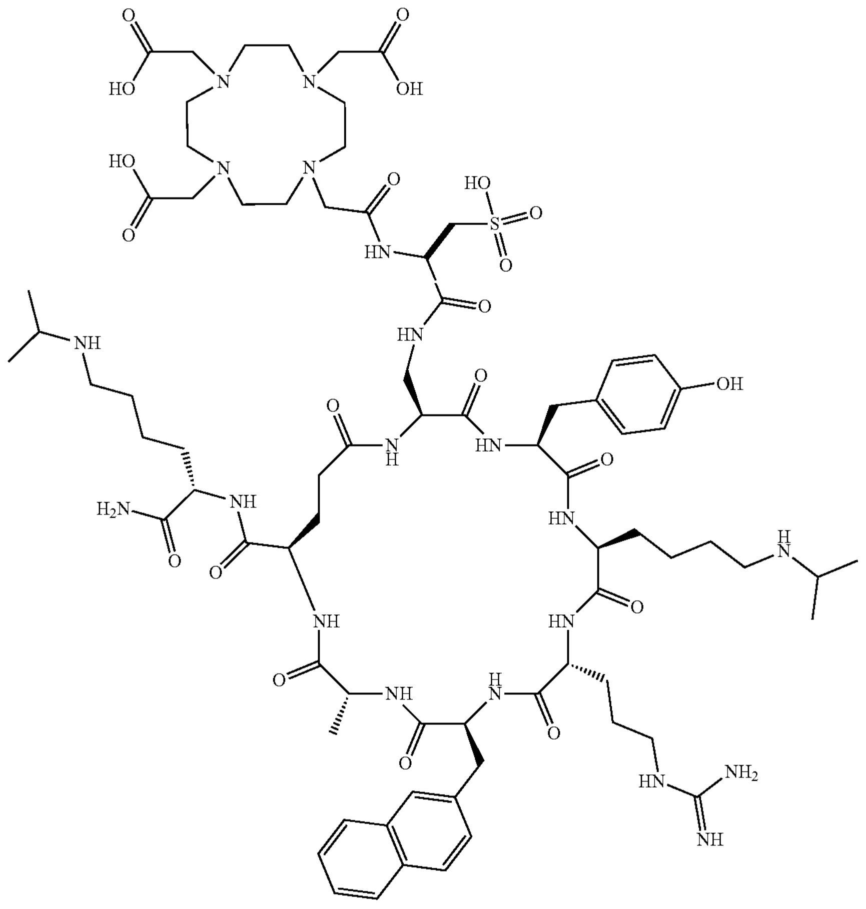 [SMILES: CC(C)NCCCC[C@H](NC(=O)[C@H]1CCC(=O)N[C@@H](CNC(=O)[C@H](CS(=O)(=O)O)NC(=O)CN2CCN(CC(=O)O)CCN(CC(=O)O)CCN(CC(=O)O)CC2)C(=O)N[C@@H](Cc2ccc(O)cc2)C(=O)N[C@@H](CCCCNC(C)C)C(=O)N[C@H](CCCNC(=N)N)C(=O)N[C@@H](Cc2ccc3ccccc3c2)C(=O)N[C@H](C)C(=O)N1)C(N)=O]

At a 0.1 mmol scale, Fmoc-Rink Amide MBHA resin (CEM, 0.56 mmol/g) was deprotected with 20% v/v piperidine in DMF for 1 min at 90° C. twice and washed with 3 mL of DMF 5 times. At a 0.02 mmol scale, Fmoc-Lys(iPr, Boc)-OH was then conjugated to the Rink Amide MBHA resin. The Fmoc group was removed with 20% v/v piperidine in DMF for 1 min at 90° C. The resin was washed three times with 3 mL DMF after each deprotection. Fmoc-D-Glu (OAll)-OH, Fmoc-D-Ala-OH (coupled twice), Fmoc-2-Nal-OH (coupled twice), Fmoc-D-Arg(Pbf)-OH (coupled twice), Fmoc-Lys(iPr, Boc)-OH, Fmoc-Tyr(tBu)-OH, and Fmoc-Dap(Mtt)-OH (coupled twice) were sequentially coupled to the peptidyl resin following similar procedures. The —OAllyl protecting group on D-Glu was removed using $Pd(PPh_3)_4$ (20 mg)/Phenylsilane (300 μL) in DCM (6 mL) (2×6 min at 35° C.). The $N^{\alpha}$-Fmoc on Dap(Mtt) was then removed, and cyclization was performed using DIC/HOBt in DMF (3×10 min at 90° C.). Following cyclization, the Mtt group was removed via adding 3 mL of 2/5/93 TFA/TIS/DCM for 5 minutes, with 5 cycles. Fmoc-CysAcid-OH was then coupled (coupled twice) and the Fmoc group removed. $DOTA(tBu)_3$ was then coupled at room temperature using HATU and DIEA in DMF using 4/4/8 equivalents. The peptide was deprotected and simultaneously cleaved from the resin by treating with a cocktail solution of 92.5/5/2.5 TFA/TIS/$H_2O$ for 3 h at 35° C. After filtration, the TFA was removed in vacuo and the peptide was precipitated by the addition of cold diethyl ether. The crude peptide was purified by preparative HPLC using the preparative column eluted with 12-32% acetonitrile (0.1% TFA) in $H_2O$ (0.1% TFA) in 20 mins at a flow rate of 30 mL/min. The retention time of BL45 was 9.85 min with the preparative column. ESI-MS: calculated $[M+2H]^{2+}$ for $C_{76}H_{120}N_{20}O_{21}S$ 840.43; found $[M+2H]^{2+}$ 840.49.

Cell Culture

The Z138 mantle cell lymphoma cell line was given by Dr. Christian Steidl (BC Cancer) as a gift. The CHO:CXCR4 cell line was given by Drs. David McDermott and Xiaoyuan Chen (National Institutes of Health) as a gift. The cell line was cultured in a 5% $CO_2$ atmosphere at 37° C. in a humidified incubator. The Z138 cells were incubated with IMDM medium (Life Technologies Corporations) and the CHO:CXCR4 cells were incubated with F12K medium (Life Technologies Corporations), both of which were supplemented with 10% fetal bovine serum (Sigma-Aldrich), 100 I.U./mL penicillin, and 100 μg/mL streptomycin (Penicillin-Streptomycin Solution).

Competitive Binding Assay

CHO:CXCR4 cells were seeded at a density of $1\times10^5$ cells/well in 24-well poly-D-lysine coated plates (Corning BioCoat) and incubated with [$^{125}$1]SDF-1α (0.01 nM, PerkinElmer) and competing nonradioactive ligands (1 μM to 0.1 μM). The cells, radioligand, and competing peptides were incubated for 1 h at 27° C. with moderate shaking. Following the incubation period, the supernatant was aspirated, followed by three washes with 1 mL of ice-cold PBS. Cells were harvested with 200 μL of trypsin and counted on a y counter. Data were plotted in GraphPad Prism 7 to determine $IC_{50}$ values (GraphPad Software, Inc., La Jolla, CA). The values are reported as mean±standard deviation. Results for a subset of compounds are shown in Table 5.

Radiolabeling $^{68}$Ga-Labeling: [$^{68}$Ga]$GaCl_3$ was eluted from an iThemba Labs generator with a total of 4 mL of 0.1 M HCl. The eluted [$^{68}$Ga]$GaCl_3$ solution was added to 2 mL of concentrated HCl. This radioactive mixture was then added to a DGA resin column and washed with 3 mL of 5 M HCl. The column was then dried with air and the [$^{68}$Ga]$GaCl_3$ (0.10-0.50 GBq) was eluted with 0.5 mL of water into a vial containing a solution of the unlabeled precursor (25 μg) in 0.7 mL HEPES buffer (2 M, pH 5.3). The reaction mixture was heated in a microwave oven (Danby; DMW7700WDB) for 1 min at power setting 2. The mixture was purified by semi-prep HPLC and quality control was performed via analytical HPLC with the co-injection of the unlabeled standard with a one-twelfth of the radiotracer. Radiochemical yields (decay-corrected) were >50% and radiochemical purities were >95%.

$^{177}$Lu-Labeling:

[$^{177}$Lu]$LuCl_3$ was purchased from ITM Isotopen Technologien Munchen AG. [$^{177}$Lu]$LuCl_3$ (0.1-3.0 GBq) in 0.04 M HCl (10-300 μL) was added to a solution of the unlabeled precursor (25 μg) in 0.5 mL of NaOAc buffer (0.1 M, pH 4.5). The reaction mixture was incubated at 100° C. for 15 min. The mixture was purified by semi-prep HPLC and quality control was performed via analytical HPLC with the co-injection of the unlabeled standard with a one-twelfth of the radiotracer. Radiochemical yields (decay-corrected) were >50% and radiochemical purities were >95%.

Animal Model

Animal experiments were performed in accordance with guidelines established by the Canadian Council on Animal Care, under a research protocol approved by the Animal Ethics Committee of the University of British Columbia. For all studies, male NOD.Cg-Rag1tm1Momll2rgtm1Wjl/SzJ (NRG) mice were used and cells injected in a 100 μL solution of 1:1 ratio of PBS/Matrigel. For preclinical imaging and biodistribution studies, $5\times10^6$ cells of Z138, cells were subcutaneously inoculated on the left or right flank and tumors were grown to a size of 200-300 $mm^3$. For radionuclide therapy studies, $4\times10^6$Z138 cells (p.n. 5-10) were subcutaneously inoculated on the left flank and grown for 19 days.

PET/CT Imaging

PET and CT scans were performed on a Siemens Inveon microPET/CT. Tumor-bearing mice were briefly sedated with isoflurane (2-2.5% isoflurane in 2 L/min 02) for i.v. injection of 4-7 MBq of [$^{68}$Ga]Ga-BL34. The animals were allowed to roam freely during the uptake period (50 or 110 minutes), after which they were sedated and scanned. The CT scan was obtained for attenuation correction and anatomical localization (80 kV; 500 μA; 3 bed positions; 34% overlap; 220° continuous rotation) followed by a 10 min PET acquisition at 1 or 2 h p.i. of the radiotracer. PET data were acquired in list mode, reconstructed using 3-dimensional ordered-subsets expectation maximization (2 iterations) followed by a fast maximum a priori algorithm (18 iterations) with CT-based attenuation correction. Images were analyzed using the Inveon Research Workplace software (Siemens Healthineers). Results for compound BL34 is shown in FIG. 1.

SPECT/CT Imaging

The CT scan was performed first, at 60 kV and 615 μA. The SPECT scan was performed via a 60 min static emission scan acquired in list mode using the U-SPECT II scanner (MILabs), equipped with an extra ultra-high sensitivity big mouse (2 mm pinhole size) collimator. The imaging dataset was reconstructed via the U-SPECT 11 software with a 20% window width on three energy windows. The photopeak window was centered at 208 keV, with the lower and upper scatter windows at 187.2 and 228.8 keV, respectively. The images were reconstructed using the ordered subset expectation maximization algorithm (4 iterations, 32 subsets) and a 1 mm post-processing Gaussian filter (collimator dependent calibration factor=10012.659). Images were decay corrected to the injection time in PMOD (PMOD Technologies) and then converted to DICOM for qualitative visualization in the Inveon Research Workplace software (Siemens Medical Solutions US).

Biodistribution Studies

Under brief isoflurane sedation (2-2.5% isoflurane in 2 L/min $O_2$) for the injection only, the mice were injected intravenously with 0.8-3.0 MBq of the radiotracer, allowed to roam freely afterwards in their cage, and euthanized at the selected timepoints. Additional groups of mice received 7.5 μg (0.25-0.3 mg/kg) LY2510924 as a blocking control i.p. 15 min before radiotracer injection and euthanized 1 h p.i.

Radioligand Therapy Studies

When the Z138 xenografts had grown to a volume of 500±180 $mm^3$, the mice were randomized into two groups (n=8 each). Z138 xenograft mice were briefly sedated (2-2.5% isoflurane in 2 L/min $O_2$) and injected with either [$^{177}$Lu]Lu-BL34 or PBS (100 μL). Both treatment groups were longitudinally monitored for tumor volume, body weight, and behaviour every other day until 60 days or until mice reached the volume endpoint (>1500 $mm^3$), loss of body weight (>15%) or unwell behavioural signs (e.g. lethargy, loss of appetite). Tumors were measured using a Biopticon Imager 2.

TABLE 5

Binding Affinity of Select Peptides to CXCR4

| Peptide | $IC_{50}$ (nM) |
|---|---|
| cyclo[Phe-Tyr-Lys(iPr)-D-Arg-2Nal-D-Gln-D-Glu]-Lys(iPr) | 1-10 |
| cyclo[Phe-(3-I)Tyr-Lys(iPr)-D-Arg-2-Nal-Gly-D-Glu]-Lys(iPr) | 10-50 |
| cyclo[Phe-Tyr-Lys(iPr)-D-Arg-2Nal-D-Ala-D-Glu]-Lys(iPr) | 1-10 |

TABLE 5-continued

| Binding Affinity of Select Peptides to CXCR4 | |
|---|---|
| Peptide | $IC_{50}$ (nM) |
| cyclo[Phe-(4-$NH_2$)Phe-Lys(iPr)-D-Arg-2-Nal-Gly-D-Glu]-Lys(iPr) | 1-10 |
| cyclo[Phe-(4-$NO_2$)Phe-Lys(iPr)-D-Arg-2-Nal-Gly-D-Glu]-Lys(iPr) | 10-50 |
| cyclo[Phe-hTyr-Lys(iPr)-D-Arg-2-Nal-Gly-D-Glu]-Lys(iPr) | 1-10 |
| cyclo[Phe-hTyr-Lys(iPr)-D-Arg-2-Nal-D-Ala-D-Glu]-Lys(iPr) | 50-100 |
| cyclo[Phe-(4-$NH_2$)Phe-Lys(iPr)-D-Arg-2-Nal-D-Ala-D-Glu]-Lys(iPr) | 10-50 |
| cyclo[Lys(Ac)-Tyr-Lys(iPr)-D-Arg-Trp-D-Ala-D-Glu]-Lys(iPr) | 10-50 |
| cyclo[Phe-Tyr-Lys(iPr)-D-Arg-(4-$NH_2$)Phe-D-Ala-D-Glu]-Lys(iPr) | 10-50 |
| cyclo[Lys(Ac)-Glu-Lys(iPr)-D-Arg-2Nal-D-Ala-D-Glu]-Lys(iPr) | 50-100 |
| cyclo[Phe-Tyr-Lys(iPr)-D-Arg-2Nal-D-His-D-Glu]-Lys(iPr) | 1-10 |
| cyclo[Lys(Ac)-Gln-Lys(iPr)-D-Arg-2Nal-D-Ala-D-Glu]-Lys(iPr) | 10-50 |
| cyclo[Phe-Tyr-Lys(iPr)-D-Arg-2Nal-His-D-Glu]-Lys(iPr) | 10-50 |
| cyclo[Phe-D-Tyr-Lys(iPr)-D-Arg-2Nal-D-Ala-D-Glu]-Lys(iPr) | 50-100 |
| cyclo[Phe-Tyr-Lys(iPr)-D-Arg-2Nal-D-Ser-D-Glu]-Lys(iPr) | 1-10 |
| cyclo[Phe-Tyr-Lys(iPr)-D-Arg-2Nal-D-Leu-D-Glu]-Lys(iPr) | 50-100 |
| cyclo[Phe-Tyr-Lys(iPr)-D-Arg-2Nal-D-Asn-D-Glu]-Lys(iPr) | 1-10 |
| cyclo[Phe-Tyr-Arg(Me)-D-Arg-2Nal-D-Ala-D-Glu]-Lys(iPr) | 1-10 |
| cyclo[Phe-Tyr-Lys(iPr)-D-Arg-2Nal-D-Glu-D-Glu]-Lys(iPr) | 10-50 |
| cyclo[Phe-Tyr-Lys(iPr)-D-Arg-2Nal-D-Dab-D-Glu]-Lys(iPr) | 1-10 |
| cyclo[Phe-Tyr-Lys(iPr)-D-Arg-(2-Ant)Ala-Gly-D-Glu]-Lys(iPr) | 1-10 |
| cyclo(isoindole)[Phe-Tyr-Lys(iPr)-D-Arg-(2-Ant) Ala-Gly-D-Cys]-Lys(iPr) | 10-50 |
| cyclo(isoindole)[Phe-Tyr-Lys(iPr)-D-Arg-(2-Ant)Ala-Gly-Cys]-Lys(iPr) | 10-50 |
| cyclo[Lys(Ac)-Tyr-Lys(iPr)-D-Arg-2Nal-Gly-D-Glu]-Lys(iPr) | 1-10 |
| cyclo[Lys(CysAcid-DOTA(Ga))-Tyr-Lys(iPr)-D-Arg-2Nal-D-Ala-D-Glu]-Lys(iPr) (Ga-BL34) | 1-10 |
| cyclo[Lys(CysAcid-amido-N,N-dimethyl-ammoniomethyl-trifluoroborate)-Tyr-Lys(iPr)-D-Arg-2Nal-D-Ala-D-Glu]-Lys(iPr) (Pep$BF_3$-BL40) | 10-50 |
| cyclo[Lys(CysAcid-triazole-N, N-dimethyl-ammoniomethyl-trifluoroborate)-Tyr-Lys(iPr)-D-Arg-2Nal-D-Ala-D-Glu]-Lys(iPr) (AM$BF_3$-BL41) | 10-50 |

TABLE 6

Biodistribution data (% ID/g) of [$^{68}$Ga]Ga-BL34 in Z138 tumor-bearing mice at selected time points. Mice in the 1 h blocked group received an injection of 7.5 μg of LY2510924 (i.p.) 15 min before tracer administration.

| | 1 h | | | 1 h blocked | | | 2 h | | |
|---|---|---|---|---|---|---|---|---|---|
| [$^{68}$Ga]Ga-BL34 | Mean | SD | n | Mean | SD | n | Mean | SD | n |
| Blood | 0.37 | 0.16 | 2 | 0.61 | NA | 1 | 0.10 | 0.04 | 3 |
| Fat | 0.03 | 0.01 | 2 | 0.10 | NA | 1 | 0.02 | 0.01 | 3 |
| Testes | 0.16 | 0.07 | 2 | 0.28 | NA | 1 | 0.06 | 0.01 | 3 |
| Intestine | 0.28 | 0.06 | 2 | 0.43 | NA | 1 | 0.12 | 0.04 | 3 |
| Stomach | 0.06 | 0.01 | 2 | 0.12 | NA | 1 | 0.02 | 0.12 | 3 |
| Spleen | 0.41 | 0.09 | 2 | 0.38 | NA | 1 | 0.25 | 0.05 | 3 |
| Liver | 0.75 | 0.06 | 2 | 0.69 | NA | 1 | 0.73 | 0.10 | 3 |
| Pancreas | 0.09 | 0.04 | 2 | 0.18 | NA | 1 | 0.04 | 0.01 | 3 |
| Adrenals | 0.15 | 0.06 | 2 | 0.12 | NA | 1 | 0.04 | 0.09 | 3 |
| Kidney | 2.95 | 0.33 | 2 | 4.30 | NA | 1 | 2.32 | 0.21 | 3 |
| Lung | 0.64 | 0.08 | 2 | 0.79 | NA | 1 | 0.20 | 0.05 | 3 |
| Heart | 0.13 | 0.03 | 2 | 0.25 | NA | 1 | 0.06 | 0.01 | 3 |
| Muscle | 0.07 | 0.03 | 2 | 0.15 | NA | 1 | 0.03 | 0.01 | 3 |
| Bone | 0.20 | 0.07 | 2 | 0.11 | NA | 1 | 0.07 | 0.04 | 3 |
| Brain | 0.03 | 0.02 | 2 | 0.03 | NA | 1 | 0.01 | 0.01 | 3 |
| Tumor | 18.99 | 5.12 | 2 | 3.18 | NA | 1 | 18.66 | 3.95 | 3 |
| Ratios | | | | | | | | | |
| Tumor:Blood | 59.41 | 38.85 | 2 | 5.22 | NA | 1 | 192.96 | 49.97 | 3 |
| Tumor:Liver | 25.85 | 8.99 | 2 | 4.58 | NA | 1 | 25.38 | 2.68 | 3 |
| Tumor:Spleen | 48.87 | 23.40 | 2 | 8.29 | NA | 1 | 80.31 | 22.99 | 3 |
| Tumor:Muscle | 318.49 | 211.64 | 2 | 21.26 | NA | 1 | 752.72 | 273.87 | 3 |
| Tumor:Bone | 106.23 | 63.90 | 2 | 28.89 | NA | 1 | 284.15 | 92.30 | 3 |
| Tumor:Lung | 30.36 | 11.86 | 2 | 4.04 | NA | 1 | 99.84 | 31.31 | 3 |
| Tumor:Kidney | 6.57 | 2.47 | 2 | 0.74 | NA | 1 | 8.06 | 0.69 | 3 |

TABLE 7

Biodistribution data (% ID/g) of [$^{177}$Lu]Lu-BL34 in Z138 tumor-bearing mice at selected time points. Mice in the 1 h blocked group received an injection of 7.5 μg of LY2510924 (i.p.) 15 min before tracer administration.

| | 1 h | | | 1 h blocked | | | 4 h | | | 24 h | | | 72 h | | |
|---|---|---|---|---|---|---|---|---|---|---|---|---|---|---|---|
| [$^{177}$Lu]Lu-BL34 | Mean | SD | n | Mean | SD | n | Mean | SD | n | Mean | SD | n | Mean | SD | n |
| Blood | 0.45 | 0.14 | 6 | 1.20 | 0.86 | 6 | 0.04 | 0.02 | 6 | 0.01 | 0.01 | 6 | 0.01 | 0.00 | 5 |
| Testes | 0.21 | 0.06 | 6 | 0.32 | 0.13 | 6 | 0.04 | 0.01 | 6 | 0.03 | 0.00 | 6 | 0.02 | 0.00 | 5 |
| Intestines | 0.37 | 0.13 | 6 | 0.60 | 0.16 | 6 | 0.06 | 0.01 | 6 | 0.06 | 0.02 | 6 | 0.07 | 0.07 | 5 |
| Spleen | 0.37 | 0.13 | 6 | 0.71 | 0.22 | 5 | 0.28 | 0.06 | 6 | 0.23 | 0.01 | 5 | 0.34 | 0.15 | 5 |
| Liver | 0.70 | 0.13 | 6 | 0.86 | 0.22 | 6 | 0.73 | 0.09 | 6 | 0.53 | 0.08 | 6 | 0.39 | 0.09 | 5 |
| Pancreas | 0.11 | 0.02 | 6 | 0.69 | 0.65 | 6 | 0.04 | 0.01 | 6 | 0.02 | 0.00 | 6 | 0.01 | 0.00 | 5 |
| Adrenal glands | 0.15 | 0.03 | 6 | 0.75 | 0.33 | 6 | 0.10 | 0.08 | 6 | 0.04 | 0.02 | 6 | 0.04 | 0.01 | 4 |
| Kidney | 2.73 | 0.50 | 6 | 5.57 | 3.13 | 6 | 2.43 | 0.36 | 6 | 0.88 | 0.02 | 5 | 0.48 | 0.14 | 5 |
| Lungs | 0.77 | 0.41 | 6 | 1.39 | 0.87 | 6 | 0.22 | 0.04 | 6 | 0.08 | 0.01 | 6 | 0.05 | 0.02 | 5 |
| Heart | 0.17 | 0.04 | 6 | 0.43 | 0.25 | 6 | 0.05 | 0.01 | 6 | 0.02 | 0.00 | 6 | 0.02 | 0.00 | 5 |
| Tumor | 14.30 | 2.51 | 6 | 5.86 | 2.89 | 6 | 15.20 | 1.34 | 6 | 9.39 | 1.80 | 6 | 4.00 | 1.26 | 5 |
| Muscle | 0.12 | 0.06 | 5 | 0.31 | 0.13 | 6 | 0.02 | 0.00 | 5 | 0.01 | 0.01 | 6 | 0.01 | 0.00 | 5 |
| Bone | 0.21 | 0.08 | 6 | 0.67 | 0.37 | 6 | 0.06 | 0.05 | 6 | 0.03 | 0.01 | 6 | 0.03 | 0.01 | 5 |
| Brain | 0.01 | 0.00 | 5 | 0.05 | 0.02 | 6 | 0.01 | 0.00 | 5 | 0.00 | 0.00 | 5 | 0.00 | 0.00 | 5 |
| Stomach | 0.18 | 0.12 | 6 | 0.24 | 0.08 | 6 | 0.03 | 0.00 | 6 | 0.10 | 0.08 | 6 | 0.16 | 0.26 | 4 |
| Ratios | | | | | | | | | | | | | | | |
| Tumour:Blood | 33.10 | 7.42 | 6 | 8.74 | 7.47 | 6 | 476.00 | 181.00 | 6 | 988.00 | 490.00 | 6 | 993.00 | 927.00 | 5 |
| Tumour:Liver | 20.50 | 3.69 | 6 | 7.77 | 5.22 | 6 | 21.10 | 3.40 | 6 | 17.70 | 1.43 | 6 | 10.40 | 3.24 | 5 |
| Tumour:Spleen | 41.40 | 13.40 | 6 | 9.13 | 8.20 | 5 | 56.10 | 12.90 | 6 | 42.40 | 6.04 | 5 | 12.70 | 4.01 | 5 |
| Tumour:Muscle | 155.00 | 81.80 | 5 | 24.02 | 16.12 | 6 | 861.00 | 134.00 | 5 | 814.00 | 325.00 | 6 | 776.00 | 457.00 | 5 |
| Tumour:Bone | 78.50 | 33.10 | 6 | 13.02 | 11.82 | 6 | 340.00 | 200.00 | 6 | 353.00 | 145.00 | 6 | 149.00 | 40.30 | 5 |
| Tumour:Lung | 21.20 | 7.70 | 6 | 6.87 | 6.16 | 6 | 72.30 | 15.40 | 6 | 122.30 | 22.60 | 6 | 90.60 | 23.00 | 5 |

TABLE 8

Biodistribution data (% ID/g) of [$^{68}$Ga]Ga-BL36 in Z138 tumor-bearing mice at selected time points.

| | 1 h | | | 2 h | | |
|---|---|---|---|---|---|---|
| [$^{68}$Ga]Ga-BL36 | Mean | SD | n | Mean | SD | n |
| Blood | 0.39 | 0.02 | 2 | 0.16 | 0.02 | 2 |
| Fat | 0.03 | 0.00 | 2 | 0.01 | 0.00 | 2 |
| Testes | 0.28 | 0.07 | 2 | 0.08 | 0.01 | 2 |
| Intestine | 0.34 | 0.01 | 2 | 0.20 | 0.00 | 2 |
| Stomach | 0.05 | 0.01 | 2 | 0.02 | 0.01 | 2 |
| Spleen | 0.35 | 0.06 | 2 | 0.25 | 0.02 | 2 |
| Liver | 0.68 | 0.07 | 2 | 0.71 | 0.03 | 2 |
| Pancreas | 0.08 | 0.01 | 2 | 0.04 | 0.00 | 2 |
| Adrenals | 0.14 | 0.06 | 2 | 0.03 | 0.01 | 2 |
| Kidney | 2.98 | 0.28 | 2 | 2.66 | 0.49 | 2 |
| Lung | 0.68 | 0.09 | 2 | 0.39 | 0.00 | 2 |
| Heart | 0.14 | 0.01 | 2 | 0.07 | 0.02 | 2 |
| Muscle | 0.10 | 0.00 | 2 | 0.03 | 0.00 | 2 |
| Bone | 0.20 | 0.14 | 2 | 0.07 | 0.00 | 2 |
| Brain | 0.01 | 0.00 | 2 | 0.01 | 0.00 | 2 |
| Tumor | 12.19 | 0.78 | 2 | 10.35 | 1.09 | 2 |
| Ratios | | | | | | |
| Tumor:Blood | 31.30 | 0.52 | 2 | 64.40 | 2.19 | 2 |
| Tumor:Liver | 18.07 | 0.77 | 2 | 16.17 | 2.22 | 2 |
| Tumor:Spleen | 35.06 | 3.83 | 2 | 46.93 | 8.01 | 2 |
| Tumor:Muscle | 119.04 | 11.24 | 2 | 337.03 | 13.67 | 2 |
| Tumor:Bone | 77.38 | 48.78 | 2 | 143.14 | 6.81 | 2 |
| Tumor:Lung | 18.00 | 1.15 | 2 | 28.69 | 2.97 | 2 |
| Tumor:Kidney | 4.10 | 0.12 | 2 | 4.82 | 1.15 | 2 |

TABLE 9

Biodistribution data (% ID/g) of [$^{68}$Ga]Ga-BL37 in Z138 tumor-bearing mice at selected time points. Mice in the 1 h blocked group received an injection of 7.5 μg of LY2510924 (i.p.) 15 min before tracer administration.

| | 1 h | | | 1 h blocked | | | 2 h | | |
|---|---|---|---|---|---|---|---|---|---|
| [$^{68}$Ga]Ga-BL37 | Mean | SD | n | Mean | SD | n | Mean | SD | n |
| Blood | 0.50 | 0.13 | 3 | 1.10 | NA | 1 | 0.18 | 0.02 | 4 |
| Fat | 0.05 | 0.02 | 3 | 0.11 | NA | 1 | 0.05 | 0.01 | 4 |
| Testes | 0.15 | 0.03 | 3 | 0.30 | NA | 1 | 0.07 | 0.01 | 4 |
| Intestine | 0.27 | 0.13 | 3 | 0.51 | NA | 1 | 0.15 | 0.04 | 4 |
| Stomach | 0.07 | 0.03 | 3 | 0.09 | NA | 1 | 0.04 | 0.02 | 4 |
| Spleen | 0.26 | 0.05 | 3 | 0.33 | NA | 1 | 0.26 | 0.06 | 4 |
| Liver | 0.65 | 0.05 | 3 | 0.65 | NA | 1 | 0.69 | 0.09 | 4 |
| Pancreas | 0.11 | 0.03 | 3 | 0.23 | NA | 1 | 0.07 | 0.02 | 4 |
| Adrenals | 0.42 | 0.48 | 3 | 0.59 | NA | 1 | 0.13 | 0.06 | 4 |
| Kidney | 3.20 | 0.34 | 3 | 4.79 | NA | 1 | 2.83 | 0.18 | 4 |
| Lung | 0.57 | 0.08 | 3 | 1.06 | NA | 1 | 0.29 | 0.04 | 4 |
| Heart | 0.17 | 0.05 | 3 | 0.33 | NA | 1 | 0.08 | 0.02 | 4 |
| Muscle | 0.09 | 0.02 | 3 | 0.19 | NA | 1 | 0.08 | 0.04 | 4 |
| Bone | 0.16 | 0.04 | 3 | 0.19 | NA | 1 | 0.16 | 0.08 | 4 |
| Brain | 0.04 | 0.03 | 3 | 0.03 | NA | 1 | 0.01 | 0.00 | 4 |
| Tumor | 6.15 | 0.56 | 3 | 0.75 | NA | 1 | 4.51 | 0.74 | 4 |
| Ratios | | | | | | | | | |
| Tumor:Blood | 12.73 | 2.57 | 3 | 1.46 | NA | 1 | 25.35 | 1.23 | 4 |
| Tumor:Liver | 9.43 | 0.53 | 3 | 2.46 | NA | 1 | 6.51 | 0.27 | 4 |
| Tumor:Spleen | 24.31 | 4.01 | 3 | 4.81 | NA | 1 | 18.13 | 5.65 | 4 |
| Tumor:Muscle | 68.67 | 12.44 | 3 | 8.66 | NA | 1 | 62.92 | 16.27 | 4 |
| Tumor:Bone | 38.59 | 5.76 | 3 | 8.51 | NA | 1 | 39.30 | 34.86 | 4 |
| Tumor:Lung | 10.76 | 0.71 | 3 | 1.51 | NA | 1 | 15.76 | 1.35 | 4 |
| Tumor:Kidney | 1.93 | 0.24 | 3 | 0.34 | NA | 1 | 1.59 | 0.23 | 4 |

TABLE 10

Biodistribution data (% ID/g) of [$^{18}$F]BL40 in Z138 tumor-bearing mice at selected time points. Mice in the 1 h blocked group received an injection of 7.5 μg of LY2510924 (i.p.) 15 min before tracer administration.

| | 1 h | | | 1 h blocked | | | 2 h | | |
|---|---|---|---|---|---|---|---|---|---|
| [$^{18}$F]BL40 | Mean | SD | n | Mean | SD | n | Mean | SD | n |
| Blood | 0.42 | 0.14 | 5 | 1.36 | 0.62 | 4 | 0.07 | 0.01 | 6 |
| Fat | 0.08 | 0.06 | 5 | 0.23 | 0.11 | 4 | 0.03 | 0.01 | 6 |
| Testes | 0.18 | 0.07 | 5 | 0.37 | 0.17 | 4 | 0.06 | 0.01 | 6 |
| Intestines | 0.31 | 0.09 | 5 | 0.42 | 0.18 | 4 | 0.14 | 0.05 | 6 |
| Spleen | 0.49 | 0.14 | 5 | 0.75 | 0.27 | 4 | 0.30 | 0.02 | 6 |
| Liver | 0.97 | 0.05 | 5 | 0.86 | 0.23 | 4 | 0.96 | 0.19 | 6 |
| Pancreas | 0.15 | 0.07 | 5 | 1.32 | 0.36 | 4 | 0.10 | 0.08 | 6 |
| Adrenal glands | 0.27 | 0.11 | 5 | 0.41 | 0.18 | 4 | 0.21 | 0.11 | 6 |
| Kidney | 3.14 | 0.35 | 5 | 0.76 | 0.56 | 4 | 2.76 | 0.28 | 6 |
| Lungs | 0.64 | 0.18 | 5 | 13.62 | 7.48 | 4 | 0.27 | 0.02 | 6 |
| Heart | 0.16 | 0.03 | 5 | 1.60 | 0.64 | 4 | 0.06 | 0.01 | 6 |
| Z138 | 21.13 | 2.09 | 5 | 0.48 | 0.17 | 4 | 20.72 | 1.92 | 6 |
| Muscle | 0.11 | 0.05 | 5 | 5.75 | 1.79 | 4 | 0.06 | 0.02 | 6 |
| Bone | 0.31 | 0.15 | 5 | 0.31 | 0.14 | 4 | 0.31 | 0.16 | 6 |
| Brain | 0.02 | 0.01 | 5 | 0.70 | 0.32 | 4 | 0.03 | 0.04 | 6 |
| Stomach | 0.19 | 0.15 | 5 | 0.05 | 0.01 | 4 | 0.06 | 0.01 | 6 |
| Ratios | | | | | | | | | |
| Tumor:Blood | 54.28 | 12.76 | 5 | 5.06 | 2.85 | 4 | 298.10 | 57.49 | 6 |
| Tumor:Liver | 21.86 | 2.15 | 5 | 4.47 | 1.39 | 4 | 22.16 | 3.81 | 6 |
| Tumor:Spleen | 45.03 | 10.08 | 5 | 7.63 | 2.94 | 4 | 69.73 | 8.27 | 6 |
| Tumor:Muscle | 207.70 | 73.53 | 5 | 21.49 | 11.85 | 4 | 381.50 | 90.28 | 6 |
| Tumor:Bone | 80.68 | 34.58 | 5 | 10.08 | 5.92 | 4 | 76.47 | 26.76 | 6 |
| Tumor:Lung | 34.94 | 8.74 | 5 | 4.18 | 2.31 | 4 | 76.59 | 9.20 | 6 |
| Tumor:Kidney | 6.76 | 0.66 | 5 | 0.60 | 0.47 | 4 | 7.55 | 0.92 | 6 |

TABLE 11

Biodistribution data (% ID/g) of [$^{18}$F]BL41 in Z138 tumor-bearing mice at selected time points. Mice in the 1 h blocked group received an injection of 7.5 μg of LY2510924 (i.p.) 15 min before tracer administration.

| | 1 h | | | 1 h blocked | | | 2 h | | |
|---|---|---|---|---|---|---|---|---|---|
| [$^{18}$F]BL41 | Mean | SD | n | Mean | SD | n | Mean | SD | n |
| Blood | 0.37 | 0.06 | 3 | 1.20 | 0.86 | 4 | 0.09 | 0.01 | 7 |
| Fat | 0.05 | 0.01 | 3 | 0.18 | 0.11 | 4 | 0.03 | 0.02 | 7 |
| Testes | 0.15 | 0.04 | 3 | 0.32 | 0.13 | 4 | 0.05 | 0.01 | 7 |
| Intestines | 0.26 | 0.04 | 3 | 0.60 | 0.16 | 4 | 0.17 | 0.06 | 7 |
| Spleen | 0.46 | 0.08 | 3 | 0.71 | 0.22 | 4 | 0.36 | 0.06 | 7 |
| Liver | 0.73 | 0.14 | 3 | 0.86 | 0.22 | 4 | 0.73 | 0.11 | 7 |
| Pancreas | 0.11 | 0.02 | 3 | 0.69 | 0.65 | 4 | 0.07 | 0.02 | 7 |
| Adrenal glands | 0.18 | 0.07 | 3 | 0.75 | 0.33 | 4 | 0.12 | 0.04 | 7 |
| Kidney | 2.83 | 0.43 | 3 | 5.57 | 3.13 | 4 | 2.25 | 0.24 | 7 |
| Lungs | 0.77 | 0.18 | 3 | 1.39 | 0.87 | 4 | 0.35 | 0.13 | 7 |
| Heart | 0.16 | 0.04 | 3 | 0.43 | 0.25 | 4 | 0.06 | 0.01 | 7 |
| Z138 | 16.90 | 3.25 | 3 | 5.86 | 2.89 | 4 | 17.62 | 1.85 | 6 |
| Muscle | 0.12 | 0.03 | 3 | 0.31 | 0.13 | 4 | 0.13 | 0.03 | 7 |
| Bone | 0.25 | 0.02 | 3 | 0.67 | 0.37 | 4 | 0.21 | 0.05 | 7 |
| Brain | 0.03 | 0.01 | 3 | 0.05 | 0.02 | 4 | 0.05 | 0.04 | 7 |
| Stomach | 0.09 | 0.03 | 3 | 0.24 | 0.08 | 4 | 0.07 | 0.03 | 7 |
| Ratios | | | | | | | | | |
| Tumor:Blood | 46.01 | 7.45 | 3 | 8.74 | 7.47 | 4 | 198.30 | 18.88 | 7 |
| Tumor:Liver | 23.15 | 1.88 | 3 | 7.77 | 5.22 | 4 | 24.50 | 3.29 | 7 |
| Tumor:Spleen | 37.16 | 7.35 | 3 | 9.13 | 8.20 | 4 | 49.39 | 8.94 | 7 |
| Tumor:Muscle | 147.30 | 46.31 | 3 | 24.02 | 16.12 | 4 | 146.80 | 41.09 | 7 |
| Tumor:Bone | 67.49 | 8.07 | 3 | 13.02 | 11.82 | 4 | 88.06 | 19.37 | 7 |
| Tumor:Lung | 23.18 | 8.03 | 3 | 6.87 | 6.16 | 4 | 53.31 | 11.47 | 7 |
| Tumor:Kidney | 5.94 | 0.40 | 3 | 1.63 | 1.40 | 4 | 7.87 | 0.63 | 7 |

TABLE 12

Biodistribution data (% ID/g) of [$^{68}$Ga]Ga-BL42 in Z138 tumor-bearing mice at selected time points.

| | 1 h | | |
|---|---|---|---|
| [$^{68}$Ga]Ga-BL42 | Mean | SD | n |
| Blood | 0.43 | 0.05 | 3 |
| Fat | 0.08 | 0.02 | 3 |
| Testes | 0.18 | 0.04 | 3 |
| Intestines | 0.36 | 0.03 | 3 |
| Spleen | 4.67 | 1.22 | 3 |
| Liver | 15.50 | 2.29 | 3 |
| Pancreas | 0.16 | 0.02 | 3 |
| Adrenal glands | 0.96 | 0.18 | 3 |
| Kidney | 6.11 | 1.39 | 3 |
| Lungs | 2.80 | 2.04 | 3 |
| Heart | 0.24 | 0.01 | 3 |
| Z138 | 16.26 | 1.34 | 3 |
| Muscle | 0.18 | 0.03 | 3 |
| Bone | 2.51 | 1.55 | 3 |
| Brain | 0.03 | 0.02 | 3 |
| Stomach | 0.16 | 0.02 | 3 |
| Ratios | | | |
| Tumor:Blood | 37.93 | 6.98 | 3 |
| Tumor:Liver | 1.06 | 0.18 | 3 |
| Tumor:Spleen | 3.61 | 0.82 | 3 |
| Tumor:Muscle | 91.81 | 23.29 | 3 |
| Tumor:Bone | 9.83 | 8.54 | 3 |
| Tumor:Lung | 8.00 | 4.99 | 3 |
| Tumor:Kidney | 2.75 | 0.68 | 3 |

TABLE 13

Biodistribution data (% ID/g) of [$^{68}$Ga]Ga-BL43 in Z138 tumor-bearing mice at selected time points.

| | 1 h | | |
|---|---|---|---|
| [$^{68}$Ga]Ga-BL43 | Mean | SD | n |
| Blood | 0.63 | 0.27 | 5 |
| Fat | 0.15 | 0.08 | 5 |
| Testes | 0.29 | 0.12 | 5 |
| Intestines | 0.48 | 0.11 | 5 |
| Spleen | 0.45 | 0.16 | 5 |
| Liver | 1.92 | 0.40 | 5 |
| Pancreas | 0.20 | 0.13 | 5 |
| Adrenal glands | 0.25 | 0.14 | 5 |
| Kidney | 4.48 | 1.46 | 5 |
| Lungs | 0.89 | 0.27 | 5 |
| Heart | 0.28 | 0.12 | 5 |
| Z138 | 11.81 | 2.42 | 5 |
| Muscle | 0.23 | 0.18 | 5 |
| Bone | 0.34 | 0.16 | 5 |
| Brain | 0.02 | 0.01 | 5 |
| Stomach | 0.16 | 0.07 | 5 |
| Ratios | | | |
| Tumor:Blood | 20.60 | 6.85 | 5 |
| Tumor:Liver | 6.25 | 1.17 | 5 |
| Tumor:Spleen | 28.27 | 9.20 | 5 |
| Tumor:Muscle | 79.03 | 48.29 | 5 |
| Tumor:Bone | 39.49 | 15.03 | 5 |
| Tumor:Lung | 13.94 | 3.60 | 5 |
| Tumor:Kidney | 2.78 | 0.80 | 5 |

TABLE 14

Biodistribution data (% ID/g) of [$^{68}$Ga]Ga-BL44 in Z138 tumor-bearing mice at selected time points.

| | 1 h | | |
|---|---|---|---|
| [$^{68}$Ga]Ga-BL44 | Mean | SD | n |
| Blood | 0.26 | 0.08 | 3 |
| Fat | 0.09 | 0.03 | 3 |
| Testes | 0.16 | 0.07 | 3 |
| Intestines | 0.19 | 0.04 | 3 |
| Spleen | 0.20 | 0.03 | 3 |
| Liver | 0.50 | 0.07 | 3 |
| Pancreas | 0.07 | 0.02 | 3 |
| Adrenal glands | 0.16 | 0.06 | 3 |
| Kidney | 2.47 | 0.21 | 3 |
| Lungs | 0.41 | 0.10 | 3 |
| Heart | 0.10 | 0.02 | 3 |
| Z138 | 18.35 | 1.76 | 3 |
| Muscle | 0.16 | 0.17 | 3 |
| Bone | 0.23 | 0.11 | 3 |
| Brain | 0.02 | 0.00 | 3 |
| Stomach | 0.05 | 0.01 | 3 |
| Ratios | | | |
| Tumor:Blood | 73.09 | 15.89 | 3 |
| Tumor:Liver | 36.78 | 3.31 | 3 |
| Tumor:Spleen | 92.14 | 19.84 | 3 |
| Tumor:Muscle | 221.68 | 171.40 | 3 |
| Tumor:Bone | 91.52 | 34.62 | 3 |
| Tumor:Lung | 46.07 | 9.46 | 3 |
| Tumor:Kidney | 7.45 | 0.51 | 3 |

TABLE 15

Biodistribution data (% ID/g) of [$^{68}$Ga]Ga-BL45 in Z138 tumor-bearing mice at selected time points.

| | 1 h | | |
|---|---|---|---|
| [$^{68}$Ga]Ga-BL45 | Mean | SD | n |
| Blood | 0.46 | 0.11 | 3 |
| Fat | 0.04 | 0.01 | 2 |
| Testes | 0.39 | 0.20 | 3 |
| Intestines | 0.31 | 0.08 | 3 |
| Spleen | 0.22 | 0.05 | 3 |
| Liver | 0.40 | 0.02 | 3 |
| Pancreas | 0.14 | 0.04 | 3 |
| Adrenal glands | 0.23 | 0.17 | 3 |
| Kidney | 2.84 | 0.14 | 3 |
| Lungs | 0.48 | 0.06 | 3 |
| Heart | 0.15 | 0.04 | 3 |
| Z138 | 14.39 | 5.01 | 3 |
| Muscle | 0.35 | 0.25 | 3 |
| Bone | 0.19 | 0.09 | 3 |
| Brain | 0.02 | 0.00 | 3 |
| Stomach | 0.06 | 0.01 | 3 |
| Ratios | | | |
| Tumor:Blood | 31.04 | 4.36 | 3 |
| Tumor:Liver | 36.07 | 10.76 | 3 |
| Tumor:Spleen | 64.39 | 16.76 | 3 |
| Tumor:Muscle | 51.16 | 24.92 | 3 |

TABLE 15-continued

| Biodistribution data (% ID/g) of $[^{68}Ga]$Ga-BL45 in Z138 tumor-bearing mice at selected time points. | | | |
|---|---|---|---|
| | 1 h | | |
| $[^{68}Ga]$Ga-BL45 | Mean | SD | n |
| Tumor:Bone | 87.49 | 39.63 | 3 |
| Tumor:Lung | 30.41 | 12.13 | 3 |
| Tumor:Kidney | 5.12 | 2.02 | 3 |

NUMBERED EMBODIMENTS

1. A compound of Formula A or a salt or solvate of Formula A:

[Formula A]

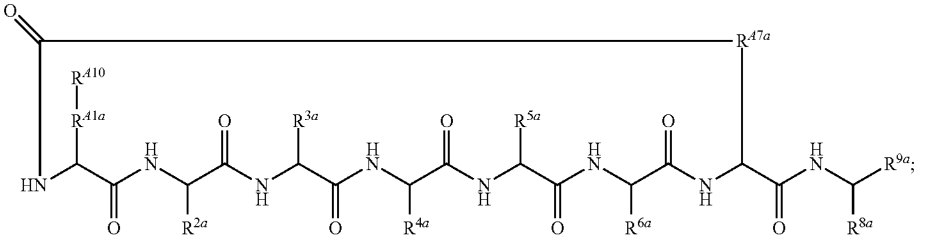

$R^{2a}$ is —($CH_2$)—($R^{2b}$)-(phenyl), wherein $R^{2b}$ is absent, —$CH_2$—, —NH—, —S— or —O—, wherein the phenyl is 4-substituted with —$NH_2$, —$NO_2$, —OH, —$OR^{2c}$, —SH, —$SR^{2c}$, or —O-phenyl, wherein the phenyl is optionally 3-substituted with halogen or —OH, wherein the phenyl is optionally 5-subsituted with halogen or —OH, wherein the —O-phenyl ring is optionally 4-substituted with —$NH_2$, —$NO_2$, —OH, —$OR^{2c}$, —SH, or —$SR^{2c}$, wherein the —O-phenyl ring is optionally 3-substituted with halogen or —OH, wherein the —O-phenyl ring is optionally 5-subsituted with halogen or —OH, wherein each $R^{2c}$ is independently a $C_1$-$C_3$ linear or branched alkyl group;

$R^{3a}$ is $R^{3b}R^{3c}$ wherein $R^{3b}$ is a linear $C_1$-$C_5$ alkylenyl, alkenylenyl, or alkynylenyl, wherein 0-2 carbons in $C_2$-$C_5$ are independently replaced with one or more N, S, and/or O heteroatoms, wherein $R^{3c}$ is —$N(R^{3d})_{2\text{-}3}$ or guanidino, wherein each $R^{3d}$ is independently —H or a linear or branched $C_1$-$C_3$ alkyl;

$R^{4a}$ is $R^{4b}R^{4c}$ wherein $R^{4b}$ is a linear $C_1$-$C_5$ alkylenyl, alkenylenyl, or alkynylenyl, in which 0-2 carbons in $C_2$-$C_5$ are independently replaced with one or more N, S, and/or O heteroatoms, wherein $R^{4c}$ is —$N(R^{4d})_{2\text{-}3}$ or guanidino, wherein each $R^{4d}$ is independently —H or a linear or branched $C_1$-$C_3$ alkyl;

$R^{5a}$ is —$(CH_2)_{1\text{-}3}$—$R^{5b}$, wherein 1 carbon in —$(CH_2)_{2\text{-}3}$— is optionally replaced with a N, S, or O heteroatom, wherein $R^{5b}$ is:

phenyl optionally substituted with one or a combination of the following: 4-substituted with —$NH_2$, —$NO_2$, —OH, —$OR^{5c}$, —SH, —$SR^{5c}$, or —O-phenyl; 3-substituted with halogen or —OH; and/or 5-subsituted with halogen or —OH; wherein the —O-phenyl ring is optionally 4-substituted with —$NH_2$, —$NO_2$, —OH, —$OR^{5c}$, —SH, or —$SR^{5c}$, wherein the —O-phenyl ring is optionally 3-substituted with halogen or —OH, wherein the —O-phenyl ring is optionally 5-subsituted with halogen or —OH; or a fused bicyclic or fused tricyclic aryl group wherein one or more carbons are optionally independently replaced by N, S, and/or O heteroatoms, and independently optionally substituted with one or a combination of halogen, —OH, —$OR^{5c}$, amino, —$NHR^{5c}$, and/or $N(R^{5c})_2$;

wherein each $R^{5c}$ is independently a $C_1$-$C_3$ linear or branched alkyl group;

either $R^{6a}$ is absent, methyl, ethyl, —C≡CH, —CH═$CH_2$, —C≡C—$(CH_2)_{1\text{-}3}$—OH, —C≡C—$(CH_2)_{1\text{-}3}$—SH, —C≡C—$(CH_2)_{1\text{-}3}$—$NH_2$, —C≡C—$(CH_2)_{1\text{-}3}$—COOH, —C≡C—$(CH_2)_{1\text{-}3}$—CONH, —C≡C—$(CH_2)_{1\text{-}3}R^{6b}R^{6c}$, —CH═CH—$(CH_2)_{1\text{-}3}$—OH, —CH═CH—$(CH_2)_{1\text{-}3}$—SH, —CH═CH—$(CH_2)_{1\text{-}3}$—$NH_2$, —CH═CH—$(CH_2)_{1\text{-}3}$—COOH, —CH═CH—$(CH_2)_{1\text{-}3}$—CONH, —CH═CH—$(CH_2)_{1\text{-}3}R^{6b}R^{6c}$, —$CH_2$—$R^{6b}$—OH, —$CH_2$—$R^{6b}$—COOH, —$CH_2$—$(R^{6b})_{1\text{-}3}$—$NH_2$, —$CH_2$—$R^{6b}$—CONH, or —$CH_2$—$R^{6b}R^{6c}$, wherein each $R^{6b}$ is independently absent, —$CH_2$—, —NH—, —S— or —O—, and wherein $R^{6c}$ is:

a 5 or 6 membered aromatic ring wherein one or more carbons are optionally independently replaced by N, S, and/or O heteroatoms, and optionally substituted with one or more groups independently selected from oxo, hydroxyl, sulfhydryl, nitro, amino, and/or halogen;

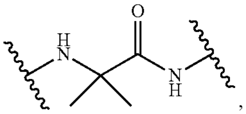,
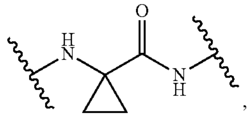,
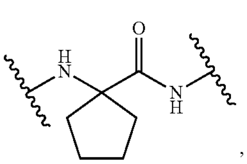,
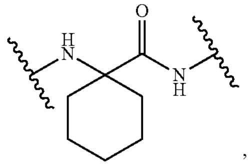,
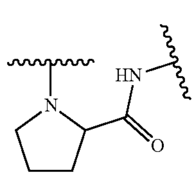, or
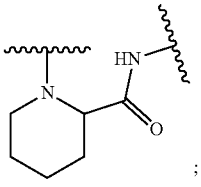;

or —NH—CH($R^{6a}$)—C(O)—NH— is replaced with:

$R^{A7a}$ is a linear $C_1$-$C_5$ alkylenyl wherein 0-2 carbons in $C_2$-$C_5$ are independently replaced with one or more N, S, and/or O heteroatoms;

$R^{8a}$ is $R^{8b}R^{8c}$ wherein $R^{8b}$ is a linear $C_1$-$C_5$ alkylenyl, alkenylenyl, or alkynylenyl, in which 0-2 carbons in $C_2$-$C_5$ are independently replaced with one or more N, S, and/or O heteroatoms, wherein $R^{8c}$ is —N($R^{8d}$)$_{2-3}$ or guanidino, wherein each $R^{8d}$ is independently —H or a linear or branched $C_1$-$C_3$ alkyl;

$R^{9a}$ is: —C(O)$NH_2$, —C(O)—OH, —$CH_2$—C(O)$NH_2$, —$CH_2$—C(O)—OH, —$CH_2$—$NH_2$, —$CH_2$—OH, —$CH_2$—$CH_2$—$NH_2$, —$R^{9b}$—$R^{9c}$, or —$R^{9b}$-[linker]-$R^X_{n1}$, wherein:

$R^{9b}$ is —$CH_2$—NH—C(O)—, —$CH_2$—C(O)—, —$CH_2$—O—, —C(O)NH—, —C(O)—N($CH_3$)—, —$CH_2$—NHC(S)—, —C(S)NH—, —$CH_2$—N($CH_3$)C(S)—, —C(O)N($CH_3$)—, —$CH_2$—N($CH_3$)C(O)—, —C(S)N($CH_3$)—, —$CH_2$—NHC(S)NH—, —$CH_2$—NHC(O)NH—, —$CH_2$—S—, —$CH_2$—S(O)—, —$CH_2$—S(O)$_2$—, —$CH_2$—S(O)$_2$—NH—, —$CH_2$—S(O)—NH—, —$CH_2$—Se—, —$CH_2$—Se(O)—, —$CH_2$—Se(O)$_2$—, —$CH_2$—NHNHC(O)—, —C(O)NHNH—, —$CH_2$—OP(O)($O^-$)O—, —$CH_2$-phosphamide-, —$CH_2$-thiophosphodiester-, —$CH_2$—S-tetrafluorophenyl-S—,

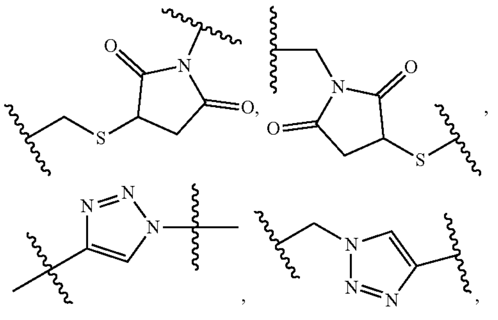

or polyethylene glycol; and $R^{9c}$ is hydrogen or a linear, branched, and/or cyclic $C_1$-$C_{20}$ alkyl, alkenyl or alkynyl, wherein 0-6 carbons in $C_2$-$C_{20}$ are independently replaced by N, S, and/or O heteroatoms, and substituted with 0-3 groups independently selected from one or a combination of oxo, hydroxyl, sulfhydryl, halogen, guanidino, carboxylic acid, sulfonic acid, sulfinic acid, and/or phosphoric acid;

$R^{A10}$ is absent or -[linker]-$R^X_{n1}$;

when $R^{A10}$ is absent, then $R^{A1a}$ is:

a linear $C_1$-$C_5$ alkyl, alkenyl, or alkynyl, wherein 0-2 carbons in $C_2$-$C_5$ are independently replaced by one or more N, S, and/or O heteroatoms, optionally C-substituted with a single substituent selected from: —SH, —OH, amino, carboxy, guanidino, —NH—C(O)—$CH_3$, —S—C(O)—$CH_3$, —O—C(O)—$CH_3$, —NH—C(O)-(phenyl), —S—C(O)-(phenyl), —O—C(O)-(phenyl), —NH—($CH_3$)$_{1-2}$, —$NH_2$—$CH_3$, —N($CH_3$)$_{2-3}$, —S—$CH_3$, or —O—$CH_3$;

a branched $C_1$-$C_{10}$ alkyl, alkenyl, or alkynyl, wherein 0-3 carbons in $C_2$-$C_{10}$ are independently replaced by one or more N, S, and/or O heteroatoms; or $R^{A1b}R^{A1c}$, wherein $R^{A1b}$ is a linear $C_1$-$C_3$ alkylenyl, wherein $C_2$ alkylenyl or $C_3$ alkylenyl is optionally replaced with a N, S, or O heteroatom, wherein $R^{A1c}$ is:

a 5 or 6 membered aromatic ring wherein one or more carbons are optionally independently replaced by N, S, and/or O heteroatoms, and optionally substituted with one or more groups independently selected from oxo, hydroxyl, sulfhydryl, nitro, amino, and/or halogen; or a fused bicyclic or fused tricyclic aryl group wherein one or more carbons are optionally independently replaced by N, S, and/or O heteroatoms, and optionally substituted with one or more groups independently selected from halogen, —OH, —$OR^{A1d}$, amino, —$NHR^{A1d}$and/or N($R^{A1d}$)$_2$, wherein each $R^{A1d}$ is independently a $C_1$-$C_3$ linear or branched alkyl group;

when $R^{A10}$ is -[linker]-$R^X_{n1}$, then $R^{A1a}$ is $R^{A1e}R^{A1f}$, wherein $R^{A1e}$ is a linear $C_1$-$C_5$ alkylenyl, alkenylenyl, or alkynylenyl, in which 0-2 carbons in $C_2$-$C_5$ are independently replaced with N, S, and/or O heteroatoms, and $R^{A1f}$ is —NH—C(O)—, —C(O)—, —O—, —C(O)NH—, —C(O)—N($CH_3$)—, —NHC(S)—, —C(S)NH—, —N($CH_3$)C(S)—, —C(O)N($CH_3$)—, —N($CH_3$)C(O)—, —C(S)N($CH_3$)—, —NHC(S)NH—, —NHC(O)NH—, —S—, —S(O)—, —S(O)—O—, —S(O)$_2$—, —S(O)$_2$—O—, —S(O)$_2$—NH—, —S(O)—NH—, —Se—, —Se(O)—, —Se(O)$_2$—, —NHNHC(O)—, —C(O)NHNH—, —OP(O)($O^-$)O—, -phosphamide-, -thiophosphodiester-, —S-tetrafluorophenyl-S—,

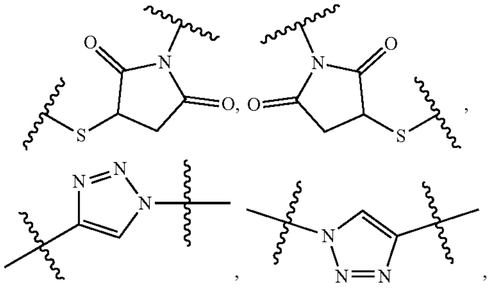

or polyethylene glycol;

each n1 is independently 0, 1 or 2;

each $R^X$ is an albumin binder, a therapeutic moiety, a fluorescent label, a radiolabeled group, or a group capable of being radiolabelled;

wherein 0-3 peptide backbone amides are independently replaced with

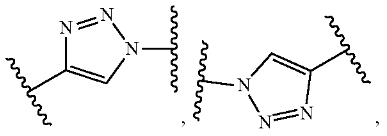

or thioamide;

wherein 0-3 peptide backbone amides are N-methylated;

with the proviso that Formula A excludes the following combination:

—NH—CH($R^{2a}$)—C(O)— forms a Tyr residue;

—NH—CH($R^{4a}$)—C(O)— forms a D-Arg residue;

—NH—CH($R^{5a}$)—C(O)— forms a 2Nal residue; and $R^{6a}$ is absent.

2. The compound of Embodiment 1, wherein —NH—CH($R^{A1a}$)—C(O)— forms an L-amino acid residue.

3. The compound of Embodiment 1 or 2, wherein $R^{A10}$ is absent.

4. The compound of Embodiment 3, wherein $R^{A1a}$ is a linear $C_1$-$C_5$ alkyl, alkenyl, or alkynyl, optionally substituted with a single substituent selected from: —SH, —OH, amino, carboxy, guanidino, —NH—C(O)—$CH_3$, —S—C(O)—$CH_3$, —O—C(O)—$CH_3$, —NH—C(O)-(phenyl), —S—C(O)— (phenyl), —O—C(O)-(phenyl), —NH—($CH_3$)$_{1-2}$, —$NH_2$—$CH_3$, —N($CH_3$)$_{2-3}$, —S—$CH_3$, or —O—$CH_3$.

5. The compound of Embodiment 3, wherein $R^{A1a}$ is a linear $C_1$-$C_5$ alkyl optionally substituted with a single substituent selected from: —SH, —OH, amino, carboxy, guanidino, —NH—C(O)—$CH_3$, —S—C(O)—$CH_3$, —O—C(O)—$CH_3$, —NH—C(O)-(phenyl), —S—C(O)-(phenyl), —O—C(O)-(phenyl), —NH—$(CH_3)_{1-2}$, —$NH_2$—$CH_3$, —$N(CH_3)_{2-3}$, —S—$CH_3$, or —O—$CH_3$.

6. The compound of Embodiment 3, wherein $R^{A1a}$ is a branched $C_1$-$C_{10}$ alkyl, alkenyl, or alkynyl.

7. The compound of Embodiment 3, wherein $R^{A1a}$ is a branched $C_1$-$C_{10}$ alkyl.

8. The compound of Embodiment 3, wherein $R^{A1a}$ is $R^{A1b}R^{A1c}$.

9. The compound of Embodiment 8, wherein $R^{A1b}$ is a linear $C_1$-$C_3$ alkylenyl.

10. The compound of Embodiment 8 or 9, wherein $R^{A1}c$ is a 5 or 6 membered aromatic ring wherein 0-4 carbons are independently replaced by N, S, and/or O heteroatoms, and substituted with 0-4 groups independently selected from oxo, hydroxyl, sulfhydryl, nitro, amino, and/or halogen.

11. The compound of Embodiment 8 or 9, wherein $R^{A1c}$ is a fused bicyclic or fused tricyclic aryl group wherein 0-6 carbons are independently replaced by N, S, and/or O heteroatoms, and optionally substituted with 0-6 groups independently selected from halogen, —OH, —$OR^{A1d}$, amino, —$NHR^{A1d}$, and/or $N(R^{A1d})_2$.

12. The compound of any one of Embodiments 1 to 3, wherein —NH—CH($R^{A1a}$). C(O)— forms a Phe residue.

13. The compound of any one of Embodiments 1 to 3, wherein —NH—CH($R^{A1a}$)—C(O)— forms a 1-Nal residue.

14. The compound of any one of Embodiments 1 to 3, wherein —NH—CH($R^{A1a}$)—C(O)— forms a 2-Nal residue.

15. The compound of any one of Embodiments 1 to 3, wherein —NH—CH($R^{A1a}$)—C(O)— forms a Tyr residue.

16. The compound of any one of Embodiments 1 to 3, wherein —NH—CH($R^{A1a}$)—C(O)— forms a Trp residue.

17. The compound of any one of Embodiments 1 to 3, wherein —NH—CH($R^{A1a}$)—C(O)— forms a Lys(Ac) residue.

18. The compound of Embodiment 1 or 2, wherein $R^{A10}$ is -[linker]-$R^{X}_{n1}$.

19. The compound of Embodiment 18, wherein $R^{A1e}$ is a linear $C_1$-$C_5$ alkylenyl, alkenylenyl, or alkynylenyl 20. The compound of Embodiment 18, wherein $R^{A1e}$ is a linear $C_1$-$C_5$ alkylenyl.

21. The compound of any one of Embodiments 18 to 20, wherein $R^{A1f}$ is —NH—C(O)—, —C(O)—, —O—, —C(O)NH—, —C(O)—N($CH_3$)—, —NHC(S)—, —C(S)NH—, —N($CH_3$)C(S)—, —C(O)N($CH_3$)—, —N($CH_3$)C(O)—, —C(S)N($CH_3$)—, —NHC(S)NH—, —NHC(O)NH—, —S—, —S(O)—, —S(O)—O—, —$S(O)_2$—, —$S(O)_2$—NH—, —S(O)—NH—, —NHNHC(O)—, —C(O)NHNH—,

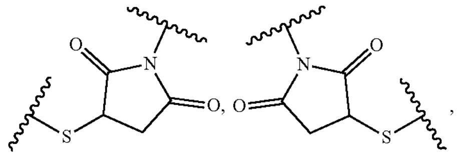
,

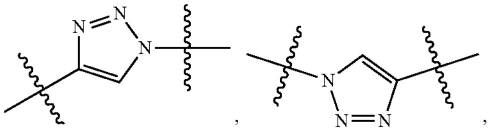
, , or polyethylene glycol.

22. The compound of any one of Embodiments 1 to 21, wherein —NH—CH($R^{A7a}$)—C(O)— forms a D-amino acid residue.

23. The compound of any one of Embodiments 1 to 22, wherein $R^{A7a}$ is $C_1$-$C_3$ alkyenyl.

24. The compound of Embodiment 23, wherein $R^{A7a}$ is —$CH_2$—$CH_2$—.

25. A compound of Formula B or a salt or solvate of Formula B:

[Formula B]

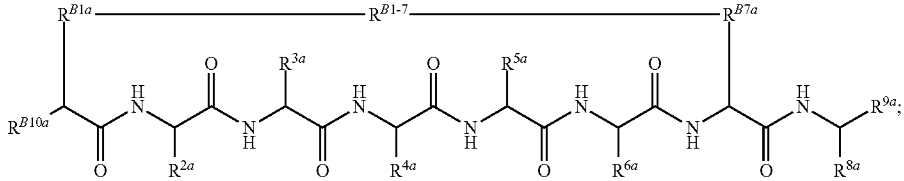

$R^{B1a}$ is a linear, branched, and/or cyclic $C_1$-$C_{10}$ alkylenyl, alkenylenyl, or alkynylenyl, wherein one or more carbons in $C_2$-$C_{10}$ are optionally independently replaced with N, S, and/or O heteroatoms $R^{B1-7}$ is:

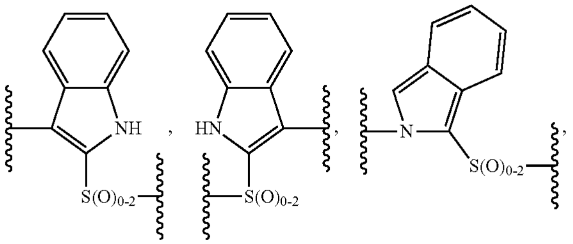

or

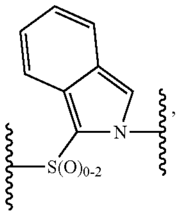

wherein the indole and the isoindole are optionally substituted with one or more of —F, —Br, —Cl, —I, —OH, —O—$R^{B1-7b}$, —CO—, —COOH, —$CONH_2$, —CN, —O-aryl, —$NH_2$, —$NHR^{B1-7b}$, $N_3$, —NH, —CHO, and/or —$R^{B1-7b}$, wherein each $R^{B1-7b}$ is a linear or branched $C_1$-$C_3$ alkyl, alkenyl, or alkynyl;

$R^{B7a}$ is a linear $C_1$-$C_5$ alkylenyl wherein 0-2 carbons in $C_2$-$C_5$ are independently replaced with one or more N, S, and/or O heteroatoms;

$R^{2a}$ is —($CH_2$)—($R^{2b}$)-(phenyl), wherein $R^{2b}$ is absent, —$CH_2$—, —NH—, —S— or —O—, wherein the phenyl is 4-substituted with —$NH_2$, —$NO_2$, —OH, —$OR^{2c}$, —SH, —$SR^{2c}$, or —O-phenyl, wherein the phenyl is optionally 3-substituted with halogen or —OH, wherein the phenyl is optionally 5-subsituted with halogen or —OH, wherein the —O-phenyl ring is optionally 4-substituted with —$NH_2$, —$NO_2$, —OH, —$OR^{2a}$, —SH, or —$SR^{2c}$, wherein the —O-phenyl ring is optionally 3-substituted with halogen or —OH, wherein the —O-phenyl ring is optionally 5-subsituted with halogen or —OH, wherein each $R^{2c}$ is independently a $C_1$-$C_3$ linear or branched alkyl group;

$R^{3a}$ is $R^{3b}R^{3c}$ wherein $R^{3b}$ is a linear $C_1$-$C_5$ alkylenyl, alkenylenyl, or alkynylenyl, wherein 0-2 carbons in $C_2$-$C_5$ are independently replaced with one or more N, S, and/or O heteroatoms, wherein $R^{3c}$ is —$N(R^{3d})_{2-3}$ or guanidino, wherein each $R^{3d}$ is independently —H or a linear or branched $C_1$-$C_3$ alkyl;

$R^{4a}$ is $R^{4b}R^{4c}$ wherein $R^{4b}$ is a linear $C_1$-$C_5$ alkylenyl, alkenylenyl, or alkynylenyl, in which 0-2 carbons in $C_2$-$C_5$ are independently replaced with one or more N, S, and/or O heteroatoms, wherein $R^{4c}$ is —$N(R^{4d})_{2-3}$ or guanidino, wherein each $R^{4d}$ is independently —H or a linear or branched $C_1$-$C_3$ alkyl;

$R^{5a}$ is —$(CH_2)_{1-3}$—$R^{5b}$, wherein 1 carbon in —$(CH_2)_{2-3}$— is optionally replaced with a N, S, or O heteroatom, wherein $R^{5b}$ is:

phenyl optionally substituted with one or a combination of the following: 4-substituted with —$NH_2$, —$NO_2$, —OH, —$OR^{5c}$, —SH, —$SR^{5c}$, or —O-phenyl; 3-substituted with halogen or —OH; and/or 5-subsituted with halogen or —OH; wherein the —O-phenyl, ring is optionally 4-substituted with —$NH_2$, —$NO_2$, —OH, —$OR^{5c}$, —SH, or —$SR^{5c}$, wherein the —O-phenyl ring is optionally 3-substituted with halogen or —OH, wherein the —O-phenyl ring is optionally 5-subsituted with halogen or —OH; or a fused bicyclic or fused tricyclic aryl group wherein one or more carbons are optionally independently replaced by N, S, and/or O heteroatoms, and optionally independently substituted with one or a combination of halogen, —OH, —$OR^{5c}$, amino, —$NHR^{5c}$, and/or $N(R^{5c})_2$;

wherein each $R^{5c}$ is independently a $C_1$-$C_3$ linear or branched alkyl group;

either $R^{6a}$ is absent, methyl, ethyl, —C≡CH, —CH═$CH_2$, —C≡C—$(CH_2)_{1-3}$—OH, —C≡C—$(CH_2)_{1-3}$—SH, —C≡C—$(CH_2)_{1-3}$—$NH_2$, —C≡C—$(CH_2)_{1-3}$—COOH, —C≡C—$(CH_2)_{1-3}$—CONH, —C≡C—$(CH_2)_{1-3}R^{6b}R^{6c}$, —CH═CH—$(CH_2)_{1-3}$—OH, —CH═CH—$(CH_2)_{1-3}$—SH, —CH═CH—$(CH_2)_{1-3}$—$NH_2$, —CH═CH—$(CH_2)_{1-3}$—COOH, —CH═CH—$(CH_2)_{1-3}$—CONH, —CH═CH—$(CH_2)_{1-3}R^{6b}R^{6c}$, —$CH_2$—$R^{6b}$—OH, —$CH_2$—$R^{6b}$—COOH, —$CH_2$—$(R^{6b})_{1-3}$—$NH_2$, —$CH_2$—$R^{6b}$—CONH, or —$CH_2$—$R^{6b}R^{6c}$, wherein each $R^{6b}$ is independently absent, —$CH_2$—, —NH—, —S— or —O—, and wherein $R^{6c}$ is:

a 5 or 6 membered aromatic ring wherein one or more carbons are optionally independently replaced by N, S, and/or O heteroatoms, and optionally substituted with one or more groups independently selected from oxo, hydroxyl, sulfhydryl, nitro, amino, and/or halogen;

or —NH—CH($R^{6a}$)—((O)—NH— is replaced with:

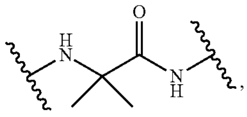,
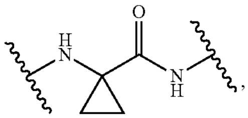,
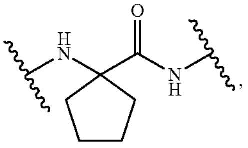,
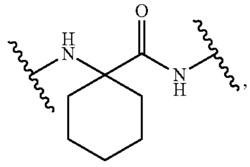,
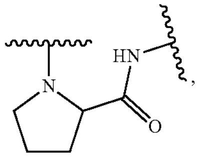, or 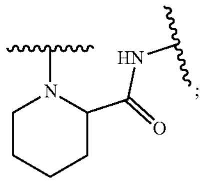;

$R^{8a}$ is $R^{8b}R^{8c}$ wherein $R^{8b}$ is a linear $C_1$-$C_5$ alkylenyl, alkenylenyl, or alkynylenyl, in which 0-2 carbons in $C_2$-$C_5$ are independently replaced with one or more N, S, and/or O heteroatoms, wherein $R^{8c}$ is —$N(R^{8d})_{2-3}$ or guanidino, wherein each $R^{8d}$ is independently —H or a linear or branched $C_1$-$C_3$ alkyl;

$R^{9a}$ is: —C(O)$NH_2$, —C(O)—OH, —$CH_2$—C(O)$NH_2$, —$CH_2$—C(O)—OH, —$CH_2$—$NH_2$, —$CH_2$—OH, —$CH_2$—$CH_2$—$NH_2$, —$R^{9b}$—$R^{9c}$, or —$R^{9b}$-[linker]-$R^{X}_{n1}$, wherein:

$R^{9b}$ is —$CH_2$—NH—C(O)—, —$CH_2$—C(O)—, —$CH_2$—O—, —C(O)NH—, —C(O)—N($CH_3$)—, —$CH_2$—NHC(S)—, —C(S)NH—, —$CH_2$—N($CH_3$)C(S)—, —C(O)N($CH_3$)—, —$CH_2$—N($CH_3$)C(O)—, —C(S)N($CH_3$)—, —$CH_2$—NHC(S)NH—, —$CH_2$—NHC(O)NH—, —$CH_2$—S—, —$CH_2$—S(O)—, —$CH_2$—$S(O)_2$—, —$CH_2$—$S(O)_2$—NH—, —$CH_2$—S(O)—NH—, —$CH_2$—Se—, —$CH_2$—Se(O)—, —$CH_2$—$Se(O)_2$—, —$CH_2$—NHNHC(O)—, —C(O)NHNH—, —$CH_2$—OP(O)($O^-$)O—, —$CH_2$-phosphamide-, —$CH_2$-thiophosphodiester-, —$CH_2$—S-tetrafluorophenyl-S—,

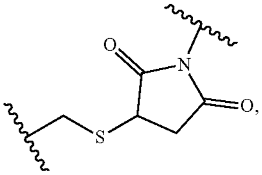,
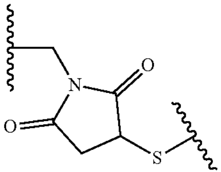,
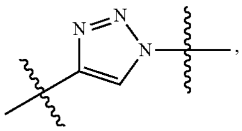,
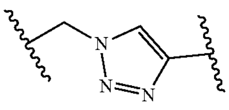, or polyethylene glycol;

$R^{9c}$ is hydrogen or a linear, branched, and/or cyclic $C_1$-$C_{20}$ alkyl, alkenyl or alkynyl, wherein 0-6 carbons in $C_2$-$C_{20}$ are independently replaced by N, S, and/or O heteroatoms, and substituted with 0-3 groups independently selected from one or a combination of oxo, hydroxyl, sulfhydryl, halogen, guanidino, carboxylic acid, sulfonic acid, sulfinic acid, and/or phosphoric acid;

$R^{B10a}$ is: amine, —NH—$(CH_3)_{1-2}$, —$N(CH_3)_{2-3}$, —NH—C(O)—$CH_3$, —NH—C(O)-(phenyl), or —$R^{B10b}$-[linker]-$R^{X}_{n1}$ wherein $R^{B10b}$ is:

—NH—C(O)—, —C(O)—, —O—, —C(O)NH—, —C(O)—N($CH_3$)—, —NHC(S)—, —C(S)NH—, —N($CH_3$)C(S)—, —C(O)N($CH_3$)—, —N($CH_3$)C(O)—, —C(S)N($CH_3$)—, —NHC(S)NH—, —NHC(O)NH—, —S—, —S(O)—, —S(O)—O—, —$S(O)_2$—, —$S(O)_2$—O—, —$S(O)_2$—NH—, —S(O)—NH—, —Se—, —Se(O)—, —$Se(O)_2$—, —NHNHC(O)—, —C(O)NHNH—, —OP(O)($O^-$)O—, -phosphamide-, -thiophosphodiester-, —S-tetrafluorophenyl-S—,

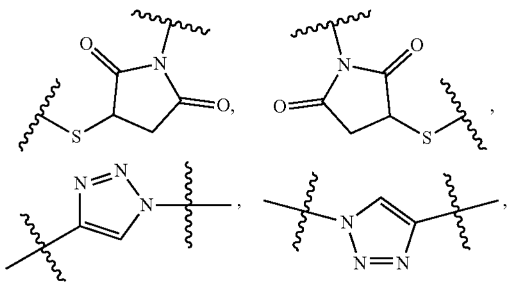

or polyethylene glycol;

each n1 is independently 0, 1 or 2;

each $R^X$ is an albumin binder, a therapeutic moiety, a fluorescent label, a radiolabeled group, or a group capable of being radiolabelled;

wherein 0-3 peptide backbone amides are independently replaced with

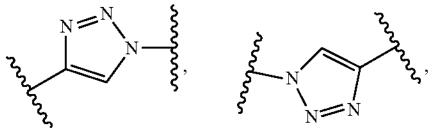 [SMILES: *c1cn(*)nn1 ; *c1cn(*)nn1]

or thioamide; and wherein 0-3 peptide backbone amides are N-methylated.

26. The compound of Embodiment 25, wherein $R^{B1-7}$ is

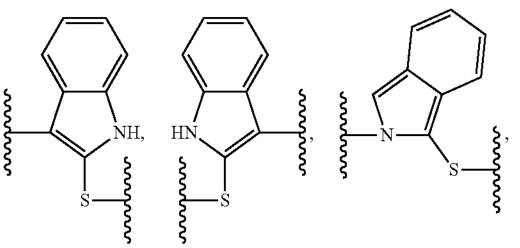

or

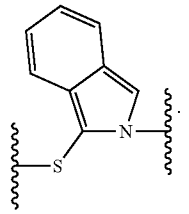

27. The compound of Embodiment 25, wherein $R^{B1a}$ is —$(CH_2)_{1-2}$—, $R^{B1-7}$ is

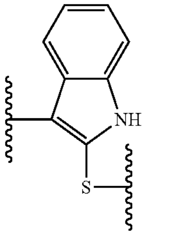

or

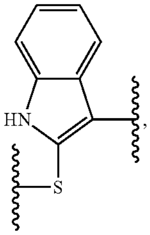

and $R^{B7a}$ is —$(CH_2)_{1-2}$—.

28. The compound of Embodiment 25, wherein $R^{B1a}$—$R^{B1-7}$—$R^{B7a}$ is

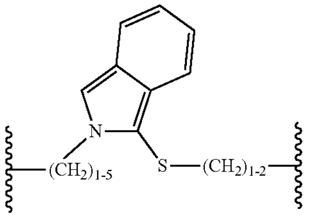

or

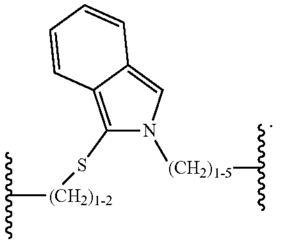

29. The compound of any one of Embodiments 25 to 28, wherein —NH—CH($R^{B7a}$)—C(O)— forms a D-amino acid residue.

30. The compound of any one of Embodiments 25 to 29, wherein $R^{B10a}$ is: amine, —NH—$(CH_3)_{1-2}$, —$N(CH_3)_{2-3}$, —NH—C(O)—$CH_3$, or —NH—C(O)-(phenyl).

31. The compound of any one of Embodiments 25 to 29, wherein $R^{B10a}$ is —$R^{B10b}$-[linker]-$R^{X}_{n1}$.

32. The compound of Embodiment 31, wherein $R^{B10b}$ is: —NH—C(O)—, —C(O)—, —O—, —C(O)NH—, —C(O)—N($CH_3$)—, —NHC(S)—, —C(S)NH—, —N($CH_3$)C(S)—, —C(O)N($CH_3$)—, —N($CH_3$)C(O)—, —C(S)N($CH_3$)—, —NHC(S)NH—, —NHC(O)NH—, —NHNHC(O)—, —C(O)NHNH—,

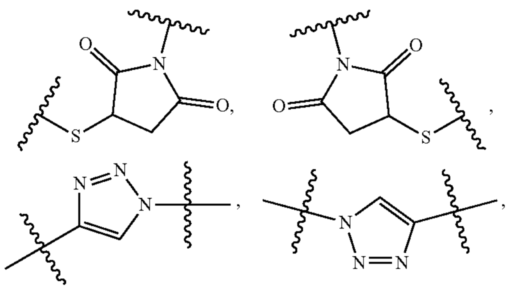

or polyethylene glycol.

33. The compound of Embodiment 31, wherein $R^{B10a}$ is —NHC(O)—[linker]-$R^{X}_{n1}$ or —N($CH_3$)C(O)—[linker]-$R^{X}_{n1}$.

34. A compound of Formula C or a salt or solvate of Formula C:

[Formula C]

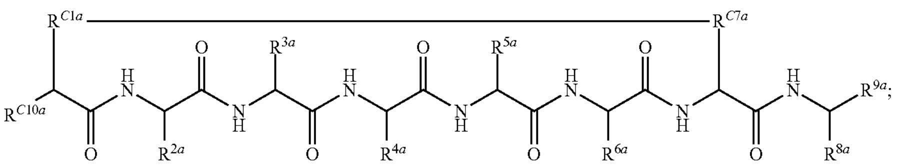

$R^{C1a}$ is:

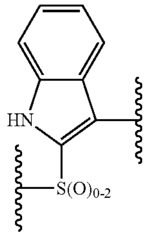

or

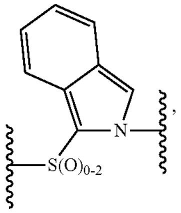

wherein the indole and the isoindole are optionally substituted with one or more of —F, —Br, —Cl, —I, —OH, —O—$R^{C1b}$, —CO—, —COOH, —$CONH_2$, —CN, —O-aryl, —$NH_2$, —$NHR^{C1b}$, $N_3$, —NH, —CHO, and/or —$R^{C1b}$, wherein each $R^{C1b}$ is a linear or branched $C_1$-$C_3$ alkyl, alkenyl, or alkynyl;

$R^{2a}$ is —($CH_2$)—($R^{2b}$)-(phenyl), wherein $R^{2b}$ is absent, —$CH_2$—, —NH—, —S— or —O—, wherein the phenyl is 4-substituted with —$NH_2$, —$NO_2$, —OH, —$OR^{2c}$, —SH, —$SR^{2c}$, or —O-phenyl, wherein the phenyl is optionally 3-substituted with halogen or —OH, wherein the phenyl is optionally 5-subsituted with halogen or —OH, wherein the —O-phenyl ring is optionally 4-substituted with —$NH_2$, —$NO_2$, —OH, —$OR^{2c}$, —SH, or —$SR^{2c}$, wherein the —O-phenyl ring is optionally 3-substituted with halogen or —OH, wherein the —O-phenyl ring is optionally 5-subsituted with halogen or —OH, wherein each $R^{2c}$ is independently a $C_1$-$C_3$ linear or branched alkyl group;

$R^{3a}$ is $R^{3b}R^{3c}$ wherein $R^{3b}$ is a linear $C_1$-$C_5$ alkylenyl, alkenylenyl, or alkynylenyl, wherein 0-2 carbons in $C_2$-$C_5$ are independently replaced with one or more N, S, and/or O heteroatoms, wherein $R^{3c}$ is —$N(R^{3d})_{2-3}$ or guanidino, wherein each $R^{3d}$ is independently —H or a linear or branched $C_1$-$C_3$ alkyl;

$R^{4a}$ is $R^{4b}R^{4c}$ wherein $R^{4b}$ is a linear $C_1$-$C_5$ alkylenyl, alkenylenyl, or alkynylenyl, in which 0-2 carbons in $C_2$-$C_5$ are independently replaced with one or more N, S, and/or O heteroatoms, wherein $R^{4c}$ is —$N(R^{4d})_{2-3}$ or guanidino, wherein each $R^{4d}$ is independently —H or a linear or branched $C_1$-$C_3$ alkyl;

$R^{5a}$ is —$(CH_2)_{1-3}$—$R^{5b}$, wherein 1 carbon in —$(CH_2)_{2-3}$— is optionally replaced with a N, S, or O heteroatom, wherein $R^{5b}$ is:

phenyl optionally substituted with one or a combination of the following: 4-substituted with —$NH_2$, —$NO_2$, —OH, —$OR^{5c}$, —SH, —$SR^{5c}$, or —O-phenyl; 3-substituted with halogen or —OH; and/or 5-subsituted with halogen or —OH; wherein the —O-phenyl ring is optionally 4-substituted with —$NH_2$, —$NO_2$, —OH, —$OR^{5c}$, —SH, or —$SR^{5c}$, wherein the —O-phenyl ring is optionally 3-substituted with halogen or —OH, wherein the —O-phenyl ring is optionally 5-subsituted with halogen or —OH; or a fused bicyclic or fused tricyclic aryl group wherein one or more carbons are optionally independently replaced by N, S, and/or O heteroatoms, and optionally independently substituted with one or a combination of halogen, —OH, —$OR^{5c}$, amino, —$NHR^{5c}$, and/or $N(R^{5c})_2$;

wherein each RSC is independently a $C_1$-$C_3$ linear or branched alkyl group;

either $R^{6a}$ is H, methyl, ethyl, —C≡CH, —CH═$CH_2$, —C≡C—$(CH_2)_{1-3}$—OH, —C≡C—$(CH_2)_{1-3}$—SH, —C≡C—$(CH_2)_{1-3}$—$NH_2$, —C≡C—$(CH_2)_{1-3}$—COOH, —C≡C—$(CH_2)_{1-3}$—CONH, —C≡C—$(CH_2)_{1-3}R^{6b}R^{6c}$, —CH═CH—$(CH_2)_{1-3}$-OH, —CH═CH—$(CH_2)_{1-3}$—SH, —CH═CH—$(CH_2)_{1-3}$—$NH_2$, —CH═CH—$(CH_2)_{1-3}$—COOH, —CH═CH—$(CH_2)_{1-3}$—CONH, —CH═CH—$(CH_2)_{1-3}R^{6b}R^{6c}$, —$CH_2$—$R^{6b}$—OH, —$CH_2$—$R^{6b}$—COOH, —$CH_2$—$(R^{6b})_{1-3}$—$NH_2$, —$CH_2$—$R^{6b}$—CONH, or —$CH_2$—$R^{6b}R^{6c}$, wherein each $R^{6b}$ is independently absent, —$CH_2$—, —NH—, —S— or —O—, and wherein $R^{6c}$ is:

a 5 or 6 membered aromatic ring wherein one or more carbons are optionally independently replaced by N, S, and/or O heteroatoms, and optionally substituted with one or more groups independently selected from oxo, hydroxyl, sulfhydryl, nitro, amino, and/or halogen;

or —NH—CH($R^{6a}$)—C(O)—NH— is replaced with:

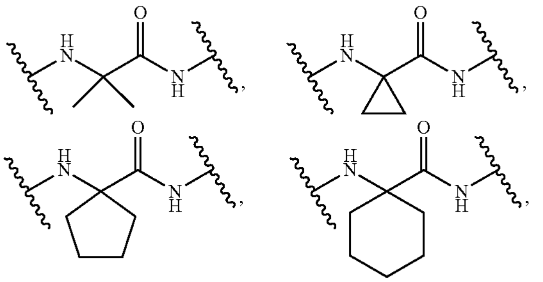

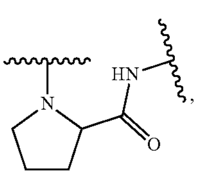

or

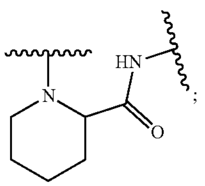

$R^{C7a}$ is a linear $C_1$-$C_5$ alkylenyl wherein optionally 0-2 carbons in $C_2$-$C_5$ are independently replaced with one or more N, S, and/or O heteroatoms;

$R^{8a}$ is $R^{8b}R^{8c}$ wherein $R^{8b}$ is a linear $C_1$-$C_5$ alkylenyl, alkenylenyl, or alkynylenyl, in which 0-2 carbons in $C_2$-$C_5$ are independently replaced with one or more N, S, and/or O heteroatoms, wherein $R^{80}$ is —$N(R^{8d})_{2-3}$ or guanidino, wherein each $R^{8d}$ is independently —H or a linear or branched $C_1$-$C_3$ alkyl;

$R^{9a}$ is: —C(O)$NH_2$, —C(O)—OH, —$CH_2$—C(O)$NH_2$, —$CH_2$—C(O)—OH, —$CH_2$—$NH_2$, —$CH_2$—OH, —$CH_2$—$CH_2$—$NH_2$, —$R^{9b}$—$R^{9c}$; or —$R^{9b}$-[linker]-$R^X_{n1}$, wherein:

$R^{9b}$ is —$CH_2$—NH—C(O)—, —$CH_2$—C(O)—, —$CH_2$—O—, —C(O)NH—, —C(O)—N($CH_3$)—, —$CH_2$—NHC(S)—, —C(S)NH—, —$CH_2$—N($CH_3$)C(S)—, —C(O)N($CH_3$)—, —$CH_2$—N($CH_3$)C(O)—, —C(S)N($CH_3$)—, —$CH_2$—NHC(S)NH—, —$CH_2$—NHC(O)NH—, —$CH_2$—S—, —$CH_2$—S(O)—, —$CH_2$—S$(O)_2$—, —$CH_2$—S$(O)_2$—NH—, —$CH_2$—S(O)—NH—, —$CH_2$—Se—, —$CH_2$—Se(O)—, —$CH_2$—Se$(O)_2$—, —$CH_2$—NHNHC(O)—, —C(O)NHNH—, —$CH_2$—OP(O)($O^-$)O—, —$CH_2$-phosphamide-, —$CH_2$-thiophosphodiester-, —$CH_2$—S-tetrafluorophenyl-S—,

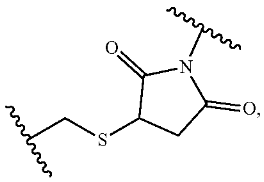

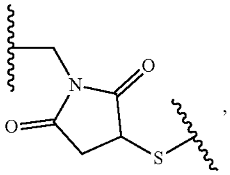
,

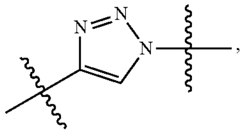
,

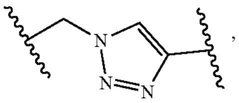
, or polyethylene glycol; and $R^{9c}$ is hydrogen or a linear, branched, and/or cyclic $C_1$-$C_{20}$ alkyl, alkenyl or alkynyl, wherein 0-6 carbons in $C_2$-$C_{20}$ are independently replaced by N, S, and/or O heteroatoms, and substituted with 0-3 groups independently selected from one or a combination of oxo, hydroxyl, sulfhydryl, halogen, guanidino, carboxylic acid, sulfonic acid, sulfinic acid, and/or phosphoric acid;

$R^{C10a}$ is $R^{C10b}$—$R^{C10c}$-[linker]-$R^X_{n1}$ or $R^{C10d}$, wherein:

$R^{C10b}$ is a linear $C_1$-$C_5$ alkylenyl, alkenylenyl, or alkynylenyl, in which 0-2 carbons in $C_2$-$C_5$ are independently replaced with N, S, and/or O heteroatoms;

$R^{C10c}$ is —NH—C(O)—, —C(O)—, —O—, —C(O)NH—, —C(O)—N($CH_3$)—, —NHC(S)—, —C(S)NH—, —N($CH_3$)C(S)—, —C(O)N($CH_3$)—, —N($CH_3$)C(O)—, —C(S)N($CH_3$)—, —NHC(S)NH—, —NHC(O)NH—, —S—, —S(O)—, —S(O)—O—, —S$(O)_2$—, —S$(O)_2$—O—, —S$(O)_2$—NH—, —S(O)—NH—, —Se—, —Se(O)—, —Se$(O)_2$—, —NHNHC(O)—, —C(O)NHNH—, —OP(O)($O^-$)O—, -phosphamide-, -thiophosphodiester-, —S-tetrafluorophenyl-S—,

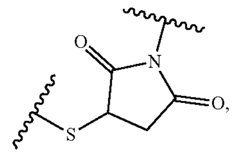

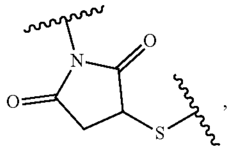
,

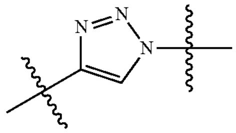
,

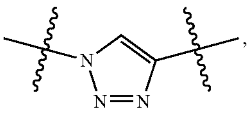
, or polyethylene glycol; and $R^{C10d}$ is:

a linear $C_1$-$C_5$ alkyl, alkenyl, or alkynyl, wherein 0-2 carbons in $C_2$-$C_5$ are independently replaced by N, S, and/or O heteroatoms, optionally C-substituted with a single substituent selected from: —SH, —OH, amino, carboxy, guanidino, —NH—C(O)—$CH_3$, —S—C(O)—$CH_3$, —O—C(O)—$CH_3$, —NH—C(O)-(phenyl), —S—C(O)-(phenyl), —O—C(O)-(phenyl), —NH—$(CH_3)_{1-2}$, —$NH_2$—$CH_3$, —N$(CH_3)_{2-3}$, —S—$CH_3$, or —O—$CH_3$;

a branched $C_1$-$C_{10}$ alkyl, alkenyl, or alkynyl, wherein 0-3 carbons in $C_2$-$C_{10}$ are independently replaced by N, S, and/or O heteroatoms; or $R^{C10e}R^{C10f}$, wherein $R^{C10e}$ is a linear $C_1$-$C_3$ alkyl, wherein $C_2$ alkyl or $C_3$ alkyl is optionally replaced with N, S, or O heteroatom, wherein $R^{C10f}$ is:

a 5 or 6 membered aromatic ring wherein one or more carbons are optionally independently replaced by N, S, and/or O heteroatoms, and optionally substituted with one or more groups independently selected from oxo, hydroxyl, sulfhydryl, nitro, amino, and/or halogen;

a fused bicyclic or fused tricyclic aryl group wherein one or more carbons are optionally independently replaced by N, S, and/or O heteroatoms, and optionally substituted with one or more groups independently selected from halogen, —OH, —$OR^{C10g}$, amino, —$NHR^{C10g}$ and/or $N(R^{C10g})_2$, wherein $R^{C10g}$ is $C_1$-$C_3$ linear or branched alkyl;

each n1 is independently 0, 1 or 2;

each $R^X$ is an albumin binder, a therapeutic moiety, a fluorescent label, a radiolabeled group, or a group capable of being radiolabelled;

wherein 0-3 peptide backbone amides are independently replaced with

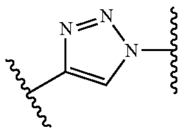
,

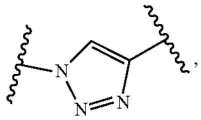
, or thioamide; and wherein 0-3 peptide backbone amides are N-methylated.

35. The compound of Embodiment 34, wherein —NH—CH($R^{C7a}$)—C(O)— forms a D-amino acid residue.

36. The compound of Embodiment 34 or 35, wherein $R^{C7a}$ is a linear $C_1$-$C_5$ alkylenyl.

37. The compound of Embodiment 34 or 35, wherein $R^{C7a}$ is —$(CH_2)_{1-2}$—.

38. The compound of any one of Embodiments 34 to 37, wherein $R^{C10a}$ is $R^{C10b}$—$R^{C10c}$-[linker]-$R^X_{n1}$.

39. The compound of Embodiment 38, wherein $R^{C10b}$ is a linear $C_1$-$C_5$ alkylenyl, alkenylenyl, or alkynylenyl.

40. The compound of Embodiment 38, wherein $R^{C10b}$ is a linear $C_1$-$C_5$ alkylenyl.

41. The compound of any one of Embodiment 38 to 40, wherein $R^{C10c}$ is:

—NH—C(O)—, —C(O)—, —O—, —C(O)NH—, —C(O)—N($CH_3$)—, —NHC(S)—, —C(S)NH—, —N($CH_3$)C(S)—, —C(O)N($CH_3$)—, —N($CH_3$)C(O)—, —C(S)N($CH_3$)—, —NHC(S)NH—, —NHC(O)NH—, —NHNHC(O)—, —C(O)NHNH—,

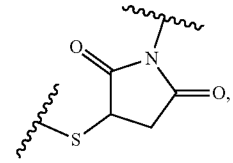 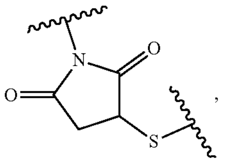 ,

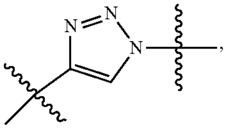 , 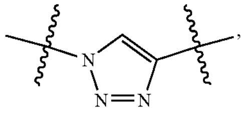 , or polyethylene glycol.

42. The compound of any one of Embodiments 38 to 40, wherein $R^{C10c}$ is —NHC(O)— or —N($CH_3$)C(O)—.

43. The compound of any one of Embodiments 34 to 37, wherein $R^{C10a}$ is $R^{C10d}$.

44. The compound of Embodiment 43, wherein $R^{C10d}$ is a linear $C_1$-$C_5$ alkyl, alkenyl, or alkynyl, wherein 0-2 carbons in $C_2$-$C_5$ are independently replaced by N, S, and/or O heteroatoms, optionally C-substituted with a single substituent selected from: —SH, —OH, amino, carboxy, guanidino, —NH—C(O)—$CH_3$, —S—C(O)—$CH_3$, —O—C(O)—$CH_3$, —NH—C(O)-(phenyl), —S—C(O)— (phenyl), —O—C(O)-(phenyl), —NH—$(CH_3)_{1-2}$, —$NH_2$—$CH_3$, —$N(CH_3)_{2-3}$, —S—$CH_3$, or —O—$CH_3$.

45. The compound of Embodiment 43, wherein $R^{C10d}$ is a linear $C_1$-$C_5$ alkyl, alkenyl, or alkynyl, optionally C-substituted with a single substituent selected from: —SH, —OH, amino, carboxy, guanidino, —NH—C(O)—$CH_3$, —S—C(O)—$CH_3$, —O—C(O)—$CH_3$, —NH—C(O)-(phenyl), —S—C(O)-(phenyl), —O—C(O)-(phenyl), —NH—$(CH_3)_{1-2}$, —$NH_2$—$CH_3$, —$N(CH_3)_{2-3}$, —S—$CH_3$, or —O—$CH_3$.

46. The compound of Embodiment 43, wherein $R^{C10d}$ is a linear $C_1$-$C_5$ alkyl optionally C-substituted with a single substituent selected from: —SH, —OH, amino, carboxy, guanidino, —NH—C(O)—$CH_3$, —S—C(O)—$CH_3$, —O—C(O)—$CH_3$, —NH—C(O)-(phenyl), —S—C(O)-(phenyl), —O—C(O)-(phenyl), —NH—$(CH_3)_{1-2}$, —$NH_2$—$CH_3$, —$N(CH_3)_{2-3}$, —S—$CH_3$, or —O—$CH_3$.

47. The compound of Embodiment 43, wherein $R^{C10d}$ is a branched $C_1$-$C_{10}$ alkyl, alkenyl, or alkynyl, wherein 0-3 carbons in $C_2$-$C_{10}$ are independently replaced by N, S, and/or O heteroatoms.

48. The compound of Embodiment 43, wherein $R^{C10d}$ is a branched $C_1$-$C_{10}$ alkyl, alkenyl, or alkynyl.

49. The compound of Embodiment 43, wherein $R^{C10d}$ is a branched $C_1$-$C_{10}$ alkyl.

50. The compound of Embodiment 43, wherein $R^{C10d}$ is $R^{C10e}R^{C10f}$.

51. The compound of Embodiment 50, wherein $R^{C10e}$ is a linear $C_1$-$C_3$ alkyl.

52. The compound of Embodiment 50 or 51, wherein $R^{C10f}$ is a 5 or 6 membered aromatic ring wherein 0-4 carbons are independently replaced by N, S, and/or O heteroatoms, and substituted with 0-4 groups independently selected from oxo, hydroxyl, sulfhydryl, nitro, amino, and/or halogen.

53. The compound of Embodiment 50 or 51, wherein $R^{C10f}$ of is a fused bicyclic or fused tricyclic aryl group wherein 0-6 carbons are independently replaced by N, S, and/or O heteroatoms, and substituted with 0-6 groups independently selected from halogen, —OH, —$OR^{C10g}$, amino, —$NHR^{C10g}$, and/or $N(R^{C10g})_2$, wherein $R^{C10g}$ is $C_1$-$C_3$ linear or branched alkyl.

54. The compound of Embodiment 53, wherein $R^{C10g}$ is methyl.

55. The compound of any one of Embodiments 1 to 54, wherein zero peptide backbone amides are replaced.

56. The compound of any one of Embodiments 1 to 55, wherein zero peptide backbone amides are N-methylated.

57. The compound of any one of Embodiments 1 to 56, wherein $R^{2b}$ is absent or —$CH_2$—.

58. The compound of any one of Embodiments 1 to 56 wherein $R^{2a}$ is —($CH_2$)—($R^{2b}$)-(phenyl), wherein $R^{2b}$ is absent or —$CH_2$—, wherein the phenyl is 4-substituted with —$NH_2$, —$NO_2$, —OH, —SH, or —O-phenyl.

59. The compound of any one of Embodiments 1 to 58, wherein —NH—CH($R^{2a}$)—C(O)— forms an L-amino acid residue.

60. The compound of any one of Embodiments 1 to 58, wherein —NH—CH($R^{2a}$)—C(O)— forms a Tyr residue.

61. The compound of any one of Embodiments 1 to 58, wherein —NH—CH($R^{2a}$)—C(O)— forms a Phe residue.

62. The compound of any one of Embodiments 1 to 58, wherein —NH—CH($R^{2a}$)—C(O)— forms a (4-$NO_2$)-Phe residue.

63. The compound of any one of Embodiments 1 to 58, wherein —NH—CH($R^{2a}$). C(O)— forms a (4-$NH_2$)-Phe residue.

64. The compound of any one of Embodiments 1 to 58, wherein —NH—CH($R^{2a}$)—C(O)— forms a hTyr residue.

65. The compound of any one of Embodiments 1 to 58, wherein —NH—CH($R^{2a}$)—C(O)— forms a (3-I)Tyr residue.

66. The compound of any one of Embodiments 1 to 58, wherein —NH—CH($R^{2a}$)—C(O)— forms a Glu residue.

67. The compound of any one of Embodiments 1 to 58, wherein —NH—CH($R^{2a}$). C(O)— forms a Gln residue.

68. The compound of any one of Embodiments 1 to 58, wherein —NH—CH($R^{2a}$)—C(O)— forms a D-Tyr residue.

69. The compound of any one of Embodiments 1 to 68, wherein $R^{3a}$ is $R^{3b}R^{3a}$, wherein $R^{3b}$ is a linear $C_1$-$C_5$ alkylenyl, alkenylenyl, or alkynylenyl, wherein $R^{3c}$ is —$N(R^{3d})_{2-3}$ or guanidino, wherein each $R^{3d}$ is independently —H or a linear or branched $C_1$-$C_3$ alkyl.

70. The compound of any one of Embodiments 1 to 69, wherein $R^{3b}$ is a linear $C_1$-$C_5$ alkylenyl, alkenylenyl, or alkynylenyl.

71. The compound of any one of Embodiments 1 to 69, wherein $R^{3b}$ is a linear $C_1$-$C_5$ alkylenyl.

72. The compound of any one of Embodiments 1 to 71, wherein each $R^{3d}$ is independently —H or methyl.

73. The compound of any one of Embodiments 1 to 71, wherein $R^{3c}$ is —$NH_2$ or —$NH_3$.

74. The compound of any one of Embodiments 1 to 71, wherein $R^{3c}$ is guanidino.

75. The compound of any one of Embodiments 1 to 74, wherein —NH—CH($R^{3a}$)—C(O)— forms an L-amino acid residue.

76. The compound of any one of Embodiments 1 to 74, wherein —NH—CH($R^{3a}$)—C(O)— forms a Lys(iPr) residue.

77. The compound of any one of Embodiments 1 to 74, wherein —NH—CH($R^{3a}$)—C(O)— forms a $Arg(Me)_2$ (asymmetrical) residue.

78. The compound of any one of Embodiments 1 to 74, wherein —NH—CH($R^{3a}$)—C(O)— forms a Arg(Me) residue.

79. The compound of any one of Embodiments 1 to 78, wherein $R^{4a}$ is $R^{4b}R^{4c}$, wherein $R^{4b}$ is a linear $C_1$-$C_5$ alkylenyl, alkenylenyl, or alkynylenyl, wherein $R^{4c}$ is —$N(R^{4d})_{2-3}$ or guanidino, wherein each $R^{4d}$ is independently —H or a linear or branched $C_1$-$C_3$ alkyl.

80. The compound of any one of Embodiments 1 to 79, wherein $R^{4b}$ is a linear $C_1$-$C_5$ alkylenyl, alkenylenyl, or alkynylenyl.

81. The compound of any one of Embodiments 1 to 79, wherein $R^{4b}$ is a linear $C_1$-$C_5$ alkylenyl.

82. The compound of any one of Embodiments 1 to 81, wherein each $R^{4d}$ is independently —H or methyl.

83. The compound of any one of Embodiments 1 to 81, wherein $R^{4c}$ is —$NH_2$ or —$NH_3$.

84. The compound of any one of Embodiments 1 to 81, wherein $R^{4c}$ is guanidino.

85. The compound of any one of Embodiments 1 to 78, wherein —NH—CH($R^{4a}$)—C(O)— forms a D-amino acid residue.

86. The compound of any one of Embodiments 1 to 78, wherein —NH—CH($R^{4a}$)—C(O)— forms a D-Arg residue.

87. The compound of any one of Embodiments 1 to 78, wherein —NH—CH($R^{4a}$)—C(O)— forms a D-hArg residue.

88. The compound of any one of Embodiments 1 to 87, wherein $R^{5a}$ is —$CH_2$—$R^{5b}$, —$CH_2$—$CH_2$—$R^{5b}$, or —$CH_2$—$CH_2$—$CH_2$—$R^{5b}$.

89. The compound of any one of Embodiments 1 to 88, wherein $R^{5b}$ is phenyl optionally substituted with one or a combination of the following: 4-substituted with —$NH_2$, —$NO_2$, —OH, —$OR^{5c}$, —SH, —$SR^{5c}$, or —O-phenyl; 3-substituted with halogen or —OH; and/or 5-subsituted with halogen or —OH; wherein the —O-phenyl ring is optionally 4-substituted with —$NH_2$, —$NO_2$, —OH, —$OR^{5c}$, —SH, or —$SR^{5c}$, wherein the —O-phenyl ring is optionally 3-substituted with halogen or —OH, wherein the —O-phenyl ring is optionally 5-subsituted with halogen or —OH.

90. The compound of any one of Embodiments 1 to 88, wherein $R^{5b}$ is phenyl optionally substituted with one or a combination of the following: 4-substituted with —$NH_2$, —$NO_2$, —OH, —SH, or —O-phenyl; 3-substituted with halogen or —OH; and/or 5-subsituted with halogen or —OH.

91. The compound of any one of Embodiments 1 to 88, wherein $R^{5b}$ is a fused bicyclic or fused tricyclic aryl group wherein one or more carbons are optionally independently replaced by N, S, and/or O heteroatoms, and optionally independently substituted with one or a combination of halogen, —OH, —$OR^{5c}$, amino, —$NHR^{5c}$, and/or $N(R^{5c})_2$.

92. The compound of any one of Embodiments 1 to 88, wherein $R^{5b}$ is a fused bicyclic or fused tricyclic aryl group wherein 0-3 carbons are independently replaced by N, S, and/or O heteroatoms, and optionally independently substituted with one or a combination of halogen, —OH, and/or amino.

93. The compound of any one of Embodiments 1 to 88, wherein $R^{5b}$ excludes 9-linked anthracenyl.

94. The compound of any one of Embodiments 1 to 87, wherein —NH—CH($R^{5a}$)—C(O)— forms an L-amino acid residue.

95. The compound of any one of Embodiments 1 to 87, wherein —NH—CH($R^{5a}$)—C(O)— forms a 2-(Ant)Ala residue.

96. The compound of any one of Embodiments 1 to 87, wherein —NH—CH($R^{5a}$)—C(O)— forms a 2-Nal residue.

97. The compound of any one of Embodiments 1 to 87, wherein —NH—CH($R^{5a}$)—C(O)— forms a Trp residue.

98. The compound of any one of Embodiments 1 to 87, wherein —NH—CH($R^{5a}$)—C(O)— forms a (4-$NH_2$)Phe residue.

99. The compound of any one of Embodiments 1 to 87, wherein —NH—CH($R^{5a}$)—C(O)— forms a hTyr residue.

100. The compound of any one of Embodiments 1 to 87, wherein —NH—CH($R^{5a}$)—C(O)— forms a Tyr residue.

101. The compound of any one of Embodiments 1 to 100, wherein $R^{6a}$ is absent or methyl, ethyl, —C≡CH, —CH═$CH_2$, —$CH_2$—$R^{6b}$—OH, —$CH_2$—$R^{6b}$—COOH, —$CH_2$—$(R^{6b})_{1-3}$—$NH_2$, —$CH_2$—$R^{6b}$—CONH, or —$CH_2$—$R^{6b}R^{6c}$, wherein each $R^{6b}$ is independently absent, —$CH_2$—, —NH—, —S— or —O—.

102. The compound of any one of Embodiments 1 to 101, wherein $R^{6c}$ is a 5 or 6 membered aromatic ring wherein 0-3 carbons are independently replaced by N, S, and/or O heteroatoms, and optionally substituted with 0-3 groups independently selected from oxo, hydroxyl, sulfhydryl, nitro, amino, and/or halogen.

103. The compound of any one of Embodiments 1 to 101, wherein —NH—CH($R^{6a}$)—C(O)—NH— is replaced with:

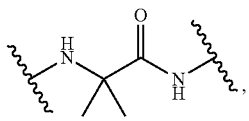,
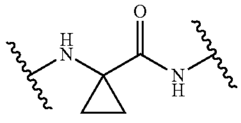,
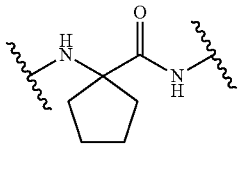,
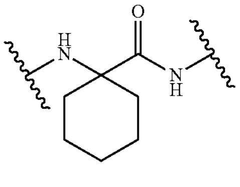.

104. The compound of any one of Embodiments 1 to 101, wherein —NH—CH($R^{6a}$)—C(O)—NH— is replaced with:

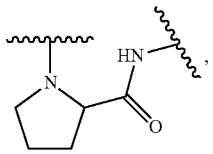, or
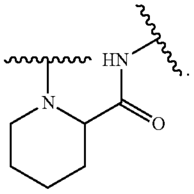.

105. The compound of any one of Embodiments 1 to 101, wherein $R^{6a}$ is absent.

106. The compound of any one of Embodiments 1 to 102, wherein —NH—CH($R^{6a}$)—C(O)— forms a D-amino acid residue.

107. The compound of any one of Embodiments 1 to 102, wherein —NH—CH($R^{6a}$)—C(O)— forms a His residue.

108. The compound of any one of Embodiments 1 to 102, wherein —NH—CH($R^{6a}$)—C(O)— forms a D-His residue.

109. The compound of any one of Embodiments 1 to 102, wherein —NH—CH($R^{6a}$)—C(O)— forms a D-Glu residue.

110. The compound of any one of Embodiments 1 to 102, wherein —NH—CH($R^{6a}$)—C(O)— forms a D-Gln residue.

111. The compound of any one of Embodiments 1 to 102, wherein —NH—CH($R^{6a}$)—C(O)— forms a D-Ala residue.

112. The compound of any one of Embodiments 1 to 102, wherein —NH—CH($R^{6a}$)—C(O)— forms a D-Phe residue.

113. The compound of any one of Embodiments 1 to 102, wherein —NH—CH($R^{6a}$)—C(O)— forms a D-Ser residue.

114. The compound of any one of Embodiments 1 to 102, wherein —NH—CH($R^{6a}$)—C(O)— forms a D-Dab residue.

115. The compound of any one of Embodiments 1 to 102, wherein —NH—CH($R^{6a}$)—C(O)— forms a D-Dap residue.

116. The compound of any one of Embodiments 1 to 115, wherein $R^{8a}$ is $R^{8b}R^{8c}$, wherein $R^{8b}$ is a linear $C_1$-$C_5$ alkylenyl, alkenylenyl, or alkynylenyl, wherein $R^{8c}$ is —N($R^{8d}$)$_{2-3}$ or guanidino, wherein each $R^{8d}$ is independently —H or a linear or branched $C_1$-$C_3$ alkyl.

117. The compound of any one of Embodiments 1 to 116, wherein $R^{8b}$ is a linear $C_1$-$C_5$ alkylenyl, alkenylenyl, or alkynylenyl.

118. The compound of any one of Embodiments 1 to 116, wherein $R^{8b}$ is a linear $C_1$-$C_5$ alkylenyl.

119. The compound of any one of Embodiments 1 to 118, wherein each $R^{8d}$ is independently —H or methyl.

120. The compound of any one of Embodiments 1 to 118, wherein $R^{8c}$ is —$NH_2$ or —$NH_3$.

121. The compound of any one of Embodiments 1 to 118, wherein $R^{8c}$ is guanidino.

122. The compound of any one of Embodiments 1 to 121, wherein —NH—CH($R^{8a}$)—C(O)— forms an L-amino acid residue.

123. The compound of any one of Embodiments 1 to 115, wherein —NH—CH($R^{8a}$)—C(O)— forms a Lys(iPr) residue.

residue.

124. The compound of any one of Embodiments 1 to 141, wherein $R^{9a}$ is: —C(O)$NH_2$, —C(O)—OH, —$CH_2$—C(O)$NH_2$, —$CH_2$—C(O)—OH, or —$R^{9b}$—$R^{9c}$, wherein $R^{9b}$ is —C(O)NH—.

125. The compound of any one of Embodiments 1 to 124, wherein $R^{9c}$ is

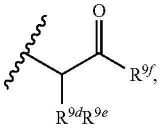

wherein $R^{9d}$ is a linear or branched $C_1$-$C_5$ alkylenyl, alkenylenyl, or alkynylenyl, in which 0-2 carbons in $C_2$-$C_5$ are independently replaced with N, S, and/or O heteroatoms, wherein $R^{9e}$ is carboxylic acid, sulfonic acid, sulfinic acid, phosphoric acid, amino, guanidino, —SH, —OH, —NH—C(O)—$CH_3$, —S—C(O)—$CH_3$, —O—C(O)—$CH_3$, —NH—C(O)-(phenyl), —S—C(O)-(phenyl), —O—C(O)-(phenyl), —NH—$CH_3$, —N($CH_3$)$_2$, —S—$CH_3$, —O—$CH_3$, and phenyl, and wherein $R^{9f}$ is amino or —OH.

126. The compound of Embodiment 125, wherein $R^{9d}$ is a linear or branched $C_1$-$C_5$ alkylenyl, alkenylenyl, or alkynylenyl.

127. The compound of Embodiment 125, wherein $R^{9d}$ is a linear or branched $C_1$-$C_5$ alkylenyl.

128. The compound of any one of Embodiments 1 to 124, wherein $R^{9a}$ is —$R^{9b}$-[linker]-$R^{X}_{n1}$.

129. The compound of Embodiment 128, wherein $R^{9b}$ is —C(O)NH—.

130. The compound of any one of Embodiments 1 to 129, wherein each linker, if present, is independently a linear or branched chain of 1-10 units of $X^1L^1$ and/or $X^1(L^1)_2$, wherein:

each $X^1$ is, independently, a linear, branched, and/or cyclic $C_1$-$C_{15}$ alkylenyl, alkenylenyl or alkynylenyl wherein 0-6 carbons are independently replaced by N, S, and/or O heteroatoms, and substituted with 0-3 groups independently selected from one or a combination of oxo, hydroxyl, sulfhydryl, halogen, guanidino, carboxylic acid, sulfonic acid, sulfinic acid, and/or phosphoric acid;

each $L^1$ is independently —NH—C(O)—, —C(O)—, —O—, —C(O)NH—, —C(O)—N($CH_3$)—, —NHC(S)—, —C(S)NH—, —N($CH_3$)C(S)—, —C(O)N($CH_3$)—, —N($CH_3$)C(O)—, —C(S)N($CH_3$)—, —NHC(S)NH—, —NHC(O)NH—, —S—, —S(O)—, —S(O)—O—, —S(O)$_2$—, —S(O)$_2$—O—, —S(O)$_2$—NH—, —S(O)—NH—, —Se—, —Se(O)—, —Se(O)$_2$—, —NHNHC(O)—, —C(O)NHNH—, —OP(O)($O^-$)O—, -phosphamide-, -thiophosphodiester-, —S-tetrafluorophenyl-S—,

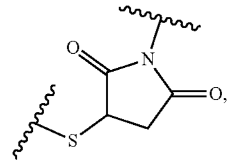
,
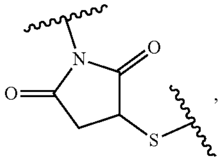
,
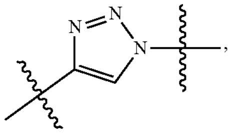
,
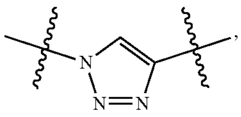
, or polyethylene glycol.

131. The compound of Embodiment 130, wherein each $L^1$ is independently —S—, —NHC(O)—, —C(O)NH—, —N($CH_3$)C(O)—, —C(O)N($CH_3$)—, —NHC(S)—, —C(S)NH—, —N($CH_3$)C(S)—, —C(S)N($CH_3$)—, NHC(S)NH—, —S—, —O—, —S(O)—, —S(O)$_2$—, —Se—, —Se(O)—, —Se(O)$_2$—, —NHNHC(O)—, —C(O)NHNH—, —OP(O)($O^-$)O—, —OP(O)($S^-$)O—,

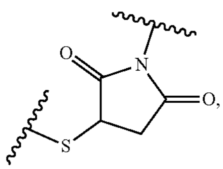
,
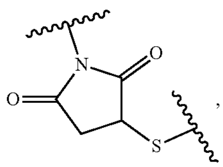
,

-continued

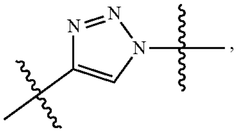, or 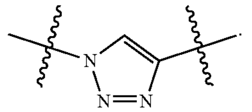.

131. The compound of Embodiment 130, wherein each $L^1$ is independently —S—, —NHC(O)—, —C(O)NH—, —$N(CH_3)C(O)$—, —$C(O)N(CH_3)$—,

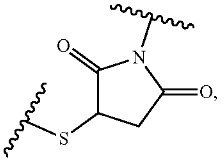 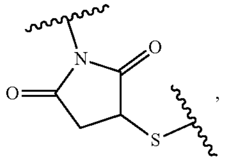,

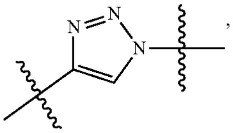, or 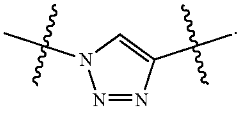.

132. The compound of 130, wherein at least one linker comprises at least one carboxylic acid, sulfonic acid, sulfinic acid, or phosphoric acid, and has a net negative charge at physiological pH.

133. The compound of any one of Embodiments 130 to 132, wherein at least one linker consists of 1-8 units of $X^1L^1$ and 0-2 units of $X^1(L^1)_2$.

134. The compound of any one of Embodiments 130 to 133, wherein each $X^1$ is independently a linear, branched, and/or cyclic $C_1$-$C_{15}$ alkylenyl.

135. The compound of any one of Embodiments 130 to 133, wherein each $X^1$ is independently: —CH—;

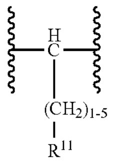

$R^{11}$ wherein each $R^{11}$ is independently carboxylic acid, sulfonic acid, sulfinic acid, or phosphoric acid; or

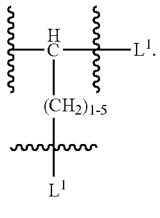

136. The compound of any one of Embodiments 130 to 135, wherein each $L^1$ between two $X^1$ groups is independently —NHC(O)—, —C(O)NH—, —$N(CH_3)C(O)$—, or —$C(O)N(CH_3)$—, and each $L^1$ linking an $R^X$ is independently-S—, —NHC(O)—, —C(O)NH—, —$N(CH_3)C$(O)—, —$C(O)N(CH_3)$—,

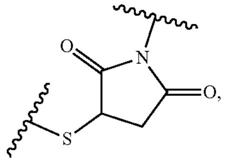 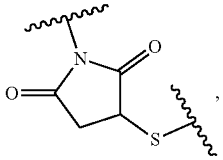,

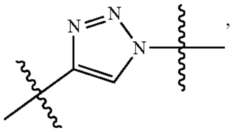, or 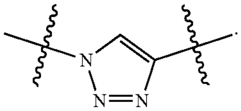.

137. The compound of any one of Embodiments 130 to 133, wherein at least one linker is a linear or branched peptide of amino acid residues selected from proteinogenic amino acid residues and/or nonproteinogenic amino acid residues listed in Table 1, wherein each $L^1$ between two $X^1$ groups is methylated or unmethylated, and wherein each $L^1$ linking an $R^X$ is independently —S—, —NHC(O)—, —C(O)NH—, —$N(CH_3)C(O)$—, —$C(O)N(CH_3)$—,

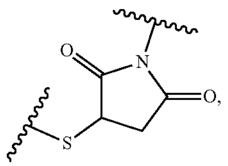 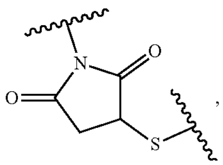,

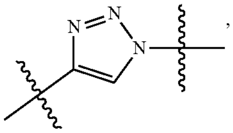, or 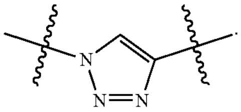.

138. The compound of Embodiment 136 or 137, wherein each $L^1$ between two $X^1$ groups is an unmethylated amide.

139. The compound of any one of Embodiments 130 to 138, wherein the linker forms a peptide linker of 1 to 3 amino acids selected from one or a combination of: cysteic acid, Glu, Asp, and/or 2-aminoadipic acid (2-Aad).

140. The compound of Embodiment 139, wherein the linker forms a single amino acid residue selected from cysteic acid, Glu, Asp, or 2-aminoadipic acid (2-Aad).

141. The compound of any one of Embodiments 130 to 140, wherein each $L^1$ linking an $R^X$ is independently —NHC (O)—, —C(O)NH—,

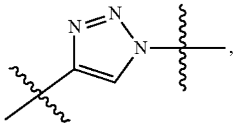, or 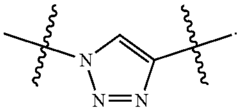.

142. The compound of any one of Embodiments 1 to 141, wherein at least one $R^X$ is an albumin binder.

143. The compound of Embodiment 142, wherein the albumin binder is bonded to an $L^1$ of the linker, wherein the albumin binder is: —$(CH_2)_{n2}$—$CH_3$ wherein n2 is 8-20; —$(CH_2)_{n3}$—C(O)OH wherein n3 is 8-20, or

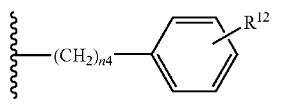

wherein n4=1-4 and $R^{12}$ is I, Br, F, Cl, H, OH, $OCH_3$, $NH_2$, $NO_2$ or $CH_3$;

144. The compound of any one of v 1 Embodiments 143, wherein at least one $R^X$ is a radiolabeled group or a group capable of being radiolabelled.

145. The compound of any one of Embodiments 1 to 144, comprising a first linker bonded to a radiolabeled group, or a group capable of being radiolabelled, and a second linker bonded to an albumin binder.

146. The compound of any one of Embodiments 1 to 144, comprising a first linker bonded to a first radiolabeled group, or a first group capable of being radiolabelled, and a second linker bonded to a second radiolabeled group, or a second group capable of being radiolabelled, optionally further comprising an albumin binder attached to either or both of the first linker and the second linker.

147. The compound of any one of Embodiments 1 to 144, comprising only a single linker bonded to 1-2 groups consisting of radiolabeled groups and/or group capable of being radiolabelled, and optionally further bonded to an albumin binder.

148. The compound of any one of Embodiments 1 to 147, wherein each group capable of being radiolabelled is independently selected from: a metal chelator optionally in complex with a radiometal or radioisotope-bound metal; a prosthetic group containing trifluoroborate (BF3); or a prosthetic group containing a silicon-fluorine-acceptor moiety, a sulphonyl fluoride, or a phosphoryl fluoride.

149. The compound of Embodiment 148, wherein the metal chelator is in complex with the radioisotope.

150. The compound of Embodiment 148 or 149, wherein the metal chelator is a polyaminocarboxylate chelator.

151. The compound of Embodiment 150, wherein the metal chelator is DOTA or a DOTA derivative.

152. The compound of any one of Embodiments 148 to 151, wherein a prosthetic group containing $BF_3$ is $—R^{13}R^{14}BF_3$ wherein $R^{13}$ is $—(CH_2)_{1-5}—$ and $—R^{14}BF_3$ is selected from Table 3 or 4 or

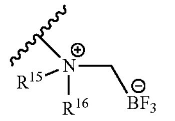

is R wherein each $R^{15}$ and each $R^{16}$ are independently a branched or linear $C_1$-$C_5$ alkyl.

153. The compound of Embodiment 152, wherein $—R^{14}BF_3$ is

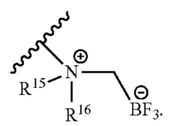

154. The compound of Embodiment 153, wherein $R^{15}$ and $R^{16}$ are each methyl.

155. The compound of any one of Embodiments 148 to 154, wherein the prosthetic group containing $BF_3$ comprises $^{18}F$.

156. The compound of any one of Embodiments 1 to 155, wherein at least $R^X$ is a therapeutic moiety.

157. The compound of any one of Embodiments 1 to 156, wherein at least one $R^X$ is fluorescent label.

158. The compound of any one of Embodiments 1 to 157, for use in imaging a CXCR4-expressing tissue in a subject or for imaging an inflammatory condition or disease, wherein at least one $R^X$ comprises or is complexed with an imaging radioisotope.

159. The compound of any one of Embodiments 1 to 158, for use in treating a disease or condition characterized by expression of CXCR4 in a subject, wherein at least one $R^X$ comprises or is complexed with a therapeutic radioisotope or at least one $R^X$ comprises a therapeutic moeity.

160. The compound of Embodiment 159, wherein the disease or condition is a CXCR4-expressing cancer.

REFERENCES

1. Murdoch, C. CXCR4: chemokine receptor extraordinaire. *Immunol. Rev.* 177, 175-184 (2000).
2. Griffith, J. W., Sokol, C. L. & Luster, A. D. Chemokines and Chemokine Receptors: Positioning Cells for Host Defense and Immunity. *Annu. Rev. Immunol.* 32, 659-702 (2014).
3. Ratajczak, M. Z. et al. The pleiotropic effects of the SDF-1-CXCR4 axis in organogenesis, regeneration and tumorigenesis. Leukemia 20, 1915-1924 (2006).
4. George, J. et al. Transfer of Endothelial Progenitor and Bone Marrow Cells Influences Atherosclerotic Plaque Size and Composition in Apolipoprotein E Knockout Mice. *Arterioscler. Thromb. Vasc. Biol.* 25, 2636-2641 (2005).
5. Wang, A. et al. CXCR4/CXCL12 Hyperexpression Plays a Pivotal Role in the Pathogenesis of Lupus. *J. Immunol.* 182, 4448-4458 (2009).
6. Wang, A. et al. Dysregulated expression of CXCR4/CXCL12 in subsets of patients with systemic lupus erythematosus. *Arthritis Rheum.* 62, 3436-3446 (2010).
7. Guo, F. et al. CXCL12/CXCR4: a symbiotic bridge linking cancer cells and their stromal neighbors in oncogenic communication networks. *Oncogene* 35, 816-26 (2016).
8. Jacobson, O. & Weiss, I. D. CXCR4 chemokine receptor overview: biology, pathology and applications in imaging and therapy. *Theranostics* 3, 1-2 (2013).
9. Balkwill, F. Cancer and the chemokine network. *Nat. Rev. Cancer* 4, 540-550 (2004).
10. Zlotnik, A., Burkhardt, A. M. & Homey, B. Homeostatic chemokine receptors and organ-specific metastasis. *Nat. Rev. Immunol.* 11, 597-606 (2011).
11. Domanska, U. M. et a. A review on CXCR4/CXCL12 axis in oncology: No place to hide. *Eur. J. Cancer* 49, 219-230 (2013).
12. Zhao, H. et a. CXCR4 over-expression and survival in cancer: a system review and meta-analysis. *Oncotarget* 6, 5022-40 (2015).
13. Woodard, L. E. & Nimmagadda, S. CXCR4-Based Imaging Agents. *J. Nucl. Med.* 52, 1665-1669 (2011).
14. Kuil, J., Buckle, T. & van Leeuwen, F. W. B. Imaging agents for the chemokine receptor 4 (CXCR4). *Chem. Soc. Rev.* 41, 5239 (2012).

15. Weiss, I. D. & Jacobson, O. Molecular Imaging of Chemokine Receptor CXCR4. *Theranostics* 3, 76-84 (2013).

16. George, G. P. C., Pisaneschi, F., Nguyen, Q.-D. & Aboagye, E. O. Positron Emission Tomographic Imaging of CXCR4 in Cancer: Challenges and Promises. *Mol. Imaging* 14, 7290.2014.00041 (2015).

17. Peng, S. et a. Identification of LY2510924, a Novel Cyclic Peptide CXCR4 Antagonist That Exhibits Antitumor Activities in Solid Tumor and Breast Cancer Metastatic Models. *Mol. Cancer Ther.* 14, 480-491 (2015).

18. Salgia, R. et al. A randomized phase II study of LY2510924 and carboplatin/etoposide versus carboplatin/etoposide in extensive-disease small cell lung cancer. *Lung Cancer* 105, 7-13 (2017).

19. Tamamura, H. et al. A Low-Molecular-Weight Inhibitor against the Chemokine Receptor CXCR4: A Strong Anti-HIV Peptide T140. *Biochem. Biophys. Res. Commun.* 253, 877-882 (1998).

20. Fujii, N. et al. Molecular-Size Reduction of a Potent CXCR4-Chemokine Antagonist Using Orthogonal Combination of Conformation- and Sequence-Based Libraries. *Angew. Chemie Int. Ed.* 42, 3251-3253 (2003).

21. Todorovic, M. et al. Fluorescent Isoindole Crosslink (FlICk) Chemistry: A Rapid, User-friendly Stapling Reaction. *Angew. Chemie Int. Ed.* 58, 14120-14124 (2019).

SEQUENCE LISTING

```
Sequence total quantity: 1
SEQ ID NO: 1            moltype = AA  length = 5
FEATURE                 Location/Qualifiers
REGION                  1..5
                        note = synthetic construct
VARIANT                 1..5
                        note = replace with Dpr, Dbu, Orn, homoarginine, 2-amino-4-
                         guanidinobutyric acid, 2-amino-3-guanidinopropionic acid,
                         4- (2-aminoethyl)-1-carboxymethyl-piperazine,
                         4-amino-1-carboxymethyl- piperidine, or N-epsilon,
                         N-epsilon, N-epsilon-trimethyl-lysine
SITE                    1..5
                        note = an amino group in each amino acid residue is
                         optionally methylated
VARIANT                 2..5
                        note = Each amino acid may be present or absent
source                  1..5
                        mol_type = protein
                        organism = synthetic construct
SEQUENCE: 1
RRRRR                                                                     5
```

What is claimed is:

1. A compound of Formula A-II or salt or solvate thereof:

[Formula A-II]

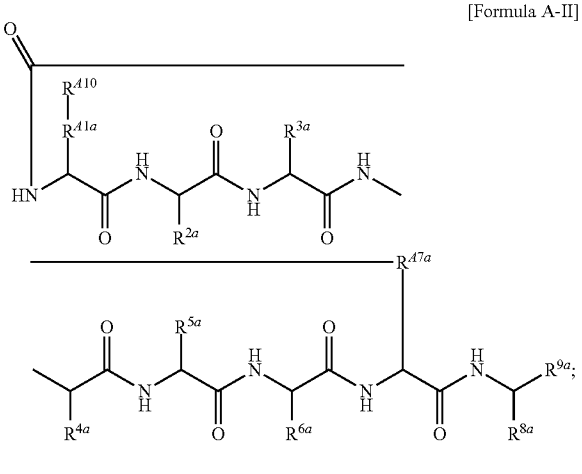

wherein:

—NH—CH($R^{2a}$)—C(O)— in Formula A-II forms a Tyr residue, a Phe residue, a (4-$NO_2$)-Phe residue, a (4-$NH_2$)-Phe residue, a hTyr residue, a (3-I)Tyr residue, a Glu residue, a Gln residue, or a D-Tyr residue;

—NH—CH($R^{3a}$)—C(O)— in Formula A-II forms a Lys (iPr) residue, an asymmetric Arg(Me)$_2$ residue, or a Arg(Me) residue;

—NH—CH($R^{4a}$)—C(O)— in Formula A-II forms a D-Arg residue or a D-hArg residue;

—NH—CH($R^{5a}$)—C(O)— in Formula A-II forms a 2-(Ant)Ala residue, a 2-Nal residue, a Trp residue, a (4-$NH_2$)Phe residue, a hTyr residue, or a Tyr residue;

—NH—CH($R^{6a}$)—C(O)— in Formula A-II forms a His residue, a D-His residue, a D-Glu residue, a D-Gln residue, a D-Ala residue, a D-Phe residue, a D-Ser residue, a D-Dab residue, a D-Dap residue;

$R^{8a}$ is $R^{8b}R^{8c}$, wherein $R^{8b}$ is a linear $C_1$-$C_5$ alkylenyl, $C_2$-$C_5$alkenylenyl, or $C_2$-$C_5$ alkynylenyl, wherein $R^{8c}$ is —N($R^{8d}$)$_{2\text{-}3}$ or guanidino, wherein each $R^{8d}$ is independently —H or a linear or branched $C_1$-$C_3$ alkyl;

$R^{9a}$ is —C(O)$NH_2$, —C(O)—OH, or —$R^{9b}$-[linker]-$R^{X}{}_{n1}$;

$R^{9b}$ is —C(O)NH—;

$R^{A7a}$ is $C_1$-$C_3$ alkylenyl;

$R^{A10}$ is absent or -[linker]-$R^{X}{}_{n1}$;

when $R^{A10}$ is absent, then $R^{A1a}$ is a linear $C_1$-$C_5$ alkyl optionally substituted with a single substituent selected from: —SH, —OH, amino, carboxy, guanidino, —NH—C(O)—$CH_3$, —S—C(O)—$CH_3$, —O—C(O)—$CH_3$, —NH—C(O)-(phenyl), —S—C(O)-(phenyl), —O—C(O)-(phenyl), —NH—($CH_3$)$_{1\text{-}2}$, —$NH_2$—$CH_3$, —N($CH_3$)$_{2\text{-}3}$, —S—$CH_3$, —O—$CH_3$, or a branched $C_1$-$C_{10}$ alkyl, alkenyl, or alkynyl;

when $R^{A10}$ is -[linker]-$R^{X}{}_{n1}$, then $R^{A1a}$ is $R^{A1e}R^{A1f}$, wherein $R^{A1e}$ is a linear $C_1$-$C_5$ alkylenyl, $C_2$-$C_5$ alkenylenyl, or $C_2$-$C_5$ alkynylenyl, and $R^{A1f}$ is —NH—C(O)—, —C(O)—, —O—, —C(O)NH—, —C(O)—N $(CH_3)$—, —NHC(S)—, —C(S)NH—, —N$(CH_3)$C(S)—, —C(O)N$(CH_3)$—, —N$(CH_3)$C(O)—, —C(S)N$(CH_3)$—, —NHC(S)NH—, —NHC(O)NH—, —S—, —S(O)—, —S(O)—O—, —$S(O)_2$—, —$S(O)_2$—NH—, —S(O)—NH—, —NHNHC(O)—, —C(O)NHNH—,

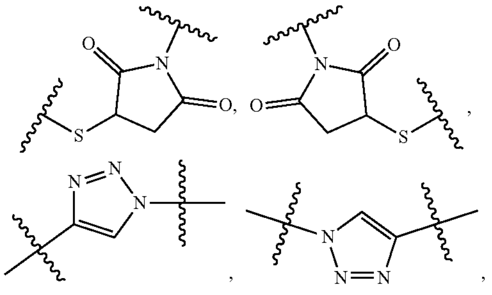

or polyethylene glycol;

the linker is each independently a linear or branched chain of 1-10 units of $X^1L^1$ and/or $X^1(L^1)_2$, wherein:

each $X^1$ is, independently, a linear, branched, and/or cyclic $C_1$-$C_{15}$ alkylenyl, $C_2$-$C_{15}$ alkenylenyl or $C_2$-$C_{15}$ alkynylenyl wherein 0-6 carbons are independently replaced by N, S, and/or O heteroatoms, and substituted with 0-3 groups independently selected from one or a combination of oxo, hydroxyl, sulfhydryl, halogen, guanidino, carboxylic acid, sulfonic acid, sulfinic acid, and/or phosphoric acid;

each $L^1$ is independently —NH—C(O)—, —NH—, —C(O)—, —O—, —C(O)NH—, —C(O)—N$(CH_3)$—, —NHC(S)—, —C(S)NH—, —N$(CH_3)$C(S)—, —C(O)N$(CH_3)$—, —N$(CH_3)$C(O)—, —C(S)N$(CH_3)$—, —NHC(S)NH—, —NHC(O)NH—, —S—, —S(O)—, —S(O)—O—, —$S(O)_2$—, —$S(O)_2$—O—, —$S(O)_2$—NH—, —S(O)—NH—, —Se—, —Se(O)—, —$Se(O)_2$—, —NHNHC(O)—, —C(O)NHNH—, —OP(O)($O^-$)O—, -phosphamide-, -thiophosphodiester-, —S-tetrafluorophenyl-S—,

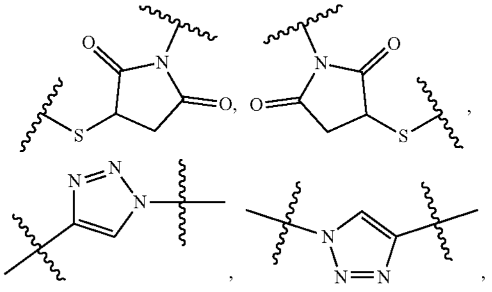

or polyethylene glycol; or alternatively, the linker together with $R^{A1f}$ forms a linear or branched peptide linker $(Xaa)_{1-5}$, wherein each Xaa is independently selected from a proteinogenic amino acid residue or a nonproteinogenic amino acid residue; and wherein the amino group in each Xaa is optionally methylated;

each n1 is independently 0, 1 or 2;

each $R^X$ is a therapeutic moiety, a fluorescent label, a radiolabeled group, a group capable of being radiolabelled, or a group capable of being radiolabelled that is in complex with a radioisotope or a radioisotope-bound metal;

wherein 0-3 peptide backbone amides are independently replaced with

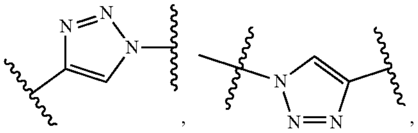 [SMILES: *c1cn(*)nn1 ; *c1cn(*)nn1]

or thioamide;

wherein 0-3 peptide backbone amides are N-methylated; and optionally, the compound is C-terminally amidated.

2. The compound of claim 1, wherein $R^{A10}$ is -[linker]-$R^X{}_{n1}$.

3. The compound of claim 1, wherein the linker is $X^1L^1$, $X^1L^1X^1L^1$, or $X^1L^1X^1L^1X^1L^1$, wherein each $X^1$ is same or different and each $L^1$ is same or different; and $X^1$ is

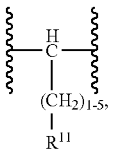

wherein each $R^{11}$ is independently a carboxylic acid, a sulfonic acid, a sulfinic acid, or a phosphoric acid.

4. The compound of claim 3, wherein each $X^1$ is

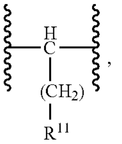

wherein each $R^{11}$ is independently a carboxylic acid, a sulfonic acid, a sulfinic acid, or a phosphoric acid.

5. The compound of claim 1, wherein the linker together with $R^{A1f}$ forms a linear or branched peptide linker $(Xaa)_{1-5}$, wherein:

a) at least one Xaa is selected from cysteic acid, Glu, Asp, or 2-aminoadipic acid (2-Aad); and wherein the group in each Xaa is optionally methylated; or b) at least one Xaa is selected from Dap, Dab, Orn, Arg, hArg, Agb, Agp, Acp, Pip, or NE, $N^\epsilon$, $N^\epsilon$-trimethyl-lysine; and wherein the group in each Xaa is optionally methylated.

6. The compound of claim 1, wherein the linker together with $R^{A1f}$ forms a single amino acid residue selected from:

a) cysteic acid, Glu, Asp, or 2-aminoadipic acid (2-Aad); and wherein the group in Xaa is optionally methylated; or b) D-Arg, L-Arg, D-hArg, L-hArg, or Pip; and wherein the group in Xaa is optionally methylated.

7. The compound of claim 1, wherein zero peptide backbone amides are replaced.

8. The compound of claim 1, wherein zero peptide backbone amides are N-methylated.

9. The compound of claim 1, wherein the compound of Formula A-II, or a salt or solvate thereof have the following combinations:

—NH—CH($R^{2a}$)—C(O)— forms a Tyr residue;

—NH—CH($R^{3a}$)—C(O)— forms a Lys(iPr) residue;

—NH—CH($R^{4a}$)—C(O)— forms a D-Arg residue;

—NH—CH($R^{A7a}$)—C(O)— forms a D-amino acid residue, wherein $R^{A7a}$ is $C_1$-$C_3$ alkyenyl; and —NH—CH($R^{8a}$)— together with —C(O)— from $R^{9a}$ forms a Lys(iPr) residue.

10. The compound of claim 9, wherein —NH—CH($R^{6a}$)—C(O)— forms a D-Ala residue or a D-Gln residue; and —NH—CH($R^{5a}$)—C(O)— forms a 2-Nal residue or a (4-$NH_2$)Phe residue.

11. The compound of claim 9, wherein $R^{A10}$ is -[linker]-$R^{X}_{n1}$, $R^{A1e}$ is linear $C_1$-$C_5$ alkylenyl, and $R^{A1f}$ is —NH—C(O)—.

12. The compound of claim 1, wherein at least one $R^X$ is a radiolabeled group or a group capable of being radiolabelled, wherein each group capable of being radiolabelled is independently selected from: a metal chelator optionally in complex with a radiometal or radioisotope-bound metal; a prosthetic group containing trifluoroborate ($BF_3$); or a prosthetic group containing a silicon-fluorine-acceptor moiety, a sulphonyl fluoride, or a phosphoryl fluoride.

13. The compound of claim 12, wherein the metal chelator is in complex with the radioisotope.

14. The compound of claim 12, wherein the metal chelator is a polyaminocarboxylate chelator or selected from Table 2.

15. The compound of claim 12, wherein the metal chelator is 1,4,7,10-tetraazacyclododecane-1,4,7,10-tetraacetic acid (DOTA), N,N'-bis[(6-carboxy-2-pyridil)methyl]-4,13-diaza-18-crown-6 ($H_2$-MACROPA), 2,2',2",2'"-(1,10-dioxa-4,7,13,16-tetraazacyclooctadecane-4,7,13,16-tetrayl)tetraacetic acid (CROWN), or a derivative thereof.

16. The compound of claim 12, wherein the prosthetic group containing $BF_3$ is —$R^{13}R^{14}BF_3$ wherein $R^{13}$ is —$(CH_2)_{1-5}$— and —$R^{14}BF_3$ is selected from Table 3 or Table 4 or is

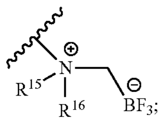

wherein each $R^{15}$ and each $R^{16}$ are independently a branched or linear $C_1$-$C_5$ alkyl.

17. The compound of claim 16, wherein —$R^{14}BF_3$ is

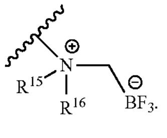

18. The compound of claim 17, wherein $R^{15}$ and $R^{16}$ are each methyl.

19. The compound of claim 12, wherein the prosthetic group containing $BF_3$ comprises at least one $^{18}F$.

20. The compound of claim 1, wherein at least one $R^X$ is a therapeutic moiety or at least one $R^X$ is fluorescent label.

21. A compound selected from:

cyclo[Phe-Tyr-Lys(iPr)-D-Arg-2Nal-D-Gln-D-Glu]-Lys(iPr);

cyclo[Phe-(3-I)Tyr-Lys(iPr)-D-Arg-2-Nal-Gly-D-Glu]-Lys(iPr);

cyclo[Phe-Tyr-Lys(iPr)-D-Arg-2Nal-D-Ala-D-Glu]-Lys(iPr);

cyclo[Phe-(4-$NH_2$)Phe-Lys(iPr)-D-Arg-2-Nal-Gly-D-Glu]-Lys(iPr);

cyclo[Phe-(4-$NO_2$)Phe-Lys(iPr)-D-Arg-2-Nal-Gly-D-Glu]-Lys(iPr);

cyclo[Phe-hTyr-Lys(iPr)-D-Arg-2-Nal-Gly-D-Glu]-Lys(iPr);

cyclo[Phe-hTyr-Lys(iPr)-D-Arg-2-Nal-D-Ala-D-Glu]-Lys(iPr);

cyclo[Phe-(4-$NH_2$)Phe-Lys(iPr)-D-Arg-2-Nal-D-Ala-D-Glu]-Lys(iPr);

cyclo[Lys(Ac)-Tyr-Lys(iPr)-D-Arg-Trp-D-Ala-D-Glu]-Lys(iPr);

cyclo[Phe-Tyr-Lys(iPr)-D-Arg-(4-$NH_2$)Phe-D-Ala-D-Glu]-Lys(iPr);

cyclo[Lys(Ac)-Glu-Lys(iPr)-D-Arg-2Nal-D-Ala-D-Glu]-Lys(iPr);

cyclo[Phe-Tyr-Lys(iPr)-D-Arg-2Nal-D-His-D-Glu]-Lys(iPr);

cyclo[Lys(Ac)-Gln-Lys(iPr)-D-Arg-2Nal-D-Ala-D-Glu]-Lys(iPr);

cyclo[Phe-Tyr-Lys(iPr)-D-Arg-2Nal-His-D-Glu]-Lys(iPr);

cyclo[Phe-D-Tyr-Lys(iPr)-D-Arg-2Nal-D-Ala-D-Glu]-Lys(iPr);

cyclo[Phe-Tyr-Lys(iPr)-D-Arg-2Nal-D-Ser-D-Glu]-Lys(iPr);

cyclo[Phe-Tyr-Lys(iPr)-D-Arg-2Nal-D-Leu-D-Glu]-Lys(iPr);

cyclo[Phe-Tyr-Lys(iPr)-D-Arg-2Nal-D-Asn-D-Glu]-Lys(iPr);

cyclo[Phe-Tyr-Arg(Me)-D-Arg-2Nal-D-Ala-D-Glu]-Lys(iPr);

cyclo[Phe-Tyr-Arg($Me_2$)(asym)-D-Arg-2Nal-Gly-D-Glu]-Lys(iPr);

cyclo[Phe-Tyr-Lys(iPr)-D-Arg-2Nal-D-Glu-D-Glu]-Lys(iPr);

cyclo[Phe-Tyr-Lys(iPr)-D-Arg-2Nal-D-Dab-D-Glu]-Lys(iPr);

cyclo[Phe-Tyr-Lys(iPr)-D-Arg-(2-Ant)Ala-Gly-D-Glu]-Lys(iPr);

cyclo(isoindole)[Phe-Tyr-Lys(iPr)-D-Arg-(2-Ant)Ala-Gly-D-Cys]-Lys(iPr);

cyclo(isoindole)[Phe-Tyr-Lys(iPr)-D-Arg-(2-Ant)Ala-Gly-Cys]-Lys(iPr);

cyclo[Lys(Ac)-Tyr-Lys(iPr)-D-Arg-2Nal-Gly-D-Glu]-Lys(iPr);

cyclo[Lys(CysAcid)-Tyr-Lys(iPr)-D-Arg-2Nal-D-Ala-D-Glu]-Lys(iPr);

cyclo[Orn(CysAcid)-Tyr-Lys(iPr)-D-Arg-2Nal-D-Ala-D-Glu]-Lys(iPr);

cyclo[Dap(CysAcid)-Tyr-Lys(iPr)-D-Arg-2Nal-D-Ala-D-Glu]-Lys(iPr);

cyclo[Lys(CysAcid)-(3-I)Tyr-Lys(iPr)-D-Arg-2Nal-D-Ala-D-Glu]-Lys(iPr);

cyclo[Lys(D-Arg)-Tyr-Lys(iPr)-D-Arg-2Nal-D-Ala-D-Glu]-Lys(iPr); or cyclo(tryptathionine)[Tyr-Lys(iPr)-D-Arg-2Nal-D-Ala-D-Cys]-Lys(iPr);

or a salt or solvate thereof;

wherein the compound is optionally bound to a radiolabeled group, a group capable of being radiolabelled, or a group capable of being radiolabelled that is in complex with a radioisotope or a radioisotope-bound metal, optionally through a linker; and wherein the compound is optionally C-terminally amidated.

22. The compound of claim 21, selected from cyclo[Lys(CysAcid-DOTA)-Tyr-Lys(iPr)-D-Arg-2Nal-D-Ala-D-Glu]-Lys(iPr);

cyclo[Lys(CysAcid-amido-N,N-dimethyl-ammoniomethyl-trifluoroborate)-Tyr-Lys(iPr)-D-Arg-2Nal-D-Ala-D-Glu]-Lys(iPr); or cyclo[Lys(CysAcid-triazole-N,N-dimethyl-ammoniomethyl-trifluoroborate)-Tyr-Lys(iPr)-D-Arg-2Nal-D-Ala-D-Glu]-Lys(iPr);

or a salt or solvate thereof, wherein the compound is optionally C-terminally amidated.

23. The compound of claim 22, wherein cyclo[Lys(CysAcid-DOTA)-Tyr-Lys(iPr)-D-Arg-2Nal-D-Ala-D-Glu]-Lys(iPr) is in complex with a radioisotope, wherein the radioisotope is $^{64}$Cu, $^{67}$Cu, $^{90}$Y, $^{153}$Sm $^{149}$Tb, $^{161}$Tb, $^{17}$Lu, $^{225}$Ac, $^{213}$Bi, $^{224}$Ra, $^{212}$Bi, $^{212}$Pb, $^{227}$Th, $^{223}$Ra, $^{47}$Sc, $^{186}$Re, $^{188}$Re, $^{94m}$Tc, $^{68}$Ga, $^{61}$Cu, $^{67}$Ga, $^{99m}$Tc, $^{111}$In $^{44}$Sc, $^{86}$Y, $^{89}$Zr, $^{90}$Nb, $^{117m}$Sn, $^{165}$Er, $^{211}$As, $^{203}$Pb, $^{166}$Ho, $^{149}$Pm, $^{159}$Gd, $^{105}$Rh, $^{109}$Pd, $^{198}$Au, $^{199}$Au, $^{175}$Yb, $^{142}$Pr, or $^{114m}$In.

24. The compound of claim 12, wherein the radioisotope is:

a) $^{64}$Cu, $^{67}$Cu, $^{90}$Y, $^{153}$Sm, $^{149}$Tb, $^{161}$Tb, $^{177}$Lu, $^{225}$Ac, $^{213}$Bi, $^{224}$Ra, $^{212}$Bi, $^{212}$Pb, $^{227}$Th, $^{223}$Ra, $^{47}$Sc, $^{186}$Re, $^{188}$Re, $^{94m}$Tc, $^{68}$Ga, $^{61}$Cu, $^{67}$Ga, $^{99m}$Tc, $^{111}$In, $^{44}$Sc, $^{86}$Y, $^{89}$Zr, $^{90}$Nb, $^{117m}$Sn, $^{165}$Er, $^{211}$As, $^{203}$Pb, $^{166}$Ho, $^{149}$Pm, $^{159}$Gd, $^{105}$Rh, $^{109}$Pd, $^{198}$Au, $^{199}$Au, $^{175}$Yb, $^{142}$Pr, or $^{114m}$In; or b) $^{177}$Lu, $^{111}$In, $^{213}$Bi, $^{68}$Ga, $^{67}$Ga $^{203}$Pb, $^{212}$Pb, $^{44}$Sc, $^{47}$Sc, $^{90}$Y, $^{86}$Y, $^{225}$Ac, $^{117m}$Sn, $^{153}$Sm, $^{149}$Tb, $^{161}$Tb, $^{165}$Er, $^{224}$Ra, $^{212}$Bi, $^{227}$Th, $^{223}$Ra, $^{64}$Cu, or $^{67}$Cu.

25. The compound of claim 12, wherein the radioisotope is $^{177}$Lu or $^{225}$Ac.

26. The compound of claim 9, wherein —NH—CH($R^{6a}$)—C(O)— forms a D-Ala residue and —NH—CH($R^{5a}$)—C(O)— forms a 2-Nal residue.

27. The compound of claim 22, wherein the trifluoroborate group in cyclo[Lys(CysAcid-amido-N,N-dimethyl-ammoniomethyl-trifluoroborate)-Tyr-Lys(iPr)-D-Arg-2Nal-D-Ala-D-Glu]-Lys(iPr) or cyclo[Lys(CysAcid-triazole-N,N-dimethyl-ammoniomethyl-trifluoroborate)-Tyr-Lys(iPr)-D-Arg-2Nal-D-Ala-D-Glu]-Lys(iPr) comprises at least one $^{18}$F.

28. The compound of claim 23, wherein cyclo[Lys(CysAcid-DOTA)-Tyr-Lys(iPr)-D-Arg-2Nal-D-Ala-D-Glu]-Lys(iPr) is in complex with a radioisotope, and wherein the radioisotope is $^{177}$Lu or $^{225}$Ac.

* * * * *